United States Patent
Xu et al.

(10) Patent No.: US 11,946,928 B2
(45) Date of Patent: Apr. 2, 2024

(54) METHODS AND COMPOSITIONS RELATING TO AIRWAY DYSFUNCTION

(71) Applicants: TRUSTEES OF BOSTON UNIVERSITY, Boston, MA (US); THE BRIGHAM AND WOMEN'S HOSPITAL, INC., Boston, MA (US)

(72) Inventors: Ke Xu, Cambridge, MA (US); Marc E. Lenburg, Brookline, MA (US); Ehab Billatos, Milton, MA (US); Alejandro A. Diaz, Boston, MA (US)

(73) Assignees: TRUSTEES OF BOSTON UNIVERSITY; THE BRIGHAM AND WOMEN'S HOSPITAL, INC.

( * ) Notice: Subject to any disclaimer, the term of this patent is extended or adjusted under 35 U.S.C. 154(b) by 62 days.

(21) Appl. No.: 17/748,404

(22) Filed: May 19, 2022

(65) Prior Publication Data
US 2022/0373537 A1    Nov. 24, 2022

Related U.S. Application Data

(60) Provisional application No. 63/191,080, filed on May 20, 2021.

(51) Int. Cl.
*G01N 33/50* (2006.01)
*C12Q 1/6883* (2018.01)

(52) U.S. Cl.
CPC ....... *G01N 33/5023* (2013.01); *C12Q 1/6883* (2013.01); *C12Q 2539/10* (2013.01); *C12Q 2600/118* (2013.01); *C12Q 2600/158* (2013.01); *G01N 2800/50* (2013.01)

(58) Field of Classification Search
CPC .............. C12Q 1/6883; C12Q 2539/10; C12Q 2600/118; C12Q 2600/158; G01N 33/5023; G01N 2800/50
See application file for complete search history.

(56) References Cited

U.S. PATENT DOCUMENTS

| | | | | |
|---|---|---|---|---|
| 2003/0228617 A1* | 12/2003 | Aune | ................... | C12Q 1/6883 435/6.16 |
| 2012/0015904 A1* | 1/2012 | Sharp | ........................ | A61P 9/10 435/6.12 |
| 2015/0299807 A1* | 10/2015 | Ross | .................... | C12Q 1/6886 435/193 |
| 2017/0137883 A1* | 5/2017 | Murphy | ............... | A61K 31/365 |

(Continued)

FOREIGN PATENT DOCUMENTS

| | | |
|---|---|---|
| WO | 2009/078793 A1 | 6/2009 |
| WO | 2020/229361 A1 | 11/2020 |

OTHER PUBLICATIONS

Hackett et al. (PLoS One, 2011, 6(5): e18378, doi: 10.1371/journal.pone.0018378) (Year: 2011).*

(Continued)

*Primary Examiner* — Jeremy C Flinders
(74) *Attorney, Agent, or Firm* — NIXON PEABODY LLP; Ronald I. Eisenstein; Nicole D. Kling

(57) ABSTRACT

Described herein are methods relating to the diagnosis, prognosis, and treatment of airway dysfunction, e.g., bronchiectasis by detecting gene expression in a sample obtained from a subject. Exemplary samples include a bronchial brushing, nasal brushing, sputum, or peripheral blood sample.

28 Claims, 12 Drawing Sheets

(56) References Cited

U.S. PATENT DOCUMENTS

| | | | |
|---|---|---|---|
| 2019/0144942 A1* | 5/2019 | Shalek | A61K 35/15 |
| | | | 424/93.7 |
| 2020/0057053 A1* | 2/2020 | Beane-Ebel | G01N 33/57423 |
| 2020/0248274 A1 | 8/2020 | Brody et al. | |
| 2021/0095334 A1* | 4/2021 | Heintz | C12Q 1/6806 |

OTHER PUBLICATIONS

Affymetrix HG-U133 Plus 2.0 microchip data sheet (Year: 2007).*
Goyal et al. (Pediatric Pulmonology, 2016, 51:450-469) (Year: 2016).*
Chalmers et al. (N Engl J Med, 2020, 383:2127-37) (Year: 2020).*
Maertzdorf et al. (PLoS One, 2011, 6(10)e26938) (Year: 2011).*
Penzo et al. (Cells, 2020, 9:387) (Year: 2020).*
Steiling et al. (Am J Respir Crit Care Med, 2013, 187(9):933-942) (Year: 2013).*
Doyle et al. (J. Med. Chem., 2016, 59(2):9457-9472) (Year: 2016).*
Chalmers et al. "Neutrophil elastase activity is associated with exacerbations and lung function decline in bronchiectasis." American journal of respiratory and critical care medicine 195.10 (2017): 1384-1393.
Chen et al. "Airway cells from protracted bacterial bronchitis and bronchiectasis share similar gene expression profiles." Pediatric Pulmonology 53.5 (2018): 575-582.
Guan et al. "Aetiology of bronchiectasis in G uangzhou, southern C hina." Respirology 20.5 (2015): 739-748.
Fang. "Consensus analysis via weighted gene co-expression network analysis (WGCNA) reveals genes participating in early phase of acute respiratory distress syndrome (ARDS) induced by sepsis". Bioengineered . . . Apr. 5, 2021; abstract; p. 1162, col. 2, "Methods: Data Collection and Quality Control" section; p. 1170, col. 2, "Conclusion" section.
"Palmer. ""Dipeptidyl Peptidase 1 Inhibitor AZD7986 Induces a Sustained, Exposure-Dependent Reduction in Neutrophil Elastase Activity in Healthy Subjects"". Clinical Pharmacology & Therapeutics . . . Apr. 16, 2018; abstract; p. 1155, ""Study Highlights"" Box, ""How Might This Change Clinical Pharmacology or Translational Science?"" section; p. 1162, col. 2, first paragraph (continued from p. 1161 ); p. 1163, col. 2, paragraph 2".
Shen. "Antibodies against low-density lipoprotein receptor-related protein 4 induce myasthenia gravis". The Journal of Clinical Investigation . . . Dec. 2, 2013; abstract.

* cited by examiner

METHODS AND COMPOSITIONS RELATING TO AIRWAY DYSFUNCTION

CROSS-REFERENCE TO RELATED APPLICATIONS

This application claims benefit under 35 U.S.C. § 119(e) of U.S. Provisional Application No. 63/191,080 filed May 20, 2021, the contents of which are incorporated herein by reference in their entirety.

GOVERNMENT SUPPORT

This invention was made with government support under Grant No. W81XWH-11-2-0161 awarded by the Department of the Army and Grant No. CA196408 awarded by the National Institutes of Health. The government has certain rights in the invention.

TECHNICAL FIELD

The technology described herein relates to the diagnosis, prognosis, and treatment of airway dysfunction.

BACKGROUND

Bronchiectasis (BE) is a pathologic dilation of bronchi in the lungs. Once considered an orphan disease that affects less than 200,000 people in the United States (US), BE has become increasingly common in the US, with over 70,000 new diagnoses in 2013 and between 340,000 and 522,000 prevalent cases requiring treatment. Bronchiectasis diagnosis currently requires a CT scan to diagnose, as the early symptoms (cough and phlegm production) are non-specific. Additionally, CT scans cannot detect early-stage bronchiectasis or the airway dysfunction that often leads to bronchiectasis.

SUMMARY

The inventors have now described methods of diagnosing, prognosing, and treating airway dysfunction (and bronchiectasis) that relate to detecting gene expression changes in samples, e.g., nasal or bronchial brushing samples. This permits earlier and more cost-effective medical intervention.

In one aspect of any of the embodiments, described herein is a method comprising detecting the level of expression of one or more genes selected from at least one of: at least one gene of Group A, at least one gene of Group B, at least one gene of Group C, at least one gene of Group D, and at least one gene of Group E; in a bronchial brushing, nasal brushing, sputum, or peripheral blood sample obtained from a subject. In some embodiments of any of the aspects, the sample obtained from the subject is a bronchial brushing or nasal brushing sample.

In one aspect of any of the embodiments, described herein is a method of treating airway dysfunction, the method comprising administering:
a) a chest CT, smoking cessation, and/or avoiding aspiration risk and inhalational injury to a subject determined to have a decreased level of expression of at least one of:
at least one gene of Group A, and at least one gene of Group B; and/or
an increased level of expression of at least one of:
at least one gene of Group C, at least one gene of Group D, and at least one gene of Group E;
b) an immunosuppressant and/or a more aggressive immunosuppressant regimen to a subject who had previously received and lung transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or
c) an immunosuppressant and/or a more aggressive immunosuppressant regimen to a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E;
d) an inhibitor of DPP1 to a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; and/or
e) an inhibitor of DPP1 to a subject who has COPD, asthma, or rheumatoid arthritis and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

In one aspect of any of the embodiments, described herein is a method of predicting or determining the risk of airway dysfunction, the method comprising detecting the level of expression of one or more genes selected from at least one of:
at least one gene of Group A, at least one gene of Group B, at least one gene of Group C,
at least one gene of Group D, and at least one gene of Group E.
in a sample obtained from a subject; and
determining that the subject is at an increased risk of airway dysfunction if the subject is determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

In one aspect of any of the embodiments, described herein is an immunosuppressant and/or a more aggressive immunosuppressant regimen for use in a method of treating or preventing airway dysfunction in:
a) a subject who had previously received and lung transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or b) a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E;

In one aspect of any of the embodiments, described herein is an inhibitor of DPP1 for use in a method of treating or preventing airway dysfunction in:
a. a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or
b. an inhibitor of DPP1 to a subject who has COPD, asthma, or rheumatoid arthritis and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

In some embodiments of any of the aspects, the level of expression is the level of expression in a sample obtained from the subject. In some embodiments of any of the aspects, the sample is a bronchial brushing, nasal brushing, sputum, or peripheral blood sample.

In some embodiments of any of the aspects, the subject is determined to have a decreased level of expression of one or more genes selected from Group B and/or an increased level of expression of one or more genes selected from Group C. In some embodiments of any of the aspects, the DPP1 inhibitor is AZD7986. In some embodiments of any of the aspects, the airway dysfunction is bronchial enlargement or dilation. In some embodiments of any of the aspects, the airway dysfunction is COPD, asthma, bronchiolitis, bronchiectasis, lung transplant rejection, rheumatoid arthritis, GvHD, or autoimmune prenumonitis.

In some embodiments of any of the aspects, the method comprises determining the level of, or the subject is determined to have a level of expression of, at least one gene of Group A, at least one gene of Group B, at least one gene of Group C, at least one gene of Group D, and at least one gene of Group E. In some embodiments of any of the aspects, the method comprises determining the level of, or the subject is determined to have a level of expression of, at least one gene of Group A, at least one gene of Group C, at least one gene of Group D, and at least one gene of Group E. In some embodiments of any of the aspects, the method comprises determining the level of, or the subject is determined to have a level of expression of, at least one gene of Group A, at least one gene of Group C, and at least one gene of Group E. In some embodiments of any of the aspects, the method comprises determining the level of, or the subject is determined to have a level of expression of, at least one gene of Group B and at least one gene of Group C.

In some embodiments of any of the aspects, the at least one gene of Group A is at least one of: ZNF493 and ZNF519. In some embodiments of any of the aspects, the at least one gene of Group A is ZNF493 and ZNF519. In some embodiments of any of the aspects, the at least one gene of Group A is ZNF493.

In some embodiments of any of the aspects, the at least one gene of Group B is at least one of: LRP4 and FAT2. In some embodiments of any of the aspects, the at least one gene of Group B is LRP4 and FAT2.

In some embodiments of any of the aspects, the at least one gene of Group C is at least one of: ASL and CCDC160. In some embodiments of any of the aspects, the at least one gene of Group C is ASL and CCDC160. In some embodiments of any of the aspects, the at least one gene of Group C is ASL.

In some embodiments of any of the aspects, the at least one gene of Group D is at least one of: LINC00888 and FBXO16. In some embodiments of any of the aspects, the at least one gene of Group D is LINC00888 and FBXO16. In some embodiments of any of the aspects, the at least one gene of Group D is LINC00888.

In some embodiments of any of the aspects, the at least one gene of Group E is at least one of: C8orf76 and DNAJC22. In some embodiments of any of the aspects, the at least one gene of Group E is C8orf76 and DNAJC22. In some embodiments of any of the aspects, the at least one gene of Group E is C8orf76.

In some embodiments of any of the aspects, the level of expression is the level of mRNA.

In some embodiments of any of the aspects, the sample obtained from the subject is a bronchial brushing or nasal brushing sample.

BRIEF DESCRIPTION OF THE DRAWINGS

FIG. 3A: Single-cell RNA-seq of bronchial brushings from 9 subjects (n=13,176 cells) were clustered. Cell types were previously assigned and reported by Deprez et al. (23).

FIG. 3B: UMAP projection a showing the expression pattern of genes up (left) and down-regulated (right) in widespread radiographic BE across different cell types. The cells are for low expression and high expression of metagene scores of each set of genes. FIG. 3C: Violin plot showing the metagene score for each set of gene module across the cell types. For each violin plot, metagene expression is designated as elevated or highly elevated if it is greater than one or two standard deviations above the mean metagene score, respectively. FIG. 3D: Boxplots of cell type proportions estimated by AutoGeneS in buld RNA-seq data form the bronchial brushings (n=173) obtained from the DECAMP cohort. Significant cell proportion differences among the normal, intermediate, and bronchiectatic clusters determined by Kruskal test.

DETAILED DESCRIPTION

Figure 1:
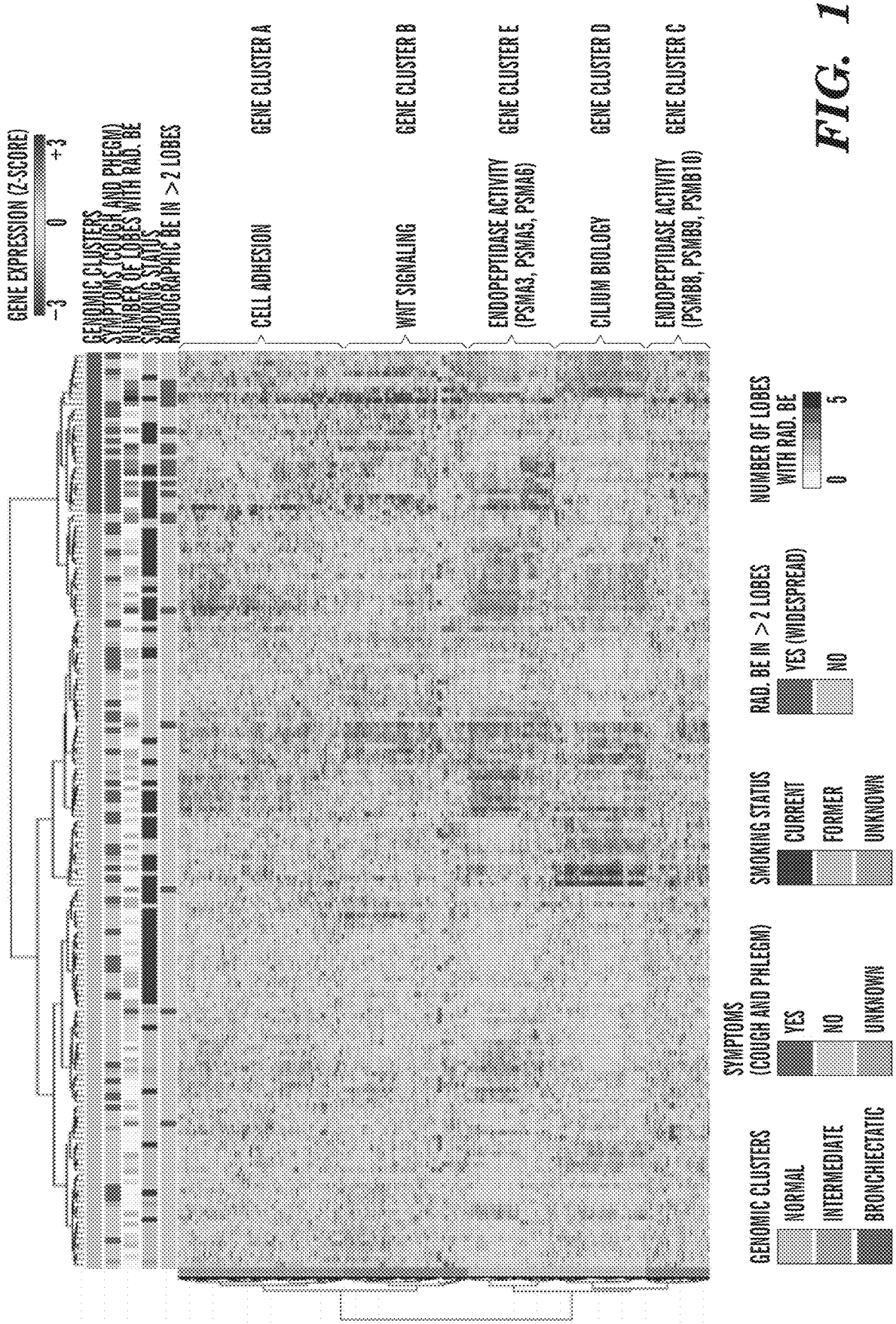
FIG. 1 depicts unsupervised heatamp of the 655 genes associated with widespread radiographic bronchiectasis (presence of radiographic BE in at least 3 lobes). Based on hierarchical clutering, participants were group into three genomic clusters, while genes were grouped into five gene clusters. Biological pathways in which these clusters of genes were enriched were shown on the side. Flase discovery rate <0.1; Fold change >0.25.

Patients with various diseases may experience airway dysfunction, e.g., thickening of central bronchial walls, abnormally mucus production that obstructs the airways, and/or thickening of the bronchi walls due to infection and/or inflammation (i.e. bronchiectasis). These changes to the lungs result in cough, breathlessness, excess sputum production, frequent respiratory infections, respiratory failure and death. Early detection of airway dysfunction is difficult, as initial symptoms such as cough or shortness of breath lack diagnostic specificity and the current clinical diagnostics rely on radiographic examinations of patients.

As described herein, the inventors have identified changes in gene expression, present in non-invasive samples such as nasal or bronchial brushing samples, that are found in subjects with airway dysfunction, including those with early stage airway dysfunction not yet detectable by radiographic examination. Specifically, the inventors have identified decreased expression of genes in Groups A and B, and increased expression of genes in Groups C, D, and E as occurring in subjects with airway dysfunction. Accordingly, in one aspect of any of the embodiments, described herein is a method comprising detecting the level of expression of one or more genes selected from at least one of: at least one gene of Group A, at least one gene of Group B, at least one gene of Group C, at least one gene of Group D, and at least one gene of Group E; in a bronchial brushing, nasal brushing, sputum, or peripheral blood sample obtained from a subject.

In some embodiments of any of the aspects, one or more genes can be one or more genes of one Group. In some embodiments of any of the aspects, one or more genes can be one or more genes of each of two Groups. In some embodiments of any of the aspects, one or more genes can be one or more genes of each of three Groups. In some embodiments of any of the aspects, one or more genes can be one or more genes of each of four Groups. In some embodiments of any of the aspects, one or more genes can be one or more genes of each Group.

In some embodiments of any of the aspects, one or more genes of a specific Group is one gene. In some embodiments of any of the aspects, one or more genes of a specific Group is two genes. In some embodiments of any of the aspects, one or more genes of a specific Group is three genes. In some embodiments of any of the aspects, one or more genes of a specific Group is four genes. In some embodiments of any of the aspects, one or more genes of a specific Group is each gene from one of Tables 12, 14, 16, 18, and 20. In some embodiments of any of the aspects, one or more genes of a specific The sequences for the genes described herein are known in the art, e.g., the human sequences for the genes described herein are available in the NCBI database, e.g, associated with the EntrezID provided in the tables herein, or the ENSEMBL database, e.g., with the entry associated with the ENSEMBL ID provided in the tables herein. In some embodiments of any of the aspects, a gene has the sequence provided in the NCBI and/or ENSEMBL databases for that ID number as of Apr. 19, 2022. In some embodiments of any of the aspects, a gene has the sequence provided in the NCBI database for that ID number as of Apr. 19, 2022.

In some embodiments of any of the aspects, a gene expression product has a sequence with at least 80%, at least 85%, at least 90%, at least 95%, at least 98%, or greater sequence identity to a sequence provided in the NCBI database for that ID number. In some embodiments of any of the aspects, a gene expression product has a sequence with at least 80%, at least 85%, at least 90%, at least 95%, at least 98%, or greater sequence identity to a sequence provided in the NCBI database for that ID number and retaining the same activity as the reference sequence. In some embodiments of any of the aspects, a gene expression product has a sequence with at least at least 95% sequence identity to a sequence provided in the NCBI database for that ID number and retaining the same activity as the reference sequence. In some embodiments of any of the aspects, a gene expression product has a sequence with at least 95% sequence identity to a sequence provided in the NCBI database for that ID number and retaining the same activity as the reference sequence.

In some embodiments of any of the aspects, the level of expression is determined/measured of one or more genes selected from Group B and/or one or more genes selected from Group C. In some embodiments of any of the aspects, the level of expression is determined/measured of one or more genes selected from Group B and one or more genes selected from Group C. In some embodiments of any of the aspects, the subject is determined to have a decreased level of expression of one or more genes selected from Group B and/or an increased level of expression of one or more genes selected from Group C. In some embodiments of any of the aspects, the subject is determined to have a decreased level of expression of one or more genes selected from Group B and an increased level of expression of one or more genes selected from Group C. This subset of the signature is referred to elsewhere herein as the "intermediate signature."

In some embodiments of any of the aspects, the level of expression is determined/measured of at least one gene of Group A, at least one gene of Group B, at least one gene of Group C, at least one gene of Group D, and at least one gene of Group E. In some embodiments of any of the aspects, subject is determined to have a decreased level of expression of least one gene of Group A, a decreased level of expression of at least one gene of Group B, an increased level of expression of at least one gene of Group C, an increased level of expression of at least one gene of Group D, and an increased level of expression of at least one gene of Group E.

In some embodiments of any of the aspects, the level of expression is determined/measured of at least one gene of Group A, at least one gene of Group C, at least one gene of Group D, and at least one gene of Group E. In some embodiments of any of the aspects, subject is determined to have a decreased level of expression of least one gene of Group A, an increased level of expression of at least one gene of Group C, an increased level of expression of at least one gene of Group D, and an increased level of expression of at least one gene of Group E.

In some embodiments of any of the aspects, the level of expression is determined/measured of at least one gene of Group A, at least one gene of Group C, and at least one gene of Group E. In some embodiments of any of the aspects, subject is determined to have a decreased level of expression of least one gene of Group A, an increased level of expression of at least one gene of Group C, and an increased level of expression of at least one gene of Group E.

In some embodiments of any of the aspects, the level of expression is determined/measured of at least one gene of Group B and at least one gene of Group C. In some embodiments of any of the aspects, subject is determined to a decreased level of expression of at least one gene of Group B and an increased level of expression of at least one gene of Group C.

As used herein, "Group A" refers to the cell adhesion genes shown in Table 12.

TABLE 12

| Ensembl_ID | GeneID | EntrezID (Gene ID) |
|---|---|---|
| ENSG00000196268 | ZNF493 | 284443 |
| ENSG00000175322 | ZNF519 | 162655 |
| ENSG00000271430 | | NA |
| ENSG00000078814 | MYH7B | 57644 |
| ENSG00000224430 | MKRN5P | NA |
| ENSG00000270574 | | NA |
| ENSG00000268521 | VN1R83P | NA |
| ENSG00000268555 | | NA |
| ENSG00000161551 | ZNF577 | 84765 |
| ENSG00000152042 | NBPF11 | c(101928050, 728912, 200030) |
| ENSG00000175356 | SCUBE2 | 57758 |
| ENSG00000101049 | SGK2 | 10110 |
| ENSG00000163141 | BNIPL | 149428 |
| ENSG00000271533 | | NA |
| ENSG00000253305 | PCDHGB6 | 56100 |
| ENSG00000123384 | LRP1 | 4035 |
| ENSG00000254122 | PCDHGB7 | 56099 |
| ENSG00000262877 | | 100507520 |
| ENSG00000114770 | ABCC5 | 10057 |
| ENSG00000067601 | PMS2P4 | 5382 |
| ENSG00000235954 | TTC28-AS1 | 284900 |
| ENSG00000257704 | PRR24 | 255783 |
| ENSG00000110651 | CD81 | 975 |
| ENSG00000205517 | RGL3 | 57139 |
| ENSG00000105426 | PTPRS | 5802 |
| ENSG00000271011 | | NA |
| ENSG00000249459 | ZNF286B | 729288 |
| ENSG00000185838 | GNB1L | 54584 |
| ENSG00000253159 | PCDHGA12 | 26025 |
| ENSG00000112394 | SLC16A10 | 117247 |
| ENSG00000160229 | ZNF66 | NA |
| ENSG00000261584 | | 101929855 |
| ENSG00000197935 | ZNF311 | 282890 |
| ENSG00000250312 | ZNF718 | NA |
| ENSG00000223745 | | c(101930643, 101930082, 100131564) |
| ENSG00000172476 | RAB40A | 142684 |
| ENSG00000268119 | | 101928983 |
| ENSG00000262576 | PCDHGA4 | 56111 |
| ENSG00000270589 | | NA |
| ENSG00000256142 | | NA |
| ENSG00000198719 | DLL1 | 28514 |
| ENSG00000224775 | BRAFP1 | NA |
| ENSG00000253873 | PCDHGA11 | c(56105, 5098) |
| ENSG00000230590 | FTX | 100302692 |
| ENSG00000059122 | FLYWCH1 | 84256 |
| ENSG00000139910 | NOVA1 | 4857 |
| ENSG00000120071 | KANSL1 | c(101929776, 284058) |
| ENSG00000231205 | ZNF826P | c(101929933, 664701) |
| ENSG00000196295 | | c(101928623, 401320) |
| ENSG00000229036 | | NA |
| ENSG00000140332 | TLE3 | 7090 |
| ENSG00000102349 | KLF8 | 11279 |
| ENSG00000170500 | LONRF2 | 164832 |
| ENSG00000248449 | PCDHGB8P | 56120 |
| ENSG00000259326 | | NA |
| ENSG00000131480 | AOC2 | 314 |
| ENSG00000108352 | RAPGEFL1 | 51195 |
| ENSG00000175414 | ARL10 | 285598 |
| ENSG00000142303 | ADAMTS10 | 81794 |

TABLE 12-continued

| Ensembl_ID | GeneID | EntrezID (Gene ID) |
|---|---|---|
| ENSG00000250303 | | c(100506870, 283140) |
| ENSG00000182463 | TSHZ2 | 128553 |
| ENSG00000189149 | CRYM-AS1 | 400508 |
| ENSG00000213971 | | NA |
| ENSG00000262470 | TVP23CP2 | NA |
| ENSG00000234978 | | NA |
| ENSG00000204366 | ZBTB12 | 221527 |
| ENSG00000261934 | PCDHGA9 | 56107 |
| ENSG00000237818 | RPS3AP29 | NA |
| ENSG00000171435 | KSR2 | 283455 |
| ENSG00000132199 | ENOSF1 | 55556 |
| ENSG00000233175 | | NA |
| ENSG00000260729 | | NA |
| ENSG00000268658 | LINC00664 | 400680 |
| ENSG00000197134 | ZNF257 | 113835 |
| ENSG00000236375 | POU5F1P5 | NA |
| ENSG00000167363 | FN3K | 64122 |
| ENSG00000204514 | ZNF814 | 730051 |
| ENSG00000165841 | CYP2C19 | 1557 |
| ENSG00000270096 | | NA |
| ENSG00000128655 | PDE11A | 50940 |
| ENSG00000248019 | FAM13A-AS1 | 285512 |
| ENSG00000156113 | KCNMA1 | 3778 |
| ENSG00000247270 | | NA |
| ENSG00000270019 | | NA |
| ENSG00000270154 | | NA |
| ENSG00000248445 | | 101927233 |
| ENSG00000234129 | | 101928302 |
| ENSG00000267169 | | 100507373 |
| ENSG00000261423 | | NA |
| ENSG00000205885 | C1RL-AS1 | 283314 |
| ENSG00000237522 | NONOP2 | NA |
| ENSG00000170615 | SLC26A5 | 375611 |
| ENSG00000247708 | STX18-AS1 | 100507266 |
| ENSG00000145020 | AMT | 275 |
| ENSG00000232626 | | NA |
| ENSG00000235834 | | 101928389 |
| ENSG00000265727 | RN7SL648P | NA |
| ENSG00000254634 | | NA |
| ENSG00000236144 | | 100506469 |
| ENSG00000229325 | ACAP2-IT1 | NA |
| ENSG00000268472 | | NA |
| ENSG00000180113 | TDRD6 | 221400 |
| ENSG00000272563 | | NA |
| ENSG00000249129 | SUDS3P1 | NA |
| ENSG00000253953 | PCDHGB4 | c(56101, 8641) |
| ENSG00000240445 | FOXO3B | 2310 |
| ENSG00000272977 | | NA |
| ENSG00000196421 | LINC00176 | 284739 |
| ENSG00000091536 | MYO15A | 51168 |
| ENSG00000240288 | GHRLOS | 100126793 |
| ENSG00000100154 | TTC28 | 23331 |
| ENSG00000271840 | | NA |
| ENSG00000203832 | NBPF20 | c(101060226, 100132406, 343505, 25832) |
| ENSG00000162738 | VANGL2 | 57216 |
| ENSG00000168970 | JMJD7-PLA2G4B | 8681 |
| ENSG00000267940 | | NA |
| ENSG00000197444 | OGDHL | 55753 |
| ENSG00000206195 | | NA |
| ENSG00000172059 | KLF11 | 8462 |
| ENSG00000263327 | TAPT1-AS1 | 202020 |
| ENSG00000105696 | TMEM59L | 25789 |
| ENSG00000144476 | ACKR3 | 57007 |
| ENSG00000184441 | | NA |
| ENSG00000108773 | KAT2A | 2648 |
| ENSG00000261052 | SULT1A3 | c(101929857, 445329, 6818) |
| ENSG00000116991 | SIPA1L2 | 57568 |
| ENSG00000229994 | RPL5P4 | NA |

TABLE 12-continued

| Ensembl_ID | GeneID | EntrezID (Gene ID) |
|---|---|---|
| ENSG00000174080 | CTSF | 8722 |
| ENSG00000160321 | ZNF208 | 7757 |
| ENSG00000130649 | CYP2E1 | 1571 |
| ENSG00000185513 | L3MBTL1 | 26013 |
| ENSG00000162373 | BEND5 | 79656 |
| ENSG00000076555 | ACACB | 32 |
| ENSG00000261087 | | NA |
| ENSG00000100968 | NFATC4 | 4776 |
| ENSG00000172824 | CES4A | 283848 |
| ENSG00000198939 | ZFP2 | 80108 |
| ENSG00000164061 | BSN | 8927 |
| ENSG00000254469 | | NA |
| ENSG00000144026 | ZNF514 | 84874 |
| ENSG00000176593 | | NA |
| ENSG00000232116 | | NA |
| ENSG00000115507 | OTX1 | 5013 |
| ENSG00000269918 | | NA |
| ENSG00000135407 | AVIL | 10677 |
| ENSG00000271971 | | NA |
| ENSG00000155970 | MICU3 | 286097 |
| ENSG00000089351 | GRAMD1A | 57655 |
| ENSG00000133466 | C1QTNF6 | 114904 |
| ENSG00000084731 | KIF3C | 3797 |
| ENSG00000186919 | ZACN | 353174 |
| ENSG00000229917 | RPL7P46 | NA |
| ENSG00000168907 | PLA2G4F | 255189 |
| ENSG00000213599 | SLX1A-SULT1A3 | 100526830 |
| ENSG00000176293 | ZNF135 | 7694 |
| ENSG00000228960 | OR2A9P | c(441295, 401428) |
| ENSG00000165548 | TMEM63C | 57156 |
| ENSG00000042832 | TG | 7038 |
| ENSG00000261502 | | NA |
| ENSG00000152487 | ARL5B-AS1 | NA |
| ENSG00000214534 | ZNF705E | NA |
| ENSG00000240764 | PCDHGC5 | c(56097, 5098) |
| ENSG00000175265 | GOLGA8A | 23015 |
| ENSG00000054690 | PLEKHH1 | 57475 |
| ENSG00000162407 | PPAP2B | 8613 |
| ENSG00000267481 | | NA |
| ENSG00000238228 | OR7E7P | NA |
| ENSG00000259585 | | NA |
| ENSG00000225210 | | 440157 |
| ENSG00000212122 | TSSK1B | 83942 |
| ENSG00000215022 | | NA |
| ENSG00000242866 | STRC | c(101930630, 161497) |
| ENSG00000250290 | | NA |
| ENSG00000246922 | UBAP1L | 390595 |
| ENSG00000264112 | | 645460 |
| ENSG00000237489 | LINC00959 | NA |
| ENSG00000189419 | SPATA41 | 388182 |
| ENSG00000213139 | CRYGS | 1427 |
| ENSG00000106479 | ZNF862 | 643641 |
| ENSG00000225032 | | NA |
| ENSG00000179715 | PCED1B | 91523 |
| ENSG00000137834 | SMAD6 | 4091 |
| ENSG00000264538 | | NA |
| ENSG00000137218 | FRS3 | 10817 |
| ENSG00000256139 | | NA |
| ENSG00000223705 | NSUN5P1 | 155400 |
| ENSG00000090006 | LTBP4 | 8425 |
| ENSG00000267053 | | NA |
| ENSG00000171282 | | 57597 |
| ENSG00000253537 | PCDHGA7 | 56108 |
| ENSG00000196208 | GREB1 | 9687 |
| ENSG00000229186 | ADAM1A | NA |
| ENSG00000251323 | | 101928865 |
| ENSG00000271917 | | NA |
| ENSG00000253366 | | NA |
| ENSG00000225241 | | NA |
| ENSG00000137070 | IL11RA | 3590 |
| ENSG00000146001 | PCDHB18 | 54660 |
| ENSG00000255495 | FAM85A | 619423 |
| ENSG00000242435 | UPK3BP1 | NA |
| ENSG00000115361 | ACADL | 33 |
| ENSG00000236055 | | NA |
| ENSG00000267508 | ZNF285 | c(646915, 26974) |
| ENSG00000239665 | | c(101928524, 101928497) |

In some embodiments of any of the aspects, one or more genes of Group A comprises one or more genes of Table 13. In some embodiments of any of the aspects, one or more genes of Group A comprises the genes of Table 13. In some embodiments of any of the aspects, one or more genes of Group A consists of the genes of Table 13.

TABLE 13

| Ensembl_ID | GeneID | EntrezID (Gene ID) |
|---|---|---|
| ENSG00000196268 | ZNF493 | 284443 |
| ENSG00000175322 | ZNF519 | 162655 |
| ENSG00000078814 | MYH7B | 57644 |
| ENSG00000161551 | ZNF577 | 84765 |
| ENSG00000175356 | SCUBE2 | 57758 |
| ENSG00000101049 | SGK2 | 10110 |
| ENSG00000163141 | BNIPL | 149428 |
| ENSG00000253305 | PCDHGB6 | 56100 |
| ENSG00000123384 | LRP1 | 4035 |
| ENSG00000254122 | PCDHGB7 | 56099 |
| ENSG00000114770 | ABCC5 | 10057 |
| ENSG00000067601 | PMS2P4 | 5382 |
| ENSG00000235954 | TTC28-AS1 | 284900 |
| ENSG00000257704 | PRR24 | 255783 |
| ENSG00000110651 | CD81 | 975 |
| ENSG00000205517 | RGL3 | 57139 |
| ENSG00000105426 | PTPRS | 5802 |
| ENSG00000249459 | ZNF286B | 729288 |
| ENSG00000185838 | GNB1L | 54584 |
| ENSG00000253159 | PCDHGA12 | 26025 |
| ENSG00000112394 | SLC16A10 | 117247 |
| ENSG00000197935 | ZNF311 | 282890 |
| ENSG00000172476 | RAB40A | 142684 |
| ENSG00000262576 | PCDHGA4 | 56111 |
| ENSG00000198719 | DLL1 | 28514 |
| ENSG00000230590 | FTX | 100302692 |
| ENSG00000059122 | FLYWCH1 | 84256 |
| ENSG00000139910 | NOVA1 | 4857 |
| ENSG00000140332 | TLE3 | 7090 |
| ENSG00000102349 | KLF8 | 11279 |
| ENSG00000170500 | LONRF2 | 164832 |
| ENSG00000248449 | PCDHGB8P | 56120 |
| ENSG00000131480 | AOC2 | 314 |
| ENSG00000108352 | RAPGEFL1 | 51195 |
| ENSG00000175414 | ARL10 | 285598 |
| ENSG00000142303 | ADAMTS10 | 81794 |
| ENSG00000182463 | TSHZ2 | 128553 |
| ENSG00000189149 | CRYM-AS1 | 400508 |
| ENSG00000204366 | ZBTB12 | 221527 |
| ENSG00000261934 | PCDHGA9 | 56107 |
| ENSG00000171435 | KSR2 | 283455 |
| ENSG00000132199 | ENOSF1 | 55556 |
| ENSG00000268658 | LINC00664 | 400680 |
| ENSG00000197134 | ZNF257 | 113835 |
| ENSG00000167363 | FN3K | 64122 |
| ENSG00000204514 | ZNF814 | 730051 |
| ENSG00000165841 | CYP2C19 | 1557 |
| ENSG00000128655 | PDE11A | 50940 |
| ENSG00000248019 | FAM13A-AS1 | 285512 |
| ENSG00000156113 | KCNMA1 | 3778 |
| ENSG00000205885 | C1RL-AS1 | 283314 |
| ENSG00000170615 | SLC26A5 | 375611 |
| ENSG00000247708 | STX18-AS1 | 100507266 |
| ENSG00000145020 | AMT | 275 |
| ENSG00000180113 | TDRD6 | 221400 |

TABLE 13-continued

| Ensembl_ID | GeneID | EntrezID (Gene ID) |
|---|---|---|
| ENSG00000240445 | FOXO3B | 2310 |
| ENSG00000196421 | LINC00176 | 284739 |
| ENSG00000091536 | MYO15A | 51168 |
| ENSG00000240288 | GHRLOS | 100126793 |
| ENSG00000100154 | TTC28 | 23331 |
| ENSG00000162738 | VANGL2 | 57216 |
| ENSG00000168970 | JMJD7-PLA2G4B | 8681 |
| ENSG00000197444 | OGDHL | 55753 |
| ENSG00000172059 | KLF11 | 8462 |
| ENSG00000263327 | TAPT1-AS1 | 202020 |
| ENSG00000105696 | TMEM59L | 25789 |
| ENSG00000144476 | ACKR3 | 57007 |
| ENSG00000108773 | KAT2A | 2648 |
| ENSG00000116991 | SIPA1L2 | 57568 |
| ENSG00000174080 | CTSF | 8722 |
| ENSG00000160321 | ZNF208 | 7757 |
| ENSG00000130649 | CYP2E1 | 1571 |
| ENSG00000185513 | L3MBTL1 | 26013 |
| ENSG00000162373 | BEND5 | 79656 |
| ENSG00000076555 | ACACB | 32 |
| ENSG00000100968 | NFATC4 | 4776 |
| ENSG00000172824 | CES4A | 283848 |
| ENSG00000198939 | ZFP2 | 80108 |
| ENSG00000164061 | BSN | 8927 |
| ENSG00000144026 | ZNF514 | 84874 |
| ENSG00000115507 | OTX1 | 5013 |
| ENSG00000135407 | AVIL | 10677 |
| ENSG00000155970 | MICU3 | 286097 |
| ENSG00000089351 | GRAMD1A | 57655 |
| ENSG00000133466 | C1QTNF6 | 114904 |
| ENSG00000084731 | KIF3C | 3797 |
| ENSG00000186919 | ZACN | 353174 |
| ENSG00000168907 | PLA2G4F | 255189 |
| ENSG00000213599 | SLX1A-SULT1A3 | 100526830 |
| ENSG00000176293 | ZNF135 | 7694 |
| ENSG00000165548 | TMEM63C | 57156 |
| ENSG00000042832 | TG | 7038 |
| ENSG00000175265 | GOLGA8A | 23015 |
| ENSG00000054690 | PLEKHH1 | 57475 |
| ENSG00000162407 | PPAP2B | 8613 |
| ENSG00000212122 | TSSK1B | 83942 |
| ENSG00000246922 | UBAP1L | 390595 |
| ENSG00000189419 | SPATA41 | 388182 |
| ENSG00000213139 | CRYGS | 1427 |
| ENSG00000106479 | ZNF862 | 643641 |
| ENSG00000179715 | PCED1B | 91523 |
| ENSG00000137834 | SMAD6 | 4091 |
| ENSG00000137218 | FRS3 | 10817 |
| ENSG00000223705 | NSUN5P1 | 155400 |
| ENSG00000090006 | LTBP4 | 8425 |
| ENSG00000253537 | PCDHGA7 | 56108 |
| ENSG00000196208 | GREB1 | 9687 |
| ENSG00000137070 | IL11RA | 3590 |
| ENSG00000146001 | PCDHB18 | 54660 |
| ENSG00000255495 | FAM85A | 619423 |
| ENSG00000115361 | ACADL | 33 |

As used herein, "Group B" refers to the Wnt signaling genes shown in Table 14.

TABLE 14

| Ensembl_ID | GeneID | EntrezID (Gene) |
|---|---|---|
| ENSG00000134569 | LRP4 | 4038 |
| ENSG00000258405 | ZNF578 | 147660 |
| ENSG00000086570 | FAT2 | 2196 |
| ENSG00000068078 | FGFR3 | 2261 |
| ENSG00000171444 | MCC | 4163 |
| ENSG00000174502 | SLC26A9 | 115019 |
| ENSG00000186260 | MKL2 | 57496 |
| ENSG00000226555 | AGKP1 | NA |
| ENSG00000171346 | KRT15 | 3866 |
| ENSG00000178662 | CSRNP3 | 80034 |
| ENSG00000081277 | PKP1 | 5317 |
| ENSG00000070404 | FSTL3 | 10272 |
| ENSG00000137954 | NEURL1 | 9148 |
| ENSG00000184916 | JAG2 | 3714 |
| ENSG00000164488 | DACT2 | 168002 |
| ENSG00000067445 | TRO | 7216 |
| ENSG00000104419 | NDRG1 | 10397 |
| ENSG00000078295 | ADCY2 | 108 |
| ENSG00000143061 | IGSF3 | 3321 |
| ENSG00000165246 | NLGN4Y | 22829 |
| ENSG00000165821 | SALL2 | 6297 |
| ENSG00000143502 | SUSD4 | 55061 |
| ENSG00000141337 | ARSG | 22901 |
| ENSG00000119866 | BCL11A | 53335 |
| ENSG00000141622 | RNF165 | 494470 |
| ENSG00000073282 | TP63 | 8626 |
| ENSG00000244122 | UGT1A7 | 54577:54576 |
| ENSG00000141837 | CACNA1A | c(100507353, 773) |
| ENSG00000182752 | PAPPA | 5069 |
| ENSG00000196562 | SULF2 | 55959 |
| ENSG00000091844 | RGS17 | 26575 |
| ENSG00000145675 | PIK3R1 | 5295 |
| ENSG00000174226 | SNX31 | 169166 |
| ENSG00000188153 | COL4A5 | 1287 |
| ENSG00000019549 | SNAI2 | 6591 |
| ENSG00000240224 | UGT1A5 | 54579 |
| ENSG00000100321 | SYNGR1 | 9145 |
| ENSG00000213963 | | 100130691 |
| ENSG00000159164 | SV2A | 9900 |
| ENSG00000066468 | FGFR2 | 2263 |
| ENSG00000107104 | KANK1 | 23189 |
| ENSG00000114851 | WNT5A | 7474 |
| ENSG00000155760 | FZD7 | 8324 |
| ENSG00000177679 | SRRM3 | 222183 |
| ENSG00000112902 | SEMA5A | 9037 |
| ENSG00000196263 | ZNF471 | 57573 |
| ENSG00000188266 | HYKK | 123688 |
| ENSG00000163590 | PPM1L | 151742 |
| ENSG00000088756 | ARHGAP28 | 79822 |
| ENSG00000241635 | UGT1A8 | c(54659, 54658, 54600, 54579, 54576) |
| ENSG00000104728 | ARHGEF10 | 9639 |
| ENSG00000187193 | MT1X | 4501 |
| ENSG00000109101 | FOXN1 | 8456 |
| ENSG00000185652 | NTF3 | 4908 |
| ENSG00000112562 | SMOC2 | 64094 |
| ENSG00000136014 | USP44 | 84101 |
| ENSG00000127585 | FBXL16 | 146330 |
| ENSG00000116016 | EPAS1 | 2034 |
| ENSG00000146648 | EGFR | 1956 |
| ENSG00000144724 | PTPRG | 5793 |
| ENSG00000183091 | NEB | 4703 |
| ENSG00000248587 | GDNF-AS1 | 100861519 |
| ENSG00000138439 | FAM117B | 150864 |
| ENSG00000134533 | RERG | 85004 |
| ENSG00000114853 | ZBTB47 | 92999 |
| ENSG00000241684 | ADAMTS9-AS2 | 100507098 |
| ENSG00000100767 | PAPLN | 89932 |
| ENSG00000176771 | NCKAP5 | 344148 |
| ENSG00000169302 | STK32A | 202374 |
| ENSG00000196159 | FAT4 | 79633 |
| ENSG00000133067 | LGR6 | 59352 |
| ENSG00000253771 | TPTE2P1 | NA |
| ENSG00000184564 | SLITRK6 | 84189 |
| ENSG00000041982 | TNC | 3371 |
| ENSG00000214860 | EVPLL | 645027 |
| ENSG00000085998 | POMGNT1 | 55624 |
| ENSG00000153885 | KCTD15 | 79047 |
| ENSG00000179314 | WSCD1 | c(339166, 23302) |

TABLE 14-continued

| Ensembl_ID | GeneID | EntrezID (Gene) |
|---|---|---|
| ENSG00000166813 | KIF7 | 374654 |
| ENSG00000130294 | KIF1A | 547 |
| ENSG00000138759 | FRAS1 | 80144 |
| ENSG00000186081 | KRT5 | 3852 |
| ENSG00000174171 | | NA |
| ENSG00000140937 | CDH11 | 1009 |
| ENSG00000196867 | ZFP28 | 140612 |
| ENSG00000198932 | GPRASP1 | 9737 |
| ENSG00000099725 | PRKY | 5616 |
| ENSG00000197565 | COL4A6 | 1288 |
| ENSG00000185565 | LSAMP | 4045 |
| ENSG00000105137 | SYDE1 | 85360 |
| ENSG00000271880 | | NA |
| ENSG00000182175 | RGMA | 56963 |
| ENSG00000144857 | BOC | 91653 |
| ENSG00000109667 | SLC2A9 | 56606 |
| ENSG00000134245 | WNT2B | 7482 |
| ENSG00000148600 | CDHR1 | 92211 |
| ENSG00000248705 | | NA |
| ENSG00000092969 | TGFB2 | 7042 |
| ENSG00000149294 | NCAM1 | 4684 |
| ENSG00000213903 | LTB4R | 1241 |
| ENSG00000065717 | TLE2 | 7089 |
| ENSG00000103723 | AP3B2 | 8120 |
| ENSG00000163827 | LRRC2 | 79442 |
| ENSG00000162591 | MEGF6 | 1953 |
| ENSG00000178222 | RNF212 | 285498 |
| ENSG00000077942 | FBLN1 | 2192 |
| ENSG00000173930 | SLCO4C1 | 353189 |
| ENSG00000154342 | WNT3A | 89780 |
| ENSG00000197497 | ZNF665 | 79788 |
| ENSG00000158220 | ESYT3 | 83850 |
| ENSG00000150893 | FREM2 | 341640 |
| ENSG00000136002 | ARHGEF4 | c(101930241, 50649) |
| ENSG00000171357 | LURAP1 | 541468 |
| ENSG00000214244 | SETP21 | NA |
| ENSG00000114270 | COL7A1 | 1294 |
| ENSG00000182272 | B4GALNT4 | 338707 |
| ENSG00000166147 | FBN1 | 2200 |
| ENSG00000213988 | ZNF90 | 7643 |
| ENSG00000168702 | LRP1B | 53353 |
| ENSG00000069431 | ABCC9 | 10060 |
| ENSG00000256995 | | NA |
| ENSG00000180739 | S1PR5 | 53637 |
| ENSG00000100842 | EFS | 10278 |
| ENSG00000171246 | NPTX1 | 4884 |
| ENSG00000260197 | | NA |
| ENSG00000228445 | UGT1A2P | NA |
| ENSG00000147100 | SLC16A2 | 6567 |
| ENSG00000117643 | MAN1C1 | 57134 |
| ENSG00000155254 | MARVELD1 | 83742 |
| ENSG00000102678 | FGF9 | 2254 |
| ENSG00000136425 | CIB2 | 10518 |
| ENSG00000139292 | LGR5 | 8549 |
| ENSG00000183853 | KIRREL | c(101928229, 55243) |
| ENSG00000213906 | LTB4R2 | 56413 |
| ENSG00000070182 | SPTB | 6710 |
| ENSG00000198885 | ITPRIPL1 | 150771 |
| ENSG00000019144 | PHLDB1 | c(102466719, 23187) |
| ENSG00000164056 | SPRY1 | 10252 |
| ENSG00000155792 | DEPTOR | 64798 |
| ENSG00000116106 | EPHA4 | 2043 |
| ENSG00000229236 | TTTY10 | 246119 |
| ENSG00000138336 | TET1 | 80312 |
| ENSG00000198046 | ZNF667 | 63934 |
| ENSG00000106123 | EPHB6 | 2051 |
| ENSG00000250685 | | NA |
| ENSG00000271738 | | NA |
| ENSG00000141753 | IGFBP4 | 3487 |
| ENSG00000240771 | ARHGEF25 | 115557 |
| ENSG00000165125 | TRPV6 | 55503 |
| ENSG00000182674 | KCNB2 | 9312 |
| ENSG00000136158 | SPRY2 | 10253 |
| ENSG00000171462 | DLK2 | 65989 |
| ENSG00000079101 | CLUL1 | 27098 |

In some embodiments of any of the aspects, one or more genes of Group B comprises one or more genes of Table 15. In some embodiments of any of the aspects, one or more genes of Group B comprises the genes of Table 15. In some embodiments of any of the aspects, one or more genes of Group B consists of the genes of Table 15.

TABLE 15

| Ensembl_ID | GeneID | EntrezID (GeneID) |
|---|---|---|
| ENSG00000134569 | LRP4 | 4038 |
| ENSG00000258405 | ZNF578 | 147660 |
| ENSG00000086570 | FAT2 | 2196 |
| ENSG00000068078 | FGFR3 | 2261 |
| ENSG00000171444 | MCC | 4163 |
| ENSG00000174502 | SLC26A9 | 115019 |
| ENSG00000186260 | MKL2 | 57496 |
| ENSG00000171346 | KRT15 | 3866 |
| ENSG00000178662 | CSRNP3 | 80034 |
| ENSG00000081277 | PKP1 | 5317 |
| ENSG00000070404 | FSTL3 | 10272 |
| ENSG00000107954 | NEURL1 | 9148 |
| ENSG00000184916 | JAG2 | 3714 |
| ENSG00000164488 | DACT2 | 168002 |
| ENSG00000067445 | TRO | 7216 |
| ENSG00000104419 | NDRG1 | 10397 |
| ENSG00000078295 | ADCY2 | 108 |
| ENSG00000143061 | IGSF3 | 3321 |
| ENSG00000165246 | NLGN4Y | 22829 |
| ENSG00000165821 | SALL2 | 6297 |
| ENSG00000143502 | SUSD4 | 55061 |
| ENSG00000141337 | ARSG | 22901 |
| ENSG00000119866 | BCL11A | 53335 |
| ENSG00000141622 | RNF165 | 494470 |
| ENSG00000073282 | TP63 | 8626 |
| ENSG00000244122 | UGT1A7 | 54577:54576 |
| ENSG00000182752 | PAPPA | 5069 |
| ENSG00000196562 | SULF2 | 55959 |
| ENSG00000091844 | RGS17 | 26575 |
| ENSG00000145675 | PIK3R1 | 5295 |
| ENSG00000174226 | SNX31 | 169166 |
| ENSG00000188153 | COL4A5 | 1287 |
| ENSG00000019549 | SNAI2 | 6591 |
| ENSG00000240224 | UGT1A5 | 54579 |
| ENSG00000100321 | SYNGR1 | 9145 |
| ENSG00000159164 | SV2A | 9900 |
| ENSG00000066468 | FGFR2 | 2263 |
| ENSG00000107104 | KANK1 | 23189 |
| ENSG00000114251 | WNT5A | 7474 |
| ENSG00000155760 | FZD7 | 8324 |
| ENSG00000177679 | SRRM3 | 222183 |
| ENSG00000112902 | SEMA5A | 9037 |
| ENSG00000196263 | ZNF471 | 57573 |
| ENSG00000188266 | HYKK | 123688 |
| ENSG00000163590 | PPM1L | 151742 |
| ENSG00000088756 | ARHGAP28 | 79822 |
| ENSG00000104728 | ARHGEF10 | 9639 |
| ENSG00000187193 | MT1X | 4501 |
| ENSG00000109101 | FOXN1 | 8456 |
| ENSG00000185652 | NTF3 | 4908 |
| ENSG00000112562 | SMOC2 | 64094 |
| ENSG00000136014 | USP44 | 84101 |
| ENSG00000127585 | FBXL16 | 146330 |
| ENSG00000116016 | EPAS1 | 2034 |
| ENSG00000146648 | EGFR | 1956 |
| ENSG00000144724 | PTPRG | 5793 |
| ENSG00000183091 | NEB | 4703 |
| ENSG00000248587 | GDNF-AS1 | 100861519 |

TABLE 15-continued

| Ensembl_ID | GeneID | EntrezID (GeneID) |
|---|---|---|
| ENSG00000138439 | FAM117B | 150864 |
| ENSG00000134533 | RERG | 85004 |
| ENSG00000114853 | ZBTB47 | 92999 |
| ENSG00000241684 | ADAMTS9-AS2 | 100507098 |
| ENSG00000100767 | PAPLN | 89932 |
| ENSG00000176771 | NCKAP5 | 344148 |
| ENSG00000169302 | STK32A | 202374 |
| ENSG00000196159 | FAT4 | 79633 |
| ENSG00000133067 | LGR6 | 59352 |
| ENSG00000184564 | SLITRK6 | 84189 |
| ENSG00000041982 | TNC | 3371 |
| ENSG00000214860 | EVPLL | 645027 |
| ENSG00000085998 | POMGNT1 | 55624 |
| ENSG00000153885 | KCTD15 | 79047 |
| ENSG00000166813 | KIF7 | 374654 |
| ENSG00000130294 | KIF1A | 547 |
| ENSG00000138759 | FRAS1 | 80144 |
| ENSG00000186081 | KRT5 | 3852 |
| ENSG00000140937 | CDH11 | 1009 |
| ENSG00000196867 | ZFP28 | 140612 |
| ENSG00000198932 | GPRASP1 | 9737 |
| ENSG00000099725 | PRKY | 5616 |
| ENSG00000197565 | COL4A6 | 1288 |
| ENSG00000185565 | LSAMP | 4045 |
| ENSG00000105137 | SYDE1 | 85360 |
| ENSG00000182175 | RGMA | 56963 |
| ENSG00000144857 | BOC | 91653 |
| ENSG00000109667 | SLC2A9 | 56606 |
| ENSG00000134245 | WNT2B | 7482 |
| ENSG00000148600 | CDHR1 | 92211 |
| ENSG00000092969 | TGFB2 | 7042 |
| ENSG00000149294 | NCAM1 | 4684 |
| ENSG00000213903 | LTB4R | 1241 |
| ENSG00000065717 | TLE2 | 7089 |
| ENSG00000103723 | AP3B2 | 8120 |
| ENSG00000163827 | LRRC2 | 79442 |
| ENSG00000162591 | MEGF6 | 1953 |
| ENSG00000178222 | RNF212 | 285498 |
| ENSG00000077942 | FBLN1 | 2192 |
| ENSG00000173930 | SLCO4C1 | 353189 |
| ENSG00000154342 | WNT3A | 89780 |
| ENSG00000197497 | ZNF665 | 79788 |
| ENSG00000158220 | ESYT3 | 83850 |
| ENSG00000150893 | FREM2 | 341640 |
| ENSG00000171357 | LURAP1 | 541468 |
| ENSG00000114270 | COL7A1 | 1294 |
| ENSG00000182272 | B4GALNT4 | 338707 |
| ENSG00000166147 | FBN1 | 2200 |
| ENSG00000213988 | ZNF90 | 7643 |
| ENSG00000168702 | LRP1B | 53353 |
| ENSG00000069431 | ABCC9 | 10060 |
| ENSG00000180739 | S1PR5 | 53637 |
| ENSG00000100842 | EFS | 10278 |
| ENSG00000171246 | NPTX1 | 4884 |
| ENSG00000147100 | SLC16A2 | 6567 |
| ENSG00000117643 | MAN1C1 | 57134 |
| ENSG00000155254 | MARVELD1 | 83742 |
| ENSG00000102678 | FGF9 | 2254 |
| ENSG00000136425 | CIB2 | 10518 |
| ENSG00000139292 | LGR5 | 8549 |
| ENSG00000213906 | LTB4R2 | 56413 |
| ENSG00000070182 | SPTB | 6710 |
| ENSG00000198885 | ITPRIPL1 | 150771 |
| ENSG00000164056 | SPRY1 | 10252 |
| ENSG00000155792 | DEPTOR | 64798 |
| ENSG00000116106 | EPHA4 | 2043 |
| ENSG00000229236 | TTTY10 | 246119 |
| ENSG00000138336 | TET1 | 80312 |
| ENSG00000198046 | ZNF667 | 63934 |
| ENSG00000106123 | EPHB6 | 2051 |
| ENSG00000141753 | IGFBP4 | 3487 |
| ENSG00000240771 | ARHGEF25 | 115557 |
| ENSG00000165125 | TRPV6 | 55503 |
| ENSG00000182674 | KCNB2 | 9312 |
| ENSG00000136158 | SPRY2 | 10253 |
| ENSG00000171462 | DLK2 | 65989 |
| ENSG00000079101 | CLUL1 | 27098 |

As used herein, "Group C" refers to the endopeptidase activity genes shown in Table 16.

TABLE 16

| Ensembl_ID | GeneID | EntrezID (Gene ID) |
|---|---|---|
| ENSG00000258545 | | NA |
| ENSG00000257512 | | NA |
| ENSG00000126522 | ASL | 435 |
| ENSG00000203952 | CCDC160 | 347475 |
| ENSG00000259120 | SMIM6 | 100130933 |
| ENSG00000182621 | PLCB1 | 23236 |
| ENSG00000179178 | TMEM125 | 128218 |
| ENSG00000171695 | C20orf201 | 198437 |
| ENSG00000004468 | CD38 | 952 |
| ENSG00000268129 | | 100289361 |
| ENSG00000134198 | TSPAN2 | 10100 |
| ENSG00000070190 | DAPP1 | 27071 |
| ENSG00000182054 | IDH2 | 3418 |
| ENSG00000100336 | APOL4 | 80832 |
| ENSG00000133328 | HRASLS2 | 54979 |
| ENSG00000183784 | C9orf66 | 157983 |
| ENSG00000125864 | BFSP1 | 631 |
| ENSG00000227375 | DLG1-AS1 | 100507086 |
| ENSG00000185905 | C16orf54 | c(101929877, 283897) |
| ENSG00000078081 | LAMP3 | 27074 |
| ENSG00000140280 | LYSMD2 | 256586 |
| ENSG00000240065 | PSMB9 | 5698 |
| ENSG00000116833 | NR5A2 | 2494 |
| ENSG00000005189 | | 81691 |
| ENSG00000100473 | COCH | 1690 |
| ENSG00000165325 | CCDC67 | 159989 |
| ENSG00000047597 | XK | 7504 |
| ENSG00000184669 | OR7E14P | 10819 |
| ENSG00000251191 | LINC00589 | 619351 |
| ENSG00000198734 | F5 | 2153 |
| ENSG00000172572 | PDE3A | 5139 |
| ENSG00000136514 | RTP4 | 64108 |
| ENSG00000253474 | | NA |
| ENSG00000163297 | ANTXR2 | 118429 |
| ENSG00000237669 | HCG4P3 | NA |
| ENSG00000147378 | FATE1 | 89885 |
| ENSG00000140092 | FBLN5 | 10516 |
| ENSG00000259153 | | 100506411 |
| ENSG00000123609 | NMI | 9111 |
| ENSG00000231901 | | NA |
| ENSG00000204264 | PSMB8 | 5696 |
| ENSG00000172058 | SERF1A | c(728492, 8293) |
| ENSG00000075643 | MOCOS | 55034 |
| ENSG00000134184 | GSTM1 | 2944 |
| ENSG00000132329 | RAMP1 | 10267 |
| ENSG00000186369 | LINC00643 | 646113 |
| ENSG00000185532 | PRKG1 | 5592 |
| ENSG00000225335 | | NA |
| ENSG00000048540 | LMO3 | 55885 |
| ENSG00000270659 | | NA |
| ENSG00000242689 | CNTF | 1270 |
| ENSG00000272463 | | NA |
| ENSG00000260552 | | 101927809 |
| ENSG00000022267 | FHL1 | 2273 |
| ENSG00000121621 | KIF18A | 81930 |
| ENSG00000133321 | RARRES3 | 5920 |
| ENSG00000183578 | TNFAIP8L3 | 388121 |
| ENSG00000205220 | PSMB10 | 5699 |
| ENSG00000227053 | | NA |
| ENSG00000011332 | DPF1 | 8193 |
| ENSG00000099984 | GSTT2 | 2953 |
| ENSG00000106565 | TMEM176B | 28959 |

TABLE 16-continued

| Ensembl_ID | GeneID | EntrezID (Gene ID) |
|---|---|---|
| ENSG00000213876 | RPL7AP64 | NA |
| ENSG00000129355 | CDKN2D | 1032 |
| ENSG00000196826 |  | 163051 |
| ENSG00000205277 | MUC12 | 10071 |
| ENSG00000260806 |  | NA |
| ENSG00000122694 | GLIPR2 | 152007 |
| ENSG00000184979 | USP18 | 11274 |
| ENSG00000238837 |  | NA |
| ENSG00000214212 | C19orf38 | 255809 |
| ENSG00000023839 | ABCC2 | 1244 |
| ENSG00000110002 | VWA5A | 4013 |
| ENSG00000163535 | SGOL2 | 151246 |
| ENSG00000135549 | PKIB | 5570 |
| ENSG00000134962 | KLB | 152831 |
| ENSG00000206432 | TMEM200C | 645369 |
| ENSG00000164690 | SHH | 6469 |

In some embodiments of any of the aspects, one or more genes of Group C comprises one or more genes of Table 17. In some embodiments of any of the aspects, one or more genes of Group C comprises the genes of Table 17. In some embodiments of any of the aspects, one or more genes of Group C consists of the genes of Table 17.

TABLE 17

| Ensembl_ID | GeneID | EntrezID (Gene ID) |
|---|---|---|
| ENSG00000126522 | ASL | 435 |
| ENSG00000203952 | CCDC160 | 347475 |
| ENSG00000259120 | SMIM6 | 100130933 |
| ENSG00000182621 | PLCB1 | 23236 |
| ENSG00000179178 | TMEM125 | 128218 |
| ENSG00000171695 | C20orf201 | 198437 |
| ENSG00000004468 | CD38 | 952 |
| ENSG00000134198 | TSPAN2 | 10100 |
| ENSG00000070190 | DAPP1 | 27071 |
| ENSG00000182054 | IDH2 | 3418 |
| ENSG00000100336 | APOL4 | 80832 |
| ENSG00000133328 | HRASLS2 | 54979 |
| ENSG00000183784 | C9orf66 | 157983 |
| ENSG00000125864 | BFSP1 | 631 |
| ENSG00000227375 | DLG1-AS1 | 100507086 |
| ENSG00000078081 | LAMP3 | 27074 |
| ENSG00000140280 | LYSMD2 | 256586 |
| ENSG00000240065 | PSMB9 | 5698 |
| ENSG00000116833 | NR5A2 | 2494 |
| ENSG00000100473 | COCH | 1690 |
| ENSG00000165325 | CCDC67 | 159989 |
| ENSG00000047597 | XK | 7504 |
| ENSG00000184669 | OR7E14P | 10819 |
| ENSG00000251191 | LINC00589 | 619351 |
| ENSG00000198734 | F5 | 2153 |
| ENSG00000172572 | PDE3A | 5139 |
| ENSG00000136514 | RTP4 | 64108 |
| ENSG00000163297 | ANTXR2 | 118429 |
| ENSG00000147378 | FATE1 | 89885 |
| ENSG00000140092 | FBLN5 | 10516 |
| ENSG00000123609 | NMI | 9111 |
| ENSG00000204264 | PSMB8 | 5696 |
| ENSG00000075643 | MOCOS | 55034 |
| ENSG00000134184 | GSTM1 | 2944 |
| ENSG00000132329 | RAMP1 | 10267 |
| ENSG00000186369 | LINC00643 | 646113 |
| ENSG00000185532 | PRKG1 | 5592 |
| ENSG00000048540 | LMO3 | 55885 |
| ENSG00000242689 | CNTF | 1270 |
| ENSG00000022267 | FHL1 | 2273 |
| ENSG00000121621 | KIF18A | 81930 |
| ENSG00000133321 | RARRES3 | 5920 |
| ENSG00000183578 | TNFAIP8L3 | 388121 |
| ENSG00000205220 | PSMB10 | 5699 |
| ENSG00000011332 | DPF1 | 8193 |

TABLE 17-continued

| Ensembl_ID | GeneID | EntrezID (Gene ID) |
|---|---|---|
| ENSG00000099984 | GSTT2 | 2953 |
| ENSG00000106565 | TMEM176B | 28959 |
| ENSG00000129355 | CDKN2D | 1032 |
| ENSG00000205277 | MUC12 | 10071 |
| ENSG00000122694 | GLIPR2 | 152007 |
| ENSG00000184979 | USP18 | 11274 |
| ENSG00000214212 | C19orf38 | 255809 |
| ENSG00000023839 | ABCC2 | 1244 |
| ENSG00000110002 | VWA5A | 4013 |
| ENSG00000163535 | SGOL2 | 151246 |
| ENSG00000135549 | PKIB | 5570 |
| ENSG00000134962 | KLB | 152831 |
| ENSG00000206432 | TMEM200C | 645369 |
| ENSG00000164690 | SHH | 6469 |

As used herein, "Group D" refers to the cilium organization genes shown in Table 18.

TABLE 18

| Ensembl_ID | GeneID | EntrezID (Gene ID) |
|---|---|---|
| ENSG00000240024 | LINC00888 | 100505687 |
| ENSG00000214050 | FBXO16 | 157574 |
| ENSG00000136193 | SCRN1 | 9805 |
| ENSG00000259508 |  | NA |
| ENSG00000153363 | LINC00467 | 84791 |
| ENSG00000143158 | MPC2 | 25874 |
| ENSG00000164542 | KIAA0895 | 23366 |
| ENSG00000178980 | SEPW1 | 6415 |
| ENSG00000129007 | CALML4 | 91860 |
| ENSG00000204334 | ERICH2 | 285141 |
| ENSG00000186198 | SLC51B | 123264 |
| ENSG00000154511 | FAM69A | 388650 |
| ENSG00000259802 |  | NA |
| ENSG00000249241 |  | 101060498 |
| ENSG00000102738 | MRPS31 | 10240 |
| ENSG00000119636 | CCDC176 | 80127 |
| ENSG00000161326 | DUSP14 | 11072 |
| ENSG00000186889 | TMEM17 | 200728 |
| ENSG00000229124 | VIM-AS1 | 100507347 |
| ENSG00000084207 | GSTP1 | 2950 |
| ENSG00000132141 | CCT6B | 10693 |
| ENSG00000175792 | RUVBL1 | 8607 |
| ENSG00000267325 |  | NA |
| ENSG00000158122 | AAED1 | 195827 |
| ENSG00000151729 | SLC25A4 | 291 |
| ENSG00000188931 | C1orf192 | 257177 |
| ENSG00000143479 | DYRK3 | 8444 |
| ENSG00000111145 | ELK3 | 2004 |
| ENSG00000272092 |  | NA |
| ENSG00000231023 | LINC00326 | 285735 |
| ENSG00000123810 | B9D2 | 80776 |
| ENSG00000224843 | LINC00240 | 100133205 |
| ENSG00000119650 | IFT43 | 112752 |
| ENSG00000139117 | CPNE8 | 144402 |
| ENSG00000267795 | SMIM22 | 440335 |
| ENSG00000116793 | PHTF1 | 10745 |
| ENSG00000137691 | C11orf70 | 85016 |
| ENSG00000184831 | APOO | 79135 |
| ENSG00000104450 | SPAG1 | 6674 |
| ENSG00000139537 | CCDC65 | 85478 |
| ENSG00000166171 | DPCD | 25911 |
| ENSG00000163001 | CCDC104 | 112942 |
| ENSG00000128581 | RABL5 | 64792 |
| ENSG00000263450 |  | NA |
| ENSG00000112667 | DNPH1 | 10591 |
| ENSG00000234478 |  | NA |
| ENSG00000233170 |  | 728024 |
| ENSG00000227630 | LINC01132 | 100506810 |
| ENSG00000174628 | IQCK | 124152 |
| ENSG00000257698 |  | 100506844 |
| ENSG00000145491 | ROPN1L | 83853 |
| ENSG00000100591 | AHSA1 | 10598 |

TABLE 18-continued

| Ensembl_ID | GeneID | EntrezID (Gene ID) |
|---|---|---|
| ENSG00000159079 | C21orf59 | 56683 |
| ENSG00000261652 | C15orf65 | 145788 |
| ENSG00000271133 | | 101927811 |
| ENSG00000104432 | IL7 | 3574 |
| ENSG00000079257 | LXN | 56925 |
| ENSG00000100246 | DNAL4 | 10126 |
| ENSG00000203711 | C6orf99 | 100130967 |
| ENSG00000164114 | MAP9 | 79884 |
| ENSG00000163263 | C1orf189 | 388701 |
| ENSG00000227877 | LINC00948 | 100507027 |
| ENSG00000108406 | DHX40 | 79665 |
| ENSG00000164347 | GFM2 | 84340 |
| ENSG00000171757 | LRRC34 | 151827 |
| ENSG00000064199 | SPA17 | 53340 |
| ENSG00000261465 | | NA |
| ENSG00000256073 | C21orf119 | NA |
| ENSG00000167552 | TUBA1A | 7846 |
| ENSG00000164411 | GJB7 | 375519 |
| ENSG00000025772 | TOMM34 | 10953 |
| ENSG00000140876 | NUDT7 | 283927 |
| ENSG00000263812 | LINC00908 | NA |
| ENSG00000183346 | C10orf107 | 219621 |
| ENSG00000124237 | C20orf85 | 128602 |
| ENSG00000138175 | ARL3 | 403 |
| ENSG00000119661 | DNAL1 | 83544 |
| ENSG00000149972 | CNTN5 | 53942 |
| ENSG00000214114 | MYCBP | c(100527950, 26292) |
| ENSG00000266916 | | 101927720 |
| ENSG00000260057 | | 101927364 |
| ENSG00000120306 | CYSTM1 | 84418 |
| ENSG00000236028 | | 101927355 |
| ENSG00000143222 | UFC1 | 51506 |
| ENSG00000204711 | C9orf135 | 138255 |
| ENSG00000263011 | | NA |
| ENSG00000125868 | DSTN | 11034 |
| ENSG00000114446 | IFT57 | 55081 |
| ENSG00000160345 | C9orf16 | 138162 |
| ENSG00000188010 | MORN2 | 729967 |
| ENSG00000185250 | PPIL6 | 285755 |
| ENSG00000157578 | LCA5L | 150082 |
| ENSG00000162961 | DPY30 | 84661 |
| ENSG00000182504 | CEP97 | 79598 |
| ENSG00000186471 | AKAP14 | 158798 |
| ENSG00000272514 | | 154313 |
| ENSG00000152611 | CAPSL | 133690 |
| ENSG00000048342 | CC2D2A | 57545 |
| ENSG00000116885 | OSCP1 | 127700 |
| ENSG00000256061 | DYX1C1 | 161582 |
| ENSG00000146453 | PNLDC1 | 154197 |
| ENSG00000150628 | SPATA4 | 132851 |
| ENSG00000197279 | ZNF165 | 7718 |
| ENSG00000163453 | IGFBP7 | 3490 |
| ENSG00000165182 | CXorf58 | 254158 |
| ENSG00000156206 | C15orf26 | 161502 |
| ENSG00000224049 | | NA |
| ENSG00000213123 | TCTEX1D2 | 255758 |
| ENSG00000196507 | TCEAL3 | 85012 |
| ENSG00000258940 | | 100288846 |
| ENSG00000138036 | DYNC2LI1 | 51626 |
| ENSG00000168734 | PKIG | 11142 |

In some embodiments of any of the aspects, one or more genes of Group D comprises one or more genes of Table 19. In some embodiments of any of the aspects, one or more genes of Group D comprises the genes of Table 19. In some embodiments of any of the aspects, one or more genes of Group D consists of the genes of Table 19.

TABLE 19

| Ensembl_ID | GeneID | EntrezID (Gene ID) |
|---|---|---|
| ENSG00000240024 | LINC00888 | 100505687 |
| ENSG00000214050 | FBXO16 | 157574 |
| ENSG00000136193 | SCRN1 | 9805 |
| ENSG00000153363 | LINC00467 | 84791 |
| ENSG00000143158 | MPC2 | 25874 |
| ENSG00000164542 | KIAA0895 | 23366 |
| ENSG00000178980 | SEPW1 | 6415 |
| ENSG00000129007 | CALML4 | 91860 |
| ENSG00000204334 | ERICH2 | 285141 |
| ENSG00000186198 | SLC51B | 123264 |
| ENSG00000154511 | FAM69A | 388650 |
| ENSG00000102738 | MRPS31 | 10240 |
| ENSG00000119636 | CCDC176 | 80127 |
| ENSG00000161326 | DUSP14 | 11072 |
| ENSG00000186889 | TMEM17 | 200728 |
| ENSG00000229124 | VIM-AS1 | 100507347 |
| ENSG00000084207 | GSTP1 | 2950 |
| ENSG00000132141 | CCT6B | 10693 |
| ENSG00000175792 | RUVBL1 | 8607 |
| ENSG00000158122 | AAED1 | 195827 |
| ENSG00000151729 | SLC25A4 | 291 |
| ENSG00000188931 | C1orf192 | 257177 |
| ENSG00000143479 | DYRK3 | 8444 |
| ENSG00000111145 | ELK3 | 2004 |
| ENSG00000231023 | LINC00326 | 285735 |
| ENSG00000123810 | B9D2 | 80776 |
| ENSG00000224843 | LINC00240 | 100133205 |
| ENSG00000119650 | IFT43 | 112752 |
| ENSG00000139117 | CPNE8 | 144402 |
| ENSG00000267795 | SMIM22 | 440335 |
| ENSG00000116793 | PHTF1 | 10745 |
| ENSG00000137691 | C11orf70 | 85016 |
| ENSG00000184831 | APOO | 79135 |
| ENSG00000104450 | SPAG1 | 6674 |
| ENSG00000139537 | CCDC65 | 85478 |
| ENSG00000166171 | DPCD | 25911 |
| ENSG00000163001 | CCDC104 | 112942 |
| ENSG00000128581 | RABL5 | 64792 |
| ENSG00000112667 | DNPH1 | 10591 |
| ENSG00000227630 | LINC01132 | 100506810 |
| ENSG00000174628 | IQCK | 124152 |
| ENSG00000145491 | ROPN1L | 83853 |
| ENSG00000100591 | AHSA1 | 10598 |
| ENSG00000159079 | C21orf59 | 56683 |
| ENSG00000261652 | C15orf65 | 145788 |
| ENSG00000104432 | IL7 | 3574 |
| ENSG00000079257 | LXN | 56925 |
| ENSG00000100246 | DNAL4 | 10126 |
| ENSG00000203711 | C6orf99 | 100130967 |
| ENSG00000164114 | MAP9 | 79884 |
| ENSG00000163263 | C1orf189 | 388701 |
| ENSG00000227877 | LINC00948 | 100507027 |
| ENSG00000108406 | DHX40 | 79665 |
| ENSG00000164347 | GFM2 | 84340 |
| ENSG00000171757 | LRRC34 | 151827 |
| ENSG00000064199 | SPA17 | 53340 |
| ENSG00000167552 | TUBA1A | 7846 |
| ENSG00000164411 | GJB7 | 375519 |
| ENSG00000025772 | TOMM34 | 10953 |
| ENSG00000140876 | NUDT7 | 283927 |
| ENSG00000183346 | C10orf107 | 219621 |
| ENSG00000124237 | C20orf85 | 128602 |
| ENSG00000138175 | ARL3 | 403 |
| ENSG00000119661 | DNAL1 | 83544 |
| ENSG00000149972 | CNTN5 | 53942 |
| ENSG00000120306 | CYSTM1 | 84418 |
| ENSG00000143222 | UFC1 | 51506 |
| ENSG00000204711 | C9orf135 | 138255 |
| ENSG00000125868 | DSTN | 11034 |
| ENSG00000114446 | IFT57 | 55081 |
| ENSG00000160345 | C9orf16 | 138162 |
| ENSG00000188010 | MORN2 | 729967 |
| ENSG00000185250 | PPIL6 | 285755 |
| ENSG00000157578 | LCA5L | 150082 |
| ENSG00000162961 | DPY30 | 84661 |
| ENSG00000182504 | CEP97 | 79598 |
| ENSG00000186471 | AKAP14 | 158798 |

TABLE 19-continued

| Ensembl_ID | GeneID | EntrezID (Gene ID) |
|---|---|---|
| ENSG00000152611 | CAPSL | 133690 |
| ENSG00000048342 | CC2D2A | 57545 |
| ENSG00000116885 | OSCP1 | 127700 |
| ENSG00000256061 | DYX1C1 | 161582 |
| ENSG00000146453 | PNLDC1 | 154197 |
| ENSG00000150628 | SPATA4 | 132851 |
| ENSG00000197279 | ZNF165 | 7718 |
| ENSG00000163453 | IGFBP7 | 3490 |
| ENSG00000165182 | CXorf58 | 254158 |
| ENSG00000156206 | C15orf26 | 161502 |
| ENSG00000213123 | TCTEX1D2 | 255758 |
| ENSG00000196507 | TCEAL3 | 85012 |
| ENSG00000138036 | DYNC2LI1 | 51626 |
| ENSG00000168734 | PKIG | 11142 |

As used herein, "Group E" refers to the endopeptidase activity genes shown in Table 20.

Table 20.

In some embodiments of any of the aspects, one or more genes of Group D comprises one or more genes of Table 19. In some embodiments of any of the aspects, one or more genes of Group D comprises the genes of Table 19. In some embodiments of any of the aspects, one or more genes of Group D consists of the genes of Table 19.

TABLE 19

| Ensembl_ID | GeneID | EntrezID (GeneID) |
|---|---|---|
| ENSG00000189376 | C8orf76 | 84933 |
| ENSG00000178401 | DNAJC22 | 79962 |
| ENSG00000250508 |  | NA |
| ENSG00000101310 | SEC23B | 10483 |
| ENSG00000121073 | SLC35B1 | 10237 |
| ENSG00000108244 | KRT23 | 25984 |
| ENSG00000136522 | MRPL47 | 57129 |
| ENSG00000132603 | NIP7 | 51388 |
| ENSG00000178127 | NDUFV2 | 4729 |
| ENSG00000151364 | KCTD14 | c(100532726, 65987) |
| ENSG00000155115 | GTF3C6 | 112495 |
| ENSG00000063241 | ISOC2 | 79763 |
| ENSG00000164105 | SAP30 | 8819 |
| ENSG00000230989 | HSBP1 | 3281 |
| ENSG00000143106 | PSMA5 | 5686 |
| ENSG00000262823 |  | NA |
| ENSG00000106803 | SEC61B | 10952 |
| ENSG00000134375 | TIMM17A | 10440 |
| ENSG00000112782 | CLIC5 | 53405 |
| ENSG00000163902 | RPN1 | 6184 |
| ENSG00000179630 | LACC1 | 144811 |
| ENSG00000183617 | MRPL54 | 116541 |
| ENSG00000100804 | PSMB5 | 5693 |
| ENSG00000118939 | UCHL3 | 7347 |
| ENSG00000087302 | C14orf166 | 51637 |
| ENSG00000162972 | C2orf47 | 79568 |
| ENSG00000184203 | PPP1R2 | 5504 |
| ENSG00000113583 | C5orf15 | 56951 |
| ENSG00000086061 | DNAJA1 | 3301 |
| ENSG00000181061 | HIGD1A | 25994 |
| ENSG00000240972 | MIF | 4282 |
| ENSG00000123595 | RAB9A | 9367 |
| ENSG00000165806 | CASP7 | 840 |
| ENSG00000132963 | POMP | 51371 |
| ENSG00000183569 | SERHL2 | 253190 |
| ENSG00000107949 | BCCIP | 56647 |
| ENSG00000198873 | GRK5 | 2869 |
| ENSG00000170315 | UBB | 7314 |
| ENSG00000116288 | PARK7 | 11315 |
| ENSG00000106153 | CHCHD2 | 51142 |
| ENSG00000064763 | FAR2 | 55711 |
| ENSG00000108176 | DNAJC12 | 56521 |
| ENSG00000122643 | NT5C3A | 51251 |

TABLE 19-continued

| Ensembl_ID | GeneID | EntrezID (GeneID) |
|---|---|---|
| ENSG00000120686 | UFM1 | 51569 |
| ENSG00000134058 | CDK7 | 1022 |
| ENSG00000198937 | CCDC167 | 154467 |
| ENSG00000166226 | CCT2 | 10576 |
| ENSG00000123562 | MORF4L2 | 9643 |
| ENSG00000143933 | CALM2 | c(808, 805, 801) |
| ENSG00000154274 | C4orf19 | 55286 |
| ENSG00000205155 | PSENEN | 55851 |
| ENSG00000109971 | HSPA8 | c(85390, 85389, 3312) |
| ENSG00000137947 | GTF2B | 2959 |
| ENSG00000004779 | NDUFAB1 | 4706 |
| ENSG00000129562 | DAD1 | 1603 |
| ENSG00000102172 | SMS | 6611 |
| ENSG00000123444 | KBTBD4 | 55709 |
| ENSG00000173467 | AGR3 | 155465 |
| ENSG00000173890 | GPR160 | 26996 |
| ENSG00000120438 | TCP1 | c(677812, 6950) |
| ENSG00000100567 | PSMA3 | 5684 |
| ENSG00000101846 | STS | 412 |
| ENSG00000134248 | LAMTOR5 | 10542 |
| ENSG00000138495 | COX17 | 10063 |
| ENSG00000148154 | UGCG | 7357 |
| ENSG00000100902 | PSMA6 | 5687 |
| ENSG00000111775 | COX6A1 | 1337 |
| ENSG00000136052 | SLC41A2 | 84102 |
| ENSG00000166598 | HSP90B1 | c(100500842, 7184) |
| ENSG00000155660 | PDIA4 | 9601 |
| ENSG00000101888 | NXT2 | 55916 |
| ENSG00000147592 | LACTB2 | 51110 |
| ENSG00000135002 | RFK | 55312 |
| ENSG00000146425 | DYNLT1 | 6993 |
| ENSG00000112695 | COX7A2 | 1347 |
| ENSG00000163170 | BOLA3 | 388962 |
| ENSG00000242114 | MTFP1 | 51537 |
| ENSG00000086205 | FOLH1 | c(219595, 2346) |
| ENSG00000101843 | PSMD10 | 5716 |
| ENSG00000065518 | NDUFB4 | 4710 |
| ENSG00000154719 | MRPL39 | 54148 |
| ENSG00000197982 | C1orf122 | 127687 |
| ENSG00000168288 | MMADHC | 27249 |
| ENSG00000132432 | SEC61G | 23480 |
| ENSG00000119013 | NDUFB3 | 4709 |
| ENSG00000180879 | SSR4 | 6748 |
| ENSG00000180530 | NRIP1 | 8204 |
| ENSG00000214274 | ANG | 283 |
| ENSG00000185222 | WBP5 | 51186 |
| ENSG00000146386 | ABRACL | 58527 |
| ENSG00000100290 | BIK | 638 |
| ENSG00000134056 | MRPS36 | 92259 |
| ENSG00000101928 | MOSPD1 | 56180 |
| ENSG00000119705 | SLIRP | 81892 |
| ENSG00000172172 | MRPL13 | 28998 |
| ENSG00000185275 | CD24P4 | NA |
| ENSG00000113811 |  | 58515 |
| ENSG00000232388 | LINC00493 | 388789 |
| ENSG00000142168 | SOD1 | 6647 |
| ENSG00000167779 | IGFBP6 | 3489 |
| ENSG00000123131 | PRDX4 | 10549 |
| ENSG00000075089 | ACTR6 | 64431 |
| ENSG00000128228 | SDF2L1 | 23753 |
| ENSG00000074842 | C19orf10 | 56005 |
| ENSG00000110944 | IL23A | 51561 |
| ENSG00000198406 | BZW1P2 | NA |
| ENSG00000189377 | CXCL17 | 284340 |
| ENSG00000173915 | USMG5 | 84833 |

In some embodiments of any of the aspects, one or more genes of Group E comprises one or more genes of Table 21. In some embodiments of any of the aspects, one or more genes of Group E comprises the genes of Table 21. In some embodiments of any of the aspects, one or more genes of Group E consists of the genes of Table 21.

TABLE 21

| Ensembl_ID | GeneID | EntrezID (GeneID) |
|---|---|---|
| ENSG00000189376 | C8orf76 | 84933 |
| ENSG00000178401 | DNAJC22 | 79962 |
| ENSG00000101310 | SEC23B | 10483 |
| ENSG00000121073 | SLC35B1 | 10237 |
| ENSG00000108244 | KRT23 | 25984 |
| ENSG00000136522 | MRPL47 | 57129 |
| ENSG00000132603 | NIP7 | 51388 |
| ENSG00000178127 | NDUFV2 | 4729 |
| ENSG00000155115 | GTF3C6 | 112495 |
| ENSG00000063241 | ISOC2 | 79763 |
| ENSG00000164105 | SAP30 | 8819 |
| ENSG00000230989 | HSBP1 | 3281 |
| ENSG00000143106 | PSMA5 | 5686 |
| ENSG00000106803 | SEC61B | 10952 |
| ENSG00000134375 | TIMM17A | 10440 |
| ENSG00000112782 | CLIC5 | 53405 |
| ENSG00000163902 | RPN1 | 6184 |
| ENSG00000179630 | LACC1 | 144811 |
| ENSG00000183617 | MRPL54 | 116541 |
| ENSG00000100804 | PSMB5 | 5693 |
| ENSG00000118939 | UCHL3 | 7347 |
| ENSG00000087302 | C14orf166 | 51637 |
| ENSG00000162972 | C2orf47 | 79568 |
| ENSG00000184203 | PPP1R2 | 5504 |
| ENSG00000113583 | C5orf15 | 56951 |
| ENSG00000086061 | DNAJA1 | 3301 |
| ENSG00000181061 | HIGD1A | 25994 |
| ENSG00000240972 | MIF | 4282 |
| ENSG00000123595 | RAB9A | 9367 |
| ENSG00000165806 | CASP7 | 840 |
| ENSG00000132963 | POMP | 51371 |
| ENSG00000183569 | SERHL2 | 253190 |
| ENSG00000107949 | BCCIP | 56647 |
| ENSG00000198873 | GRK5 | 2869 |
| ENSG00000170315 | UBB | 7314 |
| ENSG00000116288 | PARK7 | 11315 |
| ENSG00000106153 | CHCHD2 | 51142 |
| ENSG00000064763 | FAR2 | 55711 |
| ENSG00000108176 | DNAJC12 | 56521 |
| ENSG00000122643 | NT5C3A | 51251 |
| ENSG00000120686 | UFM1 | 51569 |
| ENSG00000134058 | CDK7 | 1022 |
| ENSG00000198937 | CCDC167 | 154467 |
| ENSG00000166226 | CCT2 | 10576 |
| ENSG00000123562 | MORF4L2 | 9643 |
| ENSG00000154274 | C4orf19 | 55286 |
| ENSG00000205155 | PSENEN | 55851 |
| ENSG00000137947 | GTF2B | 2959 |
| ENSG00000004779 | NDUFAB1 | 4706 |
| ENSG00000129562 | DAD1 | 1603 |
| ENSG00000102172 | SMS | 6611 |
| ENSG00000123444 | KBTBD4 | 55709 |
| ENSG00000173467 | AGR3 | 155465 |
| ENSG00000173890 | GPR160 | 26996 |
| ENSG00000100567 | PSMA3 | 5684 |
| ENSG00000101846 | STS | 412 |
| ENSG00000134248 | LAMTOR5 | 10542 |
| ENSG00000138495 | COX17 | 10063 |
| ENSG00000148154 | UGCG | 7357 |
| ENSG00000100902 | PSMA6 | 5687 |
| ENSG00000111775 | COX6A1 | 1337 |
| ENSG00000136052 | SLC41A2 | 84102 |
| ENSG00000155660 | PDIA4 | 9601 |
| ENSG00000101888 | NXT2 | 55916 |
| ENSG00000147592 | LACTB2 | 51110 |
| ENSG00000135002 | RFK | 55312 |
| ENSG00000146425 | DYNLT1 | 6993 |
| ENSG00000112695 | COX7A2 | 1347 |
| ENSG00000163170 | BOLA3 | 388962 |
| ENSG00000242114 | MTFP1 | 51537 |
| ENSG00000101843 | PSMD10 | 5716 |
| ENSG00000065518 | NDUFB4 | 4710 |
| ENSG00000154719 | MRPL39 | 54148 |

TABLE 21-continued

| Ensembl_ID | GeneID | EntrezID (GeneID) |
|---|---|---|
| ENSG00000197982 | C1orf122 | 127687 |
| ENSG00000168288 | MMADHC | 27249 |
| ENSG00000132432 | SEC61G | 23480 |
| ENSG00000119013 | NDUFB3 | 4709 |
| ENSG00000180879 | SSR4 | 6748 |
| ENSG00000180530 | NRIP1 | 8204 |
| ENSG00000214274 | ANG | 283 |
| ENSG00000185222 | WBP5 | 51186 |
| ENSG00000146386 | ABRACL | 58527 |
| ENSG00000100290 | BIK | 638 |
| ENSG00000134056 | MRPS36 | 92259 |
| ENSG00000101928 | MOSPD1 | 56180 |
| ENSG00000119705 | SLIRP | 81892 |
| ENSG00000172172 | MRPL13 | 28998 |
| ENSG00000232388 | LINC00493 | 388789 |
| ENSG00000142168 | SOD1 | 6647 |
| ENSG00000167779 | IGFBP6 | 3489 |
| ENSG00000123131 | PRDX4 | 10549 |
| ENSG00000075089 | ACTR6 | 64431 |
| ENSG00000128228 | SDF2L1 | 23753 |
| ENSG00000074842 | C19orf10 | 56005 |
| ENSG00000110944 | IL23A | 51561 |
| ENSG00000189377 | CXCL17 | 284340 |
| ENSG00000173915 | USMG5 | 84833 |

In some embodiments of any of the aspects, the at least one gene of Group A is at least one of: ZNF493 and ZNF519. In some embodiments of any of the aspects, the at least one gene of Group A comprises, consists of, or is at least one of: ZNF493 and ZNF519. In some embodiments of any of the aspects, the at least one gene of Group A comprises, consists of, or is ZNF493. In some embodiments of any of the aspects, the at least one gene of Group A comprises, consists of, or is ZNF519. In some embodiments of any of the aspects, the at least one gene of Group A comprises, consists of, or is ZNF493 and ZNF519.

In some embodiments of any of the aspects, the at least one gene of Group B is at least one of: LRP2 and FAT2. In some embodiments of any of the aspects, the at least one gene of Group B comprises, consists of, or is at least one of: LRP2 and FAT2. In some embodiments of any of the aspects, the at least one gene of Group B comprises, consists of, or is LRP2. In some embodiments of any of the aspects, the at least one gene of Group B comprises, consists of, or is FAT2. In some embodiments of any of the aspects, the at least one gene of Group B comprises, consists of, or is LRP2 and FAT2.

In some embodiments of any of the aspects, the at least one gene of Group C is at least one of: ASL and CCDC160. In some embodiments of any of the aspects, the at least one gene of Group C comprises, consists of, or is at least one of: ASL and CCDC160. In some embodiments of any of the aspects, the at least one gene of Group C comprises, consists of, or is ASL. In some embodiments of any of the aspects, the at least one gene of Group C comprises, consists of, or is CCDC160. In some embodiments of any of the aspects, the at least one gene of Group C comprises, consists of, or is ASL and CCDC160.

In some embodiments of any of the aspects, the at least one gene of Group D is at least one of: LINC00888 and FBXO16. In some embodiments of any of the aspects, the at least one gene of Group D comprises, consists of, or is at least one of: LINC00888 and FBXO16. In some embodiments of any of the aspects, the at least one gene of Group D comprises, consists of, or is LINC00888. In some embodiments of any of the aspects, the at least one gene of Group D comprises, consists of, or is FBXO16. In some embodiments of any of the aspects, the at least one gene of Group D comprises, consists of, or is LINC00888 and FBXO16.

In some embodiments of any of the aspects, the at least one gene of Group E is at least one of: C8orf76 and DNAJC22. In some embodiments of any of the aspects, the at least one gene of Group E comprises, consists of, or is at least one of: C8orf76 and DNAJC22. In some embodiments of any of the aspects, the at least one gene of Group E comprises, consists of, or is C8orf76. In some embodiments of any of the aspects, the at least one gene of Group E comprises, consists of, or is DNAJC22. In some embodiments of any of the aspects, the at least one gene of Group E comprises, consists of, or is C8orf76 and DNAJC22.

combo language. For example, in some embodiments of any of the aspects, the level of expression is or has been determined/measured for any one of: ZNF493; LRP4; FAT2; ASL; LINC00888; and C8orf76. In some embodiments of any of the aspects, the level of expression is or has been determined/measured for any two of: ZNF493; LRP4; FAT2; ASL; LINC00888; and C8orf76. In some embodiments of any of the aspects, the level of expression is or has been determined/measured for any three of: ZNF493; LRP4; FAT2; ASL; LINC00888; and C8orf76. In some embodiments of any of the aspects, the level of expression is or has been determined/measured for any four of: ZNF493; LRP4; FAT2; ASL; LINC00888; and C8orf76. In some embodiments of any of the aspects, the level of expression is or has been determined/measured for any five of: ZNF493; LRP4; FAT2; ASL; LINC00888; and C8orf76. In some embodiments of any of the aspects, the level of expression is or has been determined/measured for all of: ZNF493; LRP4; FAT2; ASL; LINC00888; and C8orf76.

In some embodiments of any of the aspects, the level of expression is or has been determined for any one of: ZNF493, ZNF519; LRP4; FAT2; ASL; CCDC160; LINC00888; FBXO16; C8orf76; and DNAJC22. In some embodiments of any of the aspects, the level of expression is or has been determined for any two of: ZNF493, ZNF519; LRP4; FAT2; ASL; CCDC160; LINC00888; FBXO16; C8orf76; and DNAJC22. In some embodiments of any of the aspects, the level of expression is or has been determined for any three of: ZNF493, ZNF519; LRP4; FAT2; ASL; CCDC160; LINC00888; FBXO16; C8orf76; and DNAJC22. In some embodiments of any of the aspects, the level of expression is or has been determined for any four of: ZNF493, ZNF519; LRP4; FAT2; ASL; CCDC160; LINC00888; FBXO16; C8orf76; and DNAJC22. In some embodiments of any of the aspects, the level of expression is or has been determined for any five of: ZNF493, ZNF519; LRP4; FAT2; ASL; CCDC160; LINC00888; FBXO16; C8orf76; and DNAJC22. In some embodiments of any of the aspects, the level of expression is or has been determined for any six of: ZNF493, ZNF519; LRP4; FAT2; ASL; CCDC160; LINC00888; FBXO16; C8orf76; and DNAJC22. In some embodiments of any of the aspects, the level of expression is or has been determined for any seven of: ZNF493, ZNF519; LRP4; FAT2; ASL; CCDC160; LINC00888; FBXO16; C8orf76; and DNAJC22. In some embodiments of any of the aspects, the level of expression is or has been determined for any eight of: ZNF493, ZNF519; LRP4; FAT2; ASL; CCDC160; LINC00888; FBXO16; C8orf76; and DNAJC22. In some embodiments of any of the aspects, the level of expression is or has been determined for any nine of: ZNF493, ZNF519; LRP4; FAT2; ASL; CCDC160; LINC00888; FBXO16; C8orf76; and DNAJC22. In some embodiments of any of the aspects, the level of expression is or has been determined for all of: ZNF493, ZNF519; LRP4; FAT2; ASL; CCDC160; LINC00888; FBXO16; C8orf76; and DNAJC22.

The gene expression signatures described herein can be indicative of airway dysfunction. As used herein, "airway dysfunction" refers to one or more of: bronchial enlargement, bronchial dilation, thickening of central bronchial walls, abnormally mucus production that obstructs the airways, and/or thickening of the bronchi walls due to infection and/or inflammation (i.e. bronchiectasis). Symptoms of airway dysfunction can include cough, breathlessness, excess sputum production, frequent respiratory infections, and respiratory failure.

In some embodiments of any of the aspects, the airway dysfunction is bronchial enlargement or dilation. In some embodiments of any of the aspects, the subject with airway dysfunction has or is diagnosed as having COPD, asthma, bronchiolitis, bronchiectasis, lung transplant rejection, rheumatoid arthritis, GvHD, or autoimmune prenumonitis. In some embodiments of any of the aspects, the subject has previously received a lung transplant and the airway dysfunction is or is caused by lung transplant rejection. In some embodiments of any of the aspects, the subject has previously received a bone marrow transplant and/or blood stem cell transplant and the airway dysfunction is or is caused by GvHD.

The signatures described herein can indicate that a subject has or is at risk of developing, e.g., bronchiectasis. In some embodiments of any of the aspects, the signatures described herein can indicate that a subject has or is at risk of developing bronchiectasis. In some embodiments of any of the aspects, the signatures described herein can indicate that a subject has bronchiectasis that has not yet progressed to radiographic bronchiectasis. The signatures described herein can indicate that a subject has or is at risk of developing transplant rejection. The signatures described herein can indicate that a subject has or is at risk of developing immune-related pneumonitis or autoimmune pneumonitis.

Accordingly, in one aspect of any of the embodiments, described herein is a method of diagnosing a subject with airway dysfunction, or determining that a subject is at increased risk of airway dysfunction, the method comprising diagnosing a subject with airway dysfunction, or prognosing a subject to be at increased risk of airway dysfunction when the subject is determined to have a decreased level of expression of at least one of: at least one gene of Group A, and at least one gene of Group B; and/or an increased level of expression of at least one of: at least one gene of Group C, at least one gene of Group D, and at least one gene of Group E. In one aspect of any of the embodiments, described herein is a method of diagnosing a subject with airway dysfunction, or determining that a subject is at increased risk of airway dysfunction, the method comprising determining the level of expression of at least one of: at least one gene of Group A, and at least one gene of Group B; at least one gene of Group C, at least one gene of Group D, and at least one gene of Group E in a sample obtained from the subject and diagnosing the subject with airway dysfunction, or prognosing a subject to be at increased risk of airway dysfunction when the subject is determined to have a decreased level of expression of at least one of: at least one gene of Group A, and at least one gene of Group B; and/or an increased level of expression of at least one of: at least one gene of Group C, at least one gene of Group D, and at least one gene of Group E.

When a subject has the signature(s) described herein, the subject is at increased risk of having or developing airway dysfunction, including bronchiectasis or radiographic bronchiectasis. Accordingly, these subjects are candidates for airway dysfunction treatment. Under current treatment regimens, these subjects' symptoms (e.g., cough, mucus production, and/or shortness of breath), would not indicate that they receive treatment for airway dysfunction. In some embodiments of any of the aspects, the subject treated according to the methods described herein does not have radiographic bronchiectasis and/or has not been diagnosed with radiographic bronchiectasis.

In one aspect of any of the embodiments, described herein is a method of treating airway dysfunction, the method comprising administering:
a) a chest CT, smoking cessation, and/or avoiding aspiration risk and inhalational injury to a subject determined to have a decreased level of expression of at least one of:
  at least one gene of Group A, and at least one gene of Group B; and/or
  an increased level of expression of at least one of:
  at least one gene of Group C, at least one gene of Group D, and at least one gene of Group E;
b) an immunosuppressant and/or a more aggressive immunosuppressant regimen to a subject who had previously received and lung transplant and was determined to have a decreased level of expression of at least one of:
  at least one gene of Group A, and at least one gene of Group B; and/or
  an increased level of expression of at least one of:
  at least one gene of Group C, at least one gene of Group D, and at least one gene of Group E;
c) an immunosuppressant and/or a more aggressive immunosuppressant regimen to a subject who had previously received a bone marrow or blood stem cell transplant and was determined to have a decreased level of expression of at least one of:
  at least one gene of Group A, and at least one gene of Group B; and/or
  an increased level of expression of at least one of:
  at least one gene of Group C, at least one gene of Group D, and at least one gene of Group E;
d) an inhibitor of DPP1 to a subject who had previously received a bone marrow or blood stem cell transplant and was determined to have a decreased level of expression of at least one of:
  at least one gene of Group A, and at least one gene of Group B; and/or
  an increased level of expression of at least one of:
  at least one gene of Group C, at least one gene of Group D, and at least one gene of Group E; and/or
e) an inhibitor of DPP1 to a subject who has COPD, asthma, or rheumatoid arthritis and was determined to have a decreased level of expression of at least one of:
  at least one gene of Group A, and at least one gene of Group B; and/or
  an increased level of expression of at least one of:
  at least one gene of Group C, at least one gene of Group D, and at least one gene of Group E.

In some embodiments of any of the aspects, for a subject who had previously received a lung transplant, an immunosuppressant and/or a more aggressive immunosuppressant regimen can comprise immunosuppression via steroids (e.g., prednisone), mycophenylate, and/or other immunosuppression medicines (e.g., cyclosporine, tacrolimus, and calcineurin inhibitors, methotrexate).

In some embodiments of any of the aspects, for a subject who had previously received a bone marrow transplant or blood stem cell transplant, the presence of the signature can be indicative of GvHD. In some embodiments of any of the aspects, for a subject who had previously received a bone marrow transplant or blood stem cell transplant, an immunosuppressant and/or a more aggressive immunosuppressant regimen can comprise immunosuppression via steroids (e.g., prednisone), mycophenylate, other immunosuppression medicines (e.g., cyclosporine, tacrolimus, and calcineurin inhibitors, methotrexate), and/or anti B-cell therapy (e.g., ibrutinib).

As described herein, levels of genes of Group A and B can be decreased, and levels of genes of Groups C, D, and E can be increased in airway dysfunction and/or in subjects with airway dysfunction. Accordingly, in one aspect of any of the embodiments, described herein is a method of treating airway dysfunction in a subject in need thereof, the method comprising administering a chest CT, smoking cessation, and/or avoiding aspiration risk and inhalational injury, an immunosuppressant, a more aggressive immunosuppressant regime, and/or a DPP1 inhibitor to a subject determined to have a level of expression of one or more genes of Groups A and B that is decreased relative to a reference, and/or a level of expression of one or more genes of Groups C, D, and E that is increased relative to a reference. In one aspect of any of the embodiments, described herein is a method of treating airway dysfunction in a subject in need thereof, the method comprising: a) determining the level of expression of one or more genes of Groups A, B, C, D, and/or E in a sample obtained from a subject; and b) administering a chest CT, smoking cessation, and/or avoiding aspiration risk and inhalational injury, an immunosuppressant, a more aggressive immunosuppressant regime, and/or a DPP1 inhibitor to the subject if the level of expression of one or more genes of Groups A and B that is decreased relative to a reference, and/or the level of expression of one or more genes of Groups C, D, and E is increased relative to a reference. In some embodiments of any of the aspects, described herein is a method of treating airway dysfunction in a subject in need thereof, the method comprising: a) first determining the level of expression of one or more genes of Groups A, B, C, D, and/or E in a sample obtained from a subject; and b) then administering a chest CT, smoking cessation, and/or avoiding aspiration risk and inhalational injury, an immunosuppressant, a more aggressive immunosuppressant regime, and/or a DPP1 inhibitor to the subject if the level of expression of one or more genes of Groups A and B that is decreased relative to a reference, and/or the level of expression of one or more genes of Groups C, D, and E is increased relative to a reference. In one aspect of any of the embodiments, the method further comprises c) not administering a chest CT, and/or maintaining the same immunosuppressant regime if the level of expression of one or more genes of Groups A and B is not decreased relative to a reference, and/or the level of expression of one or more genes of Groups C, D, and E is not increased relative to a reference.

In one aspect of any of the embodiments, described herein is a method of treating airway dysfunction in a subject in need thereof, the method comprising: a) determining if the subject has a level of expression of one or more genes of Groups A and B that is decreased relative to a reference, and/or a level of expression of one or more genes of Groups C, D, and E that is increased relative to a reference; and b) administering a chest CT, smoking cessation, and/or avoiding aspiration risk and inhalational injury, an immunosuppressant, a more aggressive immunosuppressant regime, and/or a DPP1 inhibitor to the subject if the level of expression of one or more genes of Groups A and B is decreased relative to a reference, and/or the level of expression of one or more genes of Groups C, D, and E is increased relative to a reference. In some embodiments of any of the aspects, the step of determining if the subject has a certain level of expression of one or more genes can comprise i) obtaining or having obtained a sample from the subject and ii) performing or having performed an assay on the sample obtained from the subject to determine/measure the level of expression of one or more genes in the subject. In some embodiments of any of the aspects, the step of determining if the subject has a certain level of expression of one or more genes can comprise performing or having performed an assay on a sample obtained from the subject to determine/measure the level of the one or more genes in the subject. In some embodiments of any of the aspects, the step of determining if the subject has a certain level of expression of one or more genes can comprise ordering or requesting an assay on a sample obtained from the subject to determine/measure the level of the one or more genes in the subject. In some embodiments of any of the aspects, the step of determining if the subject has a certain level of expression of one or more genes can comprise receiving the results of an assay on a sample obtained from the subject to determine/measure the level of the one or more genes in the subject. In some embodiments of any of the aspects, the step of determining if the subject has a certain level of expression of one or more genes can comprise receiving a report, results, or other means of identifying the subject as a subject with a certain level of expression of the one or more genes.

In one aspect of any of the embodiments, described herein is a method of treating airway dysfunction in a subject in need thereof, the method comprising: a) determining if the subject has a level of expression of one or more genes of Groups A and B that is decreased relative to a reference, and/or a level of expression of one or more genes of Groups C, D, and E that is increased relative to a reference; and b) instructing or directing that the subject be administered a chest CT, smoking cessation, and/or avoiding aspiration risk and inhalational injury, an immunosuppressant, a more aggressive immunosuppressant regime, and/or a DPP1 inhibitor if the level of expression of one or more genes of Groups A and B is decreased relative to a reference, and/or the level of expression of one or more genes of Groups C, D, and E is increased relative to a reference. In some embodiments of any of the aspects, the step of determining the level of expression of one or more genes of Groups A, B, C, D, and/or E can comprise i) obtaining or having obtained a sample from the subject and ii) performing or having performed an assay on the sample obtained from the subject to determine/measure the level of expression of one or more genes of Groups A, B, C, D, and/or E in the subject. In some embodiments of any of the aspects, the step of determining the level of expression of one or more genes of Groups A, B, C, D, and/or E can comprise performing or having performed an assay on a sample obtained from the subject to determine/measure the level of expression of one or more genes of Groups A, B, C, D, and/or E in the subject. In some embodiments of any of the aspects, the step of determining the level of expression of one or more genes of Groups A, B, C, D, and/or E can comprise ordering or requesting an assay on a sample obtained from the subject to determine/measure the level of expression of one or more genes of Groups A, B, C, D, and/or E in the subject. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In one aspect of any of the embodiments, described herein is a method of determining if a subject has airway dysfunction, is at increased risk of airway dysfunction, is at increased risk of bronchiectasis (e.g., radiographic bronchiectasis) or is in need of treatment for airway dysfunction, the method comprising: determining the level of expression of one or more genes of Groups A, B, C, D, and/or E in a sample obtained from the subject, wherein a level of expression of one or more genes of Groups A and B that is decreased relative to a reference, and/or a level of expression of one or more genes of Groups C, D, and E that is increased relative to a reference indicates the subject has airway dysfunction, is at increased risk of airway dysfunction, is at increased risk of bronchiectasis (e.g., radiographic bronchiectasis) or is in need of treatment for airway dysfunction.

As used herein, "immunosuppressant" refers to an agent that inhibits or suppresses an immune response. Exemplary immunosuppressants can include but are not limited to steroids (e.g. prednisone), mycophenylate, calcineurin inhibitors, tacrolimus, cyclosporine, methotrexate, and anti-B cell therapies (e.g., ibrutinib).

An immunosuppressant regimen refers to the combination of: the individual immunosuppressant(s) administered, the total number of individual immunosuppressants administered, the dosage of each immunosuppressant, and the frequence of administration of each immunosuppressant. A more aggressive immunosuppressant can comprise one or more of: a higher dosage(s), more frequent administration, administration of a greater number of individual immunosuppressants, and/or administration of a immunosuppressant with stronger immunosuppressant activity.

Exemplary immunosuppressant treatments include but are not limited to, Cyclosporine (Neoral, Sandimmune, Gengraf, and Restasis), Tacrolimus (Prograf, Protopic, Astagraf XL, and Envarsus XR), Methotrexate (Trexall, Rasuvo, Rheumatrex, and Otrexup (PF)), Sirolimus (Rapamune), Mycophenolic acid (Myfortic and CellCept), Rituximab (Rituxan), etanercept (Enbrel), pentostatin (Nipent), ruxolitinib (Jakafi); chemotherapies, e.g., Methotrexate (Trexall, Rasuvo, Rheumatrex, and Otrexup (PF)), antithymocyte globulin (Atgam, Thymoglobulin); Steroids, e.g, Prednisone (Deltasone, Rayos, and Prednisone Intensol), Methylprednisolone (Medrol, Solu-Medrol, and Depo-Medrol), budesonide (Entocort EC, Uceris); Protease inhibitors, e.g. alphal-proteinase inhibitor (Zemaira); extracorporeal photopheresis; monoclonal antibodies (daclizumab (Zinbryta), basiliximab (Simulect)), Brentuximab vedotin (Adcetris), Alemtuzumab (Campath, Lemtrada), Tocilizumab (Actemra).

Mycophenolate mofetil (MMF) is 2-morpholin-4-ylethyl (E)-6-(4-hydroxy-6-methoxy-7-methyl-3-oxo-1H-2-benzofuran-5-yl)-4-methylhex-4-enoate, having the structure below. MMF is available commercially as CELLCEPT from Genentech.

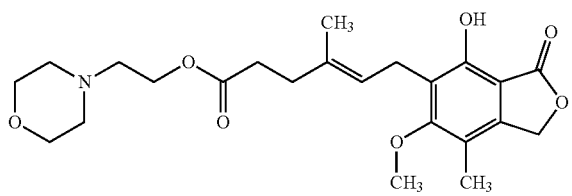 [SMILES: COc1c(C)c2c(c(O)c1C/C=C(\C)CCC(=O)OCCN1CCOCC1)C(=O)OC2]

Anti-B cell therapies are those that inhibit the growth, proliferation, and/or survival of B cells. Exemplary anti-B cell therapies include ibrutinib (IMBRUVICA), zanubrutinib (BRUKINSA), ocrelizumab (OCREVUS), ofatumumab (KESIMPTA), rituximab, obintutuzumab, and the like.

As used herein, the term "steroid" refers to a chemical substance comprising three cyclohexane rings and a cyclopentane ring. The rings are arranged to form tetracyclic cyclopentaphenanthrene, i.e. gonane. In some embodiments, the steroid is a corticosteroid.

As used herein, the term "corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydrocortisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term "corticosteroid" can include, but is not limited to, the following generic and brand name corticosteroids: cortisone (CORTONE™ ACETATE™, ADRESON™, ALTESONA™, CORTELAN™, CORTISTAB™, CORTISYL™, CORTOGEN™, CORTONE™, SCHEROSON™); dexamethasone-oral (DECADRON-ORAL™, DEXAMETH™, DEXONE™, HEXADROL-ORAL™, DEXAMETHASONE™ INTENSOL™, DEXONE 0.5™, DEXONE 0.75™, DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™ DELTA-CORTEF™, PEDIAPRED™, ADNISOLONE™, CORTALONE™, DELTACORTRIL™, DELTASOLONE™, DELTASTAB™, DI-ADRESON F™, ENCORTOLONE™, HYDROCORTANCYL™, MEDISOLONE™, METICORTELONE™, OPREDSONE™ PANAAFCORTELONE™, PRECORTISYL™, PRENISOLONA™, SCHERISOLONA™ SCHERISOLONE™); prednisone (DELTASONE™, LIQUID PRED™, METICORTEN™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™ CORDROL™ CORTAN™, DACORTIN™, DECORTIN™, DECORTISYL™, DELCORTIN™, DELLACORT™, DELTADOME™, DELTACORTENE™, DELTISONA™, DIADRESON™, ECONOSONE™, ENCORTON™, FERNISONE™, NISONA™, NOVOPREDNISONE™, PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-D™, TRI-MED™, TRIAMCOT™, TRISTOPLEX™, TRYLONE D™, U-TRILONE™). Methods of synthesizing steroids and corticosteroids are well known in the art and such compounds are also commercially available.

As used herein, "DPP1 inhibitor" refers to an inhibitor of dipeptidyl peptidase 1 (DPP1) (also known in the art as cathepsin C, NCBI Gene ID: 1075). DPP1 inhibitors include but are not limited to AZD7986 (e.g., brensocatib), ICatC (XPZ-01), and GSK2793660.

In one embodiment of any of the aspects, administration of a chest CT scan comprises administering a chest CT scan at least every 6 months (e.g., at least every 1, 2, 3, 4, 5, or 6 months). In one embodiment of any of the aspects, administration of a chest CT scan comprises instructing or directing that the patient receive a chest CT scan at least every 6 months (e.g., at least every 1, 2, 3, 4, 5, or 6 months). In one embodiment of any of the aspects, administration of a chest CT scan comprises administering a chest CT scan at least every 6 months (e.g., at least every 1, 2, 3, 4, 5, or 6 months) for 1 year. In one embodiment of any of the aspects, administration of a chest CT scan comprises instructing or directing that the patient receive a chest CT scan at least every 6 months (e.g., at least every 1, 2, 3, 4, 5, or 6 months) for 1 year. In one embodiment of any of the aspects, administration of a chest CT scan comprises administering a chest CT scan at least every 6 months (e.g., at least every 1, 2, 3, 4, 5, or 6 months) for 2 years. In one embodiment of any of the aspects, administration of a chest CT scan comprises instructing or directing that the patient receive a chest CT scan at least every 6 months (e.g., at least every 1, 2, 3, 4, 5, or 6 months) for 2 years. In one embodiment of any of the aspects, administration of a chest CT scan comprises administering a chest CT scan at least every 6 months (e.g., at least every 1, 2, 3, 4, 5, or 6 months) for 3 years. In one embodiment of any of the aspects, administration of a chest CT scan comprises instructing or directing that the patient receive a chest CT scan at least every 6 months (e.g., at least every 1, 2, 3, 4, 5, or 6 months) for 3 years. In one embodiment of any of the aspects, administration of a chest CT scan comprises administering a chest CT scan at least every 6 months (e.g., at least every 1, 2, 3, 4, 5, or 6 months) for 5 years. In one embodiment of any of the aspects, administration of a chest CT scan comprises instructing or directing that the patient receive a chest CT scan at least every 6 months (e.g., at least every 1, 2, 3, 4, 5, or 6 months) for 5 years.

In one embodiment of any of the aspects, not administering a chest CT scan comprises not administering a chest CT scan for at least 1 year. In one embodiment of any of the aspects, not administering a chest CT scan comprises instructing or directing that the patient not receive a chest CT scan for at least 1 year. In one embodiment of any of the aspects, not administering a chest CT scan comprises not administering a chest CT scan for at least 2 years. In one embodiment of any of the aspects, not administering a chest CT scan comprises instructing or directing that the patient not receive a chest CT scan for at least 2 years. In one embodiment of any of the aspects, not administering a chest CT scan comprises not administering a chest CT scan for at least 3 years. In one embodiment of any of the aspects, not administering a chest CT scan comprises instructing or directing that the patient not receive a chest CT scan for at least 3 years. In one embodiment of any of the aspects, not administering a chest CT scan comprises not administering a chest CT scan for at least 4 years. In one embodiment of any of the aspects, not administering a chest CT scan comprises instructing or directing that the patient not receive a chest CT scan for at least 4 years. In one embodiment of any of the aspects, not administering a chest CT scan comprises not administering a chest CT scan for at least 5 years. In one embodiment of any of the aspects, not administering a chest CT scan comprises instructing or directing that the patient not receive a chest CT scan for at least 5 years.

Smoking cessation refers to discontinuing smoking. In some embodiments of any of the aspects, the smoking cessation is intensive smoking cessation therapy. In some embodiments of any of the aspects, a subject is administered intensive smoking cessation therapy in accordance with the methods described herein. Intensive smoking cessation therapy can include one or more of: nicotine replacement therapy, transdermal nicotine replacement therapy, counseling, and programs such as the Gold Standard Program.

In some embodiments of any of the aspects, measurement of the level of a target and/or detection of the level or presence of a target, e.g. of an expression product (nucleic acid or polypeptide of one of the genes described herein) or a mutation can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, e.g. a mRNA or polypeptide can comprise contacting a sample obtained from a subject with a reagent (e.g. a detection reagent) which is specific for the target, e.g., a target-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for the various targets described herein are commercially available and can be used for the purposes of the invention to measure protein expression levels. Alternatively, since the amino acid sequences for the targets described herein are known and publically available at the NCBI website, one of skill in the art can raise their own antibodies against these polypeptides of interest for the purpose of the methods described herein. The amino acid sequences of the polypeptides described herein have been assigned NCBI accession numbers for different species such as human, mouse and rat.

In some embodiments of any of the aspects, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments of any of the aspects, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments of any of the aspects, the immunoassay can be a quantitative or a semi-quantitative immunoassay.

An immunoassay is a biochemical test that measures the concentration of a substance in a biological sample, typically a fluid sample such as blood or serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., any of the targets as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5"-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce significant color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests used for medical diagnostics, either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick tests, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments of any of the aspects, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, an adaptation of Western blotting (Towbin et al., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. A dot blot immobilizes a protein sample on a defined region of a support, which is then probed with antibody and labelled secondary antibody as in Western blotting. The intensity of the signal from the detectable label in either format corresponds to the amount of enzyme present, and therefore the amount of polypeptide. Levels can be quantified, for example by densitometry.

In some embodiments of any of the aspects, the level of a target can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments of any of the aspects, a detectable label can be a radiolabel including, but not limited to $^3$H, $^{125}$I, $^{35}$S, $^{14}$C, $^{32}$P, and $^{33}$P. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, CA A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylene diaminetetraacetic acid (EDTA).

In some embodiments of any of the aspects, a level which is decreased is a level which is decreased relative to a reference level. A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

In some embodiments of any of the aspects, a level which is increased is a level which is increased relative to a reference level. A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target molecule in a population of subjects who do not have or are not diagnosed as having, and/or do not exhibit signs or symptoms of airway dysfunction, cough, shortness of breath, and/or phlegm production. In some embodiments of any of the aspects, the reference can also be a level of expression of the target molecule in a control sample, a pooled sample of control individuals or a numeric value or range of values based on the same. In some embodiments of any of the aspects, the reference can be the level of a target molecule in a sample obtained from the same subject at an earlier point in time, e.g., the methods described herein can be used to determine if a subject's sensitivity or response to a given therapy is changing over time.

In some embodiments of the foregoing aspects, the expression level of a given gene can be normalized relative to the expression level of one or more reference genes or reference proteins.

In some embodiments, the reference level can be the level in a sample of similar cell type, sample type, sample processing, and/or obtained from a subject of similar age, sex and other demographic parameters as the sample/subject for which the level of expression is to be determined. In some embodiments, the test sample and control reference sample are of the same type, that is, obtained from the same biological source, and comprising the same composition, e.g. the same number and type of cells.

In some embodiments of any of the aspects, the level of expression products of no more than 2,000 other genes is determined. In some embodiments of any of the aspects, the level of expression products of no more than 1,000 other genes is determined. In some embodiments of any of the aspects, the level of expression products of no more than 500 other genes is determined. In some embodiments of any of the aspects, the level of expression products of no more than 200 other genes is determined. In some embodiments of any of the aspects, the level of expression products of no more than 100 other genes is determined. In some embodiments of any of the aspects, the level of expression products of no more than 20 other genes is determined. In some embodiments of any of the aspects, the level of expression products of no more than 10 other genes is determined.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject.

In some embodiments of any of the aspects, the sample is a bronchial brushing, nasal brushing, sputum, or peripheral blood sample. In some embodiments of any of the aspects, the sample is a bronchial brushing sample. In some embodiments of any of the aspects, the sample is a nasal brushing sample. In some embodiments of any of the aspects, the same comprises, consists of, or consists essentially of nasal cells and/or tissues. In some embodiments of any of the aspects, the same comprises, consists of, or consists essentially of nasal epithelial cells and/or tissues. In some embodiments of any of the aspects, the same comprises, consists of, or consists essentially of bronchial cells and/or tissues. In some embodiments of any of the aspects, the same comprises, consists of, or consists essentially of bronchial epithelial cells and/or tissues.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g. having or diagnosed as having) airway dysfunction or a subject at risk of or at increased risk of developing airway dysfunction as described elsewhere herein.

In some embodiments of any of the aspects, the subject is a subject that has previously received a lung transplant. In some embodiments of any of the aspects, the subject is a subject that has previously received a bone marrow transplant. In some embodiments of any of the aspects, the subject is a subject that has previously received a blood stem cell transplant. In some embodiments of any of the aspects, the subject is a subject experiencing cough and phlegm production. In some embodiments of any of the aspects, the subject is a subject experiencing cough, shortness of breath, and phlegm production.

In one aspect of any of the embodiments, described herein is a method of treating airway dysfunction in a subject in need thereof, the method comprising administering to the subject at least one agonist of at least one of: at least one gene of Group A, and at least one gene of Group B; and/or at least one inhibitor of at least one of: at least one gene of Group C, at least one gene of Group D, and at least one gene of Group E. In one aspect of any of the embodiments, described at least one agonist of at least one of: at least one gene of Group A, and at least one gene of Group B; and/or at least one inhibitor of at least one of: at least one gene of Group C, at least one gene of Group D, and at least one gene of Group E for use in a method of treating airway dysfunction in a subject in need thereof, the method comprising administering the at least one agonist and/or inhibitor to the subject. In some embodiments of any of the aspects, the subject is one determined to have a decreased level of expression of at least one of: at least one gene of Group A, and at least one gene of Group B; and/or an increased level of expression of at least one of: at least one gene of Group C, at least one gene of Group D, and at least one gene of Group E. In some embodiments of any of the aspects, the subject is further administered an immunosuppressant, DPP1 inhibitor, smoking cessation, or chest CT, e.g., as described elsewhere herein.

As used herein, the terms "drug", "compound" or "agent" are used interchangeably and refer to molecules and/or compositions. The compounds/agents include, but are not limited to, chemical compounds and mixtures of chemical compounds, e.g., small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof. In some embodiments, "drug" as used herein refers to an agent approved for medical use, e.g., by the FDA.

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide. Inhibitors can include inhibitors that act directly on the target itself (e.g., that bind to the protein or transcript, e.g., direct inhibitors).

In some embodiments of any of the aspects, an inhibitor of a specified target is an antibody, antibody reagent, or antigen-binding fragment thereof, that specifically binds to the target.

In some embodiments of any of the aspects, the agent that inhibits a gene described herein is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. In some embodiments of any of the aspects, the inhibitory nucleic acid can be a silencing RNA (siRNA), microRNA (miRNA), or short hairpin RNA (shRNA). Inhibitory nucleic acids can also include guide sequence molecules (e.g., a guide RNA) that function, e.g., in combination with an enzyme, to induce insertions, deletions, indels, and/or mutations of a target, thereby inhibiting the expression of the target.

In some embodiments of any of the aspects, an iNA comprises a sequence that is complementary to at least a portion of a target sequence described herein. In some embodiments of any of the aspects, an iNA comprises a sequence at least 15 nucleotides in length that is complementary to at least a portion of a target sequence described herein. In some embodiments of any of the aspects, an iNA comprises a sequence at least 20 nucleotides in length that is complementary to at least a portion of a target sequence described herein.

In some embodiments of any of the aspects, an iNA comprises a sequence that is the reverse complement to at least a portion of a target sequence described herein. In some embodiments of any of the aspects, an iNA comprises a sequence at least 15 nucleotides in length that is the reverse complement to at least a portion of a target sequence described herein. In some embodiments of any of the aspects, an iNA comprises a sequence at least 20 nucleotides in length that is the reverse complement to at least a portion of a target sequence described herein.

In some embodiments of any of the aspects, an iNA comprises a sequence that can specifically hybridize to at least a portion of a target sequence described herein. In some embodiments of any of the aspects, an iNA comprises a sequence at least 15 nucleotides in length that can specifically hybridize to at least a portion of a target sequence described herein. In some embodiments of any of the aspects, an iNA comprises a sequence at least 20 nucleotides in length that can specifically hybridize to at least a portion of a target sequence described herein.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target described herein. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g, siRNA, shRNA, miRNA, and/or amiRNA, which are well known in the art. One skilled in the art would be able to design further siRNA, shRNA, or miRNA to target the nucleic acid sequence of a gene or target described herein, e.g., using publically available design tools. siRNA, shRNA, or miRNA is commonly made using companies such as Dharmacon (Layfayette, CO) or Sigma Aldrich (St. Louis, MO).

In some embodiments of the various aspects described herein, the inhibitory nucleic acid is a guide nucleic acid (gNA). As used herein, the terms "guide nucleic acid," "guide sequence," "crRNA," "guide RNA," "single guide RNA," "gRNA" or "CRISPR guide sequence" refer to a nucleic acid comprising a sequence that determines the specificity of an enzyme, e.g., the Cas DNA binding protein of a CRISPR/Cas system, to a polynucleotide target. The gNA can comprise a polynucleotide sequence with at least partial complementarity with a target nucleic acid sequence, sufficient to hybridize with the target nucleic acid sequence and to direct sequence-specific binding of an enzyme, e.g, a nuclease, to the target nucleic acid sequence.

In some embodiments, the enzyme directed by the gNA is a gene-editing protein, e.g., any nuclease that induces a nick or double-strand break into a desired recognition site. Such enzymes can be native or engineered. These breaks can then be repaired by the cell in one of two ways: non-homologous end joining and homology-directed repair (homologous recombination). In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence can be used as a template for repair of the cleaved target DNA sequence, resulting in the transfer of genetic information from the donor polynucleotide to the target DNA. Therefore, new nucleic acid material may be inserted/copied into the site. The modifications of the target DNA due to NHEJ and/or homology-directed repair can be used for gene correction, gene replacement, gene tagging, transgene insertion, nucleotide deletion, gene disruption, gene mutation, etc.

In one embodiment, the gene-editing protein is a CRISPR-associated nuclease. The native prokaryotic CRISPR-associated nuclease system comprises an array of short repeats with intervening variable sequences of constant length (i.e., clusters of regularly interspaced short palindromic repeats), and CRISPR-associated ("Cas") nuclease proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a nuclease, for example, a Cas nuclease. The gRNA: nuclease complex binds a target polynucleotide sequence having a protospacer adjacent motif ("PAM") and a protospacer, which is a sequence complementary to a portion of the gRNA. The recognition and binding of the target polynucleotide by the gRNA: nuclease complex induces cleavage of the target.

Any CRISPR-associated nuclease can be used in the system and methods of the invention. CRISPR nuclease systems are known to those of skill in the art, e.g. Cas9, Cas12, Cas12a, or the like, see patents/applications U.S. Pat. No. 8,993,233, US 2015/0291965, US 2016/0175462, US 2015/0020223, US 2014/0179770, U.S. Pat. Nos. 8,697,359; 8,771,945; 8,795,965; WO 2015/191693; U.S. Pat. No. 8,889,418; WO 2015/089351; WO 2015/089486; WO 2016/028682; WO 2016/049258; WO 2016/094867; WO 2016/094872; WO 2016/094874; WO 2016/112242; US 2016/0153004; US 2015/0056705; US 2016/0090607; US 2016/0029604; U.S. Pat. Nos. 8,865,406; 8,871,445; each of which are incorporated by reference in their entirety. The nuclease can also be a phage Cas nuclease, e.g., CasΦ (e.g., Pausch et al. Science 369:333-7 (2020); which is incorporated by reference herein in its entirety).

The full-length guide nucleic acid strand can be any length. For example, the guide nucleic acid strand can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments of the various aspects described herein, a nucleic acid strand is less than about 75, 50, 45, 40, 35, 30, 25, 20, 15, 12, or fewer nucleotides in length. For example, the guide nucleic acid sequence is 10-30 nucleotides long.

In addition to a sequence that is complementary to a target nucleic acid, in some embodiments, the gNA also comprises a scaffold sequence. Expression of a gNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gNA may be referred to as a single guide RNA (sgRNA).

In some embodiments of the various aspects described herein, the guide nucleic acid is designed using a guide design tool (e.g., Benchling™; Broad Institute GPP™; CasOFFinder™; CHOPCHOP™; CRISPOR™; Deskgen™; E-CRISP™; Geneious™; GenHub™; GUIDES™ (e.g., for library design); Horizon Discovery™; IDT™; Off-Spotter™; and Synthego™; which are available on the world wide web).

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2)·nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)$_2$, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methyl-cytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist, e.g. its ability to increase the level and/or activity of the target can be determined, e.g. by measuring the level of an expression product of the target and/or the activity of the target. Methods for measuring the level of a given mRNA and/or polypeptide are known to one of skill in the art, e.g. RTPCR with primers can be used to determine the level of RNA, and Western blotting with an antibody can be used to determine the level of a polypeptide. Suitable primers for a given target are readily identified by one of skill in the art, e.g., using software widely available for this purpose (e.g., Primer3 or PrimerBank, which are both available on the world wide web). Antibodies to polypeptide gene expression products of the genes described herein are commercially available, e.g., from AbCam (Cambridge, MA). Assays for measuring the activity of the targets described herein are provided elsewhere herein. In some embodiments of any of the aspects, an agonist of a given polypeptide can be the polypeptide, a nucleic acid encoding the polypeptide, or a small molecule.

Non-limiting examples of agonists of a given polypeptide target, can include the target polypeptides or variants or functional fragments thereof and nucleic acids encoding the polypeptide or variants or functional fragments thereof. In some embodiments of any of the aspects, the agonist of a given target, is a polypeptide of that target or variants or functional fragment thereof and/or a nucleic acid encoding the polypeptide or variant or functional fragment thereof. In some embodiments of any of the aspects, the polypeptide agonist can be an engineered and/or recombinant polypeptide. In some embodiments of any of the aspects, the polypeptide agonist can be a nucleic acid encoding a polypeptide, e.g. a functional fragment thereof. In some embodiments of any of the aspects, the nucleic acid can be comprised by a vector.

In some embodiments of any of the aspects, a polypeptide agonist can comprise one of the sequences provided herein for each target. In some embodiments of any of the aspects, a polypeptide agonist can consist essentially of one of the sequences provided below herein for each target. In some embodiments of any of the aspects, a polypeptide agonist can consist of one of the sequences provided below herein for each target. In some embodiments of any of the aspects, an agonist can comprise a nucleic acid encoding one of the sequences provided below herein for each target. In some embodiments of any of the aspects, an agonist can be a polypeptide comprising a reference/wild-type sequence provided herein with at least 80%, at least 85%, at least 90%, at least 95%, or at least 98% identity to the reference/wild-type sequence and which retains the activity of the reference/wild-type sequence. In some embodiments of any of the aspects, an agonist can be a polypeptide comprising a reference/wild-type sequence provided herein with at least 95% identity to the reference/wild-type sequence and which retains the activity of the reference/wild-type sequence.

In some embodiments of any of the aspects, the agonist is an exogenous polypeptide. In some embodiments of any of the aspects, the subject is administered exogenous polypeptide, e.g., the polypeptide is produced in vitro and/or synthesized and purified polypeptide is provided to the subject. In some embodiments of any of the aspects, the agonist is an ectopic polypeptide. In some embodiments of any of the aspects, the subject is administered ectopic polypeptide, e.g., the polypeptide is produced in vitro and/or synthesized and purified polypeptide is provided to the subject.

In some embodiments of any of the aspects, the agonist can be a nucleic acid encoding a polypeptide (or a variant or functional fragment thereof) and/or a vector comprising a nucleic acid encoding a polypeptide (or a variant or functional fragment thereof). A nucleic acid encoding a polypeptide can be, e.g., an RNA molecule, a plasmid, and/or an expression vector. In some embodiments of any of the aspects, the nucleic acid encoding a polypeptide can be an mRNA. In some embodiments of any of the aspects, the nucleic acid encoding a polypeptide can be a modified mRNA. In some embodiments of any of the aspects, the agonist can be a nucleic acid encoding a polypeptide, e.g., exogenous and/or ectopic polypeptide. In some embodiments of any of the aspects, the subject is administered the nucleic acid encoding exogenous and/or ectopic polypeptide, e.g., the nucleic acid is transcribed and/or translated after the administering step to provide exogenous and/or ectopic polypeptide to the subject.

In some embodiments of any of the aspects, a polypeptide or nucleic acid as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the agonist and/or inhibitor is administered as a nucleic acid. In some embodiments of any of the aspects, a nucleic acid encoding the agonist and/or inhibitor is administered. In some embodiments of any of the aspects, the subject is administered a vector comprising a nucleic acid. Vectors can be, e.g., a DNA or RNA vector.

In some embodiments, the methods described herein relate to treating a subject having or diagnosed as having airway dysfunction. Subjects having airway dysfunction can be identified by a physician. Symptoms and/or complications of airway dysfunction which characterize these conditions and aid in diagnosis are well known in the art and include but are not limited to, cough, phlegm, shortness of breath, and/or bronchiectasis (e.g., radiographic bronchiectasis). Described herein are tests that aid in the diagnosis of airway dysfunction. A family history of airway dysfunction, or exposure to risk factors for airway dysfunction (e.g., transplant) can also aid in determining if a subject is likely to have airway dysfunction or in making a diagnosis of airway dysfunction.

The compositions and methods described herein can be administered to a subject having or diagnosed as having airway dysfunction. In some embodiments, the methods described herein comprise administering an effective amount of compositions described herein, to a subject in order to alleviate a symptom of airway dysfunction. As used herein, "alleviating a symptom" is ameliorating any condition or symptom associated with the disease, e.g., airway dysfunction. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to, oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a therapeutic, agonist, and/or inhibitor needed to alleviate at least one or more symptom of the disease or disorder, and relates to a sufficient amount of pharmacological composition to provide the desired effect. The term "therapeutically effective amount" therefore refers to an amount of a therapeutic, agonist, and/or inhibitor that is sufficient to provide a particular therapeutic effect (e.g., improvement in cough, phlegm production, shortness of breath, and/or bronchiectasis) when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an active agent which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for gene expression, among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments, the technology described herein relates to a pharmaceutical composition comprising a therapeutic, agonist, and/or inhibitor as described herein, and optionally a pharmaceutically acceptable carrier. In some embodiments, the active ingredients of the pharmaceutical composition comprise a therapeutic, agonist, and/or inhibitor as described herein. In some embodiments, the active ingredients of the pharmaceutical composition consist essentially of a therapeutic, agonist, and/or inhibitor as described herein. In some embodiments, the active ingredients of the pharmaceutical composition consist of a therapeutic, agonist, and/or inhibitor as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of compositions as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition or therapy can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, a composition or therapy as described herein is administered as a monotherapy, e.g., another treatment for the airway dysfunction is not administered to the subject.

In certain embodiments, an effective dose of a composition described herein can be administered to a patient once. In certain embodiments, an effective dose of a composition described herein can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. cough, phlegm production, shortness of breath, and/or bronchiectasis by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition or therapy, according to the methods described herein depend upon, for example, the form of the active ingredient, its potency, and the extent to which symptoms, markers, or indicators of a condition described herein are desired to be reduced, for example the percentage reduction desired for cough, phlegm production, shortness of breath, and/or bronchiectasis or the extent to which, for example, immunosuppression is desired to be induced. The dosage should not be so large as to cause adverse side effects, such as infections. Generally, the dosage will vary with the age, condition, and sex of the patient and can be determined by one of skill in the art. The dosage can also be adjusted by the individual physician in the event of any complication.

The efficacy of a composition or therapy in, e.g. the treatment of a condition described herein, or to induce a response as described herein (e.g. cough, phlegm production, shortness of breath, and/or bronchiectasis) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. cough, phlegm production, shortness of breath, and/or bronchiectasis. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. cough, phlegm, shortness of breath, and/or bronchiectasis). It is well within the ability of one skilled in the art to monitor efficacy of administration and/or treatment by measuring any one of such parameters, or any combination of parameters. Efficacy can be assessed in animal models of a condition described herein, for example treatment of airway dysfunction and/or bronchiectasis. When using an experimental animal model, efficacy of treatment is evidenced when a statistically significant change in a marker is observed, e.g. cough, phlegm production, and/or bronchiectasis.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of airway dysfunction. A subject can be male or female.

A subject can be one who has been previously diagnosed with or identified as suffering from or having a condition in need of treatment (e.g. airway dysfunction) or one or more complications related to such a condition, and optionally, have already undergone treatment for airway dysfunction or the one or more complications related to airway dysfunction. Alternatively, a subject can also be one who has not been previously diagnosed as having airway dysfunction or one or more complications related to airway dysfunction. For example, a subject can be one who exhibits one or more risk factors for airway dysfunction or one or more complications related to airway dysfunction or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, e.g. of the full length polypeptide. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of airway dysfunction as described herein.

In some embodiments, a polypeptide, e can be a variant of a sequence described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% relative to wildtype. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype, e.g. 110%, 125%, 150%, 175%, 200%, 500%, 1000% or more.

One method of identifying amino acid residues which can be substituted is to align, for example, a human protein to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide can comprise one or more amino acid substitutions or modifications. In some embodiments, the substitutions and/or modifications can prevent or reduce proteolytic degradation and/or prolong half-life of the polypeptide in a subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Marker" in the context of the present invention refers to an expression product, e.g., nucleic acid or polypeptide which is differentially present in a sample taken from subjects having airway dysfunction, as compared to a comparable sample taken from control subjects (e.g., a healthy subject). The term "biomarker" is used interchangeably with the term "marker."

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found in a given cell in its natural environment.

In some embodiments, a nucleic acid as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. airway dysfunction. The term "treating" includes reducing or alleviating at least one adverse effect or symptom of a condition, disease or disorder associated with airway dysfunction. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, treatment of airway dysfunction comprises a decrease in the frequency of cough. In some embodiments of any of the aspects, treatment of airway dysfunction comprises a decrease in the severity of cough. In some embodiments of any of the aspects, treatment of airway dysfunction comprises a decrease in the frequency and severity of cough.

In some embodiments of any of the aspects, treatment of airway dysfunction comprises a decrease in the frequency of phlegm production. In some embodiments of any of the aspects, treatment of airway dysfunction comprises a decrease in the severity of phlegm production. In some embodiments of any of the aspects, treatment of airway dysfunction comprises a decrease in the frequency and severity of phlegm production.

In some embodiments of any of the aspects, treatment of airway dysfunction comprises a decrease in the frequency of shortness of breath. In some embodiments of any of the aspects, treatment of airway dysfunction comprises a decrease in the severity of shortness of breath. In some embodiments of any of the aspects, treatment of airway dysfunction comprises a decrease in the frequency and severity of shortness of breath.

In some embodiments of any of the aspects, treatment of airway dysfunction comprises a decrease in the degree of bronchiectasis. In some embodiments of any of the aspects, treatment of airway dysfunction comprises a decrease in the rate of progression or worsening of bronchiectasis. In some embodiments of any of the aspects, treatment of airway dysfunction comprises a decrease in the degree of radiographic bronchiectasis. In some embodiments of any of the aspects, treatment of airway dysfunction comprises a decrease in the rate of progression or worsening of radiographic bronchiectasis.

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to bronchiectasis and/or radiographic bronchiectasis. Accordingly, the methods described herein can be prophylactic relative to transplant rejection and/or GvHD. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "nanoparticle" refers to particles that are on the order of about 1 to 1,000 nanometers in diameter or width. The term "nanoparticle" includes nanospheres; nanorods; nanoshells; and nanoprisms; these nanoparticles may be part of a nanonetwork. The term "nanoparticles" also encompasses liposomes and lipid particles having the size of a nanoparticle. Exemplary nanoparticles include lipid nanoparticles or ferritin nanoparticles. Lipid nanoparticles can comprise multiple components, including, e.g., ionizable lipids (such as MC3, DLin-MC3-DMA, ALC-0315, or SM-102), pegylated lipids (such as PEG2000-C-DMG, PEG2000-DMG, ALC-0159), phospholipids (such as DSPC), and cholesterol.

Exemplary liposomes can comprise, e.g., DSPC, DPPC, DSPG, Cholesterol, hydrogenated soy phosphatidylcholine, soy phosphatidyl choline, methoxypolyethylene glycol (mPEG-DSPE) phosphatidyl choline (PC), phosphatidyl glycerol (PG), distearoylphosphatidylcholine, and combinations thereof.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

In all embodiments where a sample is obtained or has been obtained or provided, the sample can be sample taken, obtained, or provided via minimally invasive methods and/or involves only a minor intervention. In some embodiments of any of the aspects, a sample is taken, obtained, or provided by one or more of a blood draw or prick, an epidermal or mucus membrane swab, buccal sampling, saliva sample, a epidermal skin sampling technique, and/or collection of a secreted or expelled bodily fluid (e.g., mucus, urine, sweat, etc), fecal sampling, semen/seminal fluid sampling, or clippings (e.g., of hair or nails). In some embodiments of any of the aspects, the sample comprises, consists of, or consists essentially of blood (or any fraction or component thereof), serum, urine, mucus, epithelial cells, saliva, buccal cells, a secreted or expelled bodily fluid, and/or hair or nail clippings.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A method comprising detecting the level of expression of one or more genes selected from at least one of:
   at least one gene of Group A, at least one gene of Group B, at least one gene of Group C,
   at least one gene of Group D, and at least one gene of Group E;
   in a bronchial brushing, nasal brushing, sputum, or peripheral blood sample obtained from a subject.

2. The method of paragraph 1, wherein the sample obtained from the subject is a bronchial brushing or nasal brushing sample.

3. A method of treating airway dysfunction, the method comprising administering:
   a) a chest CT, smoking cessation, and/or avoiding aspiration risk and inhalational injury to a subject determined to have a decreased level of expression of at least one of:
      at least one gene of Group A, and at least one gene of Group B; and/or
   an increased level of expression of at least one of:
      at least one gene of Group C, at least one gene of Group D, and at least one gene of Group E;
   b) an immunosuppressant and/or a more aggressive immunosuppressant regimen to a subject who had previously received and lung transplant and was determined to have a decreased level of expression of at least one of:
      at least one gene of Group A, and at least one gene of Group B; and/or
   an increased level of expression of at least one of:
      at least one gene of Group C, at least one gene of Group D, and at least one gene of Group E; or
   c) an immunosuppressant and/or a more aggressive immunosuppressant regimen to a subject who had previously received a bone marrow or blood stem cell transplant and was determined to have a decreased level of expression of at least one of:
      at least one gene of Group A, and at least one gene of Group B; and/or
   an increased level of expression of at least one of:
      at least one gene of Group C, at least one gene of Group D, and at least one gene of Group E;
   d) an inhibitor of DPP1 to a subject who had previously received a bone marrow or blood stem cell transplant and was determined to have a decreased level of expression of at least one of:
  at least one gene of Group A, and at least one gene of Group B; and/or
an increased level of expression of at least one of:
  at least one gene of Group C, at least one gene of Group D, and at least one gene of Group E; and/or
e) an inhibitor of DPP1 to a subject who has COPD, asthma, or rheumatoid arthritis and was determined to have a decreased level of expression of at least one of:
  at least one gene of Group A, and at least one gene of Group B; and/or
an increased level of expression of at least one of:
  at least one gene of Group C, at least one gene of Group D, and at least one gene of Group E.

4. The method of paragraph 1, wherein the subject is determined to have a decreased level of expression of one or more genes selected from Group B and/or an increased level of expression of one or more genes selected from Group C.

5. The method of paragraph 3, wherein the DPP1 inhibitor is AZD7986.

6. The method of paragraph 3, wherein the airway dysfunction is bronchial enlargement or dilation.

7. The method of paragraph 3, wherein the airway dysfunction is COPD, asthma, bronchiolitis, bronchiectasis, lung transplant rejection, rheumatoid arthritis, GvHD, or autoimmune prenumonitis.

8. The method of paragraph 3, wherein the level of expression is the level in a sample obtained from the subject.

9. The method of paragraph 8, wherein the sample is a bronchial brushing, nasal brushing, sputum, or peripheral blood sample.

10. The method of paragraph 1, wherein the method comprises determining the level of expression of, at least one gene of Group A, at least one gene of Group B, at least one gene of Group C, at least one gene of Group D, and at least one gene of Group E.

11. The method of paragraph 1, wherein the method comprises determining the level of expression of, at least one gene of Group A, at least one gene of Group C, at least one gene of Group D, and at least one gene of Group E.

12. The method of paragraph 1, wherein the method comprises determining the level of expression of, at least one gene of Group A, at least one gene of Group C, and at least one gene of Group E.

13. The method of paragraph 1, wherein the method comprises determining the level of expression of, at least one gene of Group B and at least one gene of Group C.

14. The method of paragraph 1, wherein the at least one gene of Group A is at least one of: ZNF493 and ZNF519.

15. The method of paragraph 1, wherein the at least one gene of Group A is ZNF493 and ZNF519.

16. The method of paragraph 1, wherein the at least one gene of Group A is ZNF493.

17. The method of paragraph 1, wherein the at least one gene of Group B is at least one of: LRP4 and FAT2.

18. The method of paragraph 1, wherein the at least one gene of Group B is LRP4 and FAT2.

19. The method of paragraph 1, wherein the at least one gene of Group C is at least one of: ASL and CCDC160.

20. The method of paragraph 1, wherein the at least one gene of Group C is ASL and CCDC160.

21. The method of paragraph 1, wherein the at least one gene of Group C is ASL.

22. The method of paragraph 1, wherein the at least one gene of Group D is at least one of: LINC00888 and FBXO16.

23. The method of paragraph 1, wherein the at least one gene of Group D is LINC00888 and FBXO16.

24. The method of paragraph 1, wherein the at least one gene of Group D is LINC00888.

25. The method of paragraph 1, wherein the at least one gene of Group E is at least one of: C8orf76 and DNAJC22.

26. The method of paragraph 1, wherein the at least one gene of Group E is C8orf76 and DNAJC22.

27. The method of paragraph 1, wherein the at least one gene of Group E is C8orf76.

28. The method of paragraph 1, wherein the level of expression is the level of mRNA.

29. The method of paragraph 1, wherein the sample obtained from the subject is a bronchial brushing or nasal brushing sample.

In some embodiments, the present technology may be defined in any of the following numbered paragraphs:

1. A method comprising detecting the level of expression of one or more genes selected from at least one of:
  at least one gene of Group A, at least one gene of Group B, at least one gene of Group C,
  at least one gene of Group D, and at least one gene of Group E;
  in a bronchial brushing, nasal brushing, sputum, or peripheral blood sample obtained from a subject.

2. The method of any of the preceding paragraphs, wherein the sample obtained from the subject is a bronchial brushing or nasal brushing sample.

3. A method of treating airway dysfunction, the method comprising administering:
f) a chest CT, smoking cessation, and/or avoiding aspiration risk and inhalational injury to a subject determined to have a decreased level of expression of at least one of:
  at least one gene of Group A, and at least one gene of Group B; and/or
an increased level of expression of at least one of:
  at least one gene of Group C, at least one gene of Group D, and at least one gene of Group E;
g) an immunosuppressant and/or a more aggressive immunosuppressant regimen to a subject who had previously received and lung transplant and was determined to have a decreased level of expression of at least one of:
  at least one gene of Group A, and at least one gene of Group B; and/or
an increased level of expression of at least one of:
  at least one gene of Group C, at least one gene of Group D, and at least one gene of Group E; or
h) an immunosuppressant and/or a more aggressive immunosuppressant regimen to a subject who had previously received a bone marrow or blood stem cell transplant and was determined to have a decreased level of expression of at least one of:
  at least one gene of Group A, and at least one gene of Group B; and/or
an increased level of expression of at least one of:
  at least one gene of Group C, at least one gene of Group D, and at least one gene of Group E;

i) an inhibitor of DPP1 to a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; and/or
j) an inhibitor of DPP1 to a subject who has COPD, asthma, or rheumatoid arthritis and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

4. The method of any of paragraphs 1-4, wherein the subject is determined to have a decreased level of expression of one or more genes selected from Group B and/or an increased level of expression of one or more genes selected from Group C.

5. The method of any one of paragraphs 3-4, wherein the DPP1 inhibitor is AZD7986.

6. The method of any one of paragraphs 3-5, wherein the airway dysfunction is bronchial enlargement or dilation.

7. The method of any one of paragraphs 3-6, wherein the airway dysfunction is COPD, asthma, bronchiolitis, bronchiectasis, lung transplant rejection, rheumatoid arthritis, GvHD, or autoimmune prenumonitis.

8. A method of predicting or determining the risk of airway dysfunction, the method comprising detecting the level of expression of one or more genes selected from at least one of:
at least one gene of Group A, at least one gene of Group B, at least one gene of Group C,
at least one gene of Group D, and at least one gene of Group E.
in a sample obtained from a subject; and
determining that the subject is at an increased risk of airway dysfunction if the subject is
determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

9. A immunosuppressant and/or a more aggressive immunosuppressant regimen for use in a method of treating or preventing airway dysfunction in:
a. a subject who had previously received and lung transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or
b. a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E;

10. An inhibitor of DPP1 for use in a method of treating or preventing airway dysfunction in:
a. a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or
b. an inhibitor of DPP1 to a subject who has COPD, asthma, or rheumatoid arthritis and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E.

11. The immunosuppressant, regimen, or inhibitor of any one of paragraphs 9-11, wherein the level of expression is the level of expression in a sample obtained from the subject.

12. The method, immunosuppressant, regimen, or inhibitor of any one of paragraphs 8-11, wherein the sample is a bronchial brushing, nasal brushing, sputum, or peripheral blood sample.

13. The method, immunosuppressant, regimen, or inhibitor of any one of paragraphs 8-12, wherein the subject is determined to have a decreased level of expression of one or more genes selected from Group B and/or an increased level of expression of one or more genes selected from Group C.

14. The method, immunosuppressant, regimen, or inhibitor of any one of paragraphs 8-13, wherein the DPP1 inhibitor is AZD7986.

15. The method, immunosuppressant, regimen, or inhibitor of any one of paragraphs 8-14, wherein the airway dysfunction is bronchial enlargement or dilation.

16. The method, immunosuppressant, regimen, or inhibitor of any one of paragraphs 8-15, wherein the airway dysfunction is COPD, asthma, bronchiolitis, bronchiectasis, lung transplant rejection, rheumatoid arthritis, GvHD, or autoimmune prenumonitis.

17. The method, immunosuppressant, regimen, or inhibitor of any one of the preceding paragraphs, wherein the method comprises determining the level of, or the subject is determined to have a level of expression of, at least one gene of Group A, at least one gene of Group B, at least one gene of Group C, at least one gene of Group D, and at least one gene of Group E.

18. The method, immunosuppressant, regimen, or inhibitor of any one of the preceding paragraphs, wherein the method comprises determining the level of, or the subject is determined to have a level of expression of, at least one gene of Group A, at least one gene of Group C, at least one gene of Group D, and at least one gene of Group E.

19. The method, immunosuppressant, regimen, or inhibitor of any one of the preceding paragraphs, wherein the method comprises determining the level of, or the subject is determined to have a level of expression of, at least one gene of Group A, at least one gene of Group C, and at least one gene of Group E.
20. The method, immunosuppressant, regimen, or inhibitor of any one of the preceding paragraphs, wherein the method comprises determining the level of, or the subject is determined to have a level of expression of, at least one gene of Group B and at least one gene of Group C.
21. The method, immunosuppressant, regimen, or inhibitor of any one of the preceding paragraphs, wherein the at least one gene of Group A is at least one of: ZNF493 and ZNF519.
22. The method, immunosuppressant, regimen, or inhibitor of any one of the preceding paragraphs, wherein the at least one gene of Group A is ZNF493 and ZNF519.
23. The method, immunosuppressant, regimen, or inhibitor of any one of the preceding paragraphs, wherein the at least one gene of Group A is ZNF493.
24. The method, immunosuppressant, regimen, or inhibitor of any one of the preceding paragraphs, wherein the at least one gene of Group B is at least one of: LRP4 and FAT2.
25. The method, immunosuppressant, regimen, or inhibitor of any one of the preceding paragraphs, wherein the at least one gene of Group B is LRP4 and FAT2.
26. The method, immunosuppressant, regimen, or inhibitor of any one of the preceding paragraphs, wherein the at least one gene of Group C is at least one of: ASL and CCDC160.
27. The method, immunosuppressant, regimen, or inhibitor of any one of the preceding paragraphs, wherein the at least one gene of Group C is ASL and CCDC160.
28. The method, immunosuppressant, regimen, or inhibitor of any one of the preceding paragraphs, wherein the at least one gene of Group C is ASL.
29. The method, immunosuppressant, regimen, or inhibitor of any one of the preceding paragraphs, wherein the at least one gene of Group D is at least one of: LINC00888 and FBXO16.
30. The method, immunosuppressant, regimen, or inhibitor of any one of the preceding paragraphs, wherein the at least one gene of Group D is LINC00888 and FBXO16.
31. The method, immunosuppressant, regimen, or inhibitor of any one of the preceding paragraphs, wherein the at least one gene of Group D is LINC00888.
32. The method, immunosuppressant, regimen, or inhibitor of any one of the preceding paragraphs, wherein the at least one gene of Group E is at least one of: C8orf76 and DNAJC22.
33. The method, immunosuppressant, regimen, or inhibitor of any one of the preceding paragraphs, wherein the at least one gene of Group E is C8orf76 and DNAJC22.
34. The method, immunosuppressant, regimen, or inhibitor of any one of the preceding paragraphs, wherein the at least one gene of Group E is C8orf76.
35. The method, immunosuppressant, regimen, or inhibitor of any one of the preceding paragraphs, wherein the level of expression is the level of mRNA.
36. The method, immunosuppressant, regimen, or inhibitor of any of the preceding paragraphs, wherein the sample obtained from the subject is a bronchial brushing or nasal brushing sample.

The technology described herein is further illustrated by the following examples which in no way should be construed as being further limiting.

EXAMPLES

Example 1

Described herein is a better understanding of airway dysfunction in acute and chronic respiratory conditions such as COPD, asthma, bronchiolitis and bronchiectasis. This condition manifests as a range of clinical abnormalities from cough, breathlessness, excess sputum production, frequent respiratory infections, respiratory failure and death. Radiologically, such patients may have thickening of the central bronchial walls, mucus partially or completely obstructing the airway lumen or even overt bronchiectasis. In aggregate, these conditions affect several million people in the US and early detection would allow the interception and potential prevention of advanced debilitating disease.

Described herein is a method utilizing bronchial brushing via bronchoscopy or nasal brushing, a relatively safe and non-invasive method of collecting cells, and measurement of a novel list of gene transcripts, whose abundance correlates with the clinical manifestations of central airway disease including the presence of advanced disease such as radiographic evidence of bronchiectasis. The biomarker also detects individuals with the clinical characteristics of cough and phlegm production that do not have radiographic bronchiectasis suggesting that it can detect very early disease pathophysiology related to airway dysfunction.

Also described herein are therapeutic targets for airway dysfunction and radiographic bronchiectasis. These include pathways related to cell adhesion and Wnt signaling which are expressed at higher levels in individuals with widespread radiographic bronchiectasis, and pathways related to inflammation and cilium biology which were decreased in participants with widespread radiographic bronchiectasis. Additionally, this data indicates that individuals with widespread radiographic bronchiectasis have fewer airway basal cells and more immature ciliated or deuterosomal cells.

The methods and compositions described herein are novel in utilizing one of the least invasive way of collecting tissues from patients (bronchial and nasal brushing) and the ability to detect airway dysfunction and the early structural changes in bronchiectasis, rather than much later stages of disease. The methods and compositions described herein provide a biomarker of airway dysfunction and preclinical bronchiectasis that can be used to initiate treatment with therapeutics that target pathways involved in the pathogenesis of bronchiectasis. There is evidence that the type of airway remodeling detected in radiographic bronchiectasis are also involved in the early stages of other lung diseases such as COPD, lung transplant rejection, rheumatoid arthritis and graft vs. host disease, so the biomarker and therapeutic targets we have identified can be important in the setting of these additional lung diseases.

Example 2: Bronchial Gene Expression Alterations in Current and Former Smokers Associated with Radiographic Bronchiectasis Bronchiectasis (BE) is an increasingly recognized disease characterized by pathologic dilation of airways, yet its pathophysiology is poorly understood. Identifying airway gene expression alterations associated with radiographic BE may provide insights into the molecular changes associated with BE initiation. 173 subjects without a prior clinical diagnosis for BE, with or without radiographic BE, were examined. We detected widespread radiographic BE (in 3 or more lobes) in 20 of 173 participants, who presented with more cardinal bronchiectatic symptoms such as cough and mucus production. Transcriptomic assessment of bronchial epithelial cells from mainstem bronchi revealed 298 genes with roles in cilium organization and endopeptidase activity pathways were up-regulated in participants with widespread radiographic BE; while 357 genes involved in cell adhesion and Wnt signaling pathways were down-regulated in them. Leveraging an independent single-cell RNA-seq dataset of bronchial epithelial cells, we found genes up-regulated in participants with radiographic BE were expressed at higher levels in ciliated and deuterosomal cells; and genes down-regulated were expressed at higher levels in basal cells. Deconvolution of the bulk RNA-seq samples into proportions of various cell types also showed increased presence of ciliated and deuterosomal cells, as well as decreased presence of basal cells in subjects with widespread radiographic BE, respectively. The regulatory pattern suggests a compensatory response of producing more ciliated cells in an inflammatory environment, accompanied by a loss of surface integrity in the early stage of BE.

Bronchiectasis (BE) is a pathologic dilation of bronchi[1]. Once considered an orphan disease that affects less than 200,000 people in the United States (US), BE has become increasingly common in the US, with over 70,000 new diagnoses in 2013 and between 340,000 and 522,000 prevalent cases requiring treatment[2]. Computed tomography (CT) is not only the gold standard for diagnosing BE in patients with symptomatic disease, it can also detect bronchial abnormalities in asymptomatic or mildly symptomatic individuals that are scanned for unrelated reasons. A term used for this situation is radiographic BE[1,3]. Molecular profiling of the airway epithelium in patients with radiographic BE may provide insights into the pathogenesis of BE and the possible biological pathways not yet targeted by current treatments[4-7].

Previous studies of bronchoalveolar lavage fluid and sputum have detected gene expression alterations or protein level changes related to bronchiectasis[8-10]. Yet, these studies were limited by patient numbers and a small number of genes or proteins as compared to transcriptomic profiling through RNA sequencing (RNA-seq), which allows for a comprehensive analysis of gene expression. The utility of gene expression in BE has not been sufficiently explored, possibly due to a paucity of pertinent samples at the site of the abnormality such as endobronchial tissue.

Previously, our group has used the bronchial tissue at the mainstem bronchus, from which gene expression alterations in normal-appearing airway epithelial cells could be detected in association with smoking[11], lung cancer[12], and chronic obstructive pulmonary disease[13,14]. Importantly, these gene expression alterations not only served as diagnostic biomarkers but have provided insights into the molecular events related to these lung pathologies. We hypothesize that mainstem bronchus epithelial gene expression would be especially well suited to the study of radiographic BE due to the close proximity between the profiled biospecimen and the site of disease.

Here, we aimed to characterize gene expression alterations in radiographic BE using bronchial epithelium cells and explore whether the genes show cell-type dependent expression leveraging a single-cell RNA-seq dataset of airway epithelium at the mainstem bronchus. Moreover, we examined the relationship between gene expression and clinical characteristics.

Methods

Study Participants and Sample Analysis

The Detection of Early Lung Cancer Among Military Personnel (DECAMP) is a multi-center consortium comprised of 15 military treatment facilities, Veterans Affairs (VA) hospitals, and academic centers across the United States. Participants were recruited into one of two study protocols, designated as DECAMP-1 (NCT01785342) and DECAMP-2 (NCT02504697) to develop an integrated panel of biomarkers that discriminate benign and malignant indeterminate nodules detected on CT scans. The details of this study protocol have been previously published[15].

Briefly, study participants of DECAMP-1 were adults aged 45 and older with indeterminate pulmonary nodules and heavy smoking history. Study participants of DECAMP-2 were aged 50-79 with a heavy smoking history and a family history of lung cancer or a personal history of Chronic Obstructive Pulmonary Disease (COPD). As none of the participants of this study had a clinical diagnosis of BE (participants with chronic lung disease other than COPD were excluded), it provides the opportunity to assess radiographic BE. This study was approved by the Human Research Protection Office (HRPO) for the Department of Defense, and the individual site IRBs for every participating site. All subjects were approached for written informed consent to participate in the study per IRB regulations.

Figure 4:
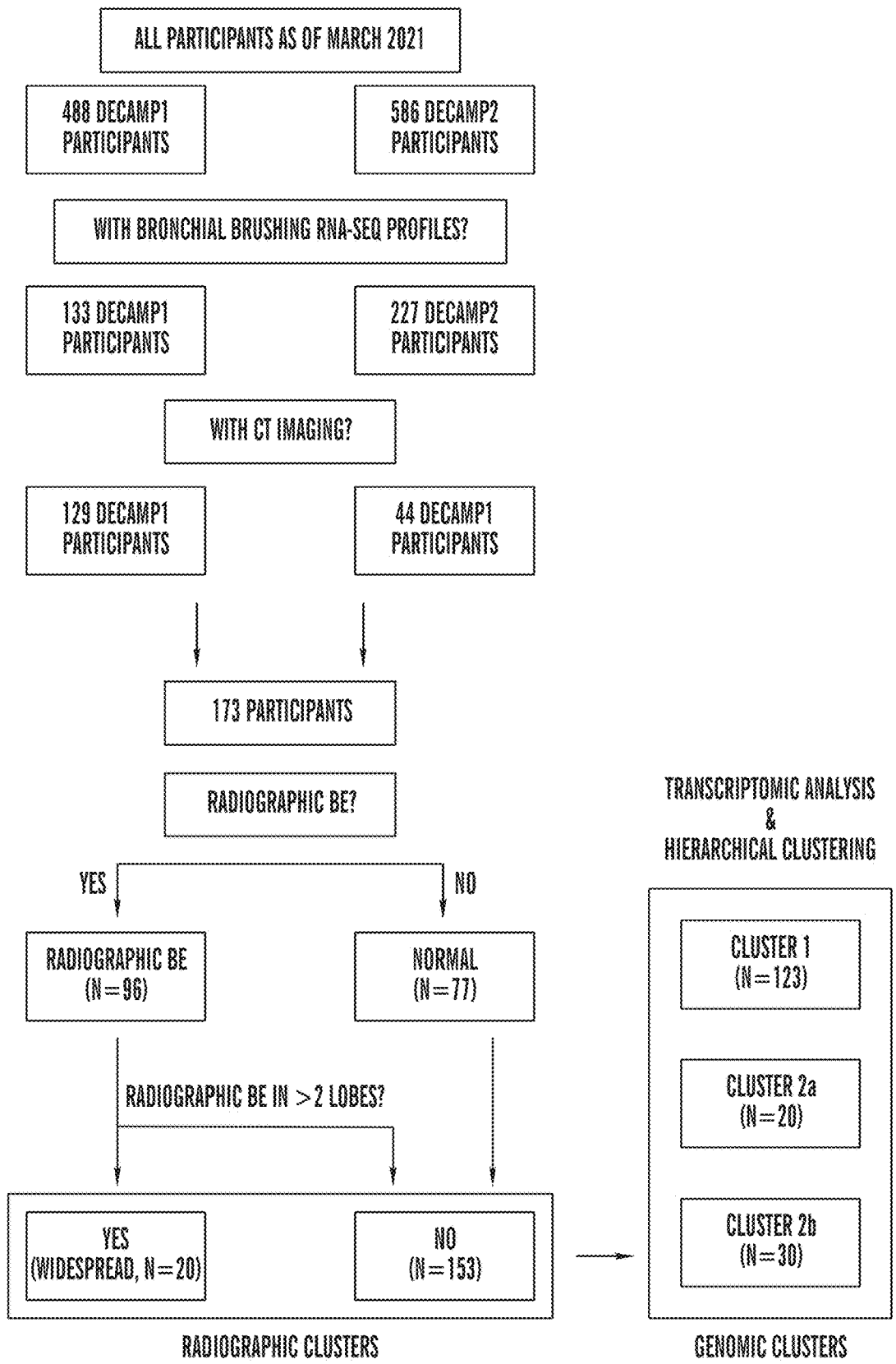
FIG. 4 depicts a schematic representation of participant clustering based on imaging and gene expressions.

From the large cohort of DECAMP of 360 subjects (169 from DECAMP-1 and 191 from DECAMP-2), 129 participants from DECAMP-1, and 44 participants from DECAMP-2 with matching RNA-seq from right mainstem bronchus and CT scans were available for analysis as of Feburary, 2021 (FIG. 4).

Computed Tomography Protocols

DECAMP-1 CT scans were collected as part of routine clinical care while DECAMP-2 used a standardized protocol for image acquisition and reconstruction. These volumetric scans were acquired with a low radiation dose helical technique on a minimum 16-slice multidetector scanner. The scans were acquired at 2.5 to 5 mm and reconstructed into 1.25 mm slice thickness using standard and high spatial frequency convolution kernels. Pertinent to this study is that the images were adequate to assess bronchiectasis.

Bronchiectasis Ascertainment

The detection of bronchiectasis was visually performed by a single reader, a pulmonologist (AD) with over 10 years of experience in lung imaging. In brief, bronchiectasis on CT was coded as yes, no, or equivocal. Radiographic bronchiectasis was defined with one or more of the following criteria: a) airway dilation (airway lumen diameter greater than adjacent pulmonary vessel diameter); b) abnormal airway tapering of any extent (no decrease in or increase in lumen moving from proximal to distal airways); and c) visualization of a bronchus within 1 cm of the pleura. A CT case was defined with at least one lobe meeting the above BE criteria. The lingula was considered a separate lobe. We further defined widespread radiographic BE when 3 or more lobes were involved.

RNA Isolation, Sequencing and Data Pre-processing

Total RNA was isolated using the miRNasey Mini Kit (Qiagen, Valencia, CA). RNA integrity was assessed by Agilent BioAnalyzer, and RNA purity was confirmed using a NanoDrop spectrophotometer. Libraries were generated using the Illumina TruSeq Stranded Total RNA kit and sequenced on Illumina NextSeq 500 and Illumina HiSeq2500 instruments with 75 base-pair paired-end reads (Illumina, San Diego, CA). We developed an automatic pipeline (github.com/compbiomed/RNA_Seq) with standard setups based on the Nextflow framework to obtain the expression levels for each gene 16. Reads were aligned to the Genome Reference Consortium human build 37 (GRCh37) using STAR[17]. Gene and transcript level counts were calculated using RSEM[18] using Ensembl v75 annotation.

Bulk RNA-Seq Analysis

The LIMMA package (version 3.10) in R (version 3.6.0) was used to assess the differential gene expression[19]. Briefly, the raw count matrix of gene expression was batch corrected using Combat-See. The corrected counts were then filtered based on counts per million (CPM) such that a gene could only be included if its CPM was greater than 1 in 10% of the total number of patients.

False discovery rate (FDR) of 0.1 and log fold change (log FC) of 0.25 were used to filter significantly differentially expressed genes. The functional analysis of the differentially expressed genes was performed using the STRING database[19]. Heatmaps were used to visualize the data and identify unsupervised participant's clusters using the "Ward.D2" algorithm. Gene set enrichment analysis (GSEA)[22] was performed on pre-ranked gene lists created by pairwise comparisons between participants' clusters using Hallmark gene sets[23]. Gene set variation analysis (GSVA) was performed using gene sets of interest using standard workflow[24].

Single Cell RNA-Seq Analysis and Deconvolution of Bulk RNA-Seq Datasets

The Seurat R package (version 3.1)[25] was used for downstream analyses including normalization, scaling, clustering of cells, and identifying cluster marker genes on a dataset from Deprez et al. [genomique.eu/cellbrowser/HCA/][26]. Cells collected from the tracheal epithelium (9 healthy volunteers, N=20519) were selected for this analysis for matching of anatomical locations.

Cells were filtered out if they met any of the following criteria: 1) bottom quantile for a total number of genes detected, 2) bottom quantile for total library size and 3) 30% of counts mapped to the mitochondrial genome. Overall, 7343 cells were filtered and 13176 cells were kept for further analysis. UMAP dimensionality reduction was performed using the first 15 principal components with a resolution setting of 0.8. Cell types were previously assigned by Deprez et al, and individually validated with previously reported cell markers. Gene set variation analysis was performed at a single-cell level. To dissect cell population proportions from bulk RNA samples, reference gene expression profiles (GEPs) were derived using the bronchial scRNA-seq data.

Marker genes of each cell type were identified using the FindMarkers function within the Seurat package using the MAST method of modeling (FDR<0.05, log FC>0.25). After generating the GEPs, we applied an optimize function within the AutoGeneS package[27] to further identify the top 1000 most informative genes from Seurat selected genes. We then applied the deconvolve function within the AutoGeneS to predict cell proportion from the bulk RNA-seq data based on the 1000 genes with model parameter set to Nu Support Vector Regression (nusvr).

Statistical Analysis

Data are presented as means and standard deviations for continuous measurements and number and percentage for categorical features. P values were calculated using a Student's T test, Fisher's exact test, Kruskal test, or ANOVA F test.

Results

Participant Demographics, Pulmonary Function, and Imaging Measurements

Of the 173 evaluated participants, 96 participants had radiographic BE. Participants with and without radiographic BE showed similar clinical characteristics (Table 3).

TABLE 3

Clinical Charateristics of the Study Population.

| | Participants with Radiographic BE (N = 96) | Participants without Radiographic BE (N = 77) | P value* |
|---|---|---|---|
| Number of lobes with Radiographic BE (median (IQR)) | 2 (1) | 0 (0) | <0.001 |
| Retrospectively identified BE (%)** | 26 (27) | 0 (0) | <0.001 |
| Age (mean (SD)) | 67 (7) | 67 (8) | 0.89 |
| Sex | | | 0.7 |
| Male (%) | 77 (80) | 64 (83) | |
| Female (%) | 19 (20) | 13 (17) | |
| Race | | | 0.88 |
| White (%) | 71 (74) | 58 (75) | |
| Black (%) | 12 (13) | 9 (12) | |
| Asian (%) | 2 (2) | 3 (4) | |
| Others/Unknown (%) | 11 (12) | 7 (9) | |
| Smoking Status | | | 0.25 |
| Current (%) | 38 (40) | 37 (48) | |
| Former (%) | 55 (57) | 35 (46) | |
| Unknown (%) | 3 (3) | 5 (7) | |
| Pack-years (mean (SD)) | 50 (25) *** | 50 (27) | 0.97 |
| FEV1 % predicted (mean (SD)) | 72 (20) | 76 (21) | 0.18 |
| FEV1/FVC (mean (SD)) | 0.6 (0.1) | 0.6 (0.1) | 0.62 |
| Having COPD (%) | 65 (68) | 54 (70) | 0.86 |
| Have malignancy | | | 0.71 |
| Yes (%) | 33 (34) | 42 (55) | |
| No (%) | 20 (20) | 31 (40) | |
| Unknown (%) | 43 (45) | 4 (5) | |
| Traction BE | | | <0.001 |
| Yes (%) | 30 (31) | 0 (0) | |
| No (%) | 61 (64) | 67 (87) | |
| Indeterminant (%) | 5 (5) | 10 (13) | |
| CT BE Score (mean (SD)) | 3.7 (3.8) | 0.1 (0.5) | <0.001 |
| Cough | | | 0.87 |
| Yes (%) | 42 (44) | 35 (46) | |
| No (%) | 46 (48) | 35 (46) | |
| Unknown (%) | 8 (8) | 7 (9) | |
| Phlegm | | | 0.87 |
| Yes (%) | 42 (44) | 34 (44) | |
| No (%) | 47 (49) | 35 (46) | |
| Unknown (%) | 7 (7) | 8 (10) | |
| Both cough and phlegm | | | 1 |
| Yes (%) | 31 (32) | 24 (31) | |
| No (%) | 58 (60) | 44 (57) | |
| Unknown (%) | 7 (7) | 9 (12) | |
| Shortness of Breath | | | 0.74 |
| Yes (%) | 56 (34) | 42 (55) | |
| No (%) | 33 (58) | 28 (36) | |
| Unknown (%) | 7 (7) | 7 (9) | |

Definition of abbreviation: BE = bronchiectasis, FEV1 = Forced expiratory volume, FVC = Forced vital capacity. The mean and standard deviation are shown for continuous variables.
*P values calculated using an ANOVA F test or Fisher's exact test.
**Missing values for 14 participants with radiographic BE.
*** Missing pack-years for 1 participant without widespread Radiographic BE in the bronchiectatic cluster.

Radiographic BE was predominant in the lower lobes (47%), whereas the lingula was the least affected (5.5%) (Table 4). We further defined widespread radiographic BE when 3 or more lobes were involved. 20 participants had widespread radiographic BE (3 females and 17 males; 66+5 yr), and 153 participants did not have widespread BE (29 females and 124 males; 67+8 yr). We found participants with and without widespread radiographic BE showed similar clinical features except those with widespread radiographic BE were more likely to report shortness of breath (p-value=0.01, Table 1).

TABLE 1

Clinical characteristics of the the participants with and without widespread BE.

| Patient Cluster | Participants with Widespread Radiographic BE (N = 20) | Participants without Widespread Radiographic BE (N = 153) | P value* |
|---|---|---|---|
| Number of lobes with Radiographic BE (median (IQR)) | 3 (1) | 0 (2) | <2e-16 |
| Retrospectively identified BE (%)** | 6 (30) | 20 (13) | 0.08 |
| Age (mean (SD)) | 66 (5) | 67 (8) | 0.62 |
| Sex | | | 1 |
| Male (%) | 17 (85) | 124 (81) | |
| Female (%) | 3 (15) | 29 (19) | |
| Race | | | 0.63 |
| White (%) | 15 (75) | 114 (74.5) | |
| Black (%) | 3 (15) | 18 (11.8) | |
| Asian (%) | 1 (5) | 4 (2.6) | |
| Others/Unknown (%) | 1 (5) | 17 (11.1) | |
| Smoking Status | | | 1 |
| Current (%) | 9 (45) | 66 (43.1) | |
| Former (%) | 10 (50) | 80 (52.3) | |
| Unknown (%) | 1 (5) | 7 (4.6) | |
| Pack-years (mean (SD)) | 45 (19) | 51 (26)*** | 0.37 |
| FEV1 % predicted (mean (SD)) | 69 (22) | 75 (20) | 0.23 |
| FEV1/FVC (mean (SD)) | 0.6 (0.2) | 0.6 (0.1) | 1 |
| Having COPD (%) | 14 (70) | 105 (69) | 1 |
| Having malignancy | | | 0.31 |
| Yes (%) | 4 (20) | 71 (46) | |
| No (%) | 6 (30) | 45 (31) | |
| Unknown (%) | 10 (50) | 37 (24) | |
| Radiographic BE | | | <0.001 |
| Yes (%) | 20 (100) | 76 (50) | |
| No (%) | 0 (0) | 77 (50) | |
| Traction BE | | | 0.081 |
| Yes (%) | 7 (35) | 23 (15) | |
| No (%) | 12 (60) | 116 (76) | |
| Indeterminant (%) | 1 (5) | 14 (9) | |
| CT BE Score (mean (SD)) | 7.7 (5.5) | 1.3 (2.0) | <0.001 |
| Cough | | | 1 |
| Yes (%) | 9 (45) | 68 (44) | |
| No (%) | 9 (45) | 72 (47) | |
| Unknown (%) | 2 (10) | 13 (9) | |
| Phlegm | | | 0.46 |
| Yes (%) | 11 (55) | 65 (43) | |
| No (%) | 8 (40) | 74 (48) | |
| Unknown (%) | 1 (5) | 14 (9) | |
| Both cough and phlegm | | | 0.804 |
| Yes (%) | 8 (40) | 47 (31) | |
| No (%) | 12 (60) | 90 (59) | |
| Unknown (%) | 0 (0) | 16 (11) | |
| Shortness of Breath | | | 0.01 |
| Yes (%) | 17 (85) | 81 (53) | |

TABLE 1-continued

Clinical characteristics of the the participants with and without widespread BE.

| Patient Cluster | Participants with Widespread Radiographic BE (N = 20) | Participants without Widespread Radiographic BE (N = 153) | P value* |
|---|---|---|---|
| No (%) | 2 (10) | 59 (39) | |
| Unknown (%) | 1 (5) | 13 (9) | |

Definition of abbreviation: BE = bronchiectasis, FEV1 = Forced expiratory volume, FVC = Forced vital capacity. The mean and standard deviation are shown for continuous variables.
*P values calculated using an ANOVA F test or Fisher's exact test.
**missing values for 12 participants without widespread radiographic BE and 2 participants with widespread radiographic BE.
***Missing pack-years for 1 participant without widespread Radiographic BE in the bronchiectatic cluster.

TABLE 4

Distribution of Radiographic BE by Lobe

| | No. | % |
|---|---|---|
| Left lung | 64 | 35.2 |
| Left upper lobe | 24 | 13.2 |
| Lingula | 10 | 5.5 |
| Left lower lobe | 30 | 16.5 |
| Right lung | 118 | 64.8 |
| Right upper lobe | 39 | 21.4 |
| Right middle lobe | 24 | 13.2 |
| Right lower lobe | 55 | 30.2 |

Identification of Three Distinct Clusters of Participants Based on Gene Expression Profiles We first performed differential gene expression analysis comparing bronchial epithelium of participants with and without radiographic BE and found no genes were differentially expressed (data not shown). We then compared participants with and without widespread radiographic BE and discovered 655 genes were significantly (false discovery rate q value <0.1, log fold change >0.25) differentially expressed when controlling for sex and smoking status (FIG. 1 and Table 10). Unsupervised clustering using the 655 genes first separated the 173 participants into two genomic clusters. The predominant cluster (N=123, left branch in FIG. 1) was primarily composed of participants without widespread radiographic BE. The smaller cluster on the right branch of the dendrogram contained two subgroups of participants, one that included most of the participants with widespread BE (N=30), and another which was composed of participants without widespread BE, yet demonstrated gene expression patterns similar to those with widespread BE (N=20).

In addition to different number of lobes with radiographic BE (p-value <0.0001), these three clusters of participants differ by the likelihood of having cardinal symptoms associated with BE—cough and phlegm production. Based on differences both in the gene expression and clinical characteristics that correlated with an increasing presentation of symptoms related to bronchiectasis, we named these three participants' clusters normal, intermediate, and bronchiectatic (FIG. 4). The bronchiectatic cluster of participants with the highest average of number lobes with radiographic BE had the highest proportion of participants complaining about both cough and phlegm (p-value=0.002). Interestingly, the intermediate cluster had a higher proportion of current smokers (p-value=0.006) but otherwise consists of individuals with similar clinical characteristics to the participants in the normal cluster with the lowest average number of lobes with radiographic BE (FIG. 1 and Table 2).

TABLE 2

Clinical characteristics of the three participants of three clusters based on gene expression profiles.

| Patient Clusters | Normal (N = 123) | Intermediate (N = 20) | Bronchiectatic (N = 30) | P value* |
|---|---|---|---|---|
| Number of lobes with Radiographic BE (median (IQR)) | 1 (2) | 1 (2) | 2 (3) | <0.0001 |
| Retrospectively identified BE (%)** | 15 (12) | 1 (5) | 10 (33) | 0.009 |
| Widespread Radiographic BE | | | | 1.18E−07 |
| Yes (%) | 4 (3) | 3 (15) | 13 (43) | |
| No (%) | 119 (97) | 17 (85) | 17 (57) | |
| Age (mean (SD)) | 67 (8) | 65 (6) | 67 (6) | 0.29 |
| Sex | | | | 0.14 |
| Male (%) | 98 (80) | 15 (75) | 28 (93) | |
| Female (%) | 25 (20) | 5 (25) | 2 (7) | |
| Race | | | | 0.22 |
| White (%) | 88 (72) | 15 (75) | 26 (87) | |
| Black (%) | 17 (14) | 2 (10) | 2 (7) | |
| Asian (%) | 2 (2) | 2 (10) | 1 (3) | |
| Others/Unknown (%) | 16 (13) | 1 (5) | 1 (3) | |
| Smoking Status | | | | 0.006 |
| Current (%) | 46 (37) | 15 (75) | 14 (47) | |
| Former (%) | 70 (57) | 4 (20) | 16 (53) | |
| Unknown (%) | 7 (6) | 1 (5) | 0 (0) | |
| Pack-years (mean (SD)) | 50 (26) | 61 (31)*** | 44 (20)*** | 0.09 |
| FEV1 % predicted (mean (SD)) | 75 (20) | 78 (20) | 68 (21) | 0.16 |
| FEV1/FVC (mean (SD)) | 0.6 (0.1) | 0.7 (0.1) | 0.6 (0.2) | 0.07 |
| Having COPD (%) | 83 (67.5) | 13 (65) | 23 (76.7) | 0.59 |
| Have malignancy | | | | 0.18 |
| Yes (%) | 56 (46) | 11 (55) | 8 (27) | |
| No (%) | 36 (29) | 4 (20) | 11 (37) | |
| Unknown (%) | 31 (25) | 5 (25) | 11 (37) | |
| Radiographic BE | | | | 0.42 |
| Yes (%) | 65 (53) | 11 (55) | 20 (67) | |
| No (%) | 58 (47) | 9 (45) | 10 (33) | |
| Traction BE | | | | 0.54 |
| Yes (%) | 19 (15) | 4 (20) | 7 (23) | |
| No (%) | 93 (76) | 13 (65) | 22 (73) | |
| Indeterminant (%) | 11 (9) | 3 (15) | 1 (3) | |
| CT BE Score (mean (SD)) | 1.6 (2.6) | 2.1 (3.4) | 3.7 (5.2) | <0.0001 |
| Cough | | | | 0.0003 |
| Yes (%) | 48 (39) | 6 (30) | 23 (77) | |
| No (%) | 66 (54) | 10 (50) | 5 (17) | |
| Unknown (%) | 9 (7) | 4 (30) | 2 (7) | |
| Phlegm | | | | 0.02 |
| Yes (%) | 49 (40) | 7 (35) | 20 (67) | |
| No (%) | 63 (51) | 11 (55) | 8 (27) | |
| Unknown (%) | 11 (9) | 2 (10) | 2 (7) | |
| Both cough and phlegm | | | | 0.002 |
| Yes (%) | 33 (27) | 4 (20) | 18 (60) | |
| No (%) | 79 (64) | 13 (65) | 10 (33) | |
| Unknown (%) | 11 (9) | 3 (15) | 2 (7) | |
| Shortness of Breath | | | | 0.15 |
| Yes (%) | 64 (52) | 13 (65) | 21 (70) | |
| No (%) | 49 (40) | 5 (25) | 7 (23) | |
| Unknown (%) | 10 (8) | 2 (10) | 2 (7) | |

Definition of abbreviation: BE = bronchiectasis, FEV1 = Forced expiratory volume, FVC = Forced vital capacity. The mean and standard deviation are shown for continuous variables.
*P values calculated using an ANOVA F test or Fisher's exact test.
**missing values for 8 participants in normal cluster, 3 participants in intermediate cluster, and 3 participants in bronchiectatic cluster.
***Missing pack-years for 1 participant without widespread Radiographic BE in the bronchiectatic cluster.

Further examination of the participants in the bronchiectatic cluster who do not have widespread radiographic BE, failed to identify significant differences in clinical characteristics compared to the participants with widespread BE within the bronchiectatic cluster (Table 5). However, when compared to the participants without widespread BE in the normal and intermediate clusters, non-BE participants in the bronchiectatic gene expression cluster exhibit an increased likelihood of cough and phlegm production (p-value=0.02) (Table 6).

TABLE 5

Clinical Characteristics of the Participants with/without Widespread BE in the Bronchiectatic Cluster.

| Patient Clusters | Bronchiectatic Participants with Widespread Radiographic BE (N = 13) | Bronchiectatic Participants without Widespread Radiographic BE (N = 17) | P value* |
|---|---|---|---|
| Number of lobes with Radiographic BE (median (IQR)) | 3 (1) | 0 (1) | <0.0001 |
| Retrospectively identified BE (%)** | 6 (46) | 20 (23) | 0.25 |
| Age (mean (SD)) | 68 (5) | 67 (7) | 0.71 |
| Sex | | | 0.18 |
| Male (%) | 11 (85) | 17 (100) | |
| Female (%) | 2 (15) | 0 (0) | |
| Race | | | 0.7 |
| White (%) | 10 (77) | 16 (94) | |
| Black (%) | 1 (8) | 1 (6) | |
| Asian (%) | 1 (8) | 0 (0) | |
| Others/Unknown (%) | 1 (8) | 0 (0) | |
| Smoking Status | | | 1 |
| Current (%) | 6 (46) | 8 (47) | |
| Former (%) | 7 (54) | 9 (53) | |
| Unknown (%) | 0 (0) | 0 (0) | |
| Pack-years (mean (SD)) | 40 (14) | 48 (23)*** | 0.3 |
| FEV1 % predicted (mean (SD)) | 66 (21) | 69 (21) | 0.68 |
| FEV1/FVC (mean (SD)) | 0.6 (0.1) | 0.6 (0.2) | 0.82 |
| Having COPD (%) | 11 (85) | 12 (71) | 0.43 |
| Have malignancy | | | 0.63 |
| Yes (%) | 2 (15) | 6 (35) | |
| No (%) | 5 (39) | 6 (35) | |
| Unknown (%) | 6 (46) | 5 (29) | |
| Radiographic BE | | | <0.0001 |
| Yes (%) | 13 (100) | 7 (41) | |
| No (%) | 0 (0) | 10 (59) | |
| Traction BE | | | 0.4 |
| Yes (%) | 4 (31) | 3 (18) | |
| No (%) | 8 (62) | 14 (82) | |
| Indeterminant (%) | 1 (8) | 0 (0) | |
| CT BE Score (mean (SD)) | 7.5 (6) | 0.9 (1.4) | 0.00015 |
| Cough | | | 0.62 |
| Yes (%) | 9 (69) | 14 (82) | |
| No (%) | 3 (23) | 2 (12) | |
| Unknown (%) | 1 (8) | 1 (6) | |
| Phlegm | | | 1 |
| Yes (%) | 9 (69) | 11 (65) | |
| No (%) | 4 (31) | 4 (24) | |
| Unknown (%) | 0 (0) | 2 (12) | |
| Both cough and phlegm | | | 1 |
| Yes (%) | 8 (62) | 10 (59) | |
| No (%) | 5 (39) | 5 (29) | |
| Unknown (%) | 0 (0) | 2 (12) | |
| Shortness of Breath | | | 0.18 |
| Yes (%) | 11 (85) | 10 (59) | |
| No (%) | 1 (8) | 6 (35) | |
| Unknown (%) | 1 (8) | 1 (6) | |

Definition of abbreviation: BE = bronchiectasis, FEV1 = Forced expiratory volume, FVC = Forced vital capacity. The mean and standard deviation are shown for continuous variables.
*P values calculated using an ANOVA F test or Fisher's exact test.
**Missing values for 2 bronchiectatic participants without widespread radiographic BE and 1 bronchiectatic participants with widespread radiographic BE.
***Missing pack-years for 1 participant without widespread Radiographic BE in the bronchiectatic cluster.

TABLE 6

Clinical Characteristics of the Participants without Widespread BE in the Three Genomic Clusters.

| Patient Clusters | Normal (N = 119) | Intermediate (N = 17) | Bronchiectatic (N = 17) | P value* |
|---|---|---|---|---|
| Number of lobes with Radiographic BE (median (IQR)) | 0 (2) | 0 (2) | 0 (1) | 0.87 |
| Retrospectively identified BE (%)** | 15 (13) | 1 (6) | 4 (24) | 0.34 |
| Age (mean (SD)) | 68 (8) | 65 (7) | 67 (7) | 0.37 |
| Sex | | | | 0.04 |
| Male (%) | 95 (80) | 12 (71) | 17 (100) | |
| Female (%) | 24 (20) | 5 (29) | 0 (0) | |
| Race | | | | 0.15 |
| White (%) | 85 (71) | 13 (77) | 16 (94) | |
| Black (%) | 16 (13) | 1 (6) | 1 (6) | |
| Asian (%) | 2 (2) | 2 (12) | 0 (0) | |
| Others/Unknown (%) | 16 (14) | 1 (6) | 0 (0) | |
| Smoking Status | | | | 0.02 |
| Current (%) | 45 (38) | 13 (77) | 8 (47) | |
| Former (%) | 68 (57) | 3 (18) | 9 (53) | |
| Unknown (%) | 6 (5) | 1 (6) | 0 (0) | |
| Pack-years (mean (SD)) | 50 (26) | 58 (31)*** | 48 (23)*** | 0.49 |
| FEV1 % predicted (mean (SD)) | 75 (20) | 78 (21) | 69 (21) | 0.42 |
| FEV1/FVC (mean (SD)) | 0.6 (0.1) | 0.6 (0.1) | 0.6 (0.2) | 0.37 |
| Having COPD (%) | 81 (68) | 12 (71) | 12 (71) | 1 |
| Having malignancy | | | | 0.66 |
| Yes (%) | 56 (47) | 9 (53) | 6 (35) | |
| No (%) | 35 (29) | 4 (24) | 6 (35) | |
| Unknown (%) | 28 (24) | 4 (24) | 5 (29) | |
| Radiographic BE | | | | 0.78 |
| Yes (%) | 61 (49) | 8 (47) | 7 (41) | |
| No (%) | 58 (51) | 9 (53) | 10 (59) | |
| Traction BE | | | | 0.78 |
| Yes (%) | 17 (14) | 3 (18) | 3 (18) | |
| No (%) | 91 (77) | 11 (65) | 14 (82) | |
| Indeterminant (%) | 11 (9) | 3 (18) | 0 (0) | |
| CT BE Score (mean (SD)) | 1.4 (2.1) | 1.3 (2.1) | 0.9 (1.4) | 0.63 |
| Cough | | | | 0.003 |
| Yes (%) | 48 (40) | 6 (35) | 14 (82) | |
| No (%) | 62 (52) | 8 (47) | 2 (12) | |
| Unknown (%) | 9 (8) | 3 (18) | 1 (6) | |
| Phlegm | | | | 0.1 |
| Yes (%) | 48 (40) | 6 (35) | 11 (65) | |
| No (%) | 61 (51) | 9 (53) | 4 (24) | |
| Unknown (%) | 10 (8) | 2 (12) | 2 (12) | |
| Both cough and phlegm | | | | 0.02 |
| Yes (%) | 33 (28) | 4 (24) | 10 (59) | |
| No (%) | 75 (63) | 10 (59) | 5 (29) | |
| Unknown (%) | 11 (9) | 3 (18) | 2 (12) | |
| Shortness of Breath | | | | 0.76 |
| Yes (%) | 61 (51) | 10 (59) | 10 (59) | |
| No (%) | 48 (40) | 5 (29) | 6 (35) | |
| Unknown (%) | 10 (8) | 2 (12) | 1 (6) | |

Definition of abbreviation: BE = bronchiectasis, FEV1 = Forced expiratory volume, FVC = Forced vital capacity. The mean and standard deviation are shown for continuous variables.
*P values calculated using an ANOVA F test or Fisher's exact test.
**Missing values for 8 normal participants, 2 intermediate participants, and 2 bronchiectatic participants without widespread BE.
***Missing pack-years for 1 participant in the intermediate cluster and 1 participant in bronchiectatic cluster.

Figure 2:
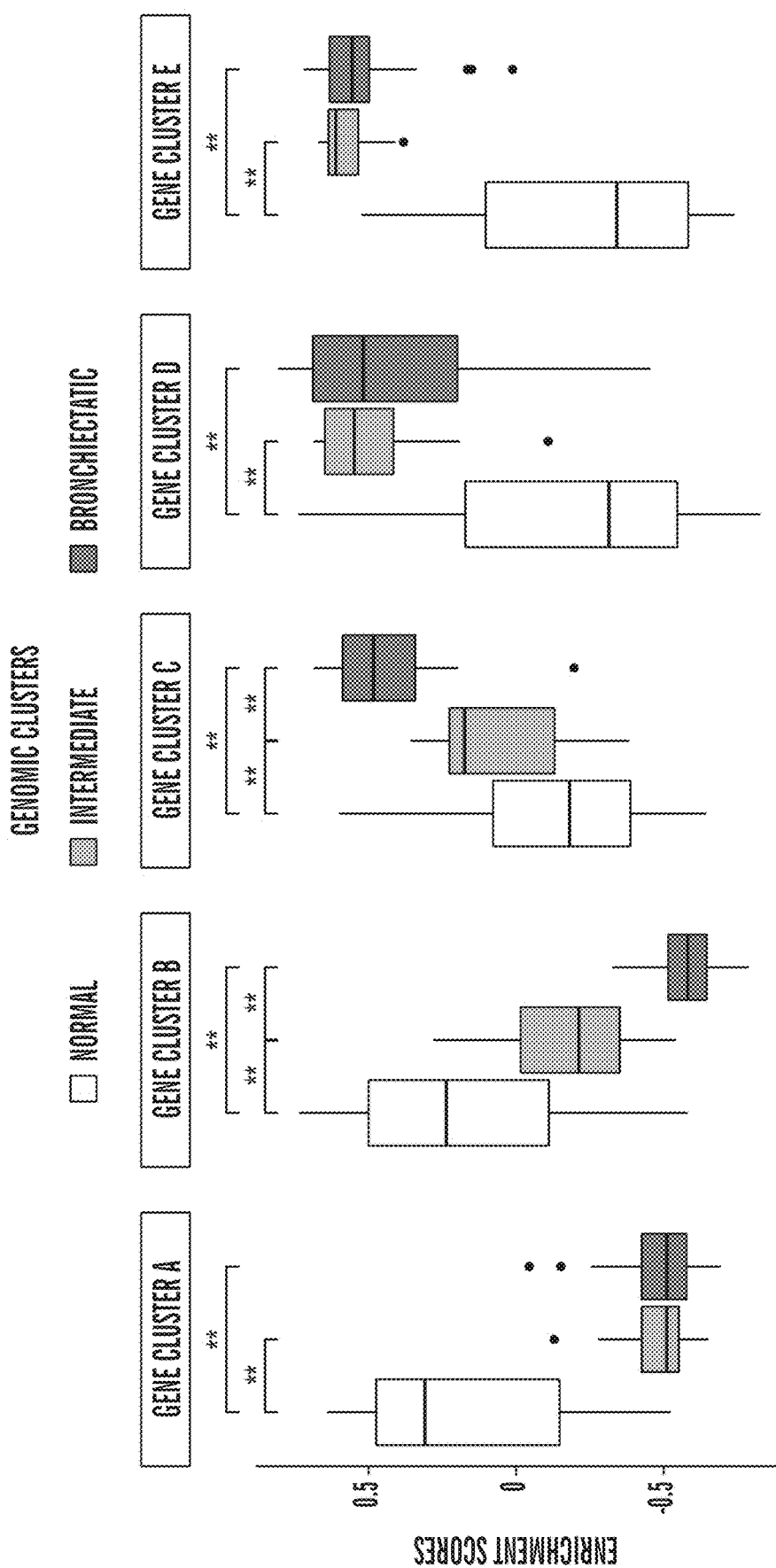
FIG. 2 depicts modular gene expressions in genomic clusters. ** Tukey adjusted P values <0.01.

Bulk RNA-Seq Analysis Reveals Molecular Pathways Associated with Widespread Radiographic BE To better understand the differences in gene expression among the three patient clusters, especially that between the intermediate cluster and either the normal or bronchiectatic cluster, we first divided the 655 genes into five co-expression clusters (A-E) based on hierarchical clustering. A composite expression score for each of the five gene clusters for each participant were then calculated using gene set variation analysis (GSVA) (FIG. 2). The normal and the bronchiectatic clusters showed clear distinctions in all gene clusters, gene clusters A and B were expressed at higher levels among participants of the normal cluster, and gene clusters C, D, and E were expressed at higher levels among participants of the bronchiectatic cluster. Participants in the intermediate cluster, however, were displaying two patterns of gene expression: one in which the intermediate and bronchiectatic clusters exhibited similar levels of gene expression relative to the normal cluster (gene cluster A, D, and E); and another pattern in which intermediate cluster exhibited gene expression intermediate between the normal and the bronchiectatic clusters (Gene clusters B and C).

Figure 5:
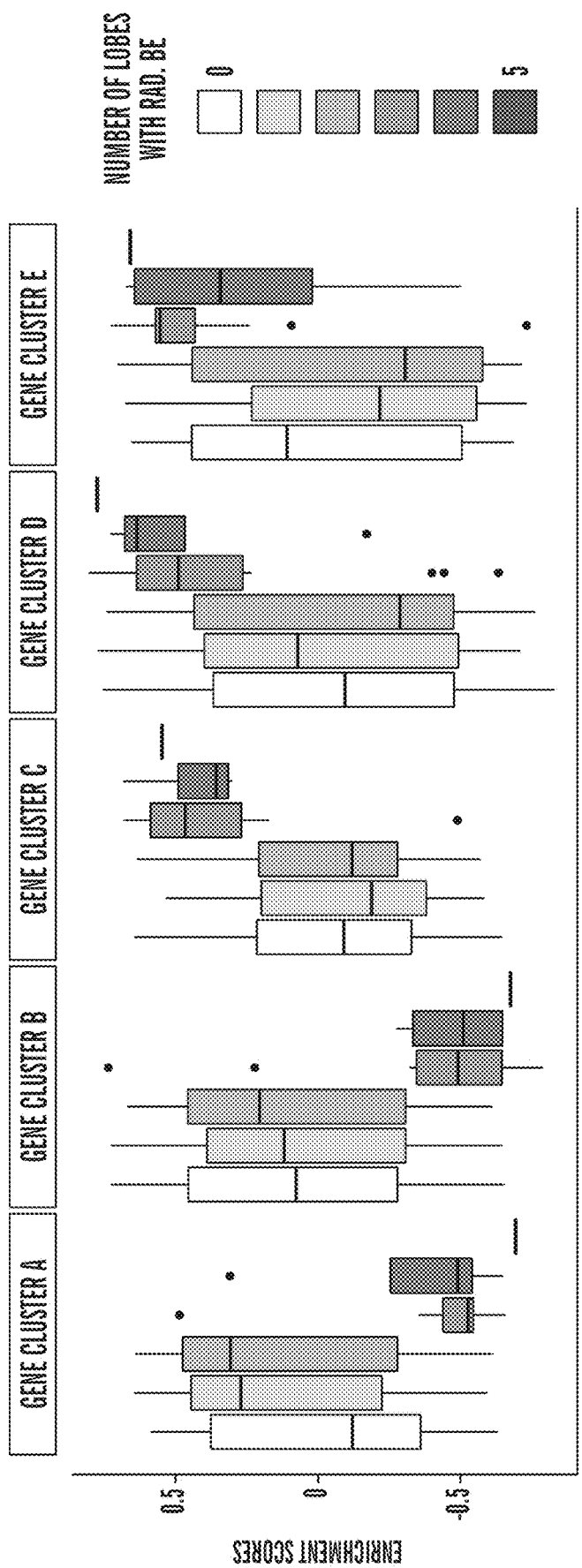
FIG. 5 depicts modular gene expression in participants with different lobes with radiographic BE.

Functional enrichment analysis showed that gene clusters A and B were significantly enriched for genes involved in cell adhesion (PCDHGA4, PCDHGA7, PCDHGA9 as well as 7 other protocadherin gamma related transcripts (PCDHG)) and Wnt signaling (WNT2B, WNT3A, WNT5A), respectively (Table 7), whereas gene clusters C and E were enriched for genes involved in endopeptidase activity (PSMA3, PSMA5, PSMA6 as well as 4 other proteasome related transcripts), and genes in cluster D were enriched for genes involved in cilium organization (TUBA1A, CC2D2A, CCDC176). When examining gene expression as a function of the number of affected lobes, we also observed a dramatic shift in expression between 2 and 3 affected lobes (FIG. 5).

TABLE 7

Functional Analysis of Differentially Expressed Genes

| Gene Cluster (number of genes) | GO-term | Description | Genes |
|---|---|---|---|
| A (N = 204) | GO: 0007156<br>GO: 0022610<br>GO: 0095609 | Hemophilic cell adhesion<br>Biological adhesion<br>Cell-cell adhesion | ACKR3, CD81, PCDHGA4, PCDHGA7, PCDHGA9, PCDHGA11, PCDHGA12, PCDHGB4, PCDHGB6, PCDHGB7, PCDHGC5, PPAP2B, PTPRS, SMAD6, STRC |
| B (N = 153) | GO: 0060828<br>GO: 0030111<br>GO: 0090263 | Regulation of canonical Wnt signaling pathway<br>Regulation of Wnt signaling pathway<br>Positive regulation of canonical Wnt signaling pathway | DACT2, EGFR, FGF9, FGFR2, FZD7, IGFBP4, KANK1, LGR5, LGR6, LRP4, MCC, SEMA5A, SNAI2, SULF2, TLE2, WNT2B, WNT3A, WNT5A |
| C (N = 78) | GO: 0004298 | Threonine-type endopeptidase activity | PSMB8, PSMB9, PSMB10 |
| D (N = 112) | GO: 0044782<br>GO: 0060271<br>GO: 0070925 | Cilium organization<br>Cilium assembly<br>Organelle assembly | ARL3, B9D2, C1orf192, C6orf165, C21orf59, CC2D2A, CCDC65, CCDC176, CEP97, DNAL1, DYNC2LI1, DYX1C1, IFT22, IFT43, MAP9, SPAG1, TCTEX1D2, TMEM17, TUBA1A |
| E (N = 108) | GO: 0004298 | Threonine-type endopeptidase activity | PSMA3, PSMA5, PSMA6, PSMB5 |

To further explore the possible biological processes contributing to the BE-associated gene expression differences, we performed gene set enrichment analysis (GSEA) using a catalog of curated Hallmark gene sets[22]. We found genes up-regulated among participants with widespread radiographic BE were enriched in interferon-gamma, oxidative phosphorylation, and interferon-alpha pathways; while genes up-regulated in participants without widespread radiographic BE were enriched in pathway down-regulated by KRAS activation, epithelial-mesenchymal transition, and pancreas beta cells pathways (Table 8).

TABLE 8

Gene set enrichment analysis showed enrichment of Hallmark genes in participants with and without radiographic BE.

| | Enrichment Scores | Normalized Enrichment Scores | FWER p-val |
|---|---|---|---|
| Pathways Enriched in Participants with Widespread Radiographic BE | | | |
| HALLMARK_INTERFERON_GAMMA_RESPONSE | 0.67 | 3.15 | 0 |
| HALLMARK_OXIDATIVE_PHOSPHORYLATION | 0.59 | 2.83 | 0 |
| HALLMARK_INTERFERON_ALPHA_RESPONSE | 0.65 | 2.69 | 0 |
| HALLMARK_MYC_TARGETS_V1 | 0.51 | 2.41 | 0 |
| HALLMARK_ALLOGRAFT_REJECTION | 0.51 | 2.34 | 0 |
| HALLMARK_COMPLEMENT | 0.47 | 2.18 | 0 |

TABLE 8-continued

Gene set enrichment analysis showed enrichment of Hallmark
genes in participants with and without radiographic BE.

|  | Enrichment Scores | Normalized Enrichment Scores | FWER p-val |
|---|---|---|---|
| HALLMARK_MTORC1_SIGNALING | 0.43 | 2.06 | 0 |
| HALLMARK_PROTEIN_SECRETION | 0.45 | 1.92 | 0.001 |
| HALLMARK_INFLAMMATORY_RESPONSE | 0.37 | 1.76 | 0.009 |
| HALLMARK_REACTIVE_OXYGEN_SPECIES_PATHWAY | 0.48 | 1.74 | 0.013 |
| HALLMARK_APOPTOSIS | 0.38 | 1.74 | 0.015 |
| HALLMARK_SPERMATOGENESIS | 0.41 | 1.7 | 0.025 |
| HALLMARK_UNFOLDED_PROTEIN_RESPONSE | 0.4 | 1.69 | 0.026 |
| HALLMARK_DNA_REPAIR | 0.35 | 1.64 | 0.044 |
| Pathways Enriched in Participants without Widespread Radiographic BE | | | |
| HALLMARK_KRAS_SIGNALING_DN | −0.53 | −2.05 | 0.002 |
| HALLMARK_EPITHELIAL_MESENCHYMAL_TRANSITION | −0.42 | −1.75 | 0.023 |
| HALLMARK_PANCREAS_BETA_CELLS | −0.61 | −1.72 | 0.027 |

Figure 6:
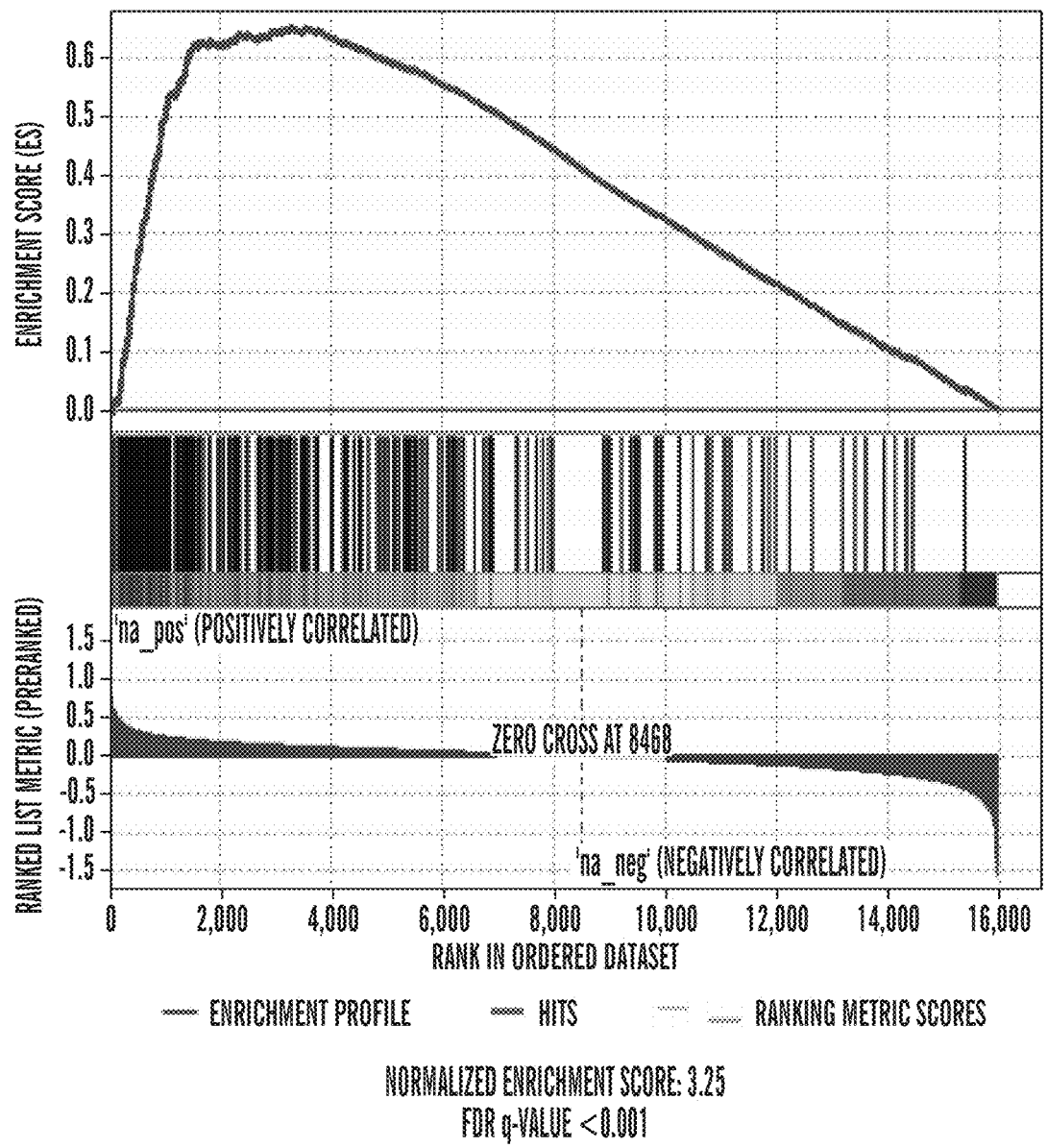
FIG. 6 depicts the enrichment of ciliogenesis-associated genes in the bronchial epithelium of participants with widespread radiographic BE.

Moreover, we compared the differentially expressed genes to a signature of ciliogenesis, which contained a list of 310 genes up-regulated with cilia organization and associated with primary ciliary dyskinesia (PCD)[28,29], a significant risk factor for BE. 42 of the 310 genes were up-regulated among patients with widespread radiographic BE (Table 9). Using GSEA, we found significant enrichment of ciliogenesis-associated genes among the genes expressed at higher levels in participants with widespread radiographic BE (FIG. 6).

Figure 3A:
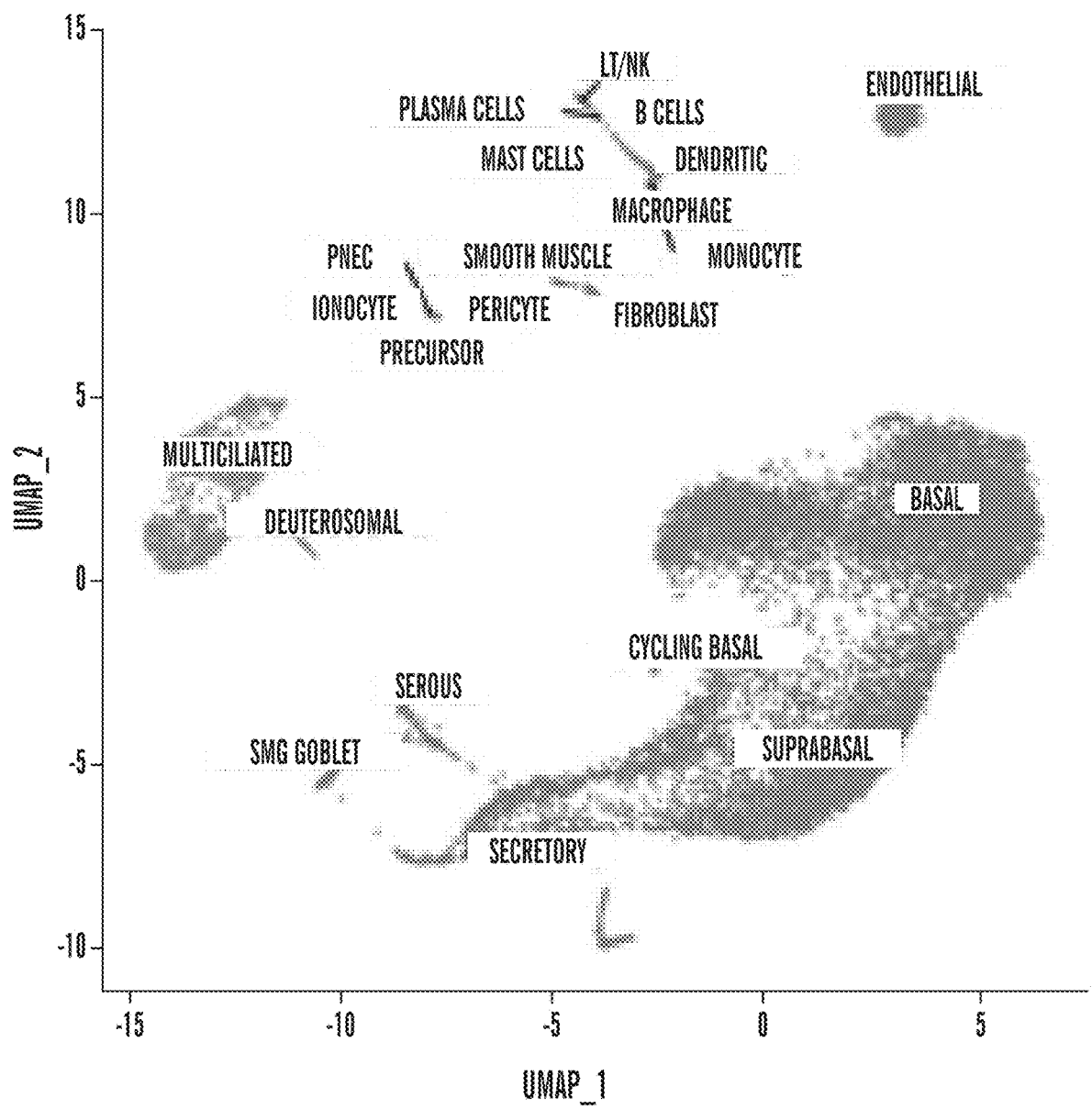
FIGS. 3A-3D.
Figure 3B:
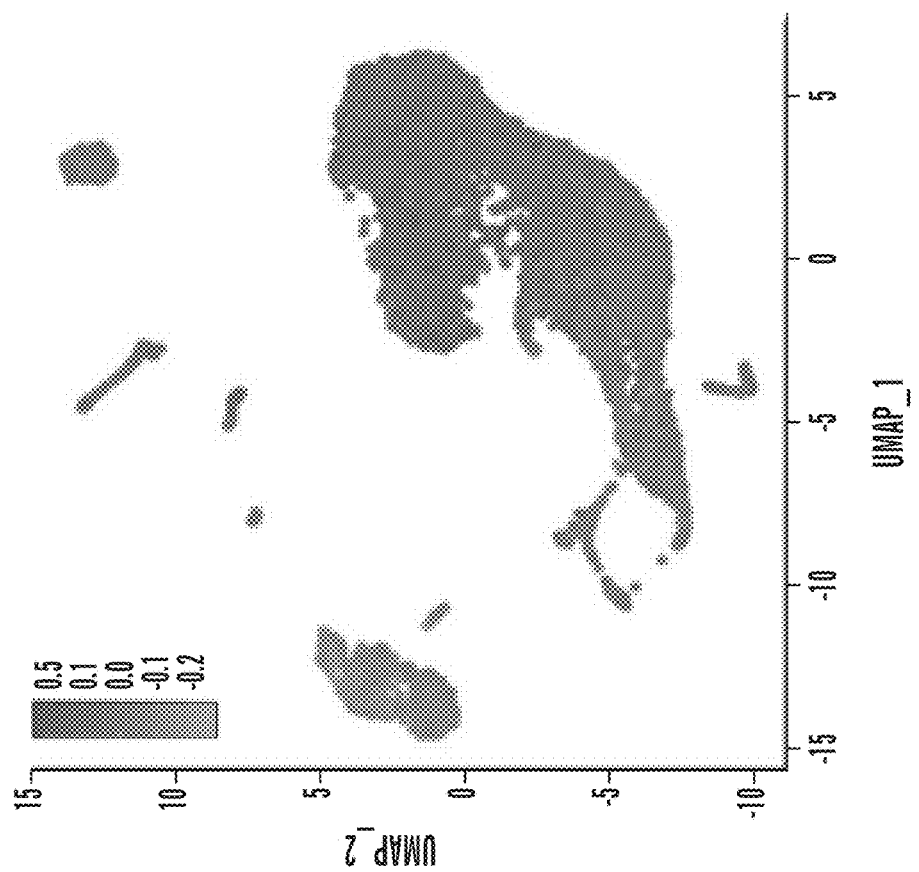
Figure 3B:
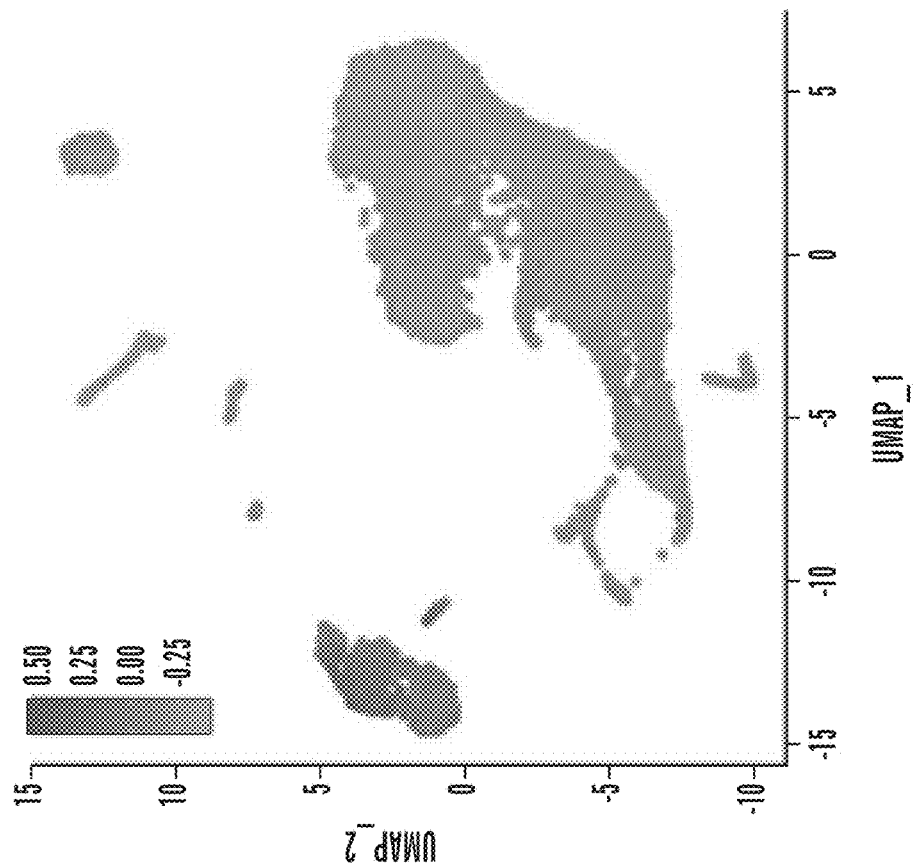
Figure 3C:
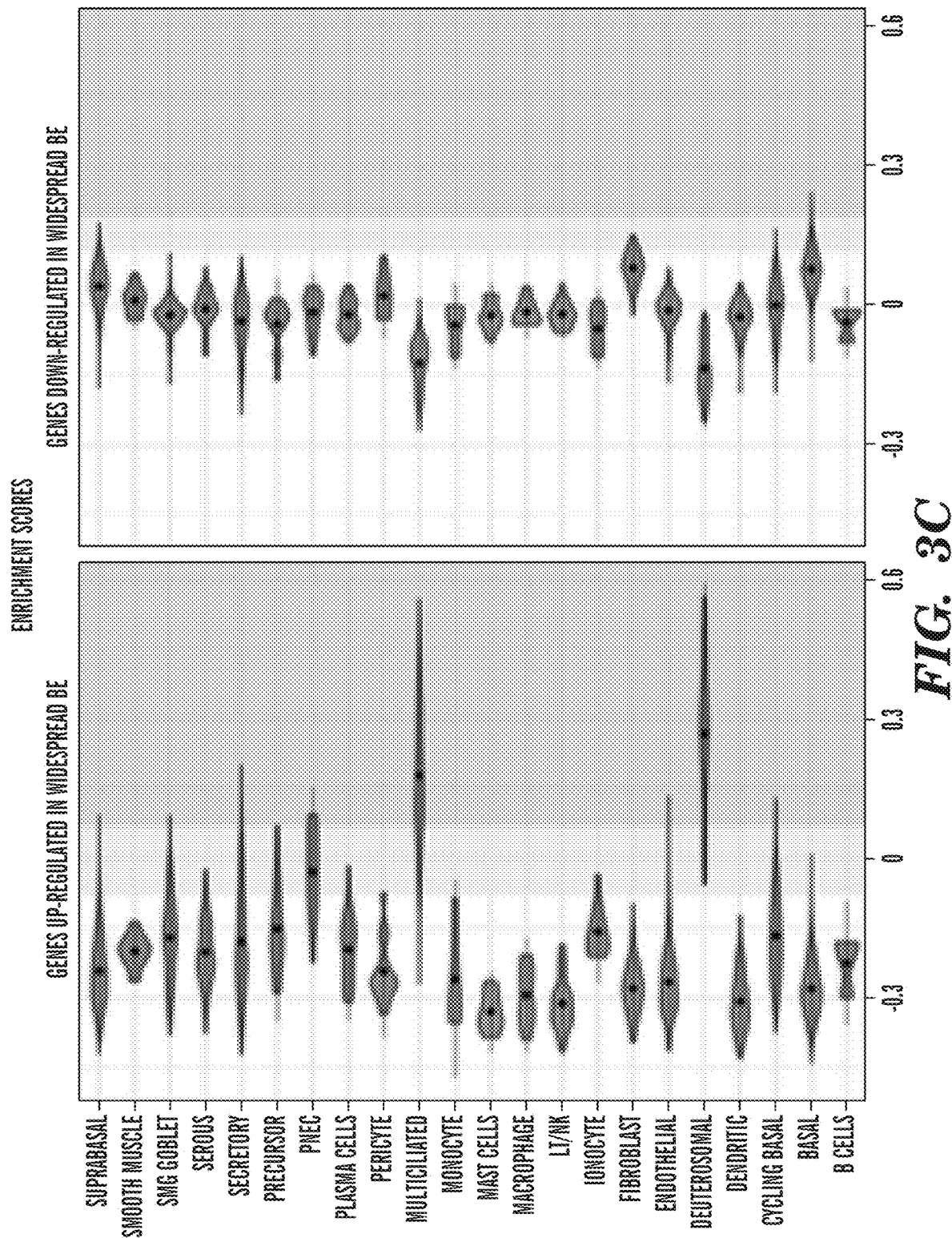
Figure 3D:
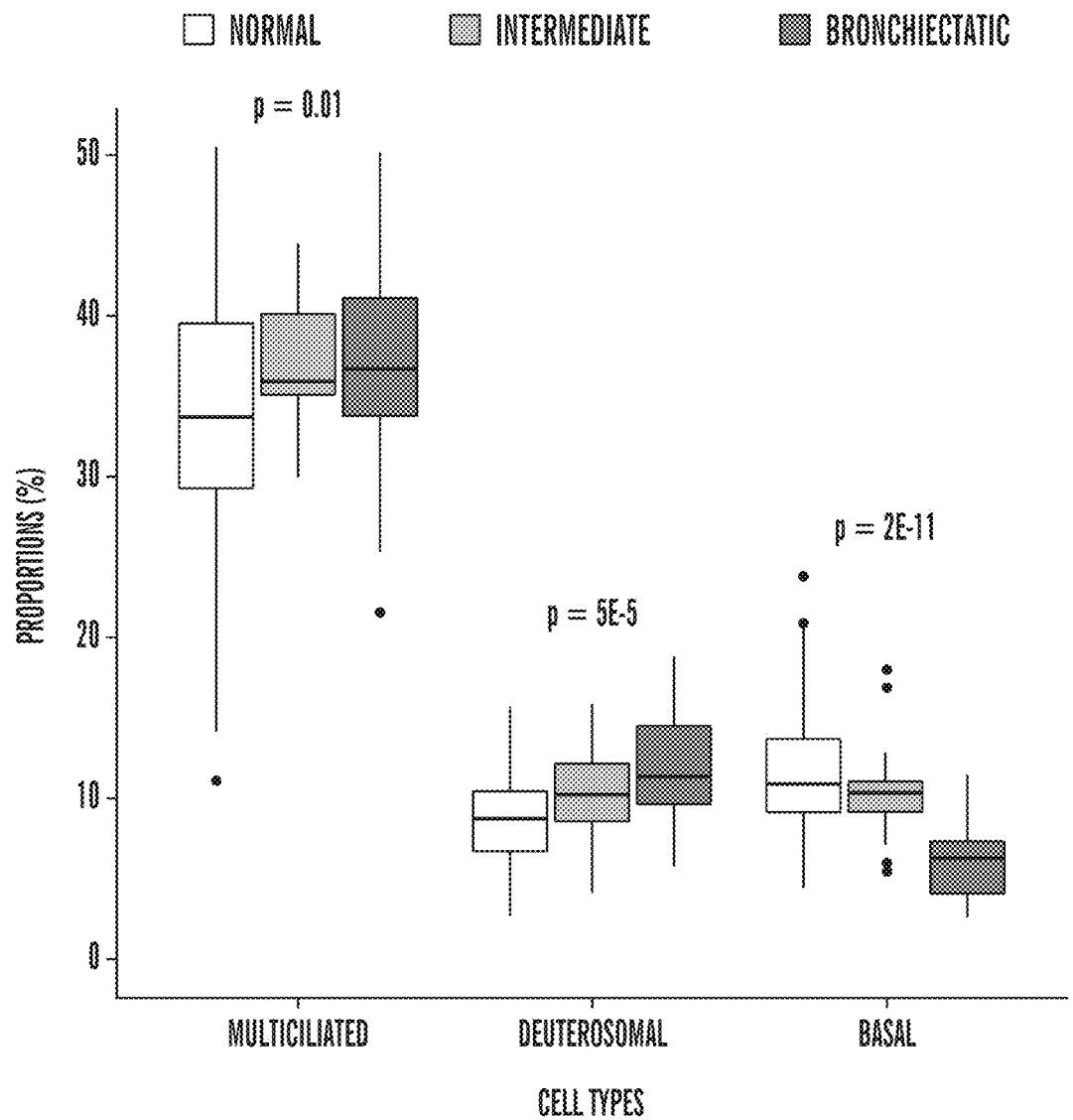
Figure 7:
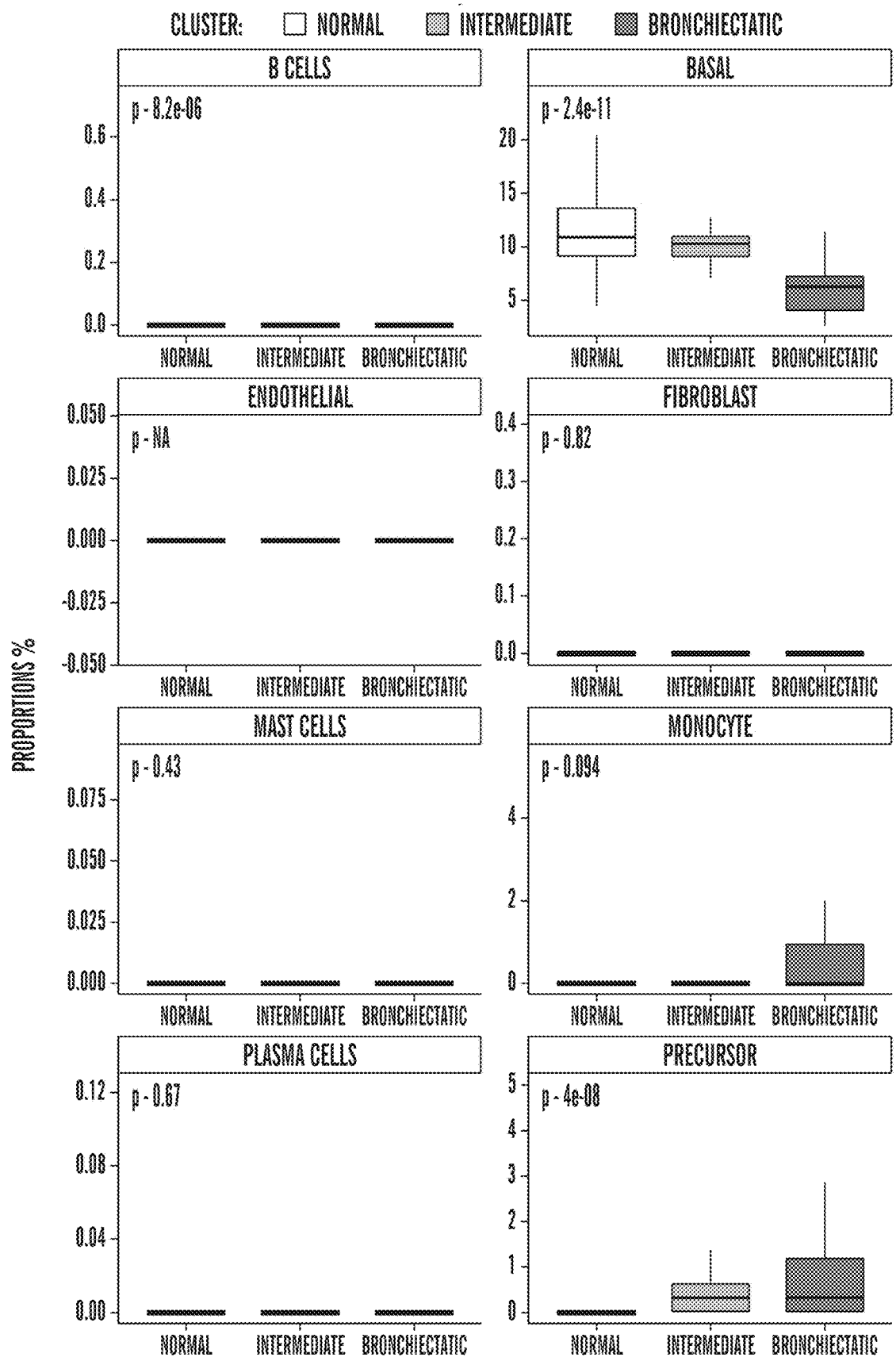
FIG. 7 demonstrates that the increased severity of radiographic BE was negatively correlated with the proportion of basal cells but positively correlated with deuterosomal cells and cilitated cells.
Figure 7:
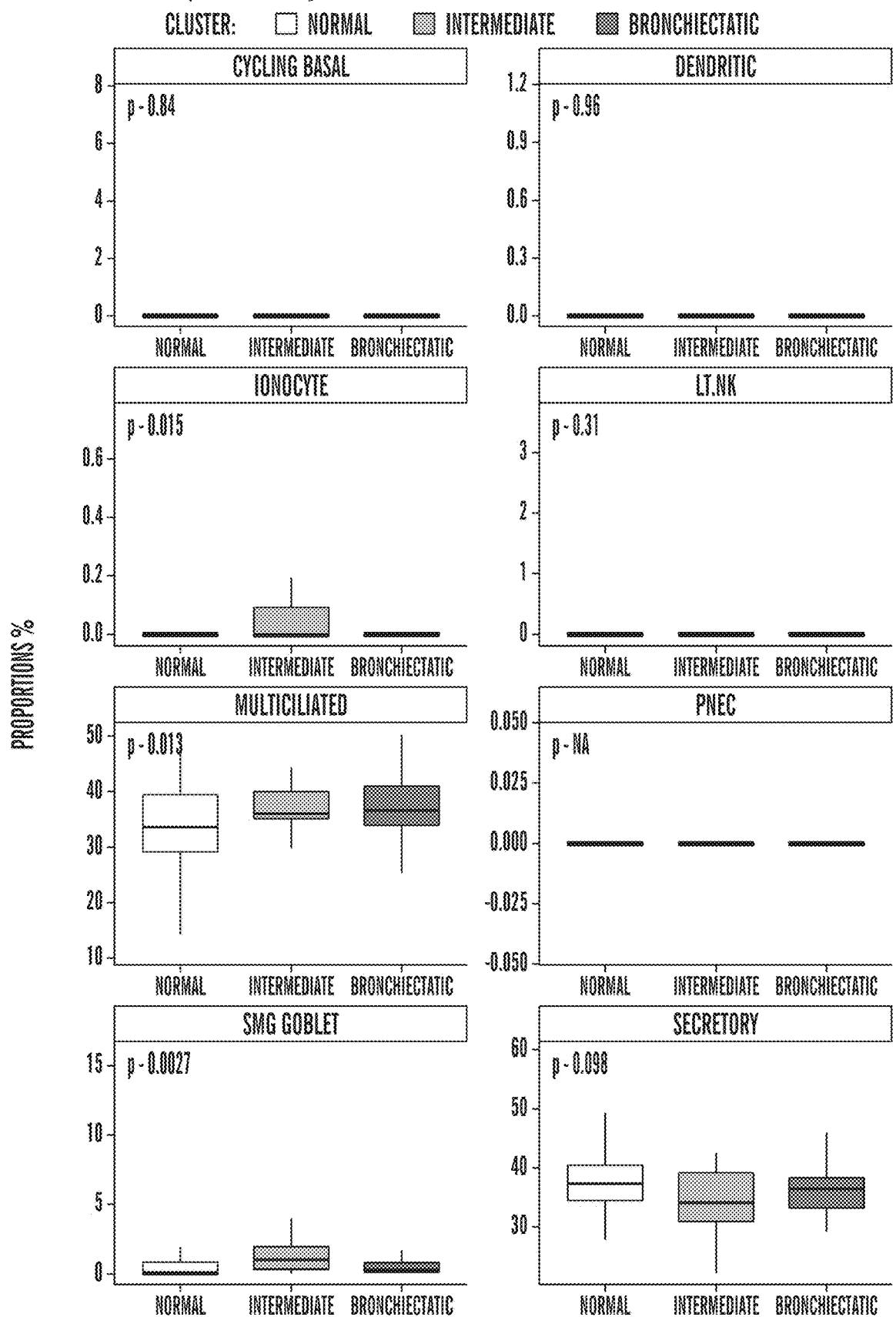
Figure 7:
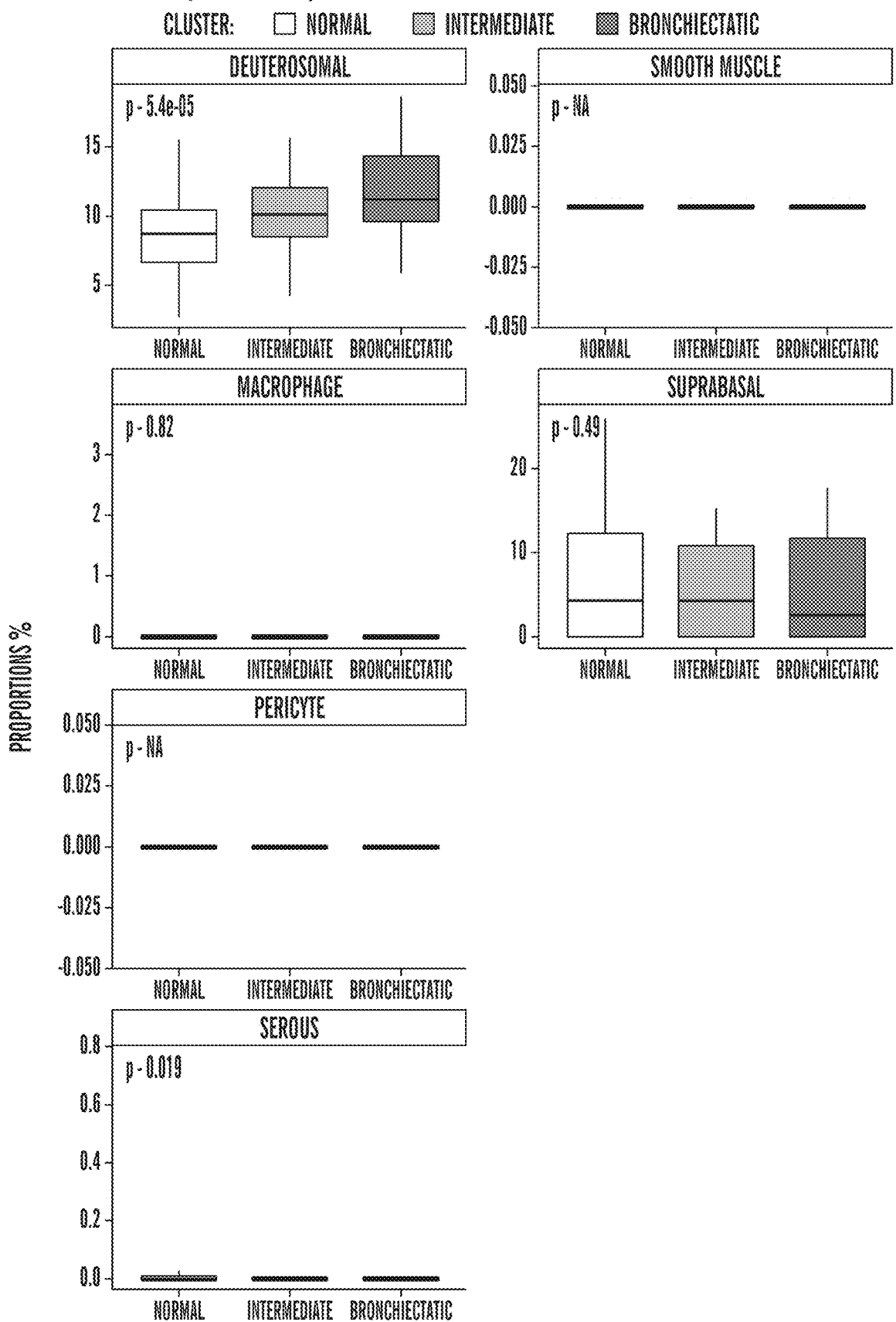

Widespread Radiographic BE Correlates with Increased Proportions of Ciliated and Deuterosomal Cells, and Decreased Proportion of Basal Cells To explore whether the observed gene expression alterations might be specific to specific cell types in the bronchial epithelium, we leveraged a single cell RNA-sequencing dataset consisting of bronchial epithelial cells collected by bronchoscopic biopsy of 9 healthy volunteers[26] and calculated a per cell GSVA enrichment scores for the Cluster A & B genes as well as the Cluster C-E genes. We found the genes increased in individuals with widespread radiographic BE (Clusters A & B) were expressed almost exclusively among the deuterosomal cells and the multiciliated cells, whereas the genes up-regulated in individuals without widespread radiographic BE (Clusters C-E) were expressed at highest levels among basal cells (FIGS. 3A-3C). To further explored the possibility that the gene expression alterations observed at the bulk level are consistent with altered epithelial cell prevalence in the bronchial airway of individuals with widespread radiographic BE, we computationally deconvolved cell population proportions in the bulk RNA-seq data using gene markers identified from the single-cell data (Table 11). The predicted proportions of both the multiciliated and deuterosomal cells increased from the normal to the intermediate and to the bronchiectatic cluster (FIG. 3 D); with the shift being most pronounced for the immature deuterosomal cells. In contrast, the proportion of basal cells incrementally decreased from the normal to the intermediate and to the bronchiectatic cluster. Of note, the proportion of goblet cells, previously shown to be correlate with cigarette smoking[30], was increased in the smoker-predominant intermediate cluster (FIG. 7).

Discussion

Current knowledge about the pathogenesis of bronchiectasis (BE) has been summarized as a "vicious cycle" model[31] in which epithelial dysfunction, chronic infection, recurring inflammation, and structural damage are involved in a cycle of events that promote the enlargement of bronchi. Our transcriptomic analysis in individuals without a previous clinical diagnosis of BE but who show signs of BE in multiple lobes on CT ("widespread radiographic BE") potentially offers insights into early molecular changes associated with BE development. Consistent with the proposed vicious cycle model, a loss of gene expression related to cell adhesion and an increased level of gene expression related to inflammation is detected in participants with radiographic BE. Our analysis also reveals two biologic pathways that may play important roles in the initiation of BE that have not been previously discussed—a decreased expression of genes in the Wnt signaling pathway and an increased expression of genes in the cilium biology pathway.

While participants with or without radiographic BE do not show clear clinical differences, the distribution of radiographic BE is consistent with existing findings that BE most commonly occurs in the lower lobes[32-34]. The decreased expression of genes involved in cell adhesion and Wnt signalling with widespread radiographic BE are consistent with the bronchial dilation observed in patients with clinical BE[32]. PCDHGA7 (Protocadherin gamma subunit A7), PCDHGB4 (Protocadherin gamma subunit B4), as well as protocadherins are members of the protocadherin gamma gene cluster, initially found as adhesion proteins most likely to play a critical role in the cell-cell connections in the brain[35,36]. Many protocadherin genes, especially PCDHA7 have been found to be down-regulated in colorectal cancer that is associated with epithelial damage[37]. Moreover, the protocadherin gene is strongly conserved between mouse and human, and plays an important role in epithelial maintenance and repair of the asthmatic mouse lung[38]. The decreased expression of these protocadherin genes, therefore, may be related to airway dilation in early BE. However, it is worth noting that while a loss of epithelial coherence and surface integrity were also noticed in chronic bronchitis, the genes associated with surface disintegration in chronic bronchitis were different from the genes associated with widespread radiographic BE[39], suggesting that the underlying molecular mechanism may be different.

Activation of the Wnt signaling pathway is important in maintaining the epithelial niche via the balance of epithelial/mesenchymal pairing[39-41]. LGR5, the gene most down-regulated in participants with widespread radiographic BE, has previously been reported to be required for maintaining the epithelial progenitor niche[40,42] Single-cell RNA-sequencing of the bronchial epithelium also suggests that genes decreased among participants with widespread BE are highly expressed among the basal cells of the bronchial airway, suggesting that these cells may be less prevalent or less active in individuals with widespread radiographic BE which may alter the structure of the airway or the ability to repair damaged airway epithelium.

Because BE is often accompanied by loss of cilia[43], we were intrigued to observe increased expression of cilia-related genes in participants with widespread radiographic BE. scRNA-seq of the bronchial epithelium also shows that these genes to be exclusively expressed among the ciliated cells. Previously, 310 genes were found to be up-regulated in ciliogenesis, the biologic process for the production of new cilium[29]. Of these 310 genes, 42 were up-regulated among participants with widespread BE. We hypothesize that the increased expression in genes important for ciliogenesis could be a response to cilium damage. A compensatory increase in ciliated cells is also supported by the deconvolution result, which predicts significant increases in the proportion of both the multiciliated cells and deuterosomal cells in samples from the bronchiectatic cluster. The predicted increase in the proportion of deuterosomal cells in samples in the bronchiectatic cluster is the most dramatic. These cells are marked by high expression of DEUP1, FOXN4, and CDC20B, have been reported as a precursor of multiciliated cells[44]. An alternative hypothesis is that the overproduction of certain cilium-related proteins contributes to faulty cilia assembly, reduced clearing capacity of the lung[41] and BE pathogenesis.

Proteasome related genes were up-regulated in individuals with widespread BE, including the constitutively expressed PSMB5 (Proteasome 20S Subunit Beta 5), and IFN-gamma inducible immunoproteasome subunits: PSMB8, PSMB9, PSMB10 (Proteasome 20S Subunit Beta 8, 9, 10)[46, 47]. The immunoproteasome enhances the generation of MHC I-associated peptide and may play important roles regulating dendritic cells[48, 49] The immunoproteasome has also been shown to facilitate the anti-viral immune response in the lung[50]. Combined with the result from GSEA, these molecular changes could reflect increased immune infiltration related to radiographic BE.

Large immunohistological studies observed the presence of CD8+ T cells[51,52], CD4+ T cells, macrophages, neutrophils, and interleukin 8 positive cells in the airways of patients with BE53. Taken together, the regulatory pattern suggests a compensatory response of producing more cilia or ciliated cells in an inflammatory environment, accompanied by a loss of surface integrity in the early stage of BE. The participants of the "bronchiectatic" gene expression cluster are characterized by having more symptoms such as cough and phlegm. Though 13 of the 30 participants in the bronchiectatic gene expression cluster have widespread radiographic BE, the other 17 do not. Interestingly, these 17 participants differ from the other participants without widespread BE in the other two gene expression clusters in that they are significantly more likely to have cough and phlegm production. Thus, the gene expression profile that defines the bronchiectatic cluster may be the consequence of two separate mechanisms—one that is associated with BE and one that is associated with cough and phlegm production that could be BE-dependent or independent. This discovery is also interesting in that it suggests not all who complain about cough and phlegm are the same, some may have transcriptomic changes in the airway that reflect radiographic BE.

While the participants in the intermediate gene expression cluster demonstrate a gene expression profile that is intermediate between the normal to the bronchiectatic clusters, they differ from those of the other clusters by being predominantly current smokers (75% compared to 37% in the normal cluster and 47% in the bronchiectatic cluster). This intermediate cluster could suggest a previously unappreciated risk of BE among smokers. Alternatively, those in the intermediate cluster may progress to develop more symptoms such as cough and phlegm production, and become more similar to those within the bronchiectatic group but without widespread BE. Longitudinal follow-up of participants of the intermediate cluster may validate whether smoking indeed leads to an increased risk for developing radiographic evidence of BE.

In conclusion, gene expression differences in individuals with radiographic signs of BE in multiple lobes reflect biologic processes that have previously been related to BE, as well as novel processes that may be associated with BE initiation. The gene expression alterations were also detected in a subpopulation of participants who present with cough and phlegm production but did not have widespread radiographic BE, and an intermediate pattern of gene expression enriched for current smokers. Longitudinal clinical follow-up and molecular profiling of the participants will provide an opportunity to explore the potential for progression and the molecular risk factors for developing radiographic BE.

REFERENCES

1. Chalmers J D, Chang A B, Chotirmall S H, Dhar R, McShane P J. Bronchiectasis. Nat Rev Dis Primer. 2018; 4(1):45. doi:10.1038/s41572-018-0042-3
2. Weycker D, Hansen G L, Seifer F D. Prevalence and incidence of noncystic fibrosis bronchiectasis among US adults in 2013. Chron Respir Dis. 2017; 14(4):377-384. doi: 10.1177/1479972317709649
3. Martinez C H, Okajima Y, Yen A, Maselli D J, Nardelli P, Rahaghi F, Young K, Kinney G, Hatt C, Galban C, Washko G R, Han M, Estépar R S J, Diaz A A. Paired C T Measures of Emphysema and Small Airways Disease and Lung Function and Exercise Capacity in Smokers with Radiographic Bronchiectasis. Acad Radiol. 2020 Mar. 23:S1076-6332(20)30099-4. doi: 10.1016/j.acra.2020.02.013. Epub ahead of print. PMID: 32217055; PMCID: PMC7508820.
4. Metersky M, Chalmers J. Bronchiectasis insanity: Doing the same thing over and over again and expecting different results? F1000Research. 2019; 8. doi:10.12688/f1000research.17295.1
5. Barker A F, O'Donnell A E, Flume P, et al. Aztreonam for inhalation solution in patients with non-cystic fibrosis bronchiectasis (AIR-BX1 and AIR-BX2): two randomised double-blind, placebo-controlled phase 3 trials. Lancet Respir Med. 2014; 2(9):738-749.doi:10.1016/S2213-2600(14)70165-1
6. De Soyza A, Aksamit T, Bandel T-J, et al. RESPIRE 1: a phase III placebo-controlled randomised trial of ciprofloxacin dry powder for inhalation in non-cystic fibrosis bronchiectasis. Eur Respir J. 2018; 51(1). doi:10.1183/13993003.02052-2017
7. Bilton D, Tino G, Barker A F, et al. Inhaled mannitol for non-cystic fibrosis bronchiectasis: a randomised, controlled trial. Thorax. 2014; 69(12):1073-1079. doi: 10.1136/thoraxjnl-2014-205587

8. Chen A C-H, Pena O M, Nel H J, et al. Airway cells from protracted bacterial bronchitis and bronchiectasis share similar gene expression profiles. Pediatr Pulmonol. 2018; 53(5):575-582. doi:10.1002/ppul.23984
9. Chalmers J D, Moffitt K L, Suarez-Cuartin G, et al. Neutrophil Elastase Activity Is Associated with Exacerbations and Lung Function Decline in Bronchiectasis. Am J Respir Crit Care Med. 2017; 195(10):1384-1393. doi: 10.1164/rccm.201605-1027OC
10. Guan W, Gao Y, Xu G, et al. Sputum matrix metalloproteinase-8 and -9 and tissue inhibitor of metalloproteinase-1 in bronchiectasis: Clinical correlates and prognostic implications. Respirology. 2015; 20(7):1073-1081. doi:https://doi.org/10.1111/resp.12582
11. Sridhar S, Schembri F, Zeskind J, et al. Smoking-induced gene expression changes in the bronchial airway are reflected in nasal and buccal epithelium. BMC Genomics. 2008; 9:259. doi: 10.1186/1471-2164-9-259
12. Spira A, Beane J E, Shah V, et al. Airway epithelial gene expression in the diagnostic evaluation of smokers with suspect lung cancer. Nat Med. 2007; 13(3):361-366. doi: 10.1038/nm1556
13. Steiling K, van den Berge M, Hijazi K, et al. A dynamic bronchial airway gene expression signature of chronic obstructive pulmonary disease and lung function impairment. Am J Respir Crit Care Med. 2013; 187(9):933-942. doi:10.1164/rccm.201208-1449OC
14. Billatos E, Ash S Y, Duan F, et al. Distinguishing smoking related lung disease phenotypes via imaging and molecular features. Chest. Published online Sep. 15, 2020. doi:10.1016/j.chest.2020.08.2115
15. Billatos E, Duan F, Moses E, et al. Detection of early lung cancer among military personnel (DECAMP) consortium: study protocols. BMC Pulm Med. 2019; 19(1):59. doi:10.1186/s12890-019-0825-7
16. Di Tommaso P, Chatzou M, Floden E W, Barja P P, Palumbo E, Notredame C. Nextflow enables reproducible computational workflows. Nat Biotechnol. 2017; 35(4):316-319. doi:10.1038/nbt.3820
17. Dobin A, Davis C A, Schlesinger F, et al. STAR: ultrafast universal RNA-seq aligner. Bioinforma Oxf Engl. 2013; 29(1):15-21. doi:10.1093/bioinformatics/bts635
18. Li B, Dewey C N. RSEM: accurate transcript quantification from RNA-Seq data with or without a reference genome. BMC Bioinformatics. 2011; 12(1):323. doi: 10.1186/1471-2105-12-323
19. Ritchie M E, Phipson B, Wu D, et al. limma powers differential expression analyses for RNA-sequencing and microarray studies. Nucleic Acids Res. 2015; 43(7):e47. doi:10.1093/nar/gkv007
20. Zhang Y, Parmigiani G, Johnson W E. ComBat-seq: batch effect adjustment for RNA-seq count data. NAR Genomics Bioinforma. 2020; 2(3). doi:10.1093/nargab/1qaa078
21. Szklarczyk D, Gable A L, Lyon D, et al. STRING v11: protein-protein association networks with increased coverage, supporting functional discovery in genome-wide experimental datasets. Nucleic Acids Res. 2019; 47(D1):D607-D613. doi:10.1093/nar/gky1131
22. Subramanian A, Tamayo P, Mootha V K, et al. Gene set enrichment analysis: a knowledge-based approach for interpreting genome-wide expression profiles. Proc Natl Acad Sci USA. 2005; 102(43):15545-15550. doi: 10.1073/pnas.0506580102
23. Liberzon A, Subramanian A, Pinchback R, Thorvaldsdóttir H, Tamayo P, Mesirov J P. Molecular signatures database (MSigDB) 3.0. Bioinforma Oxf Engl. 2011; 27(12):1739-1740. doi:10.1093/bioinformatics/btr260
24. Hänzelmann S, Castelo R, Guinney J. GSVA: gene set variation analysis for microarray and RNA-seq data. BMC Bioinformatics. 2013; 14:7. doi:10.1186/1471-2105-14-7
25. Butler A, Hoffman P, Smibert P, Papalexi E, Satija R. Integrating single-cell transcriptomic data across different conditions, technologies, and species. Nat Biotechnol. 2018; 36(5):411-420. doi:10.1038/nbt.4096
26. Deprez M, Zaragosi L E, Truchi M, Becavin C, Ruiz Garciá S, Arguel M J, Plaisant M, Magnone V, Lebrigand K, Abelanet S, Brau F, Paquet A, Pe'er D, Marquette C H, Leroy S, Barbry P. A Single-Cell Atlas of the Human Healthy Airways. Am J Respir Crit Care Med. 2020 Dec. 15; 202(12):1636-1645. doi: 10.1164/rccm.201911-2199OC. PMID: 32726565.
27. Aliee H, Theis F. AutoGeneS: Automatic gene selection using multi-objective optimization for RNA-seq deconvolution. bioRxiv. Published online Feb. 23, 2020: 2020.02.21.940650. doi: 10.1101/2020.02.21.940650
28. Horani A, Ferkol T W. Understanding Primary Ciliary Dyskinesia and Other Ciliopathies. J Pediatr. 2020 Nov. 23:S0022-3476(20)31452-9. doi: 10.1016/j.beds.2020.11.040.
29. Paff T, Kooi I E, Moutaouakil Y, et al. Diagnostic yield of a targeted gene panel in primary ciliary dyskinesia patients. Hum Mutat. 2018; 39(5):653-665. doi:https://doi.org/10.1002/humu.23403
30. Duclos G E, Teixeira V H, Autissier P, et al. Characterizing smoking-induced transcriptional heterogeneity in the human bronchial epithelium at single-cell resolution. Sci Adv. 2019; 5(12):eaaw3413. doi:10.1126/sciadv.aaw3413
31. Advances in bronchiectasis: endotyping, genetics, microbiome, and disease heterogeneity—The Lancet. Accessed Nov. 12, 2020. thelancet.com/journals/lancet/article/PIIS0140-6736(18)31767-7/fulltext
32. Whitwell F. A Study of the Pathology and Pathogenesis of Bronchiectasis *. Thorax. 1952; 7(3):213-239. 33 King P T, Holdsworth S R, Freezer N J, Villanueva E, Holmes P W. Characterisation of the onset and presenting clinical features of adult bronchiectasis. Respir Med. 2006; 100 (12):2183-2189. doi:10.1016/j.rmed.2006.03.012
34. Field C E. Bronchiectasis. Third report on a follow-up study of medical and surgical cases from childhood. Arch Dis Child. 1969; 44(237):551-561.
35. Wu Q, Maniatis T. A striking organization of a large family of human neural cadherin-like cell adhesion genes. Cell. 1999 Jun. 11; 97(6):779-90. doi: 10.1016/s0092-8674(00)80789-8. PMID: 10380929.
36. Weiner J A, Jontes J D. Protocadherins, not prototypical: a complex tale of their interactions, expression, and functions. Front Mol Neurosci. 2013; 6:4. Published 2013 Mar. 19. doi:10.3389/fnmol.2013.00004
37. Liu Y, Peng K, Xie R, Zheng J, Guo J, Wei R, Yang H, Cai C, Wei Q. Protocadherin γ-A7 is down-regulated in colorectal cancer and associated with the prognosis in patients with wild-type KRAS. Hum Pathol. 2019 January; 83:14-21. doi: 10.1016/j.humpath.2018.08.007. Epub 2018 Aug. 16. PMID: 30121367.
38. Koning H, van Oosterhout A J, Brouwer U, et al. Mouse protocadherin-1 gene expression is regulated by cigarette smoke exposure in vivo. PLoS One. 2014; 9(7):e98197. Published 2014 Jul. 3. doi:10.1371/journal.pone.0098197]

39. Samaha E, Vierlinger K, Weinhappel W, Godnic-Cvar J, Nöhammer C, Koczan D, Thiesen H J, Yanai H, Fraifeld V E, Ziesche R. Expression Profiling Suggests Loss of Surface Integrity and Failure of Regenerative Repair as Major Driving Forces for Chronic Obstructive Pulmonary Disease Progression. Am J Respir Cell Mol Biol. 2021 April; 64(4):441-452. doi: 10.1165/rcmb.2020-0270OC. PMID: 33524306.
40. Nabhan A N, Brownfield D G, Harbury P B, Krasnow M A, Desai T J. Single-cell Wnt signaling niches maintain stemness of alveolar type 2 cells. Science. 2018; 359 (6380):1118-1123. doi: 10.1126/science.aam6603
41. Yan K S, Janda C Y, Chang J, et al. Non-equivalence of Wnt and R-spondin ligands during Lgr5+ intestinal stem-cell self-renewal. Nature. 2017; 545(7653):238-242. doi: 10.1038/nature22313
42. Zepp J A, Zacharias W J, Frank D B, et al. Distinct mesenchymal lineages and niches promote epithelial self-renewal and myofibrogenesis in the lung. Cell. 2017; 170(6):1134-1148.e10. doi:10.1016/j.cell.2017.07.034
43. Barker N, van Es J H, Kuipers J, et al. Identification of stem cells in small intestine and colon by marker gene Lgr5. Nature. 2007; 449(7165):1003-1007. doi:10.1038/nature06196
44. Goddard M. Chapter 3 Histopathology of bronchiectasis. Published 2011. Accessed Nov. 12, 2020. /paper/Chapter-3-Histopathology-of-bronchiectasis-Goddard/flbbc368c49d13cbc222d22e12dfd57143676768
45. Ruiz García S, Deprez M, Lebrigand K, Cavard A, Paquet A, Arguel M J, Magnone V, Truchi M, Caballero I, Leroy S, Marquette C H, Marcet B, Barbry P, Zaragosi L E. Novel dynamics of human mucociliary differentiation revealed by single-cell RNA sequencing of nasal epithelial cultures. Development. 2019 Oct. 23; 146(20): dev177428. doi: 10.1242/dev.177428. PMID: 31558434; PMCID: PMC6826037.
46. Guo Z, Chen W, Wang L, Qian L. Clinical and Genetic Spectrum of Children with Primary Ciliary Dyskinesia in China. J Pediatr. 2020 October; 225:157-165.e5. doi: 10.1016/j jpeds.2020.05.052. Epub 2020 Jun. 2. PMID: 32502479.
47. Rouette A, Trofimov A, Haberl D, et al. Expression of immunoproteasome genes is regulated by cell-intrinsic and -extrinsic factors in human cancers. Sci Rep. 2016; 6(1):34019. doi:10.1038/srep34019
48. Basler M, Kirk C J, Groettrup M. The immunoproteasome in antigen processing and other immunological functions. Curr Opin Immunol. 2013 February; 25(1):74-80. doi: 10.1016/j.coi.2012.11.004. Epub 2012 Dec. 6. PMID: 23219269.
49. de Verteuil D, Muratore-Schroeder T L, Granados D P, Fortier M H, Hardy M P, Bramoullé A, Caron E, Vincent K, Mader S, Lemieux S, Thibault P, Perreault C. Deletion of immunoproteasome subunits imprints on the transcriptome and has a broad impact on peptides presented by major histocompatibility complex I molecules. Mol Cell Proteomics. 2010 September; 9(9):2034-47. doi: 10.1074/mcp.M900566-MCP200. Epub 2010 May 19. PMID: 20484733; PMCID: PMC2938112.
50. de Verteuil D A, Rouette A, Hardy M P, Lavallée S, Trofimov A, Gaucher É, Perreault C. Immunoproteasomes shape the transcriptome and regulate the function of dendritic cells. J Immunol. 2014 Aug. 1; 193(3):1121-32. doi: 10.4049/jimmunol.1400871. Epub 2014 Jun. 23. PMID: 24958905.
51. Keller I E, Vosyka O, Takenaka S, KloB A, Dahlmann B, Willems L I, Verdoes M, Overkleeft H S, Marcos E, Adnot S, Hauck S M, Ruppert C, Günther A, Herold S, Ohno S, Adler H, Eickelberg O, Meiners S. Regulation of immunoproteasome function in the lung. Sci Rep. 2015 May 19; 5:10230. doi: 10.1038/srep10230. PMID: 25989070; PMCID: PMC4437306.
52. Silva J R, Jones J A, Cole P J, Poulter L W. The immunological component of the cellular inflammatory infiltrate in bronchiectasis. Thorax. 1989; 44(8):668-673.
53. Lapa e Silva J R, Guerreiro D, Noble B, Poulter L W, Cole P J. Immunopathology of experimental bronchiectasis. Am J Respir Cell Mol Biol. 1989; 1(4):297-304. doi:10.1165/ajrcmb/1.4.297
54. Gaga M, Bentley A, Humbert M, et al. Increases in CD4+ T lymphocytes, macrophages, neutrophils and interleukin 8 positive cells in the airways of patients with bronchiectasis. Thorax. 1998; 53(8):685-691.

Table 9 depicts a table of 42 genes up-regulated among participants (bold) with widespread radiographic BE were previously included in a panel of genes (N=310) important in ciliogenesis.

| | | | | | |
|---|---|---|---|---|---|
| ABHD12B | C1orf158 | CCDC146 | DIXDC1 | DYNLRB2 | HAGHL |
| AGR3 | C1orf189 | CCDC147 | DNAAF1 | DYRK3 | HEATR2 |
| AK8 | C1orf192 | CCDC164 | DNAAF2 | DYX1C1 | HOOK1 |
| AKAP14 | C1orf87 | CCDC17 | DNAAF3 | DZIP1 | HYDIN |
| ANKMY1 | C20orf26 | CCDC170 | DNAH10 | DZIP3 | IFT122 |
| APOBEC4 | C20orf85 | CCDC176 | DNAH11 | EFCAB1 | IFT140 |
| ARL3 | C21orf58 | CCDC33 | DNAH12 | EFCAB6 | IFT172 |
| ARL6 | C21orf59 | CCDC37 | DNAH2 | EFHB | IFT46 |
| ARMC2 | C22orf23 | CCDC39 | DNAH3 | EFHC1 | IFT57 |
| ARMC4 | C4orf22 | CCDC40 | DNAH5 | EFHC2 | IFT74 |
| B9D1 | C6orf165 | CCDC41 | DNAH6 | ELL3 | IFT81 |
| B9D2 | C9orf116 | CCDC60 | DNAH7 | ENKD1 | IFT88 |
| BBS10 | C9orf117 | CCDC65 | DNAH9 | ENKUR | IL20RA |
| BBS2 | C9orf135 | CCDC78 | DNAI1 | FABP6 | INTU |
| BBS4 | C9orf24 | CCDC81 | DNAI2 | FAM154B | IQCD |
| BBS5 | CALML4 | CCDC89 | DNAJA1 | FAM206A | IQCG |
| BEST4 | CAPS | CCT6B | DNAJB13 | FAM216B | IQCH |
| BPHL | CAPSL | CETN2 | DNAL1 | FAM81A | IQUB |
| C10orf107 | CASC1 | CFTR | DNAL4 | FBXO15 | KATNAL2 |
| C10orf67 | CATSPERB | CLGN | DNALI1 | FOXJ1 | KBTBD4 |
| C11orf49 | CBY1 | CREB3L4 | DUSP14 | FSIP1 | KCNE1 |
| C11orf63 | CCDC103 | CSPP1 | DYDC1 | GLB1L | KIF19 |
| C11orf65 | CCDC104 | CYB5D1 | DYNC2H1 | GPR162 | KIF21A |
| C11orf70 | CCDC11 | CYB5D2 | DYNC2LI1 | GPX4 | KIF23 |
| C11orf74 | CCDC114 | DAW1 | DYNLL1 | GSTA1 | KIF24 |
| C15orf26 | CCDC135 | DHX40 | DYNLRB1 | GSTA3 | KIF27 |

-continued

| | | | | | |
|---|---|---|---|---|---|
| KIF3A | LRRC79 | NEK11 | RPGRIP1L | STX2 | TTC8 |
| KIF3B | LRRC80 | NME5 | RSPH1 | TAF1B | TUBA1A |
| KIF6 | LRRC81 | NME7 | RSPH10B | TBPL1 | TUBB4B |
| KIF9 | LRRC82 | NME8 | RSPH4A | TCTEX1D1 | TUBD1 |
| KIFAP3 | LRRC83 | NPHP1 | RSPH9 | TCTEX1D2 | TUBE1 |
| KIFAP4 | LRRC84 | NPHP4 | RTDR1 | TCTN1 | TUSC3 |
| KLHDC9 | LRRC85 | NQO1 | RUVBL1 | TCTN1 | UCHL1 |
| KTN1 | LRTOMT | NSUN7 | RUVBL2 | TEKT1 | VWA3B |
| LCA5L | LRWD1 | NUP62CL | SLC22A16 | TEKT2 | WDPCP |
| LRGUK | LZTFL1 | PACRG | SLC22A4 | TEX26 | WDR16 |
| LRRC18 | MAATS1 | PDE6B | SLC4A8 | TEX9 | WDR19 |
| LRRC23 | MAK | PFN2 | SMYD2 | THNSL1 | WDR38 |
| LRRC34 | MAP6 | PHTF1 | SOD1 | TMEM107 | WDR54 |
| LRRC43 | MAPRE3 | PIFO | SPA17 | TMEM254 | WDR60 |
| LRRC46 | MDH1B | PIH1D2 | SPAG16 | TMEM67 | WDR78 |
| LRRC48 | MEIG1 | PIH1D3 | SPAG17 | TNFAIP8L1 | WDR96 |
| LRRC49 | MKS1 | PLEKHB1 | SPAG6 | TPPP3 | WRAP53 |
| LRRC6 | MLF1 | PPIL6 | SPAG8 | TSGA10 | WRB |
| LRRC71 | MLH1 | PPOX | SPATA17 | TSNAXIP1 | XRN2 |
| LRRC72 | MNS1 | PPP1R32 | SPATA18 | TSPAN6 | ZBBX |
| LRRC73 | MORN2 | PROM1 | SPATA4 | TTC18 | ZCWPW1 |
| LRRC74 | MORN3 | RBKS | SPATA6 | TTC21A | ZMYND10 |
| LRRC75 | MPDZ | RFX3 | SPATA8 | TTC26 | ZMYND12 |
| LRRC76 | MROH9 | RGS22 | SPEF1 | TTC29 | ZNF474 |
| LRRC77 | MSMB | ROPN1L | STOML3 | TTC30A | |
| LRRC78 | MYCBP | RPGR | STRBP | TTC30B | |

Table 10 depicts a table of differentially expressed genes.

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 1 | ENSG00000196268 | ZNF493 | 284443 | p12 | -0.373862 | 5.596734994 | -5.07041 | 1.03E-06 | 0.0187688 | 5.3223 | down-regulated in participants with widespread BE | Gene Set A |
| 2 | ENSG00000175322 | ZNF519 | 162655 | p11.21 | -0.633308 | 2.0313887 | -4.28472 | 3.05E-05 | 0.0475762 | 1.9831 | down-regulated in participants with widespread BE | Gene Set A |
| 3 | ENSG00000271430 | | NA | q13.2 | -0.369932 | 5.144741026 | -4.16267 | 4.98E-05 | 0.0496081 | 1.7435 | down-regulated in participants with widespread BE | Gene Set A |
| 4 | ENSG00000078814 | MYH7B | 57644 | q11.22 | -0.885989 | 0.557843576 | -4.09903 | 6.41E-05 | 0.0496081 | 0.834 | down-regulated in participants with widespread BE | Gene Set A |
| 5 | ENSG00000224430 | MKRN5P | NA | q13.2 | -0.536838 | 1.839703911 | -3.99695 | 9.54E-05 | 0.0527906 | 1.0378 | down-regulated in participants with widespread BE | Gene Set A |
| 6 | ENSG00000270574 | | NA | q31.2 | -0.31402 | 2.228639691 | -3.93328 | 0.000122 | 0.0617796 | 0.9157 | down-regulated in participants with widespread BE | Gene Set A |
| 7 | ENSG00000268521 | VN1R83P | NA | p12 | -0.468895 | 0.166838736 | -3.84681 | 0.000169 | 0.0624298 | 0.1318 | down-regulated in participants with widespread BE | Gene Set A |
| 8 | ENSG00000268555 | | NA | p12 | -1.454442 | 1.361355155 | -3.8069 | 0.000196 | 0.0639453 | -1.154 | down-regulated in participants with widespread BE | Gene Set A |
| 9 | ENSG00000161551 | ZNF577 | 84765 | q13.41 | -0.366984 | 3.327577795 | -3.78226 | 0.000215 | 0.0663806 | 0.4816 | down-regulated in participants with widespread BE | Gene Set A |
| 10 | ENSG00000152042 | NBPF11 | c(101928050, 728912, 200030) | q21.1 | -0.282862 | 4.544081414 | -3.76939 | 0.000225 | 0.0663806 | 0.3905 | down-regulated in participants with widespread BE | Gene Set A |
| 11 | ENSG00000175356 | SCUBE2 | 57758 | p15.4 | -0.608746 | 0.993852294 | -3.73321 | 0.000257 | 0.0702506 | 0.0429 | down-regulated in participants with widespread BE | Gene Set A |
| 12 | ENSG00000101049 | SGK2 | 10110 | q13.12 | -0.809375 | 0.646456992 | -3.72698 | 0.000263 | 0.0702506 | -0.133 | down-regulated in participants with widespread BE | Gene Set A |
| 13 | ENSG00000163141 | BNIPL | 149428 | q21.3 | -0.369808 | 4.239275779 | -3.7153 | 0.000275 | 0.0702506 | 0.2319 | down-regulated in participants with widespread BE | Gene Set A |
| 14 | ENSG00000271533 | | NA | q13.2 | -0.353147 | 5.308472867 | -3.70777 | 0.000283 | 0.0702506 | 0.1579 | down-regulated in participants with widespread BE | Gene Set A |
| 15 | ENSG00000253305 | PCDHGB6 | 56100 | q31.3 | -0.373188 | 2.170772911 | -3.70474 | 0.000286 | 0.0702506 | 0.1897 | down-regulated in participants with widespread BE | Gene Set A |
| 16 | ENSG00000123384 | LRP1 | 4035 | q13.3 | -0.462369 | 7.271852355 | -3.69751 | 0.000293 | 0.0702506 | 0.1197 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 17 | ENSG00000254122 | PCDHGB7 | 56099 | q31.3 | -0.336967 | 2.746284455 | -3.6897 | 0.000302 | 0.0702506 | 0.1797 | down-regulated in participants with widespread BE | Gene Set A |
| 18 | ENSG00000262877 | | 100507520 | q25.3 | -0.66574 | 0.872650269 | -3.67639 | 0.000317 | 0.0702506 | -0.15 | down-regulated in participants with widespread BE | Gene Set A |
| 19 | ENSG00000114770 | ABCC5 | 10057 | q27.1 | -0.321034 | 7.703714819 | -3.66759 | 0.000327 | 0.0702506 | 0.0329 | down-regulated in participants with widespread BE | Gene Set A |
| 20 | ENSG00000067601 | PMS2P4 | 5382 | q11.21 | -0.321673 | 1.076438606 | -3.62496 | 0.000381 | 0.0715125 | -0.197 | down-regulated in participants with widespread BE | Gene Set A |
| 21 | ENSG00000235954 | TTC28-AS1 | 284900 | q12.1 | -0.286709 | 3.274082755 | -3.58833 | 0.000435 | 0.0715125 | -0.135 | down-regulated in participants with widespread BE | Gene Set A |
| 22 | ENSG00000257704 | PRR24 | 255783 | q13.32 | -0.354272 | 0.537175 | -3.55978 | 0.000481 | 0.0722946 | -0.494 | down-regulated in participants with widespread BE | Gene Set A |
| 23 | ENSG00000110651 | CD81 | 975 | p15.5 | -0.268316 | 7.25661036 | -3.54676 | 0.000504 | 0.0725389 | -0.367 | down-regulated in participants with widespread BE | Gene Set A |
| 24 | ENSG00000205517 | RGL3 | 57139 | p13.2 | -0.769069 | -0.040252083 | -3.53231 | 0.00053 | 0.0725389 | -0.867 | down-regulated in participants with widespread BE | Gene Set A |
| 25 | ENSG00000105426 | PTPRS | 5802 | p13.3 | -0.439135 | 6.032297635 | -3.51871 | 0.000556 | 0.0725389 | -0.468 | down-regulated in participants with widespread BE | Gene Set A |
| 26 | ENSG00000271011 | | NA | q31.2 | -0.446639 | -0.390831528 | -3.5052 | 0.000583 | 0.0725389 | -0.936 | down-regulated in participants with widespread BE | Gene Set A |
| 27 | ENSG00000249459 | ZNF286B | 729288 | p11.2 | -0.384483 | 1.440476365 | -3.49569 | 0.000603 | 0.0725389 | -0.503 | down-regulated in participants with widespread BE | Gene Set A |
| 28 | ENSG00000185838 | GNB1L | 54584 | q11.21 | -0.412889 | 0.535969192 | -3.48744 | 0.00062 | 0.0725389 | -0.691 | down-regulated in participants with widespread BE | Gene Set A |
| 29 | ENSG00000253159 | PCDHGA12 | 26025 | q31.3 | -0.519934 | 1.12782512 | -3.47913 | 0.000639 | 0.0725389 | -0.607 | down-regulated in participants with widespread BE | Gene Set A |
| 30 | ENSG00000112394 | SLC16A10 | 117247 | q21 | -0.852858 | 1.322316991 | -3.47496 | 0.000648 | 0.0725389 | -0.639 | down-regulated in participants with widespread BE | Gene Set A |
| 31 | ENSG00000160229 | ZNF66 | NA | p12 | -0.360242 | 2.322159198 | -3.46599 | 0.000669 | 0.0725389 | -0.513 | down-regulated in participants with widespread BE | Gene Set A |
| 32 | ENSG00000261584 | | 101929855 | p22.2 | -0.590419 | 1.207669902 | -3.46386 | 0.000674 | 0.0725389 | -0.654 | down-regulated in participants with widespread BE | Gene Set A |
| 33 | ENSG00000197935 | ZNF311 | 282890 | p22.1 | -0.426375 | 0.930152578 | -3.45708 | 0.00069 | 0.0725389 | -0.7 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 34 | ENSG00000250312 | ZNF718 | NA | p16.3 | -0.320308 | 3.779959522 | -3.45449 | 0.000696 | 0.0725389 | -0.572 | down-regulated in participants with widespread BE | Gene Set A |
| 35 | ENSG00000223745 | | c(101930643, 101930082, 100131564) | p22.1 | -0.309707 | 5.108950883 | -3.44472 | 0.00072 | 0.0725389 | -0.68 | down-regulated in participants with widespread BE | Gene Set A |
| 36 | ENSG00000172476 | RAB40A | 142684 | q22.2 | -0.564195 | -0.162126278 | -3.44096 | 0.000729 | 0.0725389 | -1.043 | down-regulated in participants with widespread BE | Gene Set A |
| 37 | ENSG00000268119 | | 101928983 | p12 | -1.579693 | -0.911384942 | -3.43358 | 0.000748 | 0.0725389 | -1.687 | down-regulated in participants with widespread BE | Gene Set A |
| 38 | ENSG00000262576 | PCDHGA4 | 56111 | q31.3 | -0.560551 | 0.666229443 | -3.42521 | 0.00077 | 0.0728517 | -0.848 | down-regulated in participants with widespread BE | Gene Set A |
| 39 | ENSG00000270589 | | NA | q25.2 | -0.483294 | 0.217061199 | -3.40632 | 0.000821 | 0.0731174 | -0.995 | down-regulated in participants with widespread BE | Gene Set A |
| 40 | ENSG00000256142 | | NA | p35.1 | -0.378868 | 1.744258757 | -3.39975 | 0.00084 | 0.0734175 | -0.739 | down-regulated in participants with widespread BE | Gene Set A |
| 41 | ENSG00000198719 | DLL1 | 28514 | q27 | -0.425586 | 4.141001597 | -3.37506 | 0.000914 | 0.0745239 | -0.83 | down-regulated in participants with widespread BE | Gene Set A |
| 42 | ENSG00000224775 | BRAFP1 | NA | q13.3 | -0.731281 | -0.661560336 | -3.37054 | 0.000928 | 0.0750074 | -1.438 | down-regulated in participants with widespread BE | Gene Set A |
| 43 | ENSG00000253873 | PCDHGA11 | c(56105, 5098) | q31.3 | -0.452431 | 1.577629809 | -3.35868 | 0.000966 | 0.0751012 | -0.867 | down-regulated in participants with widespread BE | Gene Set A |
| 44 | ENSG00000230590 | FTX | 100302692 | q13.2 | -0.31663 | 5.073152772 | -3.32888 | 0.001069 | 0.0768462 | -1.033 | down-regulated in participants with widespread BE | Gene Set A |
| 45 | ENSG00000059122 | FLYWCH1 | 84256 | p13.3 | -0.355272 | 4.562456257 | -3.30977 | 0.00114 | 0.0772782 | -1.06 | down-regulated in participants with widespread BE | Gene Set A |
| 46 | ENSG00000139910 | NOVA1 | 4857 | q12 | -1.230222 | 0.592614451 | -3.29905 | 0.001181 | 0.0776495 | -1.314 | down-regulated in participants with widespread BE | Gene Set A |
| 47 | ENSG00000120071 | KANSL1 | c(101929776, 284058) | q21.31 | -0.328051 | 6.40889867 | -3.29782 | 0.001186 | 0.0776495 | -1.151 | down-regulated in participants with widespread BE | Gene Set A |
| 48 | ENSG00000231205 | ZNF826P | c(101929933, 664701) | p12 | -0.437667 | 1.937316543 | -3.29268 | 0.001207 | 0.0777429 | -1.023 | down-regulated in participants with widespread BE | Gene Set A |
| 49 | ENSG00000196295 | | c(101928623, 401320) | p14.3 | -0.340357 | 5.907830918 | -3.27024 | 0.0013 | 0.0782464 | -1.231 | down-regulated in participants with widespread BE | Gene Set A |
| 50 | ENSG00000229036 | | NA | q24.2 | -0.465598 | -0.57209196 | -3.26824 | 0.001309 | 0.0782464 | -1.54 | down-regulated in participants with widespread BE | Gene Set A |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 51 | ENSG00000140332 | TLE3 | 7090 | q23 | -0.35392 | 5.048295011 | -3.26357 | 0.001329 | 0.0782464 | -1.225 | down-regulated in participants with widespread BE | Gene Set A |
| 52 | ENSG00000102349 | KLF8 | 11279 | p11.21 | -0.388384 | 3.118969843 | -3.26306 | 0.001332 | 0.0782464 | -1.098 | down-regulated in participants with widespread BE | Gene Set A |
| 53 | ENSG00000170500 | LONRF2 | 164832 | q11.2 | -0.389735 | 4.583757799 | -3.24924 | 0.001394 | 0.0782464 | -1.238 | down-regulated in participants with widespread BE | Gene Set A |
| 54 | ENSG00000248449 | PCDHGB8P | 56120 | q31.3 | -0.461523 | 1.234184376 | -3.24174 | 0.001429 | 0.0782464 | -1.213 | down-regulated in participants with widespread BE | Gene Set A |
| 55 | ENSG00000259326 | | NA | q14 | -0.385744 | 1.090192115 | -3.23378 | 0.001467 | 0.0782464 | -1.244 | down-regulated in participants with widespread BE | Gene Set A |
| 56 | ENSG00000131480 | AOC2 | 314 | q21.31 | -0.469872 | 0.653211326 | -3.23154 | 0.001478 | 0.0782464 | -1.326 | down-regulated in participants with widespread BE | Gene Set A |
| 57 | ENSG00000108352 | RAPGEF L1 | 51195 | q21.1 | -0.388695 | 5.441786917 | -3.23152 | 0.001478 | 0.0782464 | -1.334 | down-regulated in participants with widespread BE | Gene Set A |
| 58 | ENSG00000175414 | ARL10 | 285598 | q35.2 | -0.478749 | 2.437415609 | -3.22613 | 0.001505 | 0.0782464 | -1.188 | down-regulated in participants with widespread BE | Gene Set A |
| 59 | ENSG00000142303 | ADAMTS10 | 81794 | p13.2 | -0.608969 | -0.186749938 | -3.22483 | 0.001511 | 0.0782464 | -1.568 | down-regulated in participants with widespread BE | Gene Set A |
| 60 | ENSG00000250303 | | c(100506870, 283140) | q23.1 | -0.313834 | 2.734902092 | -3.22408 | 0.001515 | 0.0782464 | -1.196 | down-regulated in participants with widespread BE | Gene Set A |
| 61 | ENSG00000182463 | TSHZ2 | 128553 | q13.2 | -0.268513 | 6.400357581 | -3.22348 | 0.001518 | 0.0782464 | -1.372 | down-regulated in participants with widespread BE | Gene Set A |
| 62 | ENSG00000189149 | CRYM-AS1 | 400508 | p12.2 | -0.406337 | -0.285883813 | -3.22259 | 0.001522 | 0.0782464 | -1.547 | down-regulated in participants with widespread BE | Gene Set A |
| 63 | ENSG00000213971 | | NA | p12 | -0.344814 | 4.075772034 | -3.21667 | 0.001552 | 0.0782464 | -1.297 | down-regulated in participants with widespread BE | Gene Set A |
| 64 | ENSG00000262470 | TVP23CP2 | NA | p13.12 | -0.636787 | 0.88125449 | -3.21602 | 0.001555 | 0.0782464 | -1.349 | down-regulated in participants with widespread BE | Gene Set A |
| 65 | ENSG00000234978 | | NA | q21.1 | -0.692959 | 1.413524832 | -3.20202 | 0.001628 | 0.0793191 | -1.317 | down-regulated in participants with widespread BE | Gene Set A |
| 66 | ENSG00000204366 | ZBTB12 | 221527 | p21.33 | -0.294153 | 1.538024787 | -3.20041 | 0.001637 | 0.0795263 | -1.286 | down-regulated in participants with widespread BE | Gene Set A |
| 67 | ENSG00000261934 | PCDHGA9 | 56107 | q31.3 | -0.36223 | 2.197922519 | -3.1871 | 0.00171 | 0.0804147 | -1.295 | down-regulated in participants with widespread BE | Gene Set A |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 68 | ENSG00000237818 | RPS3AP29 | NA | q21.3 | −0.921057 | −1.102135751 | −3.18464 | 0.001724 | 0.0804147 | −1.963 | down-regulated in participants with widespread BE | Gene Set A |
| 69 | ENSG00000171435 | KSR2 | 283455 | q24.23 | −0.524362 | 1.633630002 | −3.18357 | 0.00173 | 0.0804147 | −1.332 | down-regulated in participants with widespread BE | Gene Set A |
| 70 | ENSG00000132199 | ENOSF1 | 55556 | p11.32 | −0.300739 | 6.664615427 | −3.17538 | 0.001776 | 0.0807103 | −1.51 | down-regulated in participants with widespread BE | Gene Set A |
| 71 | ENSG00000233175 | | NA | q21.31 | −0.588063 | −0.846043944 | −3.16872 | 0.001815 | 0.0807549 | −1.89 | down-regulated in participants with widespread BE | Gene Set A |
| 72 | ENSG00000260729 | | NA | q23 | −0.553629 | 1.831709842 | −3.16641 | 0.001829 | 0.0807549 | −1.368 | down-regulated in participants with widespread BE | Gene Set A |
| 73 | ENSG00000268658 | LINC00664 | 400680 | p12 | −1.457355 | −1.602545471 | −3.15988 | 0.001868 | 0.0810493 | −2.37 | down-regulated in participants with widespread BE | Gene Set A |
| 74 | ENSG00000197134 | ZNF257 | 113835 | p12 | −0.672831 | 1.478119049 | −3.15276 | 0.001912 | 0.0817261 | −1.434 | down-regulated in participants with widespread BE | Gene Set A |
| 75 | ENSG00000236375 | POU5F1P5 | NA | q21.3 | −0.538846 | −0.481763899 | −3.14533 | 0.001958 | 0.082174 | −1.785 | down-regulated in participants with widespread BE | Gene Set A |
| 76 | ENSG00000167363 | FN3K | 64122 | q25.3 | −0.422867 | 1.748016445 | −3.12632 | 0.002082 | 0.083002 | −1.47 | down-regulated in participants with widespread BE | Gene Set A |
| 77 | ENSG00000204514 | ZNF814 | 730051 | q13.43 | −0.377007 | 4.191441388 | −3.12608 | 0.002083 | 0.083002 | −1.563 | down-regulated in participants with widespread BE | Gene Set A |
| 78 | ENSG00000165841 | CYP2C19 | 1557 | q23.33 | −0.414322 | 2.594689075 | −3.12512 | 0.00209 | 0.083002 | −1.463 | down-regulated in participants with widespread BE | Gene Set A |
| 79 | ENSG00000270096 | | NA | q26.2 | −0.363082 | −0.205004095 | −3.11968 | 0.002126 | 0.0830303 | −1.744 | down-regulated in participants with widespread BE | Gene Set A |
| 80 | ENSG00000128655 | PDE11A | 50940 | q31.2 | −0.372778 | 1.124885122 | −3.11885 | 0.002132 | 0.0830303 | −1.531 | down-regulated in participants with widespread BE | Gene Set A |
| 81 | ENSG00000248019 | FAM13A-AS1 | 285512 | q22.1 | −0.387007 | 2.625005191 | −3.11188 | 0.00218 | 0.0830303 | −1.498 | down-regulated in participants with widespread BE | Gene Set A |
| 82 | ENSG00000156113 | KCNMA1 | 3778 | q22.3 | −0.658379 | 1.983806654 | −3.11078 | 0.002188 | 0.0830303 | −1.51 | down-regulated in participants with widespread BE | Gene Set A |
| 83 | ENSG00000247270 | | NA | q21 | −0.635217 | −0.203902766 | −3.11045 | 0.00219 | 0.0830303 | −1.822 | down-regulated in participants with widespread BE | Gene Set A |
| 84 | ENSG00000270019 | | NA | q14.1 | −0.292233 | 1.29677979 | −3.10978 | 0.002195 | 0.0830303 | −1.534 | down-regulated in participants with widespread BE | Gene Set A |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 85 | ENSG00000270154 | | NA | p23.1 | -0.770644 | -0.272646071 | -3.1075 | 0.002211 | 0.0830303 | -1.881 | down-regulated in participants with widespread BE | Gene Set A |
| 86 | ENSG00000248445 | | 101927233 | q23.1 | -0.391495 | 0.483453292 | -3.09985 | 0.002266 | 0.0834437 | -1.655 | down-regulated in participants with widespread BE | Gene Set A |
| 87 | ENSG00000234129 | | 101928302 | p22.2 | -0.360615 | -0.046815836 | -3.09416 | 0.002307 | 0.0838518 | -1.775 | down-regulated in participants with widespread BE | Gene Set A |
| 88 | ENSG00000267169 | | 100507373 | p13.12 | -0.388354 | 0.205727182 | -3.09375 | 0.00231 | 0.0838518 | -1.722 | down-regulated in participants with widespread BE | Gene Set A |
| 89 | ENSG00000261423 | | NA | q24.1 | -0.310419 | 1.608275128 | -3.09192 | 0.002324 | 0.0839935 | -1.563 | down-regulated in participants with widespread BE | Gene Set A |
| 90 | ENSG00000205885 | C1RL-AS1 | 283314 | p13.31 | -0.55558 | 3.119080642 | -3.09025 | 0.002336 | 0.0839935 | -1.57 | down-regulated in participants with widespread BE | Gene Set A |
| 91 | ENSG00000237522 | NONOP2 | NA | p16.1 | -0.370773 | 0.41941161 | -3.08877 | 0.002347 | 0.0840709 | -1.694 | down-regulated in participants with widespread BE | Gene Set A |
| 92 | ENSG00000170615 | SLC26A5 | 375611 | q22.1 | -0.442566 | 1.632739485 | -3.0877 | 0.002355 | 0.084104 | -1.577 | down-regulated in participants with widespread BE | Gene Set A |
| 93 | ENSG00000247708 | STX18-AS1 | 100507266 | p16.2 | -0.296965 | 2.404303214 | -3.08051 | 0.00241 | 0.0842685 | -1.579 | down-regulated in participants with widespread BE | Gene Set A |
| 94 | ENSG00000145020 | AMT | 275 | p21.31 | -0.402089 | 3.393517322 | -3.07632 | 0.002442 | 0.0842685 | -1.63 | down-regulated in participants with widespread BE | Gene Set A |
| 95 | ENSG00000232626 | | NA | q32.1 | -0.445564 | 0.734023962 | -3.07094 | 0.002484 | 0.0842685 | -1.691 | down-regulated in participants with widespread BE | Gene Set A |
| 96 | ENSG00000235834 | | 101928389 | p22.13 | -0.457789 | 1.546976599 | -3.07005 | 0.002491 | 0.0842685 | -1.623 | down-regulated in participants with widespread BE | Gene Set A |
| 97 | ENSG00000265727 | RN7SL648P | NA | q13.2 | -0.465209 | 0.550606843 | -3.06844 | 0.002504 | 0.0843097 | -1.719 | down-regulated in participants with widespread BE | Gene Set A |
| 98 | ENSG00000254634 | | NA | p11.2 | -0.283095 | 3.651578839 | -3.05913 | 0.002579 | 0.0853677 | -1.709 | down-regulated in participants with widespread BE | Gene Set A |
| 99 | ENSG00000236144 | | 100506469 | q13.12 | -0.302186 | 3.387793435 | -3.05705 | 0.002596 | 0.0854302 | -1.69 | down-regulated in participants with widespread BE | Gene Set A |
| 100 | ENSG00000229325 | ACAP2-IT1 | NA | q29 | -0.424659 | -0.026791726 | -3.05586 | 0.002606 | 0.0854302 | -1.864 | down-regulated in participants with widespread BE | Gene Set A |
| 101 | ENSG00000268472 | | NA | q23.1 | -0.540275 | 0.011708827 | -3.05549 | 0.002609 | 0.0854302 | -1.861 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 102 | ENSG00000180113 | TDRD6 | 221400 | p12.3 | −0.462516 | 1.623665598 | −3.05422 | 0.002619 | 0.0854302 | −1.661 | down-regulated in participants with widespread BE | Gene Set A |
| 103 | ENSG00000272563 | | NA | q13 | −0.58593 | −0.083362394 | −3.05331 | 0.002627 | 0.0854302 | −1.903 | down-regulated in participants with widespread BE | Gene Set A |
| 104 | ENSG00000249129 | SUDS3P1 | NA | q35.3 | −0.382349 | 1.181721544 | −3.05107 | 0.002645 | 0.0854302 | −1.691 | down-regulated in participants with widespread BE | Gene Set A |
| 105 | ENSG00000253953 | PCDHGB4 | c(56101, 8641) | q31.3 | −0.337087 | 2.120479802 | −3.04862 | 0.002666 | 0.0854302 | −1.66 | down-regulated in participants with widespread BE | Gene Set A |
| 106 | ENSG00000240445 | FOXO3B | 2310 | p11.2 | −0.432154 | 0.141961044 | −3.04664 | 0.002683 | 0.0855198 | −1.843 | down-regulated in participants with widespread BE | Gene Set A |
| 107 | ENSG00000272977 | | NA | q11.23 | −0.803751 | 2.042701138 | −3.04662 | 0.002683 | 0.0855198 | −1.674 | down-regulated in participants with widespread BE | Gene Set A |
| 108 | ENSG00000196421 | LINC00176 | 284739 | q13.33 | −0.521951 | 0.078865815 | −3.04502 | 0.002696 | 0.0855297 | −1.88 | down-regulated in participants with widespread BE | Gene Set A |
| 109 | ENSG00000091536 | MYO15A | 51168 | p11.2 | −0.472811 | 1.374116589 | −3.03524 | 0.002781 | 0.0865262 | −1.725 | down-regulated in participants with widespread BE | Gene Set A |
| 110 | ENSG00000240288 | GHRLOS | 100126793 | p25.3 | −0.557278 | 1.363090644 | −3.02576 | 0.002865 | 0.0868249 | −1.751 | down-regulated in participants with widespread BE | Gene Set A |
| 111 | ENSG00000100154 | TTC28 | 23331 | q12.1 | −0.329515 | 3.962352293 | −3.02313 | 0.002888 | 0.0868249 | −1.831 | down-regulated in participants with widespread BE | Gene Set A |
| 112 | ENSG00000271840 | | NA | p36.12 | −0.429037 | 0.544248249 | −3.02117 | 0.002906 | 0.0868249 | −1.832 | down-regulated in participants with widespread BE | Gene Set A |
| 113 | ENSG00000203832 | NBPF20 | c(101060226, 100132406, 343505, 25832) | q21.2 | −0.283172 | 3.772108048 | −3.01686 | 0.002946 | 0.0868249 | −1.837 | down-regulated in participants with widespread BE | Gene Set A |
| 114 | ENSG00000162738 | VANGL2 | 57216 | q23.2 | −0.346221 | 4.296233137 | −3.01227 | 0.002988 | 0.0868249 | −1.892 | down-regulated in participants with widespread BE | Gene Set A |
| 115 | ENSG00000168970 | JMJD7-PLA2G4B | 8681 | q15.1 | −0.446367 | 4.795563329 | −3.00963 | 0.003013 | 0.0868249 | −1.93 | down-regulated in participants with widespread BE | Gene Set A |
| 116 | ENSG00000267940 | | NA | p15.4 | −0.396583 | 0.488368366 | −3.00794 | 0.003029 | 0.0868249 | −1.87 | down-regulated in participants with widespread BE | Gene Set A |
| 117 | ENSG00000197444 | OGDHL | 55753 | q11.23 | −0.755885 | −0.508228015 | −3.00646 | 0.003043 | 0.0868249 | −2.133 | down-regulated in participants with widespread BE | Gene Set A |
| 118 | ENSG00000206195 | | NA | q11.1 | −1.358142 | −1.456089492 | −3.00482 | 0.003059 | 0.0868249 | −2.548 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 119 | ENSG00000172059 | KLF11 | 8462 | p25.1 | -0.319275 | 2.842591541 | -3.00404 | 0.003066 | 0.0868249 | -1.793 | down-regulated in participants with widespread BE | Gene Set A |
| 120 | ENSG00000263327 | TAPT1-AS1 | 202020 | p15.32 | -0.301991 | 4.090333836 | -3.00241 | 0.003082 | 0.0869183 | -1.903 | down-regulated in participants with widespread BE | Gene Set A |
| 121 | ENSG00000105696 | TMEM59L | 25789 | p13.11 | -0.849431 | -1.112063875 | -2.99389 | 0.003164 | 0.0876268 | -2.338 | down-regulated in participants with widespread BE | Gene Set A |
| 122 | ENSG00000144476 | ACKR3 | 57007 | q37.3 | -0.392783 | 3.80803321 | -2.99358 | 0.003168 | 0.0876268 | -1.892 | down-regulated in participants with widespread BE | Gene Set A |
| 123 | ENSG00000184441 | | NA | q22.3 | -0.377653 | 0.470919789 | -2.99338 | 0.003169 | 0.0876268 | -1.904 | down-regulated in participants with widespread BE | Gene Set A |
| 124 | ENSG00000108773 | KAT2A | 2648 | q21.2 | -0.31247 | 4.102967159 | -2.99158 | 0.003187 | 0.0876268 | -1.932 | down-regulated in participants with widespread BE | Gene Set A |
| 125 | ENSG00000261052 | SULT1A3 | c(101929857, 445329, 6818) | p11.2 | -0.495401 | 2.690066402 | -2.97686 | 0.003336 | 0.0884774 | -1.852 | down-regulated in participants with widespread BE | Gene Set A |
| 126 | ENSG00000116991 | SIPA1L2 | 57568 | q42.2 | -0.29547 | 4.875589283 | -2.97609 | 0.003344 | 0.0884774 | -2.036 | down-regulated in participants with widespread BE | Gene Set A |
| 127 | ENSG00000229994 | RPL5P4 | NA | p34.3 | -0.412369 | 0.560062712 | -2.9754 | 0.003351 | 0.0884774 | -1.933 | down-regulated in participants with widespread BE | Gene Set A |
| 128 | ENSG00000174080 | CTSF | 8722 | q13.2 | -0.334364 | 2.94345493 | -2.97287 | 0.003378 | 0.0884774 | -1.879 | down-regulated in participants with widespread BE | Gene Set A |
| 129 | ENSG00000160321 | ZNF208 | 7757 | p12 | -1.331024 | 0.537316643 | -2.97112 | 0.003396 | 0.0884774 | -2.094 | down-regulated in participants with widespread BE | Gene Set A |
| 130 | ENSG00000130649 | CYP2E1 | 1571 | q26.3 | -0.58003 | 0.189081914 | -2.96629 | 0.003447 | 0.08858 | -2.038 | down-regulated in participants with widespread BE | Gene Set A |
| 131 | ENSG00000185513 | L3MBTL1 | 26013 | q13.12 | -0.420395 | 4.747533594 | -2.96399 | 0.003472 | 0.08858 | -2.052 | down-regulated in participants with widespread BE | Gene Set A |
| 132 | ENSG00000162373 | BEND5 | 79656 | p33 | -0.316432 | 3.382523066 | -2.96185 | 0.003495 | 0.08858 | -1.944 | down-regulated in participants with widespread BE | Gene Set A |
| 133 | ENSG00000076555 | ACACB | 32 | q24.11 | -0.29932 | 4.968959135 | -2.96167 | 0.003497 | 0.08858 | -2.08 | down-regulated in participants with widespread BE | Gene Set A |
| 134 | ENSG00000261087 | | NA | q22.3 | -0.470303 | 0.192500505 | -2.95945 | 0.003521 | 0.0887618 | -2.03 | down-regulated in participants with widespread BE | Gene Set A |
| 135 | ENSG00000100968 | NFATC4 | 4776 | q12 | -0.38519 | 3.015229071 | -2.95533 | 0.003566 | 0.0888089 | -1.929 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 136 | ENSG00000172824 | CES4A | 283848 | q22.1 | -0.386675 | 6.467823314 | -2.95507 | 0.003569 | 0.0888089 | -2.131 | down-regulated in participants with widespread BE | Gene Set A |
| 137 | ENSG00000198939 | ZFP2 | 80108 | q35.3 | -0.27857 | 1.279205891 | -2.95187 | 0.003604 | 0.0888908 | -1.922 | down-regulated in participants with widespread BE | Gene Set A |
| 138 | ENSG00000164061 | BSN | 8927 | p21.31 | -0.498619 | 0.613900498 | -2.95081 | 0.003616 | 0.0888908 | -1.989 | down-regulated in participants with widespread BE | Gene Set A |
| 139 | ENSG00000254469 | | NA | q13.4 | -0.254281 | 2.348690856 | -2.94699 | 0.003658 | 0.089096 | -1.923 | down-regulated in participants with widespread BE | Gene Set A |
| 140 | ENSG00000144026 | ZNF514 | 84874 | q11.1 | -0.257862 | 4.660840189 | -2.9447 | 0.003684 | 0.0891181 | -2.109 | down-regulated in participants with widespread BE | Gene Set A |
| 141 | ENSG00000176593 | | NA | q13.43 | -0.434475 | 2.61160695 | -2.9408 | 0.003729 | 0.0891181 | -1.943 | down-regulated in participants with widespread BE | Gene Set A |
| 142 | ENSG00000232116 | | NA | p11.2 | -0.424457 | 2.65011455 | -2.93845 | 0.003756 | 0.0891719 | -1.95 | down-regulated in participants with widespread BE | Gene Set A |
| 143 | ENSG00000115507 | OTX1 | 5013 | p15 | -0.349948 | 4.168349989 | -2.9323 | 0.003827 | 0.0891719 | -2.096 | down-regulated in participants with widespread BE | Gene Set A |
| 144 | ENSG00000269918 | | NA | p23.1 | -0.319879 | 1.707054684 | -2.93023 | 0.003852 | 0.0891719 | -1.96 | down-regulated in participants with widespread BE | Gene Set A |
| 145 | ENSG00000135407 | AVIL | 10677 | q14.1 | -0.37943 | 3.620057634 | -2.92804 | 0.003877 | 0.0891719 | -2.052 | down-regulated in participants with widespread BE | Gene Set A |
| 146 | ENSG00000271971 | | NA | q22.1 | -0.319733 | 0.043066766 | -2.9239 | 0.003927 | 0.0893264 | -2.119 | down-regulated in participants with widespread BE | Gene Set A |
| 147 | ENSG00000155970 | MICU3 | 286097 | p22 | -0.286995 | 2.824654206 | -2.91444 | 0.004042 | 0.0905893 | -2.025 | down-regulated in participants with widespread BE | Gene Set A |
| 148 | ENSG00000089351 | GRAMD1A | 57655 | q13.11 | -0.373333 | 3.603286138 | -2.91173 | 0.004076 | 0.090932 | -2.091 | down-regulated in participants with widespread BE | Gene Set A |
| 149 | ENSG00000133466 | C1QTNF6 | 114904 | q12.3 | -0.339904 | 2.33484653 | -2.90756 | 0.004128 | 0.0910552 | -2.02 | down-regulated in participants with widespread BE | Gene Set A |
| 150 | ENSG00000084731 | KIF3C | 3797 | p23.3 | -0.315746 | 2.150411086 | -2.90593 | 0.004148 | 0.0910644 | -2.02 | down-regulated in participants with widespread BE | Gene Set A |
| 151 | ENSG00000186919 | ZACN | 353174 | q25.1 | -0.619248 | 0.099822222 | -2.90516 | 0.004158 | 0.0910644 | -2.175 | down-regulated in participants with widespread BE | Gene Set A |
| 152 | ENSG00000229917 | RPL7P46 | NA | p13.13 | -0.576638 | -0.047929785 | -2.90387 | 0.004174 | 0.091201 | -2.206 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 153 | ENSG00000168907 | PLA2G4F | 255189 | q15.1 | -0.474951 | 0.675610165 | -2.9028 | 0.004188 | 0.0912822 | -2.087 | down-regulated in participants with widespread BE | Gene Set A |
| 154 | ENSG00000213599 | SLX1A-SULT1A3 | 100526830 | p11.2 | -0.439135 | 2.461922696 | -2.89432 | 0.004297 | 0.0916715 | -2.054 | down-regulated in participants with widespread BE | Gene Set A |
| 155 | ENSG00000176293 | ZNF135 | 7694 | q13.43 | -0.370724 | 3.598201432 | -2.89279 | 0.004317 | 0.0916715 | -2.139 | down-regulated in participants with widespread BE | Gene Set A |
| 156 | ENSG00000228960 | OR2A9P | c(441295, 401428) | q35 | -0.712066 | 1.988978093 | -2.89131 | 0.004336 | 0.0916715 | -2.054 | down-regulated in participants with widespread BE | Gene Set A |
| 157 | ENSG00000165548 | TMEM63C | 57156 | q24.3 | -0.438603 | 3.018381497 | -2.88635 | 0.004402 | 0.0916715 | -2.105 | down-regulated in participants with widespread BE | Gene Set A |
| 158 | ENSG00000042832 | TG | 7038 | q24.22 | -0.466542 | 1.81586987 | -2.88482 | 0.004422 | 0.0916715 | -2.07 | down-regulated in participants with widespread BE | Gene Set A |
| 159 | ENSG00000261502 | | NA | q21 | -0.477523 | 0.669477557 | -2.88255 | 0.004453 | 0.0916715 | -2.135 | down-regulated in participants with widespread BE | Gene Set A |
| 160 | ENSG00000152487 | ARL5B-AS1 | NA | p12.31 | -0.277123 | 1.029388478 | -2.87695 | 0.004529 | 0.0916715 | -2.111 | down-regulated in participants with widespread BE | Gene Set A |
| 161 | ENSG00000214534 | ZNF705E | NA | q13.4 | -0.448403 | -0.081399512 | -2.87618 | 0.004539 | 0.0916715 | -2.249 | down-regulated in participants with widespread BE | Gene Set A |
| 162 | ENSG00000240764 | PCDHGC5 | c(56097, 5098) | q31.3 | -0.530688 | 0.242355861 | -2.8733 | 0.004579 | 0.0916715 | -2.212 | down-regulated in participants with widespread BE | Gene Set A |
| 163 | ENSG00000175265 | GOLGA8A | 23015 | q14 | -0.378735 | 6.820494933 | -2.87224 | 0.004594 | 0.0916715 | -2.349 | down-regulated in participants with widespread BE | Gene Set A |
| 164 | ENSG00000054690 | PLEKHH1 | 57475 | q24.1 | -0.379217 | 6.063871903 | -2.8717 | 0.004601 | 0.0916715 | -2.354 | down-regulated in participants with widespread BE | Gene Set A |
| 165 | ENSG00000162407 | PPAP2B | 8613 | p32.2 | -0.286677 | 5.006270836 | -2.87098 | 0.004611 | 0.0916715 | -2.325 | down-regulated in participants with widespread BE | Gene Set A |
| 166 | ENSG00000267481 | | NA | p13.11 | -0.254503 | 1.458979455 | -2.86341 | 0.004718 | 0.0916715 | -2.125 | down-regulated in participants with widespread BE | Gene Set A |
| 167 | ENSG00000238228 | OR7E7P | NA | q21.3 | -0.505684 | 0.301994148 | -2.8601 | 0.004765 | 0.0916715 | -2.23 | down-regulated in participants with widespread BE | Gene Set A |
| 168 | ENSG00000259585 | | NA | q14 | -0.394597 | 0.506748248 | -2.85709 | 0.004808 | 0.0916715 | -2.205 | down-regulated in participants with widespread BE | Gene Set A |
| 169 | ENSG00000225210 | | 440157 | q11.2 | -1.304194 | 0.007224636 | -2.85678 | 0.004813 | 0.0916715 | -2.385 | down-regulated in participants with widespread BE | Gene Set A |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 170 | ENSG00000212122 | TSSK1B | 83942 | q22.2 | -0.692483 | 0.340685035 | -2.85624 | 0.00482 | 0.0916715 | -2.259 | down-regulated in participants with widespread BE | Gene Set A |
| 171 | ENSG00000215022 | | NA | p24.1 | -0.452937 | 0.144151418 | -2.84499 | 0.004986 | 0.0925016 | -2.281 | down-regulated in participants with widespread BE | Gene Set A |
| 172 | ENSG00000242866 | STRC | c(101930630, 161497) | q15.3 | -0.660217 | 1.072400078 | -2.8405 | 0.005053 | 0.0927491 | -2.213 | down-regulated in participants with widespread BE | Gene Set A |
| 173 | ENSG00000250290 | | NA | q24.12 | -0.542333 | -0.40348882 | -2.8363 | 0.005117 | 0.0927491 | -2.401 | down-regulated in participants with widespread BE | Gene Set A |
| 174 | ENSG00000246922 | UBAP1L | 390595 | q22.31 | -0.430644 | 3.365246862 | -2.83615 | 0.005119 | 0.0927491 | -2.26 | down-regulated in participants with widespread BE | Gene Set A |
| 175 | ENSG00000264112 | | 645460 | q22 | -0.33353 | 4.969103436 | -2.83582 | 0.005125 | 0.0927491 | -2.414 | down-regulated in participants with widespread BE | Gene Set A |
| 176 | ENSG00000237489 | LINC00959 | NA | q26.3 | -0.364103 | 0.741124331 | -2.83481 | 0.00514 | 0.0927491 | -2.229 | down-regulated in participants with widespread BE | Gene Set A |
| 177 | ENSG00000189419 | SPATA41 | 388182 | q26.3 | -0.421428 | -0.615950545 | -2.8306 | 0.005205 | 0.093061 | -2.428 | down-regulated in participants with widespread BE | Gene Set A |
| 178 | ENSG00000213139 | CRYGS | 1427 | q27.3 | -0.276504 | 1.38359494 | -2.82967 | 0.005219 | 0.0931029 | -2.205 | down-regulated in participants with widespread BE | Gene Set A |
| 179 | ENSG00000106479 | ZNF862 | 643641 | q36.1 | -0.267752 | 4.562087693 | -2.82614 | 0.005275 | 0.0932239 | -2.414 | down-regulated in participants with widespread BE | Gene Set A |
| 180 | ENSG00000225032 | | NA | q34.11 | -0.494271 | 1.670001923 | -2.82562 | 0.005283 | 0.0932239 | -2.213 | down-regulated in participants with widespread BE | Gene Set A |
| 181 | ENSG00000179715 | PCED1B | 91523 | q13.11 | -0.414414 | 0.988997536 | -2.82417 | 0.005306 | 0.0932239 | -2.239 | down-regulated in participants with widespread BE | Gene Set A |
| 182 | ENSG00000137834 | SMAD6 | 4091 | q22.31 | -0.540528 | -0.718919286 | -2.82099 | 0.005356 | 0.0932239 | -2.506 | down-regulated in participants with widespread BE | Gene Set A |
| 183 | ENSG00000264538 | | NA | q11.2 | -0.266002 | 2.853102855 | -2.82021 | 0.005369 | 0.0932239 | -2.266 | down-regulated in participants with widespread BE | Gene Set A |
| 184 | ENSG00000137218 | FRS3 | 10817 | p21.1 | -0.271065 | 1.255970486 | -2.81846 | 0.005397 | 0.0932239 | -2.235 | down-regulated in participants with widespread BE | Gene Set A |
| 185 | ENSG00000256139 | | NA | q24.11 | -0.374937 | 0.571693332 | -2.81652 | 0.005428 | 0.0932239 | -2.284 | down-regulated in participants with widespread BE | Gene Set A |
| 186 | ENSG00000223705 | NSUN5P1 | 155400 | q11.23 | -0.311216 | 5.031039349 | -2.81644 | 0.005429 | 0.0932239 | -2.469 | down-regulated in participants with widespread BE | Gene Set A |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 187 | ENSG00000090006 | LTBP4 | 8425 | q13.2 | -0.442523 | 4.607220474 | -2.81605 | 0.005435 | 0.0932239 | -2.433 | down-regulated in participants with widespread BE | Gene Set A |
| 188 | ENSG00000267053 | | NA | q13.12 | -0.735327 | 0.913148231 | -2.8139 | 0.00547 | 0.0934722 | -2.285 | down-regulated in participants with widespread BE | Gene Set A |
| 189 | ENSG00000171282 | | 57597 | q25.3 | -0.413302 | 3.514874387 | -2.8074 | 0.005577 | 0.0947599 | -2.351 | down-regulated in participants with widespread BE | Gene Set A |
| 190 | ENSG00000253537 | PCDHGA7 | 56108 | q31.3 | -0.41948 | 1.312051402 | -2.80407 | 0.005632 | 0.0949554 | -2.268 | down-regulated in participants with widespread BE | Gene Set A |
| 191 | ENSG00000196208 | GREB1 | 9687 | p25.1 | -0.643285 | -1.078409485 | -2.80266 | 0.005656 | 0.095212 | -2.631 | down-regulated in participants with widespread BE | Gene Set A |
| 192 | ENSG00000229186 | ADAM1A | NA | q24.13 | -0.298552 | 2.74358025 | -2.79939 | 0.005711 | 0.095212 | -2.309 | down-regulated in participants with widespread BE | Gene Set A |
| 193 | ENSG00000251323 | | 101928865 | q14.1 | -0.388487 | 0.108206692 | -2.79818 | 0.005731 | 0.095212 | -2.38 | down-regulated in participants with widespread BE | Gene Set A |
| 194 | ENSG00000271917 | | NA | q23.3 | -0.43508 | 0.043237531 | -2.79813 | 0.005732 | 0.095212 | -2.391 | down-regulated in participants with widespread BE | Gene Set A |
| 195 | ENSG00000253366 | | NA | q13.2 | -0.426281 | 0.351554561 | -2.79784 | 0.005737 | 0.095212 | -2.35 | down-regulated in participants with widespread BE | Gene Set A |
| 196 | ENSG00000225241 | | NA | q21.1 | -0.277413 | 3.643193053 | -2.79762 | 0.005741 | 0.095212 | -2.397 | down-regulated in participants with widespread BE | Gene Set A |
| 197 | ENSG00000137070 | IL11RA | 3590 | p13.3 | -0.384932 | 2.014000116 | -2.79531 | 0.00578 | 0.0954815 | -2.284 | down-regulated in participants with widespread BE | Gene Set A |
| 198 | ENSG00000146001 | PCDHB18 | 54660 | q31.3 | -0.534028 | 0.124256526 | -2.7862 | 0.005938 | 0.0961675 | -2.412 | down-regulated in participants with widespread BE | Gene Set A |
| 199 | ENSG00000255495 | FAM85A | 619423 | p23.1 | -0.55258 | 1.381180644 | -2.78373 | 0.005981 | 0.0962697 | -2.317 | down-regulated in participants with widespread BE | Gene Set A |
| 200 | ENSG00000242435 | UPK3BP1 | NA | q11.23 | -1.271832 | -1.547482383 | -2.78016 | 0.006044 | 0.0967025 | -2.933 | down-regulated in participants with widespread BE | Gene Set A |
| 201 | ENSG00000115361 | ACADL | 33 | q34 | -0.391873 | 1.512299037 | -2.77323 | 0.006169 | 0.0976297 | -2.335 | down-regulated in participants with widespread BE | Gene Set A |
| 202 | ENSG00000236055 | | NA | q21.1 | -0.824266 | -0.973820393 | -2.77297 | 0.006173 | 0.0976297 | -2.673 | down-regulated in participants with widespread BE | Gene Set A |
| 203 | ENSG00000267508 | ZNF285 | c(646915, 26974) | q13.31 | -0.522781 | 1.258035996 | -2.76547 | 0.006311 | 0.0983509 | -2.361 | down-regulated in participants with widespread BE | Gene Set A |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 204 | ENSG00000239665 | | c(101928524, 101928497) | p13 | -0.312891 | 5.120850747 | -2.7599 | 0.006415 | 0.099009 | -2.619 | down-regulated in participants with widespread BE | Gene Set A |
| 205 | ENSG00000134569 | LRP4 | 4038 | p11.2 | -0.699615 | 4.650632986 | -4.73423 | 4.60E-06 | 0.0280264 | 3.9385 | down-regulated in participants with widespread BE | Gene Set B |
| 206 | ENSG00000258405 | ZNF578 | 147660 | q13.41 | -0.78613 | -0.066970606 | -4.32732 | 2.57E-05 | 0.0475762 | 0.7906 | down-regulated in participants with widespread BE | Gene Set B |
| 207 | ENSG00000086570 | FAT2 | 2196 | q33.1 | -0.644847 | 7.645229286 | -4.09472 | 6.52E-05 | 0.0496081 | 1.4941 | down-regulated in participants with widespread BE | Gene Set B |
| 208 | ENSG00000068078 | FGFR3 | 2261 | p16.3 | -0.616231 | 6.019654035 | -4.04412 | 7.94E-05 | 0.0518618 | 1.3048 | down-regulated in participants with widespread BE | Gene Set B |
| 209 | ENSG00000171444 | MCC | 4163 | q22.2 | -0.376183 | 5.419446205 | -4.02617 | 8.52E-05 | 0.0518618 | 1.2473 | down-regulated in participants with widespread BE | Gene Set B |
| 210 | ENSG00000174502 | SLC26A9 | 115019 | q32.1 | -0.802526 | 2.732661434 | -3.96863 | 0.000106 | 0.0571392 | 1.0526 | down-regulated in participants with widespread BE | Gene Set B |
| 211 | ENSG00000186260 | MKL2 | 57496 | p13.12 | -0.392308 | 7.77089031 | -3.88264 | 0.000148 | 0.0624298 | 0.7543 | down-regulated in participants with widespread BE | Gene Set B |
| 212 | ENSG00000226555 | AGKP1 | NA | q11.221 | -0.727645 | -0.825289744 | -3.86247 | 0.000159 | 0.0624298 | -0.028 | down-regulated in participants with widespread BE | Gene Set B |
| 213 | ENSG00000171346 | KRT15 | 3866 | q21.2 | -0.584322 | 7.577481067 | -3.82508 | 0.000183 | 0.0624298 | 0.5508 | down-regulated in participants with widespread BE | Gene Set B |
| 214 | ENSG00000178662 | CSRNP3 | 80034 | q24.3 | -0.598096 | 2.591679264 | -3.79255 | 0.000207 | 0.0659672 | 0.4766 | down-regulated in participants with widespread BE | Gene Set B |
| 215 | ENSG00000081277 | PKP1 | 5317 | q32.1 | -0.610017 | 5.051598449 | -3.74108 | 0.00025 | 0.0702506 | 0.2853 | down-regulated in participants with widespread BE | Gene Set B |
| 216 | ENSG00000070404 | FSTL3 | 10272 | p13.3 | -0.522501 | 0.615273868 | -3.66254 | 0.000333 | 0.0702506 | -0.235 | down-regulated in participants with widespread BE | Gene Set B |
| 217 | ENSG00000107954 | NEURL1 | 9148 | q24.33 | -0.545798 | 0.566047438 | -3.65887 | 0.000337 | 0.0702506 | -0.269 | down-regulated in participants with widespread BE | Gene Set B |
| 218 | ENSG00000184916 | JAG2 | 3714 | q32.33 | -0.481256 | 4.569112566 | -3.58612 | 0.000438 | 0.0715125 | -0.2 | down-regulated in participants with widespread BE | Gene Set B |
| 219 | ENSG00000164488 | DACT2 | 168002 | q27 | -0.836245 | 1.129299607 | -3.5731 | 0.000459 | 0.0720393 | -0.423 | down-regulated in participants with widespread BE | Gene Set B |
| 220 | ENSG00000067445 | TRO | 7216 | p11.21 | -0.628957 | 1.687231342 | -3.54261 | 0.000511 | 0.0725389 | -0.367 | down-regulated in participants with widespread BE | Gene Set B |

-continued

| | Ensembl_ID | GeneID | EntrezID | Band | logFC | AveExpr | t | P.Value | adj.P.Val | B | Direction | GeneClusters |
|---|---|---|---|---|---|---|---|---|---|---|---|---|
| 221 | ENSG00000104419 | NDRG1 | 10397 | q24.22 | −0.555699 | 4.912777787 | −3.49928 | 0.000595 | 0.0725389 | −0.492 | down-regulated in participants with widespread BE | Gene Set B |
| 222 | ENSG00000078295 | ADCY2 | 108 | p15.31 | −0.556893 | 5.369881097 | −3.4966 | 0.000601 | 0.0725389 | −0.519 | down-regulated in participants with widespread BE | Gene Set B |
| 223 | ENSG00000143061 | IGSF3 | 3321 | p13.1 | −0.281068 | 5.633543783 | −3.48772 | 0.00062 | 0.0725389 | −0.562 | down-regulated in participants with widespread BE | Gene Set B |
| 224 | ENSG00000165246 | NLGN4Y | 22829 | q11.221 | −0.423807 | 1.743647285 | −3.48743 | 0.00062 | 0.0725389 | −0.437 | down-regulated in participants with widespread BE | Gene Set B |
| 225 | ENSG00000165821 | SALL2 | 6297 | q11.2 | −0.468971 | 1.429906277 | −3.48474 | 0.000626 | 0.0725389 | −0.55 | down-regulated in participants with widespread BE | Gene Set B |
| 226 | ENSG00000143502 | SUSD4 | 55061 | q41 | −0.409607 | 4.654086587 | −3.47468 | 0.000649 | 0.0725389 | −0.559 | down-regulated in participants with widespread BE | Gene Set B |
| 227 | ENSG00000141337 | ARSG | 22901 | q24.2 | −0.331299 | 2.97246364 | −3.46568 | 0.000669 | 0.0725389 | −0.503 | down-regulated in participants with widespread BE | Gene Set B |
| 228 | ENSG00000119866 | BCL11A | 53335 | p16.1 | −0.436449 | 3.790733131 | −3.46272 | 0.000676 | 0.0725389 | −0.539 | down-regulated in participants with widespread BE | Gene Set B |
| 229 | ENSG00000141622 | RNF165 | 494470 | q21.1 | −0.654176 | 2.612214731 | −3.44322 | 0.000723 | 0.0725389 | −0.579 | down-regulated in participants with widespread BE | Gene Set B |
| 230 | ENSG00000073282 | TP63 | 8626 | q28 | −0.607804 | 6.320482909 | −3.43674 | 0.00074 | 0.0725389 | −0.726 | down-regulated in participants with widespread BE | Gene Set B |
| 231 | ENSG00000244122 | UGT1A7 | 54577; 54576 | q37.1 | −0.621018 | 2.801081608 | −3.43453 | 0.000745 | 0.0725389 | −0.595 | down-regulated in participants with widespread BE | Gene Set B |
| 232 | ENSG00000141837 | CACNA1A | c(100507353, 773) | p13.2 | −0.748874 | 1.388111132 | −3.43331 | 0.000749 | 0.0725389 | −0.72 | down-regulated in participants with widespread BE | Gene Set B |
| 233 | ENSG00000182752 | PAPPA | 5069 | q33.1 | −1.267719 | 1.889114323 | −3.41999 | 0.000784 | 0.0731174 | −0.757 | down-regulated in participants with widespread BE | Gene Set B |
| 234 | ENSG00000196562 | SULF2 | 55959 | q13.13 | −0.293715 | 5.582543341 | −3.41118 | 0.000808 | 0.0731174 | −0.799 | down-regulated in participants with widespread BE | Gene Set B |
| 235 | ENSG00000091844 | RGS17 | 26675 | q25.2 | −0.432978 | 3.920228244 | −3.40234 | 0.000833 | 0.0731174 | −0.733 | down-regulated in participants with widespread BE | Gene Set B |
| 236 | ENSG00000145675 | PIK3R1 | 5295 | q13.1 | −0.298079 | 6.257793123 | −3.39592 | 0.000851 | 0.0740316 | −0.853 | down-regulated in participants with widespread BE | Gene Set B |
| 237 | ENSG00000174226 | SNX31 | 169166 | q22.3 | −0.8431 | 2.977764314 | −3.38648 | 0.000879 | 0.0742673 | −0.736 | down-regulated in participants with widespread BE | Gene Set B |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 238 | ENSG00000188153 | COL4A5 | 1287 | q22.3 | -0.365577 | 6.612785342 | -3.3846 | 0.000885 | 0.0742673 | -0.886 | down-regulated in participants with widespread BE | Gene Set B |
| 239 | ENSG00000019549 | SNAI2 | 6591 | q11.21 | -0.629867 | 2.574790785 | -3.37168 | 0.000924 | 0.0750074 | -0.784 | down-regulated in participants with widespread BE | Gene Set B |
| 240 | ENSG00000240224 | UGT1A5 | 54579 | q37.1 | -0.614817 | 1.680916438 | -3.36691 | 0.00094 | 0.0751012 | -0.836 | down-regulated in participants with widespread BE | Gene Set B |
| 241 | ENSG00000100321 | SYNGR1 | 9145 | q13.1 | -0.449028 | 3.800571325 | -3.36385 | 0.000949 | 0.0751012 | -0.838 | down-regulated in participants with widespread BE | Gene Set B |
| 242 | ENSG00000213963 | | 100130691 | q31.2 | -0.496021 | 2.924610032 | -3.3635 | 0.000951 | 0.0751012 | -0.801 | down-regulated in participants with widespread BE | Gene Set B |
| 243 | ENSG00000159164 | SV2A | 9900 | q21.2 | -0.718227 | 0.270683666 | -3.35131 | 0.000991 | 0.0755505 | -1.165 | down-regulated in participants with widespread BE | Gene Set B |
| 244 | ENSG00000066468 | FGFR2 | 2263 | q26.13 | -0.319114 | 6.168041752 | -3.34808 | 0.001002 | 0.0758422 | -0.999 | down-regulated in participants with widespread BE | Gene Set B |
| 245 | ENSG00000107104 | KANK1 | 23189 | p24.3 | -0.320315 | 4.919738447 | -3.34226 | 0.001021 | 0.0758422 | -0.984 | down-regulated in participants with widespread BE | Gene Set B |
| 246 | ENSG00000114251 | WNT5A | 7474 | p14.3 | -0.508005 | 4.977116685 | -3.32594 | 0.001079 | 0.0769338 | -1.026 | down-regulated in participants with widespread BE | Gene Set B |
| 247 | ENSG00000155760 | FZD7 | 8324 | q33.1 | -0.48261 | 0.880819973 | -3.32506 | 0.001082 | 0.0769338 | -1.055 | down-regulated in participants with widespread BE | Gene Set B |
| 248 | ENSG00000177679 | SRRM3 | 222183 | q11.23 | -0.637119 | -0.298885081 | -3.31263 | 0.001129 | 0.0772782 | -1.405 | down-regulated in participants with widespread BE | Gene Set B |
| 249 | ENSG00000112902 | SEMA5A | 9037 | p15.31 | -0.475111 | 6.838028967 | -3.29563 | 0.001195 | 0.0776631 | -1.155 | down-regulated in participants with widespread BE | Gene Set B |
| 250 | ENSG00000196263 | ZNF471 | 57573 | q13.43 | -0.314839 | 3.76150312 | -3.2902 | 0.001217 | 0.0777429 | -1.06 | down-regulated in participants with widespread BE | Gene Set B |
| 251 | ENSG00000188266 | HYKK | 123688 | q25.1 | -0.36594 | 2.629601783 | -3.29007 | 0.001217 | 0.0777429 | -1.009 | down-regulated in participants with widespread BE | Gene Set B |
| 252 | ENSG00000163590 | PPM1L | 151742 | q25.33 | -0.292189 | 6.414683843 | -3.28541 | 0.001236 | 0.0782464 | -1.188 | down-regulated in participants with widespread BE | Gene Set B |
| 253 | ENSG00000088756 | ARHGAP28 | 79822 | p11.31 | -0.717002 | 1.240055189 | -3.28156 | 0.001252 | 0.0782464 | -1.147 | down-regulated in participants with widespread BE | Gene Set B |
| 254 | ENSG00000241635 | UGT1A8 | c(54659, 54658, 54600, 54579, 54576) | q37.1 | -0.516814 | 4.344760926 | -3.26244 | 0.001334 | 0.0782464 | -1.174 | down-regulated in participants with widespread BE | Gene Set B |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 255 | ENSG00000104728 | ARHGEF10 | 9639 | p23.3 | −0.494707 | 3.024695755 | −3.26138 | 0.001339 | 0.0782464 | −1.097 | down-regulated in participants with widespread BE | Gene Set B |
| 256 | ENSG00000187193 | MT1X | 4501 | q13 | −0.585646 | 4.259541832 | −3.25767 | 0.001356 | 0.0782464 | −1.177 | down-regulated in participants with widespread BE | Gene Set B |
| 257 | ENSG00000109101 | FOXN1 | 8456 | q11.2 | −0.763992 | 0.209340702 | −3.24927 | 0.001394 | 0.0782464 | −1.442 | down-regulated in participants with widespread BE | Gene Set B |
| 258 | ENSG00000185652 | NTF3 | 4908 | p13.31 | −0.687096 | 0.286384515 | −3.24795 | 0.0014 | 0.0782464 | −1.416 | down-regulated in participants with widespread BE | Gene Set B |
| 259 | ENSG00000112562 | SMOC2 | 64094 | q27 | −0.759223 | 1.641125767 | −3.24394 | 0.001419 | 0.0782464 | −1.195 | down-regulated in participants with widespread BE | Gene Set B |
| 260 | ENSG00000136014 | USP44 | 84101 | q22 | −0.581224 | −0.68548371 | −3.24293 | 0.001424 | 0.0782464 | −1.688 | down-regulated in participants with widespread BE | Gene Set B |
| 261 | ENSG00000127585 | FBXL16 | 146330 | p13.3 | −0.500028 | 0.335383137 | −3.23 | 0.001486 | 0.0782464 | −1.396 | down-regulated in participants with widespread BE | Gene Set B |
| 262 | ENSG00000116016 | EPAS1 | 2034 | p21 | −0.375566 | 8.672343752 | −3.21803 | 0.001545 | 0.0782464 | −1.333 | down-regulated in participants with widespread BE | Gene Set B |
| 263 | ENSG00000146648 | EGFR | 1956 | p11.2 | −0.349276 | 7.874557529 | −3.20542 | 0.00161 | 0.0788617 | −1.394 | down-regulated in participants with widespread BE | Gene Set B |
| 264 | ENSG00000144724 | PTPRG | 5793 | p14.2 | −0.490278 | 4.541786513 | −3.19584 | 0.001662 | 0.0800848 | −1.383 | down-regulated in participants with widespread BE | Gene Set B |
| 265 | ENSG00000183091 | NEB | 4703 | q23.3 | −0.584253 | 4.86798727 | −3.19431 | 0.00167 | 0.0801049 | −1.406 | down-regulated in participants with widespread BE | Gene Set B |
| 266 | ENSG00000248587 | GDNF-AS1 | 100861519 | p13.2 | −0.672771 | 1.112541162 | −3.18456 | 0.001724 | 0.0804147 | −1.392 | down-regulated in participants with widespread BE | Gene Set B |
| 267 | ENSG00000138439 | FAM117B | 150864 | q33.2 | −0.280028 | 4.407972116 | −3.18391 | 0.001728 | 0.0804147 | −1.422 | down-regulated in participants with widespread BE | Gene Set B |
| 268 | ENSG00000134533 | RERG | 85004 | p12.3 | −0.61579 | 2.317374688 | −3.17553 | 0.001775 | 0.0807103 | −1.329 | down-regulated in participants with widespread BE | Gene Set B |
| 269 | ENSG00000114853 | ZBTB47 | 92999 | p22.1 | −0.266334 | 3.073400316 | −3.17002 | 0.001808 | 0.0807549 | −1.361 | down-regulated in participants with widespread BE | Gene Set B |
| 270 | ENSG00000241684 | ADAMTS9-AS2 | 100507098 | p14.1 | −0.902907 | 0.167381891 | −3.1606 | 0.001864 | 0.0810493 | −1.685 | down-regulated in participants with widespread BE | Gene Set B |
| 271 | ENSG00000100767 | PAPLN | 89932 | q24.2 | −0.575972 | 2.889537615 | −3.1513 | 0.001921 | 0.0817261 | −1.393 | down-regulated in participants with widespread BE | Gene Set B |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 272 | ENSG00000176771 | NCKAP5 | 344148 | q21.2 | -0.468444 | 2.364877806 | -3.15076 | 0.001924 | 0.0817261 | -1.392 | down-regulated in participants with widespread BE | Gene Set B |
| 273 | ENSG00000169302 | STK32A | 202374 | q32 | -0.521563 | 2.42928557 | -3.13585 | 0.002019 | 0.0824924 | -1.431 | down-regulated in participants with widespread BE | Gene Set B |
| 274 | ENSG00000196159 | FAT4 | 79633 | q28.1 | -0.618214 | 2.63640482 | -3.12523 | 0.002089 | 0.083002 | -1.46 | down-regulated in participants with widespread BE | Gene Set B |
| 275 | ENSG00000133067 | LGR6 | 59352 | q32.1 | -0.816813 | 2.711378516 | -3.123 | 0.002104 | 0.083002 | -1.465 | down-regulated in participants with widespread BE | Gene Set B |
| 276 | ENSG00000253771 | TPTE2P1 | NA | q12.13 | -0.649088 | 0.311370659 | -3.1091 | 0.0022 | 0.0830303 | -1.718 | down-regulated in participants with widespread BE | Gene Set B |
| 277 | ENSG00000184564 | SLITRK6 | 84189 | q31.1 | -0.463389 | 6.147664228 | -3.10566 | 0.002224 | 0.0830303 | -1.711 | down-regulated in participants with widespread BE | Gene Set B |
| 278 | ENSG00000041982 | TNC | 3371 | q33.1 | -0.647891 | 7.488437961 | -3.08968 | 0.002341 | 0.0839935 | -1.744 | down-regulated in participants with widespread BE | Gene Set B |
| 279 | ENSG00000214860 | EVPLL | 645027 | p11.2 | -0.707744 | 0.37653779 | -3.08742 | 0.002357 | 0.084104 | -1.759 | down-regulated in participants with widespread BE | Gene Set B |
| 280 | ENSG00000085998 | POMGNT1 | 55624 | p34.1 | -0.257145 | 4.073041093 | -3.08534 | 0.002373 | 0.0842685 | -1.676 | down-regulated in participants with widespread BE | Gene Set B |
| 281 | ENSG00000153885 | KCTD15 | 79047 | q13.11 | -0.295739 | 4.008122362 | -3.08239 | 0.002395 | 0.0842685 | -1.675 | down-regulated in participants with widespread BE | Gene Set B |
| 282 | ENSG00000179314 | WSCD1 | c(339166, 23302) | p13.2 | -0.684745 | -0.22057559 | -3.0773 | 0.002435 | 0.0842685 | -1.898 | down-regulated in participants with widespread BE | Gene Set B |
| 283 | ENSG00000166813 | KIF7 | 374654 | q26.1 | -0.514965 | -0.00850719 | -3.07525 | 0.00245 | 0.0842685 | -1.829 | down-regulated in participants with widespread BE | Gene Set B |
| 284 | ENSG00000130294 | KIF1A | 547 | q37.3 | -0.889067 | 2.08958412 | -3.07031 | 0.002489 | 0.0842685 | -1.613 | down-regulated in participants with widespread BE | Gene Set B |
| 285 | ENSG00000138759 | FRAS1 | 80144 | q21.21 | -0.4651 | 4.862359481 | -3.05004 | 0.002654 | 0.0854302 | -1.823 | down-regulated in participants with widespread BE | Gene Set B |
| 286 | ENSG00000186081 | KRT5 | 3852 | q13.13 | -0.542819 | 8.429103105 | -3.04073 | 0.002733 | 0.0856287 | -1.849 | down-regulated in participants with widespread BE | Gene Set B |
| 287 | ENSG00000174171 | | NA | q15.1 | -0.641869 | 0.597273924 | -3.03204 | 0.002809 | 0.0868249 | -1.839 | down-regulated in participants with widespread BE | Gene Set B |
| 288 | ENSG00000140937 | CDH11 | 1009 | q21 | -0.66659 | 3.029163516 | -3.02873 | 0.002838 | 0.0868249 | -1.724 | down-regulated in participants with widespread BE | Gene Set B |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 289 | ENSG00000196867 | ZFP28 | 140612 | q13.43 | −0.251417 | 3.122705181 | −3.02812 | 0.002844 | 0.0868249 | −1.752 | down-regulated in participants with widespread BE | Gene Set B |
| 290 | ENSG00000198932 | GPRASP1 | 9737 | q22.1 | −0.306878 | 3.881702344 | −3.02134 | 0.002905 | 0.0868249 | −1.83 | down-regulated in participants with widespread BE | Gene Set B |
| 291 | ENSG00000099725 | PRKY | 5616 | p11.2 | −0.361171 | 3.567417418 | −3.01129 | 0.002997 | 0.0868249 | −1.905 | down-regulated in participants with widespread BE | Gene Set B |
| 292 | ENSG00000197565 | COL4A6 | 1288 | q22.3 | −0.566004 | 4.01352509 | −3.0111 | 0.002999 | 0.0868249 | −1.85 | down-regulated in participants with widespread BE | Gene Set B |
| 293 | ENSG00000185565 | LSAMP | 4045 | q13.32 | −1.121177 | 0.517966124 | −3.01024 | 0.003007 | 0.0868249 | −1.974 | down-regulated in participants with widespread BE | Gene Set B |
| 294 | ENSG00000105137 | SYDE1 | 85360 | p13.12 | −0.596643 | −0.854254745 | −3.01008 | 0.003009 | 0.0868249 | −2.186 | down-regulated in participants with widespread BE | Gene Set B |
| 295 | ENSG00000271880 | | NA | q23.2 | −0.897566 | 0.609444955 | −3.00387 | 0.003068 | 0.0868249 | −1.922 | down-regulated in participants with widespread BE | Gene Set B |
| 296 | ENSG00000182175 | RGMA | 56963 | q26.1 | −0.571165 | 2.022091296 | −2.99317 | 0.003172 | 0.0876268 | −1.804 | down-regulated in participants with widespread BE | Gene Set B |
| 297 | ENSG00000144857 | BOC | 91653 | q13.2 | −0.597174 | 3.774853455 | −2.99051 | 0.003198 | 0.0876268 | −1.88 | down-regulated in participants with widespread BE | Gene Set B |
| 298 | ENSG00000109667 | SLC2A9 | 56606 | p16.1 | −0.321556 | 3.162900644 | −2.98919 | 0.003211 | 0.087805 | −1.855 | down-regulated in participants with widespread BE | Gene Set B |
| 299 | ENSG00000134245 | WNT2B | 7482 | p13.2 | −0.507664 | 3.672467682 | −2.97889 | 0.003315 | 0.0884774 | −1.908 | down-regulated in participants with widespread BE | Gene Set B |
| 300 | ENSG00000148600 | CDHR1 | 92211 | q23.1 | −0.776396 | 0.920937336 | −2.97854 | 0.003319 | 0.0884774 | −1.919 | down-regulated in participants with widespread BE | Gene Set B |
| 301 | ENSG00000248705 | | NA | q37.1 | −0.622024 | 0.053773378 | −2.97846 | 0.00332 | 0.0884774 | −2.014 | down-regulated in participants with widespread BE | Gene Set B |
| 302 | ENSG00000092969 | TGFB2 | 7042 | q41 | −0.518486 | 3.446416908 | −2.97465 | 0.003359 | 0.0884774 | −1.904 | down-regulated in participants with widespread BE | Gene Set B |
| 303 | ENSG00000149294 | NCAM1 | 4684 | q23.2 | −0.65216 | 1.322823262 | −2.96934 | 0.003415 | 0.0884774 | −1.897 | down-regulated in participants with widespread BE | Gene Set B |
| 304 | ENSG00000213903 | LTB4R | 1241 | q12 | −0.455546 | 4.098210638 | −2.96458 | 0.003466 | 0.08858 | −1.993 | down-regulated in participants with widespread BE | Gene Set B |
| 305 | ENSG00000065717 | TLE2 | 7089 | p13.3 | −0.319984 | 3.666802619 | −2.95924 | 0.003523 | 0.0887618 | −1.977 | down-regulated in participants with widespread BE | Gene Set B |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 306 | ENSG00000103723 | AP3B2 | 8120 | q25.2 | -0.404667 | 0.912455406 | -2.95478 | 0.003572 | 0.0888089 | -1.948 | down-regulated in participants with widespread BE | Gene Set B |
| 307 | ENSG00000163827 | LRRC2 | 79442 | p21.31 | -0.595272 | 1.853477836 | -2.94971 | 0.003628 | 0.0888908 | -1.916 | down-regulated in participants with widespread BE | Gene Set B |
| 308 | ENSG00000162591 | MEGF6 | 1953 | p36.32 | -0.635096 | 3.46916109 | -2.94685 | 0.00366 | 0.089096 | -1.967 | down-regulated in participants with widespread BE | Gene Set B |
| 309 | ENSG00000178222 | RNF212 | 285498 | p16.3 | -0.432545 | 0.985376736 | -2.9409 | 0.003728 | 0.0891181 | -1.975 | down-regulated in participants with widespread BE | Gene Set B |
| 310 | ENSG00000077942 | FBLN1 | 2192 | q13.31 | -0.454822 | 3.051535198 | -2.93848 | 0.003755 | 0.0891719 | -1.97 | down-regulated in participants with widespread BE | Gene Set B |
| 311 | ENSG00000173930 | SLCO4C1 | 353189 | q21.1 | -0.251544 | 4.983130287 | -2.93646 | 0.003779 | 0.0891719 | -2.151 | down-regulated in participants with widespread BE | Gene Set B |
| 312 | ENSG00000154342 | WNT3A | 89780 | q42.13 | -0.446479 | 1.340677666 | -2.93368 | 0.003811 | 0.0891719 | -1.968 | down-regulated in participants with widespread BE | Gene Set B |
| 313 | ENSG00000197497 | ZNF665 | 79788 | q13.42 | -0.351587 | 1.573915177 | -2.93319 | 0.003817 | 0.0891719 | -1.958 | down-regulated in participants with widespread BE | Gene Set B |
| 314 | ENSG00000158220 | ESYT3 | 83850 | q22.3 | -0.440665 | -0.449444168 | -2.92971 | 0.003858 | 0.0891719 | -2.2 | down-regulated in participants with widespread BE | Gene Set B |
| 315 | ENSG00000150893 | FREM2 | 341640 | q13.3 | -0.35764 | 5.697517979 | -2.92971 | 0.003858 | 0.0891719 | -2.194 | down-regulated in participants with widespread BE | Gene Set B |
| 316 | ENSG00000136002 | ARHGEF4 | c(101930241, 50649) | q21.1 | -0.306659 | 4.355885999 | -2.92704 | 0.003889 | 0.0891719 | -2.129 | down-regulated in participants with widespread BE | Gene Set B |
| 317 | ENSG00000171357 | LURAP1 | 541468 | p34.1 | -0.386037 | 1.352211948 | -2.92628 | 0.003898 | 0.0891719 | -1.983 | down-regulated in participants with widespread BE | Gene Set B |
| 318 | ENSG00000214244 | SETP21 | NA | q12.1 | -0.891291 | -0.840441636 | -2.92419 | 0.003923 | 0.0893264 | -2.405 | down-regulated in participants with widespread BE | Gene Set B |
| 319 | ENSG00000114270 | COL7A1 | 1294 | p21.31 | -0.673795 | 5.915377279 | -2.9113 | 0.004081 | 0.090932 | -2.241 | down-regulated in participants with widespread BE | Gene Set B |
| 320 | ENSG00000182272 | B4GALNT4 | 338707 | p15.5 | -0.679922 | -0.604771719 | -2.90338 | 0.00418 | 0.0912292 | -2.35 | down-regulated in participants with widespread BE | Gene Set B |
| 321 | ENSG00000166147 | FBN1 | 2200 | q21.1 | -0.617794 | 3.4916171 | -2.89122 | 0.004338 | 0.0916715 | -2.116 | down-regulated in participants with widespread BE | Gene Set B |
| 322 | ENSG00000213988 | ZNF90 | 7643 | p12 | -0.584704 | 1.581197722 | -2.89119 | 0.004338 | 0.0916715 | -2.064 | down-regulated in participants with widespread BE | Gene Set B |

-continued

| | Ensembl_ID | GeneID | EntrezID | Band | logFC | AveExpr | t | P.Value | adj. P. Val | B | Direction | GeneClusters |
|---|---|---|---|---|---|---|---|---|---|---|---|---|
| 323 | ENSG00000168702 | LRP1B | 53353 | q22.2 | -0.905547 | 1.837860989 | -2.89007 | 0.004353 | 0.0916715 | -2.064 | down-regulated in participants with widespread BE | Gene Set B |
| 324 | ENSG00000069431 | ABCC9 | 10060 | p12.1 | -0.728882 | 3.714141032 | -2.88229 | 0.004456 | 0.0916715 | -2.15 | down-regulated in participants with widespread BE | Gene Set B |
| 325 | ENSG00000256995 | | NA | p12.1 | -0.821555 | 2.863796021 | -2.88083 | 0.004476 | 0.0916715 | -2.089 | down-regulated in participants with widespread BE | Gene Set B |
| 326 | ENSG00000180739 | S1PR5 | 53637 | p13.2 | -0.586281 | 1.127282635 | -2.87818 | 0.004512 | 0.0916715 | -2.121 | down-regulated in participants with widespread BE | Gene Set B |
| 327 | ENSG00000100842 | EFS | 10278 | q11.2 | -0.373957 | 2.905779759 | -2.87784 | 0.004517 | 0.0916715 | -2.119 | down-regulated in participants with widespread BE | Gene Set B |
| 328 | ENSG00000171246 | NPTX1 | 4884 | q25.3 | -0.944807 | -0.571739856 | -2.87742 | 0.004523 | 0.0916715 | -2.424 | down-regulated in participants with widespread BE | Gene Set B |
| 329 | ENSG00000260197 | | NA | q11.222 | -0.398204 | -0.211066982 | -2.87465 | 0.00456 | 0.0916715 | -2.153 | down-regulated in participants with widespread BE | Gene Set B |
| 330 | ENSG00000228445 | UGT1A2P | NA | q37.1 | -0.697399 | 1.144024049 | -2.87043 | 0.004619 | 0.0916715 | -2.129 | down-regulated in participants with widespread BE | Gene Set B |
| 331 | ENSG00000147100 | SLC16A2 | 6567 | q13.2 | -0.401589 | 1.747764371 | -2.8699 | 0.004626 | 0.0916715 | -2.107 | down-regulated in participants with widespread BE | Gene Set B |
| 332 | ENSG00000117643 | MAN1C1 | 57134 | p36.11 | -0.374375 | 4.250696194 | -2.86902 | 0.004639 | 0.0916715 | -2.268 | down-regulated in participants with widespread BE | Gene Set B |
| 333 | ENSG00000155254 | MARVELD1 | 83742 | q24.2 | -0.417561 | 2.762334379 | -2.86813 | 0.004651 | 0.0916715 | -2.131 | down-regulated in participants with widespread BE | Gene Set B |
| 334 | ENSG00000102678 | FGF9 | 2254 | q12.11 | -0.697319 | -0.085453367 | -2.86763 | 0.004658 | 0.0916715 | -2.31 | down-regulated in participants with widespread BE | Gene Set B |
| 335 | ENSG00000136425 | CIB2 | 10518 | q25.1 | -0.464536 | 0.573488312 | -2.86692 | 0.004668 | 0.0916715 | -2.183 | down-regulated in participants with widespread BE | Gene Set B |
| 336 | ENSG00000139292 | LGR5 | 8549 | q21.1 | -1.570018 | -0.496864705 | -2.86591 | 0.004682 | 0.0916715 | -2.59 | down-regulated in participants with widespread BE | Gene Set B |
| 337 | ENSG00000183853 | KIRREL | c(101928229, 55243) | q23.1 | -0.520194 | 2.659355361 | -2.86575 | 0.004684 | 0.0916715 | -2.129 | down-regulated in participants with widespread BE | Gene Set B |
| 338 | ENSG00000213906 | LTB4R2 | 56413 | q12 | -0.409095 | 2.685791847 | -2.86497 | 0.004696 | 0.0916715 | -2.138 | down-regulated in participants with widespread BE | Gene Set B |
| 339 | ENSG00000070182 | SPTB | 6710 | q23.3 | -0.755869 | -0.096071136 | -2.86114 | 0.00475 | 0.0916715 | -2.316 | down-regulated in participants with widespread BE | Gene Set B |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 340 | ENSG00000198885 | ITPRIPL1 | 150771 | q11.2 | −0.464596 | 1.603302871 | −2.86107 | 0.004751 | 0.0916715 | −2.132 | down-regulated in participants with widespread BE | Gene Set B |
| 341 | ENSG00000019144 | PHLDB1 | c(102466719, 23187) | q23.3 | −0.405273 | 3.367459089 | −2.84441 | 0.004995 | 0.0925264 | −2.24 | down-regulated in participants with widespread BE | Gene Set B |
| 342 | ENSG00000164056 | SPRY1 | 10252 | q28.1 | −0.413213 | 4.07630567 | −2.84109 | 0.005044 | 0.0927071 | −2.317 | down-regulated in participants with widespread BE | Gene Set B |
| 343 | ENSG00000155792 | DEPTOR | 64798 | q24.12 | −0.334539 | 3.183527853 | −2.83898 | 0.005076 | 0.0927491 | −2.242 | down-regulated in participants with widespread BE | Gene Set B |
| 344 | ENSG00000116106 | EPHA4 | 2043 | q36.1 | −0.285694 | 5.288229407 | −2.83231 | 0.005178 | 0.0930091 | −2.441 | down-regulated in participants with widespread BE | Gene Set B |
| 345 | ENSG00000229236 | TTTY10 | 246119 | q11.223 | −0.450034 | 1.202197919 | −2.83015 | 0.005212 | 0.093061 | −2.416 | down-regulated in participants with widespread BE | Gene Set B |
| 346 | ENSG00000138336 | TET1 | 80312 | q21.3 | −0.377607 | 2.536806501 | −2.8254 | 0.005286 | 0.0932239 | −2.227 | down-regulated in participants with widespread BE | Gene Set B |
| 347 | ENSG00000198046 | ZNF667 | 63934 | q13.43 | −0.514325 | 2.364200109 | −2.82496 | 0.005293 | 0.0932239 | −2.218 | down-regulated in participants with widespread BE | Gene Set B |
| 348 | ENSG00000106123 | EPHB6 | 2051 | q34 | −0.438498 | 2.933087734 | −2.82278 | 0.005328 | 0.0932239 | −2.255 | down-regulated in participants with widespread BE | Gene Set B |
| 349 | ENSG00000250685 | | NA | q24.1 | −0.455902 | 1.525173736 | −2.8227 | 0.005329 | 0.0932239 | −2.222 | down-regulated in participants with widespread BE | Gene Set B |
| 350 | ENSG00000271738 | | NA | q23.1 | −0.288474 | 2.297988226 | −2.82099 | 0.005356 | 0.0932239 | −2.233 | down-regulated in participants with widespread BE | Gene Set B |
| 351 | ENSG00000141753 | IGFBP4 | 3487 | q21.2 | −0.322733 | 4.445603204 | −2.81786 | 0.005406 | 0.0932239 | −2.422 | down-regulated in participants with widespread BE | Gene Set B |
| 352 | ENSG00000240771 | ARHGEF25 | 115557 | q13.3 | −0.665429 | −0.710013782 | −2.81487 | 0.005455 | 0.0933415 | −2.539 | down-regulated in participants with widespread BE | Gene Set B |
| 353 | ENSG00000165125 | TRPV6 | 55503 | q34 | −0.58036 | 2.220718951 | −2.80493 | 0.005618 | 0.0949554 | −2.262 | down-regulated in participants with widespread BE | Gene Set B |
| 354 | ENSG00000182674 | KCNB2 | 9312 | q13.3 | −0.705551 | −0.819355999 | −2.80422 | 0.00563 | 0.0949554 | −2.566 | down-regulated in participants with widespread BE | Gene Set B |
| 355 | ENSG00000136158 | SPRY2 | 10253 | q31.1 | −0.29229 | 4.115913968 | −2.79711 | 0.005749 | 0.095212 | −2.445 | down-regulated in participants with widespread BE | Gene Set B |
| 356 | ENSG00000171462 | DLK2 | 65989 | p21.1 | −0.540041 | 2.395746291 | −2.78621 | 0.005937 | 0.0961675 | −2.312 | down-regulated in participants with widespread BE | Gene Set B |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 357 | ENSG00000079101 | CLUL1 | 27098 | p11.32 | -0.462322 | 1.027102242 | -2.77366 | 0.006161 | 0.0976003 | -2.352 | down-regulated in participants with widespread BE | Gene Set B |
| 358 | ENSG00000258545 | | NA | q24 | 1.28262 | -1.089336135 | 4.838828 | 2.91E-06 | 0.0265657 | 3.1165 | up-regulated in participants with widespread BE | Gene Set C |
| 359 | ENSG00000257512 | | NA | q22 | 0.808182 | 1.479742551 | 4.552311 | 1.01E-05 | 0.0414908 | 3.0515 | up-regulated in participants with widespread BE | Gene Set C |
| 360 | ENSG00000126522 | ASL | 435 | q11.21 | 0.253948 | 4.916527284 | 4.461225 | 1.48E-05 | 0.0414908 | 2.8568 | up-regulated in participants with widespread BE | Gene Set C |
| 361 | ENSG00000203952 | CCDC160 | 347475 | q26.2 | 0.397871 | 3.582037896 | 4.368228 | 2.17E-05 | 0.0475762 | 2.5247 | up-regulated in participants with widespread BE | Gene Set C |
| 362 | ENSG00000259120 | SMIM6 | 100130933 | q25.1 | 1.076348 | 1.531088524 | 4.320594 | 2.64E-05 | 0.0475762 | 2.2583 | up-regulated in participants with widespread BE | Gene Set C |
| 363 | ENSG00000182621 | PLCB1 | 23236 | p12.3 | 0.591813 | 3.131961042 | 4.128779 | 5.70E-05 | 0.0496081 | 1.6561 | up-regulated in participants with widespread BE | Gene Set C |
| 364 | ENSG00000179178 | TMEM125 | 128218 | p34.2 | 0.304211 | 5.289577277 | 4.013555 | 8.94E-05 | 0.0527041 | 1.1962 | up-regulated in participants with widespread BE | Gene Set C |
| 365 | ENSG00000171695 | C20orf201 | 198437 | q13.33 | 1.490508 | -1.555434273 | 3.861637 | 0.00016 | 0.0624298 | 0.0304 | up-regulated in participants with widespread BE | Gene Set C |
| 366 | ENSG00000004468 | CD38 | 952 | p15.32 | 0.487774 | 6.167052469 | 3.844314 | 0.00017 | 0.0624298 | 0.6077 | up-regulated in participants with widespread BE | Gene Set C |
| 367 | ENSG00000268129 | | 100289361 | q23 | 0.352902 | 0.280103819 | 3.819071 | 0.000187 | 0.0624298 | 0.2909 | up-regulated in participants with widespread BE | Gene Set C |
| 368 | ENSG00000134198 | TSPAN2 | 10100 | p13.2 | 0.539801 | 3.359017475 | 3.679996 | 0.000313 | 0.0702506 | 0.1252 | up-regulated in participants with widespread BE | Gene Set C |
| 369 | ENSG00000070190 | DAPP1 | 27071 | q23 | 0.27646 | 6.316178674 | 3.652647 | 0.000345 | 0.0702506 | -0.034 | up-regulated in participants with widespread BE | Gene Set C |
| 370 | ENSG00000182054 | IDH2 | 3418 | q26.1 | 0.315377 | 6.240138281 | 3.605105 | 0.000409 | 0.0715125 | -0.189 | up-regulated in participants with widespread BE | Gene Set C |
| 371 | ENSG00000100336 | APOL4 | 80832 | q12.3 | 0.733435 | 2.989014286 | 3.571563 | 0.000461 | 0.0720393 | -0.206 | up-regulated in participants with widespread BE | Gene Set C |
| 372 | ENSG00000133328 | HRASLS2 | 54979 | q12.3 | 0.478513 | 4.156744741 | 3.543772 | 0.000509 | 0.0725389 | -0.353 | up-regulated in participants with widespread BE | Gene Set C |
| 373 | ENSG00000183784 | C9orf66 | 157983 | p24.3 | 0.443252 | 0.731954854 | 3.49573 | 0.000603 | 0.0725389 | -0.518 | up-regulated in participants with widespread BE | Gene Set C |

-continued

| | Ensembl_ID | GeneID | EntrezID | Band | logFC | AveExpr | t | P.Value | adj.P.Val | B | Direction | GeneClusters |
|---|---|---|---|---|---|---|---|---|---|---|---|---|
| 374 | ENSG00000125864 | BFSP1 | 631 | p12.1 | 0.43726 | 0.62954887 | 3.495214 | 0.000604 | 0.0725389 | -0.532 | up-regulated in participants with widespread BE | Gene Set C |
| 375 | ENSG00000227375 | DLG1-AS1 | 100507086 | q29 | 0.386417 | 0.56412307 | 3.470312 | 0.000659 | 0.0725389 | -0.613 | up-regulated in participants with widespread BE | Gene Set C |
| 376 | ENSG00000185905 | C16orf54 | c(10192987, 283897) | p11.2 | 0.4272 | 3.887167154 | 3.446987 | 0.000714 | 0.0725389 | -0.638 | up-regulated in participants with widespread BE | Gene Set C |
| 377 | ENSG00000078081 | LAMP3 | 27074 | q27.1 | 0.420776 | 3.903400153 | 3.415038 | 0.000797 | 0.0731174 | -0.737 | up-regulated in participants with widespread BE | Gene Set C |
| 378 | ENSG00000140280 | LYSMD2 | 256586 | q21.2 | 0.285627 | 3.088136164 | 3.413382 | 0.000802 | 0.0731174 | -0.681 | up-regulated in participants with widespread BE | Gene Set C |
| 379 | ENSG00000240065 | PSMB9 | 5698 | p21.32 | 0.575999 | 4.062146821 | 3.408593 | 0.000815 | 0.0731174 | -0.773 | up-regulated in participants with widespread BE | Gene Set C |
| 380 | ENSG00000116833 | NR5A2 | 2494 | q32.1 | 1.00451 | -1.14380144 | 3.406806 | 0.00082 | 0.0731174 | -1.095 | up-regulated in participants with widespread BE | Gene Set C |
| 381 | ENSG00000005189 | | 81691 | p12.3 | 0.32978 | 3.263707969 | 3.39087 | 0.000866 | 0.0742673 | -0.762 | up-regulated in participants with widespread BE | Gene Set C |
| 382 | ENSG00000100473 | COCH | 1690 | q12 | 0.797041 | -0.629606741 | 3.383958 | 0.000887 | 0.0742673 | -1.015 | up-regulated in participants with widespread BE | Gene Set C |
| 383 | ENSG00000165325 | CCDC67 | 159989 | q21 | 0.370851 | 3.542580097 | 3.361337 | 0.000958 | 0.0751012 | -0.872 | up-regulated in participants with widespread BE | Gene Set C |
| 384 | ENSG00000047597 | K | 7504 | p21.1 | 0.442304 | 2.181132049 | 3.358713 | 0.000966 | 0.0751012 | -0.815 | up-regulated in participants with widespread BE | Gene Set C |
| 385 | ENSG00000184669 | OR7E14P | 10819 | p15.1 | 0.297287 | 1.570358228 | 3.350704 | 0.000993 | 0.0755505 | -0.852 | up-regulated in participants with widespread BE | Gene Set C |
| 386 | ENSG00000251191 | LINC00589 | 619351 | p12 | 0.407923 | 1.906001822 | 3.302326 | 0.001168 | 0.0776495 | -0.975 | up-regulated in participants with widespread BE | Gene Set C |
| 387 | ENSG00000198734 | F5 | 2153 | q24.2 | 0.747491 | 2.249174423 | 3.27631 | 0.001274 | 0.0782464 | -1.057 | up-regulated in participants with widespread BE | Gene Set C |
| 388 | ENSG00000172572 | PDE3A | 5139 | p12.2 | 0.855396 | -0.426990091 | 3.270309 | 0.0013 | 0.0782464 | -1.243 | up-regulated in participants with widespread BE | Gene Set C |
| 389 | ENSG00000136514 | RTP4 | 64108 | q27.3 | 0.339436 | 3.523618507 | 3.269396 | 0.001304 | 0.0782464 | -1.141 | up-regulated in participants with widespread BE | Gene Set C |
| 390 | ENSG00000253474 | | NA | q11.21 | 1.196308 | -1.915791738 | 3.230185 | 0.001485 | 0.0782464 | -1.678 | up-regulated in participants with widespread BE | Gene Set C |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 391 | ENSG00000163297 | ANTR2 | 118429 | q21.21 | 0.289633 | 4.715786928 | 3.229436 | 0.001488 | 0.0782464 | -1.332 | up-regulated in participants with widespread BE | Gene Set C |
| 392 | ENSG00000237669 | HCG4P3 | NA | p22.1 | 0.512938 | 0.578200762 | 3.224711 | 0.001512 | 0.0782464 | -1.254 | up-regulated in participants with widespread BE | Gene Set C |
| 393 | ENSG00000147378 | FATE1 | 89885 | q28 | 1.053991 | -0.486663373 | 3.217731 | 0.001547 | 0.0782464 | -1.365 | up-regulated in participants with widespread BE | Gene Set C |
| 394 | ENSG00000140092 | FBLN5 | 10516 | q32.12 | 0.320787 | 3.109741797 | 3.177535 | 0.001764 | 0.0807103 | -1.372 | up-regulated in participants with widespread BE | Gene Set C |
| 395 | ENSG00000259153 | | 100506411 | q24.2 | 0.300803 | -0.04712851 | 3.169643 | 0.00181 | 0.0807549 | -1.493 | up-regulated in participants with widespread BE | Gene Set C |
| 396 | ENSG00000123609 | NMI | 9111 | q23.3 | 0.264716 | 4.04213961 | 3.142366 | 0.001977 | 0.0821741 | -1.545 | up-regulated in participants with widespread BE | Gene Set C |
| 397 | ENSG00000231901 | | NA | q33.1 | 0.5353 | 1.057101305 | 3.124612 | 0.002093 | 0.083002 | -1.474 | up-regulated in participants with widespread BE | Gene Set C |
| 398 | ENSG00000204264 | PSMB8 | 5696 | p21.32 | 0.372373 | 5.457715768 | 3.118245 | 0.002136 | 0.0830303 | -1.675 | up-regulated in participants with widespread BE | Gene Set C |
| 399 | ENSG00000172058 | SERF1A | c(728492, 8293) | q13.2 | 0.38574 | 1.598022337 | 3.117357 | 0.002142 | 0.0830303 | -1.481 | up-regulated in participants with widespread BE | Gene Set C |
| 400 | ENSG00000075643 | MOCOS | 55034 | q12.2 | 0.379978 | 4.234614654 | 3.10457 | 0.002232 | 0.0830303 | -1.672 | up-regulated in participants with widespread BE | Gene Set C |
| 401 | ENSG00000134184 | GSTM1 | 2944 | p13.3 | 1.784552 | 0.003404175 | 3.1033 | 0.002241 | 0.0830303 | -1.534 | up-regulated in participants with widespread BE | Gene Set C |
| 402 | ENSG00000132329 | RAMP1 | 10267 | q37.3 | 0.524534 | 2.882472447 | 3.063138 | 0.002546 | 0.0850812 | -1.683 | up-regulated in participants with widespread BE | Gene Set C |
| 403 | ENSG00000186369 | LINC00643 | 646113 | q23.2 | 0.550126 | 0.862706126 | 3.033316 | 0.002797 | 0.0868249 | -1.712 | up-regulated in participants with widespread BE | Gene Set C |
| 404 | ENSG00000185532 | PRKG1 | 5592 | q11.23 | 0.854588 | 0.867544713 | 3.011163 | 0.002999 | 0.0868249 | -1.761 | up-regulated in participants with widespread BE | Gene Set C |
| 405 | ENSG00000225335 | | NA | q11.21 | 0.281821 | 0.338432172 | 3.006342 | 0.003044 | 0.0868249 | -1.828 | up-regulated in participants with widespread BE | Gene Set C |
| 406 | ENSG00000048540 | LMO3 | 55885 | p12.3 | 1.130821 | 1.616190012 | 2.981849 | 0.003285 | 0.0884774 | -1.845 | up-regulated in participants with widespread BE | Gene Set C |
| 407 | ENSG00000270659 | | NA | q34 | 0.319387 | -0.013208628 | 2.981191 | 0.003292 | 0.0884774 | -1.926 | up-regulated in participants with widespread BE | Gene Set C |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 408 | ENSG00000242689 | CNTF | 1270 | q12.1 | 0.31589 | 3.854627577 | 2.973033 | 0.003376 | 0.0884774 | -2.001 | up-regulated in participants with widespread BE | Gene Set C |
| 409 | ENSG00000272463 | NA | NA | p25.3 | 0.655049 | -1.119671506 | 2.962579 | 0.003487 | 0.08858 | -2.117 | up-regulated in participants with widespread BE | Gene Set C |
| 410 | ENSG00000260552 | | 101927809 | q12.2 | 0.406654 | 0.153052277 | 2.955828 | 0.00356 | 0.0888089 | -1.955 | up-regulated in participants with widespread BE | Gene Set C |
| 411 | ENSG00000022267 | FHL1 | 2273 | q26.3 | 0.681677 | 2.221129543 | 2.954182 | 0.003578 | 0.0888089 | -1.932 | up-regulated in participants with widespread BE | Gene Set C |
| 412 | ENSG00000121621 | KIF18A | 81930 | p14.1 | 0.330335 | 1.759328424 | 2.95298 | 0.003592 | 0.0888908 | -1.904 | up-regulated in participants with widespread BE | Gene Set C |
| 413 | ENSG00000133321 | RARRES3 | 5920 | q12.3 | 0.393676 | 6.035754633 | 2.934584 | 0.003801 | 0.0891719 | -2.185 | up-regulated in participants with widespread BE | Gene Set C |
| 414 | ENSG00000183578 | TNFAIP8L3 | 388121 | q21.2 | 0.269614 | 2.333108059 | 2.933411 | 0.003814 | 0.0891719 | -1.974 | up-regulated in participants with widespread BE | Gene Set C |
| 415 | ENSG00000205220 | PSMB10 | 5699 | q22.1 | 0.278335 | 5.253855712 | 2.931324 | 0.003839 | 0.0891719 | -2.19 | up-regulated in participants with widespread BE | Gene Set C |
| 416 | ENSG00000227053 | | NA | q22.1 | 0.525099 | 2.628998459 | 2.930305 | 0.003851 | 0.0891719 | -2.021 | up-regulated in participants with widespread BE | Gene Set C |
| 417 | ENSG00000011332 | DPF1 | 8193 | q13.2 | 0.710557 | -0.820702583 | 2.927232 | 0.003887 | 0.0891719 | -2.113 | up-regulated in participants with widespread BE | Gene Set C |
| 418 | ENSG00000099984 | GSTT2 | 2953 | q11.23 | 0.81183 | -0.627978433 | 2.918847 | 0.003988 | 0.0900354 | -2.105 | up-regulated in participants with widespread BE | Gene Set C |
| 419 | ENSG00000106565 | TMEM176B | 28959 | q36.1 | 0.616145 | 2.398432516 | 2.907901 | 0.004123 | 0.0910552 | -2.056 | up-regulated in participants with widespread BE | Gene Set C |
| 420 | ENSG00000213876 | RPL7AP64 | NA | p13.1 | 0.342226 | 0.343818944 | 2.900409 | 0.004218 | 0.0915331 | -2.072 | up-regulated in participants with widespread BE | Gene Set C |
| 421 | ENSG00000129355 | CDKN2D | 1032 | p13.2 | 0.27729 | 2.175656821 | 2.885976 | 0.004407 | 0.0916715 | -2.087 | up-regulated in participants with widespread BE | Gene Set C |
| 422 | ENSG00000196826 | | 163051 | p13.2 | 0.390658 | -0.510630355 | 2.883561 | 0.004439 | 0.0916715 | -2.206 | up-regulated in participants with widespread BE | Gene Set C |
| 423 | ENSG00000205277 | MUC12 | 10071 | q22.1 | 0.546542 | 1.686551134 | 2.881752 | 0.004464 | 0.0916715 | -2.088 | up-regulated in participants with widespread BE | Gene Set C |
| 424 | ENSG00000260806 | | NA | q32.2 | 0.267548 | 3.717146369 | 2.875144 | 0.004554 | 0.0916715 | -2.247 | up-regulated in participants with widespread BE | Gene Set C |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 425 | ENSG00000122694 | GLIPR2 | 152007 | p13.3 | 0.251408 | 5.766854405 | 2.873913 | 0.004571 | 0.0916715 | -2.35 | up-regulated in participants with widespread BE | Gene Set C |
| 426 | ENSG00000184979 | USP18 | 11274 | q11.21 | 0.288572 | 3.687504244 | 2.860452 | 0.00476 | 0.0916715 | -2.284 | up-regulated in participants with widespread BE | Gene Set C |
| 427 | ENSG00000238837 | C19orf38 | NA | q26.33 | 0.331369 | 0.83383478 | 2.847425 | 0.00495 | 0.0923449 | -2.167 | up-regulated in participants with widespread BE | Gene Set C |
| 428 | ENSG00000214212 | C19orf38 | 255809 | p13.2 | 0.46415 | -0.025604031 | 2.835118 | 0.005135 | 0.0927491 | -2.242 | up-regulated in participants with widespread BE | Gene Set C |
| 429 | ENSG00000023839 | ABCC2 | 1244 | q24.2 | 0.279066 | 1.044694011 | 2.819607 | 0.005378 | 0.0932239 | -2.227 | up-regulated in participants with widespread BE | Gene Set C |
| 430 | ENSG00000110002 | VWA5A | 4013 | q24.2 | 0.250175 | 6.556532576 | 2.806637 | 0.005589 | 0.0948862 | -2.517 | up-regulated in participants with widespread BE | Gene Set C |
| 431 | ENSG00000163535 | SGOL2 | 151246 | q33.1 | 0.283547 | 3.190150326 | 2.791251 | 0.00585 | 0.0961055 | -2.41 | up-regulated in participants with widespread BE | Gene Set C |
| 432 | ENSG00000135549 | PKIB | 5570 | q22.31 | 0.389987 | 4.783220828 | 2.788194 | 0.005903 | 0.0961055 | -2.552 | up-regulated in participants with widespread BE | Gene Set C |
| 433 | ENSG00000134962 | KLB | 152831 | p14 | 0.485717 | -0.635899287 | 2.782388 | 0.006005 | 0.0963814 | -2.424 | up-regulated in participants with widespread BE | Gene Set C |
| 434 | ENSG00000206432 | TMEM200C | 645369 | p11.31 | 0.378448 | 1.013588349 | 2.765607 | 0.006308 | 0.0983509 | -2.351 | up-regulated in participants with widespread BE | Gene Set C |
| 435 | ENSG00000164690 | SHH | 6469 | q36.3 | 0.634824 | 1.735447774 | 2.763862 | 0.006341 | 0.0985685 | -2.378 | up-regulated in participants with widespread BE | Gene Set C |
| 436 | ENSG00000240024 | LINC00888 | 100505687 | q27.1 | 0.365548 | 2.187460242 | 4.443304 | 1.59E-05 | 0.0414908 | 2.7202 | up-regulated in participants with widespread BE | Gene Set D |
| 437 | ENSG00000214050 | FBO16 | 157574 | p21.1 | 0.254774 | 3.082699356 | 4.139319 | 5.47E-05 | 0.0496081 | 1.6931 | up-regulated in participants with widespread BE | Gene Set D |
| 438 | ENSG00000136193 | SCRN1 | 9805 | p14.3 | 0.287157 | 6.236429201 | 4.0275 | 8.47E-05 | 0.0518618 | 1.2445 | up-regulated in participants with widespread BE | Gene Set D |
| 439 | ENSG00000259508 | | NA | q32.32 | 0.639592 | 1.061018455 | 3.912151 | 0.000132 | 0.0624298 | 0.7805 | up-regulated in participants with widespread BE | Gene Set D |
| 440 | ENSG00000153363 | LINC00467 | 84791 | q32.3 | 0.270217 | 2.883837499 | 3.905116 | 0.000136 | 0.0624298 | 0.8868 | up-regulated in participants with widespread BE | Gene Set D |
| 441 | ENSG00000143158 | MPC2 | 25874 | q24.2 | 0.370803 | 5.870469278 | 3.88154 | 0.000148 | 0.0624298 | 0.7323 | up-regulated in participants with widespread BE | Gene Set D |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 442 | ENSG00000164542 | KIAA0895 | 23366 | p14.2 | 0.30409 | 5.452344047 | 3.879329 | 0.000149 | 0.0624298 | 0.7257 | up-regulated in participants with widespread BE | Gene Set D |
| 443 | ENSG00000178980 | SEPW1 | 6415 | q13.33 | 0.280031 | 7.166023347 | 3.774645 | 0.000221 | 0.0663806 | 0.3855 | up-regulated in participants with widespread BE | Gene Set D |
| 444 | ENSG00000129007 | CALML4 | 91860 | q23 | 0.323418 | 6.249807166 | 3.756113 | 0.000237 | 0.0686069 | 0.308 | up-regulated in participants with widespread BE | Gene Set D |
| 445 | ENSG00000204334 | ERICH2 | 285141 | q31.1 | 0.455338 | 2.004362657 | 3.739533 | 0.000252 | 0.0702506 | 0.3285 | up-regulated in participants with widespread BE | Gene Set D |
| 446 | ENSG00000186198 | SLC51B | 123264 | q22.31 | 0.547972 | 0.733996628 | 3.691794 | 0.000299 | 0.0702506 | 0.0575 | up-regulated in participants with widespread BE | Gene Set D |
| 447 | ENSG00000154511 | FAM69A | 388650 | p22.1 | 0.317803 | 3.536488403 | 3.625749 | 0.00038 | 0.0715125 | -0.05 | up-regulated in participants with widespread BE | Gene Set D |
| 448 | ENSG00000259802 | | NA | p15.2 | 0.30622 | 0.300724431 | 3.624769 | 0.000382 | 0.0715125 | -0.255 | up-regulated in participants with widespread BE | Gene Set D |
| 449 | ENSG00000249241 | | 101060498 | p14 | 0.625764 | 1.690915418 | 3.604354 | 0.000411 | 0.0715125 | -0.099 | up-regulated in participants with widespread BE | Gene Set D |
| 450 | ENSG00000102738 | MRPS31 | 10240 | q14.11 | 0.318959 | 4.973023407 | 3.59077 | 0.000431 | 0.0715125 | -0.228 | up-regulated in participants with widespread BE | Gene Set D |
| 451 | ENSG00000119636 | CCDC176 | 80127 | q24.3 | 0.344003 | 7.061856279 | 3.584075 | 0.000441 | 0.0715125 | -0.242 | up-regulated in participants with widespread BE | Gene Set D |
| 452 | ENSG00000161326 | DUSP14 | 11072 | q12 | 0.34653 | 5.570973807 | 3.568768 | 0.000466 | 0.0721409 | -0.309 | up-regulated in participants with widespread BE | Gene Set D |
| 453 | ENSG00000186889 | TMEM17 | 200728 | p15 | 0.279558 | 3.166984824 | 3.561027 | 0.000479 | 0.0722946 | -0.233 | up-regulated in participants with widespread BE | Gene Set D |
| 454 | ENSG00000229124 | VIM-AS1 | 100507347 | p13 | 0.442825 | 4.315459004 | 3.558765 | 0.000483 | 0.0722946 | -0.31 | up-regulated in participants with widespread BE | Gene Set D |
| 455 | ENSG00000084207 | GSTP1 | 2950 | q13.2 | 0.312438 | 9.417497003 | 3.500344 | 0.000593 | 0.0725389 | -0.445 | up-regulated in participants with widespread BE | Gene Set D |
| 456 | ENSG00000132141 | CCT6B | 10693 | q12 | 0.257644 | 3.490818486 | 3.477527 | 0.000642 | 0.0725389 | -0.51 | up-regulated in participants with widespread BE | Gene Set D |
| 457 | ENSG00000175792 | RUVBL1 | 8607 | q21.3 | 0.346095 | 6.650871545 | 3.454691 | 0.000695 | 0.0725389 | -0.661 | up-regulated in participants with widespread BE | Gene Set D |
| 458 | ENSG00000267325 | | NA | q21.2 | 0.417567 | 3.695216671 | 3.452079 | 0.000702 | 0.0725389 | -0.609 | up-regulated in participants with widespread BE | Gene Set D |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 459 | ENSG00000158122 | AAED1 | 195827 | q22.33 | 0.335572 | 4.390190928 | 3.443961 | 0.000722 | 0.0725389 | -0.671 | up-regulated in participants with widespread BE | Gene Set D |
| 460 | ENSG00000151729 | SLC25A4 | 291 | q35.1 | 0.254126 | 5.221281957 | 3.441546 | 0.000728 | 0.0725389 | -0.706 | up-regulated in participants with widespread BE | Gene Set D |
| 461 | ENSG00000188931 | C1orf192 | 257177 | q23.3 | 0.427719 | 5.747199743 | 3.415286 | 0.000796 | 0.0731174 | -0.793 | up-regulated in participants with widespread BE | Gene Set D |
| 462 | ENSG00000143479 | DYRK3 | 8444 | q32.1 | 0.273075 | 4.200817344 | 3.409962 | 0.000811 | 0.0731174 | -0.764 | up-regulated in participants with widespread BE | Gene Set D |
| 463 | ENSG00000111145 | ELK3 | 2004 | q23.1 | 0.351464 | 6.62242425 | 3.405362 | 0.000824 | 0.0731174 | -0.814 | up-regulated in participants with widespread BE | Gene Set D |
| 464 | ENSG00000272092 | | NA | p11.23 | 0.294857 | 0.349949622 | 3.385983 | 0.000881 | 0.0742673 | -0.887 | up-regulated in participants with widespread BE | Gene Set D |
| 465 | ENSG00000231023 | LINC00326 | 285735 | q23.2 | 0.560581 | 1.95518756 | 3.380833 | 0.000896 | 0.0744009 | -0.751 | up-regulated in participants with widespread BE | Gene Set D |
| 466 | ENSG00000123810 | B9D2 | 80776 | q13.2 | 0.323991 | 4.071472409 | 3.345952 | 0.001009 | 0.0758422 | -0.953 | up-regulated in participants with widespread BE | Gene Set D |
| 467 | ENSG00000224843 | LINC00240 | 100133205 | p22.2 | 0.326654 | 2.095575569 | 3.342706 | 0.00102 | 0.0758422 | -0.86 | up-regulated in participants with widespread BE | Gene Set D |
| 468 | ENSG00000119650 | IFT43 | 112752 | q24.3 | 0.263938 | 5.298974276 | 3.335726 | 0.001044 | 0.0761021 | -1.032 | up-regulated in participants with widespread BE | Gene Set D |
| 469 | ENSG00000139117 | CPNE8 | 144402 | q12 | 0.280439 | 4.490857384 | 3.33294 | 0.001054 | 0.0761021 | -1.013 | up-regulated in participants with widespread BE | Gene Set D |
| 470 | ENSG00000267795 | SMIM22 | 440335 | p13.3 | 0.348891 | 5.363985306 | 3.318389 | 0.001107 | 0.0772782 | -1.086 | up-regulated in participants with widespread BE | Gene Set D |
| 471 | ENSG00000116793 | PHTF1 | 10745 | p13.2 | 0.256963 | 6.19044751 | 3.311416 | 0.001133 | 0.0772782 | -1.108 | up-regulated in participants with widespread BE | Gene Set D |
| 472 | ENSG00000137691 | C1orf70 | 85016 | q22.1 | 0.442185 | 6.352930064 | 3.299369 | 0.00118 | 0.0776495 | -1.14 | up-regulated in participants with widespread BE | Gene Set D |
| 473 | ENSG00000184831 | APOO | 79135 | p22.11 | 0.352096 | 4.449139657 | 3.259888 | 0.001346 | 0.0782464 | -1.232 | up-regulated in participants with widespread BE | Gene Set D |
| 474 | ENSG00000104450 | SPAG1 | 6674 | q22.2 | 0.259969 | 6.592191972 | 3.258679 | 0.001351 | 0.0782464 | -1.259 | up-regulated in participants with widespread BE | Gene Set D |
| 475 | ENSG00000139537 | CCDC65 | 85478 | q13.12 | 0.362714 | 6.368645696 | 3.248376 | 0.001398 | 0.0782464 | -1.293 | up-regulated in participants with widespread BE | Gene Set D |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 476 | ENSG00000166171 | DPCD | 25911 | q24.32 | 0.363541 | 5.338325061 | 3.239845 | 0.001438 | 0.0782464 | -1.32 | up-regulated in participants with widespread BE | Gene Set D |
| 477 | ENSG00000163001 | CCDC104 | 112942 | p16.1 | 0.328365 | 5.857377134 | 3.235808 | 0.001457 | 0.0782464 | -1.335 | up-regulated in participants with widespread BE | Gene Set D |
| 478 | ENSG00000128581 | RABL5 | 64792 | q22.1 | 0.338706 | 6.146694683 | 3.235158 | 0.00146 | 0.0782464 | -1.335 | up-regulated in participants with widespread BE | Gene Set D |
| 479 | ENSG00000263450 | | NA | q12.1 | 0.713935 | 0.221767111 | 3.224096 | 0.001515 | 0.0782464 | -1.277 | up-regulated in participants with widespread BE | Gene Set D |
| 480 | ENSG00000112667 | DNPH1 | 10591 | p21.1 | 0.275305 | 4.700502665 | 3.217994 | 0.001545 | 0.0782464 | -1.365 | up-regulated in participants with widespread BE | Gene Set D |
| 481 | ENSG00000234478 | | NA | q42.12 | 0.356428 | 3.460660012 | 3.212185 | 0.001575 | 0.0783812 | -1.304 | up-regulated in participants with widespread BE | Gene Set D |
| 482 | ENSG00000233170 | | 728024 | p11.23 | 0.359322 | 0.40916477 | 3.192185 | 0.001682 | 0.0802005 | -1.363 | up-regulated in participants with widespread BE | Gene Set D |
| 483 | ENSG00000227630 | LINC01132 | 100506810 | q42.3 | 0.33641 | 1.822988676 | 3.17866 | 0.001757 | 0.0806565 | -1.317 | up-regulated in participants with widespread BE | Gene Set D |
| 484 | ENSG00000174628 | IQCK | 124152 | p12.3 | 0.268133 | 5.914277548 | 3.168056 | 0.001819 | 0.0807549 | -1.533 | up-regulated in participants with widespread BE | Gene Set D |
| 485 | ENSG00000257698 | | 100506844 | q14.1 | 0.373236 | 4.251474037 | 3.166244 | 0.00183 | 0.0807549 | -1.494 | up-regulated in participants with widespread BE | Gene Set D |
| 486 | ENSG00000145491 | ROPN1L | 83853 | p15.2 | 0.32416 | 6.567567653 | 3.161452 | 0.001858 | 0.0810493 | -1.543 | up-regulated in participants with widespread BE | Gene Set D |
| 487 | ENSG00000100591 | AHSA1 | 10598 | q24.3 | 0.26848 | 6.527514446 | 3.156711 | 0.001887 | 0.0811099 | -1.559 | up-regulated in participants with widespread BE | Gene Set D |
| 488 | ENSG00000159079 | C21orf59 | 56683 | q22.11 | 0.281553 | 6.523380005 | 3.149231 | 0.001933 | 0.0817498 | -1.58 | up-regulated in participants with widespread BE | Gene Set D |
| 489 | ENSG00000261652 | C15orf65 | 145788 | q21.3 | 0.408782 | 1.642028971 | 3.136584 | 0.002014 | 0.0824924 | -1.43 | up-regulated in participants with widespread BE | Gene Set D |
| 490 | ENSG00000271133 | | 101927811 | p21.1 | 0.356435 | 1.682513804 | 3.119452 | 0.002128 | 0.0830303 | -1.475 | up-regulated in participants with widespread BE | Gene Set D |
| 491 | ENSG00000104432 | IL7 | 3574 | q21.12 | 0.283981 | 2.808017256 | 3.118601 | 0.002134 | 0.0830303 | -1.511 | up-regulated in participants with widespread BE | Gene Set D |
| 492 | ENSG00000079257 | LN | 56925 | q25.32 | 0.388165 | 5.249539923 | 3.104825 | 0.00223 | 0.0830303 | -1.71 | up-regulated in participants with widespread BE | Gene Set D |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 493 | ENSG00000100246 | DNAL4 | 10126 | q13.1 | 0.296186 | 5.35282722 | 3.082768 | 0.002393 | 0.0842685 | −1.774 | up-regulated in participants with widespread BE | Gene Set D |
| 494 | ENSG00000203711 | C6orf99 | 100130967 | q25.3 | 0.39709 | −0.193810621 | 3.080613 | 0.002409 | 0.0842685 | −1.712 | up-regulated in participants with widespread BE | Gene Set D |
| 495 | ENSG00000164114 | MAP9 | 79884 | q32.1 | 0.284247 | 6.896460971 | 3.073895 | 0.002461 | 0.0842685 | −1.785 | up-regulated in participants with widespread BE | Gene Set D |
| 496 | ENSG00000163263 | C1orf189 | 388701 | q21.3 | 0.426698 | 2.886621864 | 3.070784 | 0.002485 | 0.0842685 | −1.656 | up-regulated in participants with widespread BE | Gene Set D |
| 497 | ENSG00000227877 | LINC00948 | 100507027 | q21.2 | 0.54792 | 1.879617571 | 3.059543 | 0.002575 | 0.0853677 | −1.636 | up-regulated in participants with widespread BE | Gene Set D |
| 498 | ENSG00000108406 | DHX40 | 79665 | q23.1 | 0.260338 | 6.802353525 | 3.058439 | 0.002584 | 0.0853677 | −1.832 | up-regulated in participants with widespread BE | Gene Set D |
| 499 | ENSG00000164347 | GFM2 | 84340 | q13.3 | 0.279667 | 6.712758713 | 3.053016 | 0.002629 | 0.0854302 | −1.849 | up-regulated in participants with widespread BE | Gene Set D |
| 500 | ENSG00000171757 | LRRC34 | 151827 | q26.2 | 0.371255 | 5.606355344 | 3.037736 | 0.002759 | 0.08629 | −1.903 | up-regulated in participants with widespread BE | Gene Set D |
| 501 | ENSG00000064199 | SPA17 | 53340 | q24.2 | 0.361473 | 6.641021453 | 3.029926 | 0.002827 | 0.0868249 | −1.913 | up-regulated in participants with widespread BE | Gene Set D |
| 502 | ENSG00000261465 | | NA | p12.3 | 0.499708 | −0.666257003 | 3.015216 | 0.002961 | 0.0868249 | −1.937 | up-regulated in participants with widespread BE | Gene Set D |
| 503 | ENSG00000256073 | C21orf119 | NA | q22.11 | 0.284132 | 2.661751446 | 2.991391 | 0.003189 | 0.0876268 | −1.845 | up-regulated in participants with widespread BE | Gene Set D |
| 504 | ENSG00000167552 | TUBA1A | 7846 | q13.12 | 0.450192 | 9.550605917 | 2.991092 | 0.003192 | 0.0876268 | −1.917 | up-regulated in participants with widespread BE | Gene Set D |
| 505 | ENSG00000164411 | GJB7 | 375519 | q15 | 0.460907 | 1.847699142 | 2.984781 | 0.003255 | 0.0883538 | −1.828 | up-regulated in participants with widespread BE | Gene Set D |
| 506 | ENSG00000025772 | TOMM34 | 10953 | q13.12 | 0.289002 | 5.670442122 | 2.97917 | 0.003312 | 0.0884774 | −2.065 | up-regulated in participants with widespread BE | Gene Set D |
| 507 | ENSG00000140876 | NUDT7 | 283927 | q23.1 | 0.275788 | 2.825076209 | 2.974904 | 0.003357 | 0.0884774 | −1.9 | up-regulated in participants with widespread BE | Gene Set D |
| 508 | ENSG00000263812 | LINC00908 | NA | q23 | 0.275585 | 3.253122129 | 2.971955 | 0.003387 | 0.0884774 | −1.945 | up-regulated in participants with widespread BE | Gene Set D |
| 509 | ENSG00000183346 | C10orf107 | 219621 | q21.2 | 0.427327 | 5.790264475 | 2.970959 | 0.003398 | 0.0884774 | −2.087 | up-regulated in participants with widespread BE | Gene Set D |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 510 | ENSG00000124237 | C20orf85 | 128602 | q13.32 | 0.363114 | 7.670419999 | 2.965764 | 0.003453 | 0.08858 | -2.058 | up-regulated in participants with widespread BE | Gene Set D |
| 511 | ENSG00000138175 | ARL3 | 403 | q24.32 | 0.311216 | 5.283547651 | 2.965313 | 0.003458 | 0.08858 | -2.098 | up-regulated in participants with widespread BE | Gene Set D |
| 512 | ENSG00000119661 | DNAL1 | 83544 | q24.3 | 0.281819 | 7.499313418 | 2.9608 | 0.003506 | 0.08858 | -2.079 | up-regulated in participants with widespread BE | Gene Set D |
| 513 | ENSG00000149972 | CNTN5 | 53942 | q22.1 | 0.380065 | 2.561332743 | 2.931747 | 0.003834 | 0.0891719 | -1.999 | up-regulated in participants with widespread BE | Gene Set D |
| 514 | ENSG00000214114 | MYCBP | c(100527950, 26292) | p34.3 | 0.305465 | 6.548479228 | 2.930877 | 0.003844 | 0.0891719 | -2.188 | up-regulated in participants with widespread BE | Gene Set D |
| 515 | ENSG00000266916 | | 101927720 | q13.12 | 0.256856 | 0.216073678 | 2.915876 | 0.004024 | 0.0903654 | -2.051 | up-regulated in participants with widespread BE | Gene Set D |
| 516 | ENSG00000260057 | | 101927364 | q12.1 | 0.373091 | 2.166813295 | 2.90635 | 0.004143 | 0.0910644 | -2.038 | up-regulated in participants with widespread BE | Gene Set D |
| 517 | ENSG00000120306 | CYSTM1 | 84418 | q31.3 | 0.301098 | 6.110846413 | 2.905517 | 0.004153 | 0.0910644 | -2.263 | up-regulated in participants with widespread BE | Gene Set D |
| 518 | ENSG00000236028 | | 101927355 | q13.12 | 0.369059 | 0.533789897 | 2.901035 | 0.00421 | 0.0915331 | -2.054 | up-regulated in participants with widespread BE | Gene Set D |
| 519 | ENSG00000143222 | UFC1 | 51506 | q23.3 | 0.297012 | 7.393460547 | 2.898812 | 0.004239 | 0.0915331 | -2.249 | up-regulated in participants with widespread BE | Gene Set D |
| 520 | ENSG00000204711 | C9orf135 | 138255 | q21.12 | 0.454562 | 5.637586495 | 2.889937 | 0.004354 | 0.0916715 | -2.306 | up-regulated in participants with widespread BE | Gene Set D |
| 521 | ENSG00000263011 | | NA | p13.3 | 0.412841 | 1.286679348 | 2.889046 | 0.004366 | 0.0916715 | -2.059 | up-regulated in participants with widespread BE | Gene Set D |
| 522 | ENSG00000125868 | DSTN | 11034 | p12.1 | 0.270644 | 8.056412725 | 2.886076 | 0.004406 | 0.0916715 | -2.259 | up-regulated in participants with widespread BE | Gene Set D |
| 523 | ENSG00000114446 | IFT57 | 55081 | q13.13 | 0.344321 | 7.531635332 | 2.880581 | 0.00448 | 0.0916715 | -2.291 | up-regulated in participants with widespread BE | Gene Set D |
| 524 | ENSG00000160345 | C9orf116 | 138162 | q34.3 | 0.352016 | 6.031865176 | 2.87327 | 0.00458 | 0.0916715 | -2.35 | up-regulated in participants with widespread BE | Gene Set D |
| 525 | ENSG00000188010 | MORN2 | 729967 | p22.1 | 0.422575 | 6.650505431 | 2.866738 | 0.004671 | 0.0916715 | -2.354 | up-regulated in participants with widespread BE | Gene Set D |
| 526 | ENSG00000185250 | PPIL6 | 285755 | q21 | 0.33456 | 6.712044527 | 2.866396 | 0.004675 | 0.0916715 | -2.356 | up-regulated in participants with widespread BE | Gene Set D |

| | Ensembl_ID | GeneID | EntrezID | Band | logFC | AveExpr | t | P.Value | adj. P.Val | B | Direction | GeneClusters |
|---|---|---|---|---|---|---|---|---|---|---|---|---|
| 527 | ENSG00000157578 | LCA5L | 150082 | q22.2 | 0.276333 | 5.169814484 | 2.859923 | 0.004767 | 0.0916715 | -2.378 | up-regulated in participants with widespread BE | Gene Set D |
| 528 | ENSG00000162961 | DPY30 | 84661 | p22.3 | 0.329773 | 5.35136745 | 2.856906 | 0.004811 | 0.0916715 | -2.39 | up-regulated in participants with widespread BE | Gene Set D |
| 529 | ENSG00000182504 | CEP97 | 79598 | q12.3 | 0.255178 | 6.536663243 | 2.853574 | 0.004859 | 0.0916715 | -2.395 | up-regulated in participants with widespread BE | Gene Set D |
| 530 | ENSG00000186471 | AKAP14 | 158798 | q24 | 0.398536 | 5.42496531 | 2.850645 | 0.004902 | 0.0921207 | -2.408 | up-regulated in participants with widespread BE | Gene Set D |
| 531 | ENSG00000272514 | | 154313 | q15 | 0.364449 | 6.921726512 | 2.847665 | 0.004946 | 0.0923449 | -2.398 | up-regulated in participants with widespread BE | Gene Set D |
| 532 | ENSG00000152611 | CAPSL | 133690 | p13.2 | 0.409244 | 6.812737872 | 2.845742 | 0.004975 | 0.0925016 | -2.406 | up-regulated in participants with widespread BE | Gene Set D |
| 533 | ENSG00000048342 | CC2D2A | 57545 | p15.32 | 0.266826 | 7.63012617 | 2.845462 | 0.004979 | 0.0925016 | -2.382 | up-regulated in participants with widespread BE | Gene Set D |
| 534 | ENSG00000116885 | OSCP1 | 127700 | p34.3 | 0.311286 | 6.285588344 | 2.842359 | 0.005025 | 0.0927071 | -2.429 | up-regulated in participants with widespread BE | Gene Set D |
| 535 | ENSG00000256061 | DY1C1 | 161582 | q21.3 | 0.33886 | 5.102801112 | 2.841055 | 0.005045 | 0.0927071 | -2.426 | up-regulated in participants with widespread BE | Gene Set D |
| 536 | ENSG00000146453 | PNLDC1 | 154197 | q25.3 | 0.417202 | 1.248909721 | 2.834755 | 0.005141 | 0.0927491 | -2.189 | up-regulated in participants with widespread BE | Gene Set D |
| 537 | ENSG00000150628 | SPATA4 | 132851 | q34.2 | 0.362661 | 4.073742819 | 2.824551 | 0.0053 | 0.0932239 | -2.416 | up-regulated in participants with widespread BE | Gene Set D |
| 538 | ENSG00000197279 | ZNF165 | 7718 | p22.1 | 0.278227 | 2.59622702 | 2.822855 | 0.005327 | 0.0932239 | -2.275 | up-regulated in participants with widespread BE | Gene Set D |
| 539 | ENSG00000163453 | IGFBP7 | 3490 | q12 | 0.454981 | 6.832337867 | 2.81838 | 0.005398 | 0.0932239 | -2.475 | up-regulated in participants with widespread BE | Gene Set D |
| 540 | ENSG00000165182 | CXorf58 | 254158 | p22.11 | 0.379046 | 0.425816977 | 2.816069 | 0.005435 | 0.0932239 | -2.255 | up-regulated in participants with widespread BE | Gene Set D |
| 541 | ENSG00000156206 | C15orf26 | 161502 | q25.1 | 0.270009 | 5.423388464 | 2.805292 | 0.005612 | 0.0949554 | -2.526 | up-regulated in participants with widespread BE | Gene Set D |
| 542 | ENSG00000224049 | | NA | q27.3 | 0.56394 | 1.789413866 | 2.804476 | 0.005625 | 0.0949554 | -2.277 | up-regulated in participants with widespread BE | Gene Set D |
| 543 | ENSG00000213123 | TCTE1D2 | 255758 | q29 | 0.353651 | 4.99497215 | 2.797761 | 0.005738 | 0.095212 | -2.536 | up-regulated in participants with widespread BE | Gene Set D |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 544 | ENSG00000196507 | TCEAL3 | 85012 | q22.2 | 0.276203 | 3.60349036 | 2.790099 | 0.00587 | 0.0961055 | -2.456 | up-regulated in participants with widespread BE | Gene Set D |
| 545 | ENSG00000258940 | | 100288846 | q21.1 | 0.297988 | 0.680016869 | 2.783379 | 0.005987 | 0.0962697 | -2.319 | up-regulated in participants with widespread BE | Gene Set D |
| 546 | ENSG00000138036 | DYNC2LI1 | 51626 | p21 | 0.267865 | 5.901722483 | 2.768023 | 0.006264 | 0.0982927 | -2.626 | up-regulated in participants with widespread BE | Gene Set D |
| 547 | ENSG00000168734 | PKIG | 11142 | q13.12 | 0.294306 | 5.472779878 | 2.76764 | 0.006271 | 0.0983189 | -2.624 | up-regulated in participants with widespread BE | Gene Set D |
| 548 | ENSG00000189376 | C8orf76 | 84933 | q24.13 | 0.313096 | 4.103784513 | 4.129937 | 5.67E-05 | 0.0496081 | 1.6402 | up-regulated in participants with widespread BE | Gene Set E |
| 549 | ENSG00000178401 | DNAJC22 | 79962 | q13.12 | 0.360757 | 2.805252263 | 4.12846 | 5.71E-05 | 0.0496081 | 1.6508 | up-regulated in participants with widespread BE | Gene Set E |
| 550 | ENSG00000250508 | | NA | q13.3 | 0.572485 | 1.720171237 | 4.052134 | 7.70E-05 | 0.0518618 | 1.3236 | up-regulated in participants with widespread BE | Gene Set E |
| 551 | ENSG00000101310 | SEC23B | 10483 | p11.23 | 0.328132 | 6.52944054 | 4.051477 | 7.72E-05 | 0.0518618 | 1.3337 | up-regulated in participants with widespread BE | Gene Set E |
| 552 | ENSG00000121073 | SLC35B1 | 10237 | q21.33 | 0.266967 | 4.809216485 | 4.005039 | 9.24E-05 | 0.0527668 | 1.1753 | up-regulated in participants with widespread BE | Gene Set E |
| 553 | ENSG00000108244 | KRT23 | 25984 | q21.2 | 0.576992 | 5.375653675 | 3.83653 | 0.000176 | 0.0624298 | 0.5786 | up-regulated in participants with widespread BE | Gene Set E |
| 554 | ENSG00000136522 | MRPL47 | 57129 | q26.33 | 0.323007 | 4.307415729 | 3.821971 | 0.000185 | 0.0624298 | 0.558 | up-regulated in participants with widespread BE | Gene Set E |
| 555 | ENSG00000132603 | NIP7 | 51388 | q22.1 | 0.253381 | 4.16230053 | 3.820233 | 0.000187 | 0.0624298 | 0.5599 | up-regulated in participants with widespread BE | Gene Set E |
| 556 | ENSG00000178127 | NDUFV2 | 4729 | p11.22 | 0.340324 | 5.787490336 | 3.704869 | 0.000286 | 0.0702506 | 0.1348 | up-regulated in participants with widespread BE | Gene Set E |
| 557 | ENSG00000151364 | KCTD14 | c(100532726, 65987) | q14.1 | 0.501193 | 2.683008449 | 3.65285 | 0.000345 | 0.0702506 | 0.0663 | up-regulated in participants with widespread BE | Gene Set E |
| 558 | ENSG00000155115 | GTF3C6 | 112495 | q21 | 0.298237 | 4.119158184 | 3.651347 | 0.000347 | 0.0702506 | 0.0017 | up-regulated in participants with widespread BE | Gene Set E |
| 559 | ENSG00000063241 | ISOC2 | 79763 | q13.42 | 0.253628 | 4.277209779 | 3.630251 | 0.000374 | 0.0715125 | -0.074 | up-regulated in participants with widespread BE | Gene Set E |
| 560 | ENSG00000164105 | SAP30 | 8819 | q34.1 | 0.314754 | 3.159376036 | 3.594316 | 0.000426 | 0.0715125 | -0.13 | up-regulated in participants with widespread BE | Gene Set E |

-continued

| | Ensembl_ID | GeneID | EntrezID | Band | logFC | AveExpr | t | P.Value | adj.P.Val | B | Direction | GeneClusters |
|---|---|---|---|---|---|---|---|---|---|---|---|---|
| 561 | ENSG00000230989 | HSBP1 | 3281 | q23.3 | 0.31323 | 6.851053919 | 3.589056 | 0.000434 | 0.0715125 | -0.231 | up-regulated in participants with widespread BE | Gene Set E |
| 562 | ENSG00000143106 | PSMA5 | 5686 | p13.3 | 0.301712 | 6.036582209 | 3.530969 | 0.000533 | 0.0725389 | -0.429 | up-regulated in participants with widespread BE | Gene Set E |
| 563 | ENSG00000262823 | | NA | p13.2 | 0.444549 | -0.142212668 | 3.522327 | 0.000549 | 0.0725389 | -0.612 | up-regulated in participants with widespread BE | Gene Set E |
| 564 | ENSG00000106803 | SEC61B | 10952 | q22.33 | 0.315806 | 4.609782825 | 3.520529 | 0.000553 | 0.0725389 | -0.441 | up-regulated in participants with widespread BE | Gene Set E |
| 565 | ENSG00000134375 | TIMM17A | 10440 | q32.1 | 0.277264 | 4.855680442 | 3.509081 | 0.000575 | 0.0725389 | -0.485 | up-regulated in participants with widespread BE | Gene Set E |
| 566 | ENSG00000112782 | CLIC5 | 53405 | p21.1 | 0.330827 | 3.700895251 | 3.503787 | 0.000586 | 0.0725389 | -0.446 | up-regulated in participants with widespread BE | Gene Set E |
| 567 | ENSG00000163902 | RPN1 | 6184 | q21.3 | 0.253197 | 7.641379322 | 3.478801 | 0.000639 | 0.0725389 | -0.561 | up-regulated in participants with widespread BE | Gene Set E |
| 568 | ENSG00000179630 | LACC1 | 144811 | q14.11 | 0.29273 | 4.143657591 | 3.474307 | 0.000649 | 0.0725389 | -0.563 | up-regulated in participants with widespread BE | Gene Set E |
| 569 | ENSG00000183617 | MRPL54 | 116541 | p13.3 | 0.268756 | 3.941620204 | 3.458937 | 0.000685 | 0.0725389 | -0.597 | up-regulated in participants with widespread BE | Gene Set E |
| 570 | ENSG00000100804 | PSMB5 | 5693 | q11.2 | 0.281185 | 5.734192903 | 3.452447 | 0.000701 | 0.0725389 | -0.678 | up-regulated in participants with widespread BE | Gene Set E |
| 571 | ENSG00000118939 | UCHL3 | 7347 | q22.2 | 0.400047 | 3.1516158 | 3.439633 | 0.000732 | 0.0725389 | -0.612 | up-regulated in participants with widespread BE | Gene Set E |
| 572 | ENSG00000087302 | C14orf166 | 51637 | q22.1 | 0.273425 | 5.580142461 | 3.431561 | 0.000753 | 0.0725389 | -0.742 | up-regulated in participants with widespread BE | Gene Set E |
| 573 | ENSG00000162972 | C2orf47 | 79568 | q33.1 | 0.253392 | 3.101296108 | 3.427569 | 0.000764 | 0.0727039 | -0.639 | up-regulated in participants with widespread BE | Gene Set E |
| 574 | ENSG00000184203 | PPP1R2 | 5504 | q29 | 0.253023 | 6.190441168 | 3.411564 | 0.000807 | 0.0731174 | -0.803 | up-regulated in participants with widespread BE | Gene Set E |
| 575 | ENSG00000113583 | C5orf15 | 56951 | q31.1 | 0.263197 | 6.618345802 | 3.403861 | 0.000828 | 0.0731174 | -0.82 | up-regulated in participants with widespread BE | Gene Set E |
| 576 | ENSG00000086061 | DNAJA1 | 3301 | p21.1 | 0.342861 | 7.524831322 | 3.388106 | 0.000874 | 0.0742673 | -0.844 | up-regulated in participants with widespread BE | Gene Set E |
| 577 | ENSG00000181061 | HIGD1A | 25994 | p22.1 | 0.318956 | 5.928431826 | 3.387455 | 0.000876 | 0.0742673 | -0.878 | up-regulated in participants with widespread BE | Gene Set E |

-continued

| | Ensembl_ID | GeneID | Band | logFC | AveExpr | t | P.Value | adj. P. Val | B | Direction | GeneClusters |
|---|---|---|---|---|---|---|---|---|---|---|---|
| 578 | ENSG00000240972 | MIF | q11.23 | 0.306547 | 5.099895062 | 3.382697 | 0.00089 | 0.0742673 | -0.886 | up-regulated in participants with widespread BE | Gene Set E |
| 579 | ENSG00000123595 | RAB9A | p22.2 | 0.262776 | 4.158526879 | 3.375729 | 0.000912 | 0.0745239 | -0.866 | up-regulated in participants with widespread BE | Gene Set E |
| 580 | ENSG00000165806 | CASP7 | q25.3 | 0.282308 | 6.026516898 | 3.343948 | 0.001016 | 0.0758422 | -1.011 | up-regulated in participants with widespread BE | Gene Set E |
| 581 | ENSG00000132963 | POMP | q12.3 | 0.325732 | 5.159197088 | 3.342801 | 0.00102 | 0.0758422 | -1.009 | up-regulated in participants with widespread BE | Gene Set E |
| 582 | ENSG00000183569 | SERHL2 | q13.2 | 0.734318 | 1.537803324 | 3.336354 | 0.001042 | 0.0761021 | -0.883 | up-regulated in participants with widespread BE | Gene Set E |
| 583 | ENSG00000107949 | BCCIP | q26.2 | 0.250068 | 5.464094537 | 3.334137 | 0.00105 | 0.0761021 | -1.039 | up-regulated in participants with widespread BE | Gene Set E |
| 584 | ENSG00000198873 | GRK5 | q26.11 | 0.489212 | 0.834572302 | 3.325587 | 0.001081 | 0.0769338 | -0.965 | up-regulated in participants with widespread BE | Gene Set E |
| 585 | ENSG00000170315 | UBB | p11.2 | 0.316094 | 8.63186581 | 3.316893 | 0.001113 | 0.0772782 | -1.025 | up-regulated in participants with widespread BE | Gene Set E |
| 586 | ENSG00000116288 | PARK7 | p36.23 | 0.265877 | 6.095903701 | 3.314663 | 0.001121 | 0.0772782 | -1.099 | up-regulated in participants with widespread BE | Gene Set E |
| 587 | ENSG00000106153 | CHCHD2 | p11.2 | 0.260087 | 6.798841737 | 3.312194 | 0.00113 | 0.0772782 | -1.095 | up-regulated in participants with widespread BE | Gene Set E |
| 588 | ENSG00000064763 | FAR2 | p11.22 | 0.432405 | 4.244597197 | 3.309042 | 0.001142 | 0.0772782 | -1.079 | up-regulated in participants with widespread BE | Gene Set E |
| 589 | ENSG00000108176 | DNAJC12 | q21.3 | 0.791402 | 2.601919235 | 3.299955 | 0.001178 | 0.0776495 | -1.01 | up-regulated in participants with widespread BE | Gene Set E |
| 590 | ENSG00000122643 | NT5C3A | p14.3 | 0.292867 | 4.858381761 | 3.295749 | 0.001194 | 0.0776631 | -1.142 | up-regulated in participants with widespread BE | Gene Set E |
| 591 | ENSG00000120686 | UFM1 | q13.3 | 0.251325 | 6.307020311 | 3.276253 | 0.001275 | 0.0782464 | -1.212 | up-regulated in participants with widespread BE | Gene Set E |
| 592 | ENSG00000134058 | CDK7 | q13.2 | 0.271783 | 4.48222239 | 3.235552 | 0.001459 | 0.0782464 | -1.303 | up-regulated in participants with widespread BE | Gene Set E |
| 593 | ENSG00000198937 | CCDC167 | p21.2 | 0.345191 | 1.552847987 | 3.223303 | 0.001519 | 0.0782464 | -1.202 | up-regulated in participants with widespread BE | Gene Set E |
| 594 | ENSG00000166226 | CCT2 | q15 | 0.309508 | 6.567541566 | 3.219411 | 0.001538 | 0.0782464 | -1.375 | up-regulated in participants with widespread BE | Gene Set E |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 595 | ENSG00000123562 | MORF4L2 | 9643 | q22.2 | 0.250654 | 7.542963352 | 3.218237 | 0.001544 | 0.0782464 | -1.352 | up-regulated in participants with widespread BE | Gene Set E |
| 596 | ENSG00000143933 | CALM2 | c(808, 805, 801) | p21 | 0.314179 | 9.174811992 | 3.210063 | 0.001586 | 0.0783812 | -1.322 | up-regulated in participants with widespread BE | Gene Set E |
| 597 | ENSG00000154274 | C4orf19 | 55286 | p14 | 0.322321 | 4.176306923 | 3.185901 | 0.001716 | 0.0804147 | -1.433 | up-regulated in participants with widespread BE | Gene Set E |
| 598 | ENSG00000205155 | PSENEN | 55851 | q13.12 | 0.361966 | 6.754049948 | 3.18567 | 0.001718 | 0.0804147 | -1.468 | up-regulated in participants with widespread BE | Gene Set E |
| 599 | ENSG00000109971 | HSPA8 | c(85390, 85389, 3312) | q24.1 | 0.310312 | 10.211409 | 3.172135 | 0.001795 | 0.0807549 | -1.398 | up-regulated in participants with widespread BE | Gene Set E |
| 600 | ENSG00000137947 | GTF2B | 2959 | p22.2 | 0.282617 | 4.838715146 | 3.170513 | 0.001805 | 0.0807549 | -1.509 | up-regulated in participants with widespread BE | Gene Set E |
| 601 | ENSG00000004779 | NDUFAB1 | 4706 | p12.2 | 0.299104 | 4.980862437 | 3.163642 | 0.001845 | 0.0810493 | -1.534 | up-regulated in participants with widespread BE | Gene Set E |
| 602 | ENSG00000129562 | DAD1 | 1603 | q11.2 | 0.288065 | 5.658647712 | 3.158538 | 0.001876 | 0.0810493 | -1.56 | up-regulated in participants with widespread BE | Gene Set E |
| 603 | ENSG00000102172 | SMS | 6611 | p22.11 | 0.264835 | 5.766020895 | 3.158506 | 0.001876 | 0.0810493 | -1.561 | up-regulated in participants with widespread BE | Gene Set E |
| 604 | ENSG00000123444 | KBTBD4 | 55709 | p11.2 | 0.258125 | 5.447297598 | 3.140393 | 0.001989 | 0.0821741 | -1.611 | up-regulated in participants with widespread BE | Gene Set E |
| 605 | ENSG00000173467 | AGR3 | 155465 | p21.1 | 0.48089 | 6.554500474 | 3.134809 | 0.002026 | 0.0825572 | -1.617 | up-regulated in participants with widespread BE | Gene Set E |
| 606 | ENSG00000173890 | GPR160 | 26996 | q26.2 | 0.256005 | 4.294353096 | 3.109949 | 0.002194 | 0.0830303 | -1.653 | up-regulated in participants with widespread BE | Gene Set E |
| 607 | ENSG00000120438 | TCP1 | c(677812, 6950) | q25.3 | 0.251811 | 6.911517186 | 3.104443 | 0.002233 | 0.0830303 | -1.699 | up-regulated in participants with widespread BE | Gene Set E |
| 608 | ENSG00000100567 | PSMA3 | 5684 | q23.1 | 0.312964 | 5.350249867 | 3.095792 | 0.002295 | 0.0838518 | -1.737 | up-regulated in participants with widespread BE | Gene Set E |
| 609 | ENSG00000101846 | STS | 412 | p22.31 | 0.297508 | 5.258952853 | 3.079696 | 0.002416 | 0.0842685 | -1.779 | up-regulated in participants with widespread BE | Gene Set E |
| 610 | ENSG00000134248 | LAMTOR5 | 10542 | p13.3 | 0.25592 | 4.808240849 | 3.073879 | 0.002461 | 0.0842685 | -1.782 | up-regulated in participants with widespread BE | Gene Set E |
| 611 | ENSG00000138495 | COX17 | 10063 | q13.33 | 0.254823 | 4.177550679 | 3.073255 | 0.002466 | 0.0842685 | -1.748 | up-regulated in participants with widespread BE | Gene Set E |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 612 | ENSG00000148154 | UGCG | 7357 | q31.3 | 0.297461 | 7.372860551 | 3.067959 | 0.002508 | 0.0843097 | −1.786 | up-regulated in participants with widespread BE | Gene Set E |
| 613 | ENSG00000100902 | PSMA6 | 5687 | q13.2 | 0.282143 | 5.690626529 | 3.06295 | 0.002548 | 0.0850812 | −1.833 | up-regulated in participants with widespread BE | Gene Set E |
| 614 | ENSG00000111775 | CO6A1 | 1337 | q24.31 | 0.260676 | 6.426155716 | 3.049696 | 0.002657 | 0.0854302 | −1.864 | up-regulated in participants with widespread BE | Gene Set E |
| 615 | ENSG00000136052 | SLC41A2 | 84102 | q23.3 | 0.314947 | 4.388016976 | 3.032092 | 0.002808 | 0.0868249 | −1.88 | up-regulated in participants with widespread BE | Gene Set E |
| 616 | ENSG00000166598 | HSP90B1 | c(100500842, 7184) | q23.3 | 0.268603 | 8.559619664 | 3.023149 | 0.002888 | 0.0868249 | −1.87 | up-regulated in participants with widespread BE | Gene Set E |
| 617 | ENSG00000155660 | PDIA4 | 9601 | q36.1 | 0.25177 | 7.362121664 | 3.005906 | 0.003048 | 0.0868249 | −1.96 | up-regulated in participants with widespread BE | Gene Set E |
| 618 | ENSG00000101888 | NT2 | 55916 | q23 | 0.252093 | 4.034965088 | 2.987889 | 0.003224 | 0.088019 | −1.972 | up-regulated in participants with widespread BE | Gene Set E |
| 619 | ENSG00000147592 | LACTB2 | 51110 | q13.3 | 0.287754 | 2.946252521 | 2.985697 | 0.003246 | 0.0883538 | −1.883 | up-regulated in participants with widespread BE | Gene Set E |
| 620 | ENSG00000135002 | RFK | 55312 | q21.13 | 0.267403 | 4.674693387 | 2.983086 | 0.003273 | 0.0884774 | −2.029 | up-regulated in participants with widespread BE | Gene Set E |
| 621 | ENSG00000146425 | DYNLT1 | 6993 | q25.3 | 0.268277 | 6.821634721 | 2.977583 | 0.003329 | 0.0884774 | −2.054 | up-regulated in participants with widespread BE | Gene Set E |
| 622 | ENSG00000112695 | COX7A2 | 1347 | q14.1 | 0.341053 | 5.914333185 | 2.969662 | 0.003411 | 0.0884774 | −2.091 | up-regulated in participants with widespread BE | Gene Set E |
| 623 | ENSG00000163170 | BOLA3 | 388962 | p13.1 | 0.266922 | 2.550422148 | 2.96757 | 0.003434 | 0.08858 | −1.899 | up-regulated in participants with widespread BE | Gene Set E |
| 624 | ENSG00000242114 | MTFP1 | 51537 | q12.2 | 0.358225 | 2.220491845 | 2.941506 | 0.003721 | 0.0891181 | −1.952 | up-regulated in participants with widespread BE | Gene Set E |
| 625 | ENSG00000086205 | FOLH1 | c(219595, 2346) | p11.12 | 0.395493 | 4.208396985 | 2.933317 | 0.003815 | 0.0891719 | −2.14 | up-regulated in participants with widespread BE | Gene Set E |
| 626 | ENSG00000101843 | PSMD10 | 5716 | q22.3 | 0.278713 | 5.351508334 | 2.930939 | 0.003843 | 0.0891719 | −2.193 | up-regulated in participants with widespread BE | Gene Set E |
| 627 | ENSG00000065518 | NDUFB4 | 4710 | q13.33 | 0.28038 | 5.097972966 | 2.926096 | 0.003901 | 0.0891719 | −2.2 | up-regulated in participants with widespread BE | Gene Set E |
| 628 | ENSG00000154719 | MRPL39 | 54148 | q21.3 | 0.264371 | 3.718683222 | 2.918467 | 0.003993 | 0.0900354 | −2.134 | up-regulated in participants with widespread BE | Gene Set E |

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 629 | ENSG00000197982 | C1orf122 | 127687 | p34.3 | 0.255217 | 3.127967988 | 2.911194 | 0.004082 | 0.090932 | -2.096 | up-regulated in participants with widespread BE | Gene Set E |
| 630 | ENSG00000168288 | MMADHC | 27249 | q23.2 | 0.263099 | 6.047326745 | 2.908921 | 0.00411 | 0.0910381 | -2.255 | up-regulated in participants with widespread BE | Gene Set E |
| 631 | ENSG00000132432 | SEC61G | 23480 | p11.2 | 0.358082 | 4.424434196 | 2.907909 | 0.004123 | 0.0910552 | -2.22 | up-regulated in participants with widespread BE | Gene Set E |
| 632 | ENSG00000119013 | NDUFB3 | 4709 | q33.1 | 0.301864 | 4.694486911 | 2.904476 | 0.004166 | 0.0911434 | -2.242 | up-regulated in participants with widespread BE | Gene Set E |
| 633 | ENSG00000180879 | SSR4 | 6748 | q28 | 0.270817 | 6.338286382 | 2.899875 | 0.004225 | 0.0915331 | -2.275 | up-regulated in participants with widespread BE | Gene Set E |
| 634 | ENSG00000180530 | NRIP1 | 8204 | q21.1 | 0.256581 | 5.914743492 | 2.899131 | 0.004235 | 0.0915331 | -2.282 | up-regulated in participants with widespread BE | Gene Set E |
| 635 | ENSG00000214274 | ANG | 283 | q11.2 | 0.318993 | 4.129351636 | 2.895128 | 0.004286 | 0.0916715 | -2.232 | up-regulated in participants with widespread BE | Gene Set E |
| 636 | ENSG00000185222 | WBP5 | 51186 | q22.2 | 0.363055 | 3.464712275 | 2.871185 | 0.004608 | 0.0916715 | -2.237 | up-regulated in participants with widespread BE | Gene Set E |
| 637 | ENSG00000146386 | ABRACL | 58527 | q24.1 | 0.324632 | 3.479584525 | 2.866295 | 0.004677 | 0.0916715 | -2.25 | up-regulated in participants with widespread BE | Gene Set E |
| 638 | ENSG00000100290 | BIK | 638 | q13.2 | 0.272277 | 3.274696192 | 2.86426 | 0.004706 | 0.0916715 | -2.234 | up-regulated in participants with widespread BE | Gene Set E |
| 639 | ENSG00000134056 | MRPS36 | 92259 | q13.2 | 0.263064 | 3.528376109 | 2.854011 | 0.004853 | 0.0916715 | -2.283 | up-regulated in participants with widespread BE | Gene Set E |
| 640 | ENSG00000101928 | MOSPD1 | 56180 | q26.3 | 0.255546 | 3.872779468 | 2.853012 | 0.004867 | 0.0916715 | -2.319 | up-regulated in participants with widespread BE | Gene Set E |
| 641 | ENSG00000119705 | SLIRP | 81892 | q24.3 | 0.258311 | 3.806895895 | 2.848197 | 0.004938 | 0.0923449 | -2.325 | up-regulated in participants with widespread BE | Gene Set E |
| 642 | ENSG00000172172 | MRPL13 | 28998 | q24.12 | 0.262719 | 4.226455799 | 2.836658 | 0.005112 | 0.0927491 | -2.391 | up-regulated in participants with widespread BE | Gene Set E |
| 643 | ENSG00000185275 | CD24P4 | NA | q11.222 | 0.335756 | 4.297375471 | 2.834569 | 0.005144 | 0.0927491 | -2.408 | up-regulated in participants with widespread BE | Gene Set E |
| 644 | ENSG00000113811 | | 58515 | p21.1 | 0.297744 | 4.293766065 | 2.828633 | 0.005236 | 0.0932108 | -2.418 | up-regulated in participants with widespread BE | Gene Set E |
| 645 | ENSG00000232388 | LINC00493 | 388789 | p11.23 | 0.271123 | 4.403198516 | 2.819634 | 0.005378 | 0.0932239 | -2.448 | up-regulated in participants with widespread BE | Gene Set E |

-continued

| | Ensembl_ID | GeneID | EntrezID | Band | logFC | AveExpr | t | P. Value | adj. P. Val | B | Direction | GeneClusters |
|---|---|---|---|---|---|---|---|---|---|---|---|---|
| 646 | ENSG00000142168 | SOD1 | 6647 | q22.11 | 0.310565 | 7.306984977 | 2.800964 | 0.005684 | 0.095212 | −2.508 | up-regulated in participants with widespread BE | Gene Set E |
| 647 | ENSG00000167779 | IGFBP6 | 3489 | q13.13 | 0.57466 | 0.542162636 | 2.790446 | 0.005864 | 0.0961055 | −2.302 | up-regulated in participants with widespread BE | Gene Set E |
| 648 | ENSG00000123131 | PRD4 | 10549 | p22.11 | 0.294233 | 4.629903118 | 2.789932 | 0.005873 | 0.0961055 | −2.54 | up-regulated in participants with widespread BE | Gene Set E |
| 649 | ENSG00000075089 | ACTR6 | 64431 | q23.1 | 0.260396 | 4.799730994 | 2.788388 | 0.005899 | 0.0961055 | −2.551 | up-regulated in participants with widespread BE | Gene Set E |
| 650 | ENSG00000128228 | SDF2L1 | 23753 | q11.21 | 0.279759 | 2.829626145 | 2.787862 | 0.005909 | 0.0961055 | −2.385 | up-regulated in participants with widespread BE | Gene Set E |
| 651 | ENSG00000074842 | C19orf10 | 56005 | p13.3 | 0.287845 | 4.061776633 | 2.776583 | 0.006108 | 0.097019 | −2.536 | up-regulated in participants with widespread BE | Gene Set E |
| 652 | ENSG00000110944 | IL23A | 51561 | q13.3 | 0.488376 | −0.729806416 | 2.766512 | 0.006292 | 0.0983509 | −2.461 | up-regulated in participants with widespread BE | Gene Set E |
| 653 | ENSG00000198406 | BZW1P2 | NA | q13.31 | 0.266169 | 2.712442049 | 2.765814 | 0.006304 | 0.0983509 | −2.427 | up-regulated in participants with widespread BE | Gene Set E |
| 654 | ENSG00000189377 | CCL17 | 284340 | q13.2 | 0.357141 | 7.221167995 | 2.763617 | 0.006345 | 0.0985685 | −2.605 | up-regulated in participants with widespread BE | Gene Set E |
| 655 | ENSG00000173915 | USMG5 | 84833 | q24.33 | 0.323602 | 4.73039352 | 2.759733 | 0.006418 | 0.099009 | −2.622 | up-regulated in participants with widespread BE | Gene Set E |

Table 11 depicts a table of deconvolution results for estimated cell proportion across cohorts of bronchial epithelium.

| | Bcells | Basal | Cycling Basal | Dendritic | Deuterosomal | Endothelial | Fibroblast | Ionocyte | LT/NK | Macrophage | Mast cells |
|---|---|---|---|---|---|---|---|---|---|---|---|
| 4790-005 | 0 | 0.099879 | 0 | 0 | 0.056186 | 0 | 0 | 0 | 0 | 0.002328 | 0 |
| 4790-006 | 0 | 0.103093 | 0 | 0 | 0.073383 | 0 | 0 | 0 | 0 | 0 | 0 |
| 4790-008 | 0 | 0.036462 | 0 | 0 | 0.068103 | 0 | 0 | 0 | 0 | 0 | 0 |
| 4790-009 | 0 | 0.101899 | 0 | 0 | 0.06991 | 0 | 0 | 0 | 0 | 0 | 0 |
| 4790-011 | 0 | 0.108956 | 0 | 0 | 0.062372 | 0 | 0 | 0.001922 | 0 | 0 | 5.04E−05 |
| 4790-012 | 0 | 0.142271 | 0 | 0 | 0.069322 | 0 | 0 | 0 | 0 | 0 | 0 |
| 4790-013 | 0 | 0.105756 | 0 | 0 | 0.117906 | 0 | 0 | 0 | 0 | 0 | 0 |
| 4790-014 | 0 | 0.055011 | 0 | 0 | 0.058687 | 0 | 0 | 0 | 0 | 0 | 0.000932 |
| 4790-016 | 0 | 0.096485 | 0 | 0 | 0.057687 | 0 | 0 | 0 | 0 | 0 | 0 |
| 4790-021 | 0 | 0.117804 | 0 | 0 | 0.103562 | 0 | 0 | 0 | 0 | 0 | 0 |
| 4790-022 | 0 | 0.122813 | 0 | 0 | 0.047329 | 0 | 0 | 0 | 0 | 0 | 0 |
| 4790-023 | 0 | 0.169319 | 0 | 0 | 0.053018 | 0 | 0 | 0 | 0 | 0 | 0 |
| 4790-024 | 0 | 0.066548 | 0 | 0 | 0.088986 | 0 | 0 | 0 | 0.000328 | 0 | 0 |
| 4790-025 | 0 | 0.130453 | 0 | 0 | 0.029707 | 0 | 0 | 0 | 0 | 0 | 0 |
| 4790-026 | 0 | 0.068693 | 0 | 0 | 0.094585 | 0 | 0 | 0.001147 | 0 | 0 | 0 |
| 4790-027 | 0 | 0.070766 | 0 | 0 | 0.041903 | 0 | 0 | 0 | 0 | 0 | 0 |
| 4238-030 | 0 | 0.070934 | 0.01128 | 0 | 0.08968 | 0 | 0 | 0 | 0 | 0 | 0 |
| 4797-006 | 0 | 0.15937 | 0 | 0 | 0.071922 | 0 | 0 | 0 | 0 | 0 | 0 |
| 4797-007 | 0 | 0.138311 | 0 | 0 | 0.060744 | 0 | 0 | 0 | 0 | 0 | 0 |
| 4797-012 | 0 | 0.153757 | 0 | 0 | 0.050647 | 0 | 0 | 0 | 0 | 0 | 0 |
| 4795-013 | 0 | 0.189715 | 0 | 0 | 0.065034 | 0 | 0 | 0.000132 | 0 | 0 | 0 |
| 4795-017 | 0 | 0.084249 | 0 | 0.000635 | 0.092531 | 0 | 0 | 0 | 0.000744 | 0 | 0 |
| 4795-019 | 0 | 0.125658 | 0 | 0 | 0.047227 | 0 | 0 | 0 | 0.002808 | 0 | 0.000237 |
| 4238-017 | 0 | 0.071048 | 0 | 0 | 0.084136 | 0 | 0 | 0 | 0 | 0 | 0 |
| 4238-022 | 0 | 0.085588 | 0 | 0 | 0.078335 | 0 | 0 | 0 | 0 | 0.034016 | 0 |
| 4238-027 | 0 | 0.039818 | 0 | 0 | 0.187425 | 0 | 0 | 0 | 0.012473 | 0 | 0 |
| 4238-028 | 0 | 0.053142 | 0 | 0 | 0.087775 | 0 | 0 | 0 | 0 | 0 | 0 |
| 4238-029 | 0 | 0.060807 | 0 | 0 | 0.07363 | 0 | 0 | 0 | 0 | 0 | 0 |
| 4438-015 | 0 | 0.100708 | 0 | 0 | 0.075284 | 0 | 0 | 0 | 0 | 0 | 0 |
| 4438-032 | 0 | 0.180172 | 0 | 0 | 0.07035 | 0 | 0 | 0 | 0 | 0 | 0 |
| 4790-015 | 0.001172 | 0.057986 | 0.012671 | 0 | 0.061547 | 0 | 0 | 0 | 0.009501 | 0 | 0 |
| 4796-008 | 0 | 0.108862 | 0 | 0 | 0.08024 | 0 | 0 | 0 | 0 | 0 | 0 |
| 4796-015 | 0 | 0.168659 | 0 | 0 | 0.156818 | 0 | 0 | 0 | 0 | 0 | 0 |
| 4796-029 | 0 | 0.06542 | 0 | 0 | 0.098843 | 0 | 0 | 0 | 0 | 0.032873 | 0 |
| 4796-033 | 0 | 0.035253 | 0 | 0 | 0.141668 | 0 | 0 | 0 | 0 | 0.018624 | 0 |
| 4796-034 | 0 | 0.058724 | 0 | 0 | 0.127941 | 0 | 0 | 0 | 0 | 0 | 0 |
| 4796-036 | 0 | 0.088509 | 0 | 0 | 0.107713 | 0 | 0 | 0 | 0 | 0 | 0 |
| 4796-037 | 0 | 0.147702 | 0 | 0 | 0.086616 | 0 | 0 | 0 | 0 | 0 | 0 |
| 4796-052 | 0 | 0.083971 | 0 | 0 | 0.122559 | 0 | 0 | 0 | 0 | 0 | 0 |
| 4796-055 | 0 | 0.108947 | 0 | 0 | 0.095425 | 0 | 0 | 0 | 0 | 0 | 0 |
| 4796-064 | 0 | 0.110857 | 0 | 0 | 0.103355 | 0 | 0 | 0 | 0 | 0 | 0 |
| 4796-071 | 0 | 0.109836 | 0 | 0 | 0.109126 | 0 | 0 | 0 | 0 | 0 | 0 |
| 4796-072 | 0 | 0.083082 | 0 | 0 | 0.071058 | 0 | 0 | 0.00275 | 0 | 0 | 0 |
| 4238-019 | 0 | 0.125974 | 0 | 0 | 0.06844 | 0 | 0 | 0 | 0 | 0.00039 | 0 |
| 4238-025 | 0 | 0.120558 | 0 | 0 | 0.087487 | 0 | 0 | 0 | 0 | 0.000129 | 0 |
| 4790-053 | 0 | 0.078909 | 0 | 0 | 0.145914 | 0 | 0 | 0.000361 | 0 | 0 | 0 |
| 4795-032 | 0 | 0.099079 | 0 | 0 | 0.113787 | 0 | 0 | 0 | 0 | 0 | 0 |
| 4796-023 | 0 | 0.129773 | 0 | 0 | 0.114945 | 0 | 0 | 0 | 0 | 0.000144 | 0 |
| 4796-044 | 0 | 0.102071 | 0 | 0 | 0.041851 | 0 | 0 | 0 | 0 | 0 | 0 |
| 4796-051 | 0 | 0.11582 | 0 | 0 | 0.120478 | 0 | 0 | 0 | 0 | 0.000172 | 0 |
| 4796-060 | 0 | 0.119378 | 0 | 0 | 0.131867 | 0 | 0 | 0 | 0 | 0 | 0 |
| 4796-067 | 0 | 0.071333 | 0 | 0 | 0.073846 | 0 | 0 | 0 | 0 | 0.006297 | 0 |
| 4796-039 | 0 | 0.044475 | 0 | 0 | 0.048296 | 0 | 0 | 0 | 0 | 0 | 0 |
| 4790-032 | 0 | 0.106403 | 0 | 0.002886 | 0.095989 | 0 | 0 | 0 | 0 | 0.023457 | 0 |
| 4790-034 | 0.000616 | 0.104287 | 0 | 0 | 0.106894 | 0 | 0 | 0 | 0 | 0 | 0 |
| 4202-003 | 0.006276 | 0.166513 | 0 | 0.000795 | 0.029581 | 0 | 0 | 0 | 0.03616 | 0 | 0 |
| 4790-041 | 0 | 0.101983 | 0 | 0 | 0.092224 | 0 | 0 | 0 | 0.001396 | 0 | 0 |
| 4791-004 | 0 | 0.175073 | 0 | 0 | 0.079925 | 0 | 0 | 0.000546 | 0 | 0 | 0 |
| 4795-023 | 0 | 0.159423 | 0 | 0 | 0.098296 | 0 | 0 | 0 | 0 | 0 | 0 |
| 4795-031 | 0 | 0.120325 | 0 | 0 | 0.099236 | 0 | 0 | 0.000251 | 0 | 0 | 0 |
| 4795-035 | 0 | 0.094775 | 0 | 0 | 0.145932 | 0 | 0 | 0 | 0 | 0 | 0 |
| 4795-058 | 0 | 0.107021 | 0 | 0 | 0.12642 | 0 | 0 | 0 | 0 | 0 | 0 |
| 4795-065 | 0 | 0.077297 | 0 | 0 | 0.06092 | 0 | 0 | 0 | 0 | 0 | 0 |
| 4795-070 | 0 | 0.116618 | 0 | 0 | 0.094399 | 0 | 0 | 0 | 0 | 0 | 0 |
| 4795-071 | 0 | 0.110829 | 0 | 0 | 0.0721 | 0 | 0 | 0 | 0 | 0 | 0 |
| 4795-081 | 0 | 0.132106 | 0 | 0 | 0.130082 | 0 | 0 | 0 | 0 | 0 | 0 |
| 4795-087 | 0 | 0.186941 | 0 | 0 | 0.095583 | 0 | 0 | 0 | 0 | 0 | 0 |
| 4795-092 | 0 | 0.127615 | 0 | 0 | 0.103324 | 0 | 0 | 0 | 0 | 0 | 0 |
| 4795-096 | 0 | 0.106837 | 0 | 0 | 0.1011 | 0 | 0 | 0.003892 | 0 | 0 | 0 |
| 4797-008 | 0 | 0.083609 | 0 | 0.00017 | 0.0957 | 0 | 0 | 0 | 0 | 0 | 0.000415 |
| 4792-005 | 1.00E−05 | 0.030277 | 0 | 0 | 0.107384 | 0 | 0 | 0.002882 | 0 | 0 | 0 |
| 4790-040 | 0 | 0.102936 | 0 | 0 | 0.090001 | 0 | 0 | 0.004928 | 0 | 0 | 0 |
| 4792-010 | 0 | 0.107184 | 0 | 0 | 0.118856 | 0 | 0 | 0 | 0 | 0.00194 | 0 |

-continued

| | | | | | | | | | | | |
|---|---|---|---|---|---|---|---|---|---|---|---|
| 4238-002 | 0 | 0.078009 | 0 | 0 | 0.053596 | 0 | 0 | 0 | 0 | 0.001508 | 0 |
| 4795-012 | 0 | 0.208452 | 0 | 0 | 0.04377 | 0 | 0 | 0 | 0 | 0 | 0 |
| 4790-019 | 0 | 0.069475 | 0 | 0 | 0.084843 | 0 | 0 | 0 | 0 | 0 | 0 |
| 4790-028 | 0 | 0.116311 | 0 | 0 | 0.056261 | 0 | 0 | 0 | 0 | 0 | 0 |
| 4797-009 | 0 | 0.2045 | 0 | 0 | 0.060184 | 0 | 0 | 0 | 0 | 0 | 0 |
| 4797-011 | 0 | 0.119962 | 0 | 0 | 0.13594 | 0 | 0 | 0 | 0 | 0 | 0 |
| 4797-002 | 0 | 0.058581 | 0 | 0 | 0.044527 | 0 | 0 | 0 | 0 | 0 | 0 |
| 4797-003 | 0 | 0.04346 | 0 | 0 | 0.159411 | 0 | 0 | 0 | 0 | 0 | 0 |
| 4238-004 | 0 | 0.085492 | 0 | 0 | 0.125238 | 0 | 0 | 0 | 0 | 0 | 0 |
| 4790-003 | 0 | 0.083028 | 0 | 0 | 0.079629 | 0 | 0 | 0 | 0 | 0 | 0 |
| 4790-001 | 0 | 0.089071 | 0 | 0 | 0.121218 | 0 | 0 | 0 | 0 | 0.003253 | 0 |
| 4795-010 | 0 | 0.132933 | 0 | 0 | 0.088837 | 0 | 0 | 0 | 0 | 0 | 0 |
| 4714-001 | 0 | 0.179542 | 0 | 0 | 0.070037 | 0 | 0 | 0 | 0 | 0 | 0 |
| 4796-001 | 0 | 0.108765 | 0 | 0 | 0.079015 | 0 | 0 | 0.000825 | 0 | 0 | 0 |
| 4790-002 | 0 | 0.114599 | 0 | 0 | 0.087478 | 0 | 0 | 0.002553 | 0 | 0 | 0 |
| 4794-001 | 0 | 0.074901 | 0 | 0 | 0.112425 | 0 | 0 | 0 | 0 | 0 | 0 |
| 4791-002 | 0 | 0.164837 | 0.000451 | 0 | 0.074449 | 0 | 0 | 0.000343 | 0 | 0 | 0 |
| 4794-002 | 0 | 0.127398 | 0 | 0 | 0.073141 | 0 | 0 | 0.000306 | 0 | 0 | 0 |
| 4792-001 | 0 | 0.16119 | 0 | 0 | 0.123228 | 0 | 0 | 0 | 0 | 0 | 0 |
| 4797-010 | 0 | 0.072924 | 0.001817 | 0 | 0.133381 | 0 | 0 | 0.000422 | 0 | 0 | 0 |
| 4795-002 | 0 | 0.10914 | 0 | 0 | 0.058973 | 0 | 0 | 0 | 0 | 0 | 0 |
| 4438-004 | 0 | 0.058067 | 0 | 0.01144 | 0.062852 | 0 | 0 | 0 | 0 | 0.001569 | 0.000189 |
| 4438-005 | 0 | 0.096228 | 0 | 0 | 0.08716 | 0 | 0 | 0 | 0 | 0 | 0 |
| 4796-050 | 0 | 0.103355 | 0.017312 | 0 | 0.076084 | 0 | 0 | 0.002609 | 0 | 0 | 0 |
| 4795-051 | 0 | 0.080045 | 0 | 0 | 0.090006 | 0 | 0 | 0 | 0 | 0 | 0 |
| 4791-003 | 0 | 0.103778 | 0 | 0 | 0.151173 | 0 | 0 | 0.001443 | 0 | 0 | 0 |
| 4795-004 | 0 | 0.14506 | 0 | 0 | 0.068686 | 0 | 0 | 0 | 0 | 0 | 0 |
| 4202-004 | 0 | 0.077773 | 0 | 0 | 0.06264 | 0 | 0 | 0 | 0 | 0 | 0 |
| 4202-006 | 0 | 0.100184 | 0 | 0 | 0.11027 | 0 | 0 | 0.007465 | 0 | 0 | 0 |
| 4202-012 | 0.000375 | 0.073033 | 0 | 0 | 0.098618 | 0 | 0 | 0 | 0.006588 | 0 | 0 |
| 4238-018 | 0 | 0.135672 | 0 | 0 | 0.110618 | 0 | 0 | 0 | 0 | 0 | 0 |
| 4438-003 | 0 | 0.12301 | 0 | 0 | 0.098572 | 0 | 0 | 0.000735 | 0 | 0 | 0 |
| 4438-026 | 0 | 0.145892 | 0 | 0 | 0.108126 | 0 | 0 | 0 | 0 | 0 | 0 |
| 4795-005 | 0 | 0.17832 | 0 | 0 | 0.038922 | 0 | 0 | 0 | 0 | 0 | 0 |
| 4795-007 | 0 | 0.143238 | 0 | 0 | 0.07502 | 0 | 0.003945 | 0 | 0 | 0 | 0 |
| 4795-008 | 0 | 0.127691 | 0 | 0 | 0.099185 | 0 | 0 | 0 | 0 | 0 | 0 |
| 4795-011 | 0 | 0.107314 | 0 | 0 | 0.108105 | 0 | 0 | 0 | 0 | 0 | 0 |
| 4795-014 | 0 | 0.0952 | 0 | 0 | 0.084576 | 0 | 0 | 0.000102 | 0 | 0 | 0 |
| 4796-045 | 0 | 0.088984 | 0 | 0 | 0.090823 | 0 | 0 | 0 | 0 | 0.001459 | 0 |
| 4795-059 | 0 | 0.07197 | 0 | 0 | 0.098878 | 0 | 0 | 0 | 0 | 0 | 0 |
| 4795-038 | 0 | 0.102918 | 0 | 0 | 0.114191 | 0 | 0 | 0 | 0 | 0 | 0 |
| 4238-012 | 0 | 0.087569 | 0 | 0 | 0.116318 | 0 | 0 | 0 | 0 | 0 | 0 |
| 4795-080 | 0 | 0.065284 | 0 | 0 | 0.054078 | 0 | 0 | 0 | 0 | 0 | 0 |
| 4796-018 | 0 | 0.069842 | 0 | 0 | 0.106261 | 0 | 0 | 0 | 0 | 0 | 0 |
| 4796-016 | 0 | 0.02662 | 0 | 0 | 0.115737 | 0 | 0 | 0.002182 | 0 | 0 | 0 |
| 4796-004 | 0 | 0.082337 | 0 | 0 | 0.104255 | 0 | 0 | 0 | 0 | 0 | 0 |
| 4238-016 | 0 | 0.096088 | 0 | 0 | 0.134968 | 0 | 0 | 0 | 0 | 0 | 0 |
| 4714-005 | 0 | 0.133913 | 0 | 0 | 0.093222 | 0 | 0 | 0 | 0 | 0 | 0 |
| 4796-059 | 0 | 0.166998 | 0 | 0 | 0.064702 | 0 | 0 | 0 | 0 | 0 | 0 |
| 4796-058 | 0 | 0.098949 | 0 | 0 | 0.080271 | 0 | 0 | 0 | 0.01156 | 0 | 0.000431 |
| 4202-016 | 0 | 0.135487 | 0 | 0 | 0.095391 | 0 | 0 | 0 | 0 | 0 | 0 |
| 4714-013 | 0 | 0.137696 | 0 | 0 | 0.155996 | 0 | 0 | 0 | 0 | 0 | 0 |
| 4714-012 | 0 | 0.174502 | 0 | 0 | 0.026414 | 0 | 0 | 0 | 0 | 0 | 0 |
| 4714-009 | 0 | 0.099266 | 0 | 0 | 0.087348 | 0 | 0 | 0 | 0 | 0 | 0 |
| 4714-007 | 0 | 0.237086 | 0 | 0 | 0.053084 | 0 | 0 | 0 | 0 | 0 | 0 |
| 4790-030 | 0 | 0.134707 | 0 | 0 | 0.1382 | 0 | 0 | 0 | 0 | 0 | 0 |
| 4796-073 | 0 | 0.092364 | 0 | 0 | 0.098571 | 0 | 0 | 0 | 0 | 0.002185 | 0 |
| 4796-041 | 0 | 0.101594 | 0 | 0 | 0.057934 | 0 | 0 | 0 | 0 | 0 | 0 |
| 4790-046 | 0 | 0.086018 | 0 | 0 | 0.128784 | 0 | 0 | 0 | 0 | 0.007821 | 0 |
| 4790-038 | 0 | 0.079726 | 0 | 0 | 0.077783 | 0 | 0 | 0.005669 | 0 | 0 | 0 |
| 4790-037 | 0 | 0.105617 | 0 | 0 | 0.10612 | 0 | 0 | 0 | 0 | 0 | 0 |
| 4790-059 | 0 | 0.072357 | 0 | 0 | 0.12486 | 0 | 0 | 0 | 0 | 0.005319 | 0 |
| 4790-057 | 0 | 0.137579 | 0 | 0 | 0.107103 | 0 | 0 | 0 | 0 | 0 | 0.000193 |
| 4790-052 | 0 | 0.120232 | 0 | 0 | 0.055761 | 0 | 0 | 0 | 0 | 0 | 0 |
| 4438-037 | 0 | 0.080719 | 0 | 0 | 0.149172 | 0 | 0 | 0 | 0 | 0 | 0 |
| 4797-029 | 0 | 0.117068 | 0 | 0 | 0.136935 | 0 | 0 | 0.000836 | 0 | 0 | 0 |
| 4438-052 | 0.007203 | 0.131605 | 0 | 0 | 0.10215 | 0 | 0 | 0 | 0.014522 | 0 | 0 |
| 4793-039 | 0 | 0.139092 | 0 | 0 | 0.08322 | 0 | 0 | 0.006647 | 0 | 0.002373 | 0 |
| 4796-080 | 0 | 0.133647 | 0.008936 | 0 | 0.057222 | 0 | 0 | 0 | 0 | 0 | 0 |
| 4438-056 | 0.000334 | 0.040837 | 0 | 0 | 0.175699 | 0 | 0 | 0.001683 | 0 | 0 | 0 |
| 4790-074 | 0 | 0.093539 | 0 | 0 | 0.105865 | 0 | 0 | 0 | 0 | 0 | 0 |
| 4790-073 | 0 | 0.063405 | 0 | 0 | 0.133201 | 0 | 0 | 0 | 0 | 0 | 0 |
| 4790-070 | 0 | 0.089473 | 0 | 0 | 0.095106 | 0 | 0 | 0 | 0 | 0 | 0 |
| 4790-063 | 0 | 0.104374 | 0.076834 | 0 | 0.074394 | 0 | 0 | 0.003324 | 0 | 0 | 0 |
| 4793-006 | 0 | 0.238948 | 0 | 0 | 0.059294 | 0 | 0 | 0 | 0 | 0 | 0 |
| 4438-051 | 6.38E−05 | 0.095524 | 0 | 0 | 0.11267 | 0 | 0 | 0 | 0 | 0 | 0 |
| 4793-021 | 0 | 0.102886 | 0 | 0 | 0.111864 | 0 | 0 | 0 | 0 | 0 | 0 |
| 4793-013 | 0 | 0.102451 | 0 | 0 | 0.069054 | 0 | 0 | 0.002134 | 0 | 0 | 0 |
| 4793-035 | 0 | 0.102815 | 0 | 0 | 0.151217 | 0 | 0 | 0.001143 | 0 | 0 | 0 |

-continued

| ID | | | | | | | | | | | |
|---|---|---|---|---|---|---|---|---|---|---|---|
| 4793-028 | 0 | 0.083195 | 0 | 0 | 0.050496 | 0 | 0 | 0 | 0 | 0.008048 | 0 |
| 4793-027 | 0 | 0.147596 | 0 | 0 | 0.097069 | 0 | 0 | 0 | 0 | 0.001868 | 0 |
| 4714-023 | 0 | 0.172333 | 0 | 0 | 0.105326 | 0 | 0 | 0.001231 | 0 | 0 | 0 |
| 4238-037 | 0 | 0.054616 | 0 | 0.00415 | 0.105743 | 0 | 0 | 0 | 0 | 0.008466 | 0 |
| 4796-095 | 0 | 0.065137 | 0 | 0 | 0.150234 | 0 | 0 | 0 | 0 | 0 | 0 |
| 4796-091 | 0 | 0.062453 | 0 | 0 | 0.149624 | 0 | 0 | 0 | 0 | 0 | 0 |
| 4238-038 | 0 | 0.036453 | 0 | 0 | 0.150506 | 0 | 0 | 0 | 0 | 0 | 0 |
| 4790-080 | 0 | 0.074278 | 0 | 0 | 0.144451 | 0 | 0 | 0.001254 | 0 | 0 | 0 |
| 4790-084 | 0 | 0.062377 | 0 | 0.010346 | 0.075637 | 0 | 0 | 0 | 0 | 0.036278 | 0 |
| 4796-108 | 0 | 0.097009 | 0 | 0 | 0.129879 | 0 | 0 | 0 | 0 | 0 | 0 |
| 4438-073 | 0 | 0.035553 | 0 | 0 | 0.157682 | 0 | 0 | 0 | 0 | 0.003252 | 0 |
| 4790-081 | 0 | 0.112064 | 0 | 0 | 0.077478 | 0 | 0 | 0 | 0 | 0 | 0 |
| 4796-112 | 0 | 0.109654 | 0 | 0 | 0.093723 | 0 | 0 | 0 | 0.007194 | 0.012679 | 0.000212 |
| 4438-066 | 0 | 0.036158 | 0 | 0 | 0.097865 | 0 | 0 | 0 | 0.002429 | 0 | 0.000159 |
| 4791-006 | 0 | 0.092356 | 0 | 0 | 0.096995 | 0 | 0 | 0 | 0 | 0 | 0 |
| 4790-077 | 0 | 0.089209 | 0.020874 | 0 | 0.066981 | 0 | 0 | 0 | 0 | 0 | 0 |
| 4438-068 | 0 | 0.103194 | 0 | 0 | 0.09935 | 0 | 0 | 0.000419 | 0 | 0 | 0 |
| 4202-033 | 0 | 0.172485 | 0 | 0 | 0.064768 | 0 | 0 | 0 | 0 | 0 | 0 |
| 4202-002 | 0 | 0.176533 | 0 | 0 | 0.087473 | 0 | 0 | 2.83E-05 | 0 | 0 | 0 |
| 4797-014 | 0.001223 | 0.113795 | 0 | 0 | 0.113316 | 0 | 0 | 0 | 0 | 0 | 0 |
| 4797-005 | 0 | 0.105841 | 0 | 0 | 0.100741 | 0 | 0 | 0 | 0 | 0 | 0 |

| | Monocyte | Multi-ciliated | PNEC | Pericyte | Plasma cells | Precursor | SMG Goblet | Secretory | Serous | Smooth | Suprabasal |
|---|---|---|---|---|---|---|---|---|---|---|---|
| 4790-005 | 0.007146 | 0.474365 | 0 | 0 | 0 | 0 | 0.0008 | 0.359296 | 0 | 0 | 0 |
| 4790-006 | 0 | 0.336663 | 0 | 0 | 0 | 0 | 0 | 0.383693 | 7.26E-05 | 0 | 0.103095 |
| 4790-008 | 0 | 0.311167 | 0 | 0 | 0.000568 | 0 | 0 | 0.53687 | 7.82E-05 | 0 | 0.046751 |
| 4790-009 | 0 | 0.337289 | 0 | 0 | 0 | 0 | 0 | 0.404799 | 0.000497 | 0 | 0.085606 |
| 4790-011 | 0 | 0.351594 | 0 | 0 | 0 | 0.002824 | 0.047357 | 0.424924 | 0 | 0 | 0 |
| 4790-012 | 0 | 0.371821 | 0 | 0 | 0 | 0 | 0.001164 | 0.415422 | 0 | 0 | 0 |
| 4790-013 | 0 | 0.375475 | 0 | 0 | 0 | 0 | 0.01028 | 0.390583 | 0 | 0 | 0 |
| 4790-014 | 0.025217 | 0.349479 | 0 | 0 | 0 | 0 | 0 | 0.510007 | 0.000667 | 0 | 0 |
| 4790-016 | 0 | 0.394525 | 0 | 0 | 0 | 0 | 0.008285 | 0.417537 | 0 | 0 | 0.025481 |
| 4790-021 | 0 | 0.408585 | 0 | 0 | 0 | 0 | 0.003419 | 0.36663 | 0 | 0 | 0 |
| 4790-022 | 0.019322 | 0.352262 | 0 | 0 | 0 | 0 | 0 | 0.427809 | 2.38E-05 | 0 | 0.030442 |
| 4790-023 | 0 | 0.382976 | 0 | 0 | 0 | 0 | 0.017821 | 0.376865 | 0 | 0 | 0 |
| 4790-024 | 0 | 0.251564 | 0 | 0 | 0 | 0.000695 | 0 | 0.420864 | 0 | 0 | 0.171015 |
| 4790-025 | 0 | 0.209276 | 0 | 0 | 0 | 0.012974 | 0.042845 | 0.477853 | 0 | 0 | 0.096892 |
| 4790-026 | 0 | 0.341203 | 0 | 0 | 0 | 0.002258 | 0.054007 | 0.418468 | 0 | 0 | 0.019639 |
| 4790-027 | 0 | 0.302006 | 0 | 0 | 0 | 0.00286 | 0.007386 | 0.422776 | 0 | 0 | 0.152303 |
| 4238-030 | 0 | 0.503832 | 0 | 0 | 0 | 0 | 0.001896 | 0.322367 | 1.05E-05 | 0 | 0 |
| 4797-006 | 0 | 0.439577 | 0 | 0 | 0 | 0 | 0 | 0.329131 | 0 | 0 | 0 |
| 4797-007 | 0 | 0.256474 | 0 | 0 | 0 | 0 | 0.013499 | 0.460135 | 0.00552 | 0 | 0.065317 |
| 4797-012 | 0 | 0.26124 | 0 | 0 | 0 | 0 | 0.002613 | 0.420947 | 0.000303 | 0 | 0.110493 |
| 4795-013 | 0 | 0.307178 | 0 | 0 | 0 | 0 | 0.012338 | 0.425603 | 0 | 0 | 0 |
| 4795-017 | 0 | 0.266745 | 0 | 0 | 0 | 0 | 0 | 0.42174 | 0.000429 | 0 | 0.132928 |
| 4795-019 | 0 | 0.311517 | 0 | 0 | 0.000421 | 0 | 0.001244 | 0.37592 | 0.000675 | 0 | 0.134293 |
| 4238-017 | 0 | 0.494337 | 0 | 0 | 0 | 0 | 0.00748 | 0.342999 | 0 | 0 | 0 |
| 4238-022 | 0.030586 | 0.396402 | 0 | 0 | 0 | 0 | 0 | 0.338845 | 0 | 0 | 0.036228 |
| 4238-027 | 0.020067 | 0.336828 | 0 | 0 | 0 | 0.027338 | 0 | 0.375601 | 0.000451 | 0 | 0 |
| 4238-028 | 0 | 0.342854 | 0 | 0 | 0 | 0 | 0.000782 | 0.415219 | 0 | 0 | 0.100228 |
| 4238-029 | 0 | 0.335306 | 0 | 0 | 0 | 0 | 0 | 0.393474 | 3.77E-05 | 0 | 0.136745 |
| 4438-015 | 0.048749 | 0.314217 | 0 | 0 | 0 | 0 | 0 | 0.436246 | 0 | 0 | 0.024797 |
| 4438-032 | 0 | 0.352273 | 0 | 0 | 0 | 0 | 0 | 0.396646 | 0.000559 | 0 | 0 |
| 4790-015 | 0.028797 | 0.332387 | 0 | 0 | 0 | 0.015354 | 0.022887 | 0.457699 | 0 | 0 | 0 |
| 4796-008 | 0 | 0.364804 | 0 | 0 | 0 | 0 | 0.016592 | 0.402445 | 0 | 0 | 0.027057 |
| 4796-015 | 0 | 0.411157 | 0 | 0 | 0 | 0.002126 | 0.039372 | 0.221869 | 0 | 0 | 0 |
| 4796-029 | 0.027587 | 0.290196 | 0 | 0 | 0 | 0 | 0 | 0.356699 | 0.003265 | 0 | 0.125117 |
| 4796-033 | 0.011107 | 0.366269 | 0 | 0 | 0 | 0.001063 | 0 | 0.310217 | 0 | 0 | 0.115798 |
| 4796-034 | 0 | 0.355292 | 0 | 0 | 0 | 0.008295 | 0.025704 | 0.31719 | 0 | 0 | 0.106854 |
| 4796-036 | 0.01276 | 0.265887 | 0 | 0 | 0 | 0 | 0 | 0.381046 | 0.000127 | 0 | 0.143959 |
| 4796-037 | 0 | 0.266533 | 0 | 0 | 0 | 0 | 0 | 0.34409 | 0.000233 | 0 | 0.154826 |
| 4796-052 | 0 | 0.338993 | 0 | 0 | 0 | 0 | 0 | 0.346618 | 0 | 0 | 0.10786 |
| 4796-055 | 0 | 0.301455 | 0 | 0 | 0 | 0 | 0 | 0.358798 | 0 | 0 | 0.135375 |
| 4796-064 | 0 | 0.313229 | 0 | 0 | 0 | 0 | 0 | 0.35553 | 0.00013 | 0 | 0.116898 |
| 4796-071 | 0 | 0.323305 | 0 | 0 | 0 | 0.000586 | 0 | 0.308779 | 0.002379 | 0 | 0.145989 |
| 4796-072 | 0 | 0.289632 | 0 | 0 | 0 | 0.001936 | 0.021088 | 0.393095 | 0 | 0 | 0.137359 |
| 4238-019 | 0.000453 | 0.350704 | 0 | 0 | 0 | 0 | 0 | 0.374943 | 0.000299 | 0 | 0.078795 |
| 4238-025 | 0 | 0.300983 | 0 | 0 | 0 | 0 | 0 | 0.344073 | 6.78E-05 | 0 | 0.146702 |
| 4790-053 | 0.009244 | 0.215759 | 0 | 0 | 0 | 0.008356 | 0.000338 | 0.385861 | 0 | 0 | 0.155256 |
| 4795-032 | 0 | 0.350534 | 0 | 0 | 0 | 0.001048 | 0 | 0.312476 | 0 | 0 | 0.123075 |
| 4796-043 | 0 | 0.398554 | 0 | 0 | 0 | 0 | 0.002789 | 0.353795 | 0 | 0 | 0 |
| 4796-044 | 0 | 0.258093 | 0 | 0 | 0 | 0 | 0.085648 | 0.461329 | 0 | 0 | 0.051008 |
| 4796-051 | 0 | 0.455726 | 0 | 0 | 0 | 0 | 0 | 0.307804 | 0 | 0 | 0 |
| 4796-060 | 0 | 0.421564 | 0 | 0 | 0 | 0 | 0.012517 | 0.314674 | 0 | 0 | 0 |
| 4796-067 | 0 | 0.314178 | 0 | 0 | 0 | 0 | 0 | 0.37317 | 0 | 0 | 0.161176 |
| 4796-039 | 0.024002 | 0.197484 | 0 | 0 | 0 | 0 | 0 | 0.492099 | 0 | 0 | 0.193644 |
| 4790-032 | 0.039356 | 0.344093 | 0 | 0 | 0 | 0.001268 | 0.016992 | 0.350434 | 0 | 0 | 0.019124 |

-continued

| | | | | | | | | | | | |
|---|---|---|---|---|---|---|---|---|---|---|---|
| 4790-034 | 0.002888 | 0.365839 | 0 | 0 | 0 | 0.016245 | 0.007165 | 0.365595 | 0 | 0 | 0.030471 |
| 4202-003 | 0 | 0.11074 | 0 | 0 | 0 | 0.031372 | 0.003055 | 0.59373 | 0 | 0 | 0.021777 |
| 4790-041 | 0 | 0.312704 | 0 | 0 | 0 | 0.000928 | 0.015447 | 0.345792 | 0 | 0 | 0.129525 |
| 4791-004 | 0 | 0.433033 | 0 | 0 | 0 | 0 | 0.01293 | 0.298493 | 0 | 0 | 0 |
| 4795-023 | 0 | 0.464016 | 0 | 0 | 0 | 0 | 0 | 0.278265 | 0 | 0 | 0 |
| 4795-031 | 0 | 0.371543 | 0 | 0 | 0 | 0 | 0 | 0.348417 | 0 | 0 | 0.060227 |
| 4795-035 | 0 | 0.462502 | 0 | 0 | 0 | 0 | 0.001016 | 0.295775 | 0 | 0 | 0 |
| 4795-058 | 0 | 0.330542 | 0 | 0 | 0 | 0.00532 | 0 | 0.305722 | 6.34E−05 | 0 | 0.124912 |
| 4795-065 | 0 | 0.223746 | 0 | 0 | 0 | 0 | 0 | 0.434648 | 0.000139 | 0 | 0.203249 |
| 4795-070 | 0 | 0.277136 | 0 | 0 | 0 | 0 | 0 | 0.372775 | 7.71E−05 | 0 | 0.138994 |
| 4795-071 | 0 | 0.297681 | 0 | 0 | 0 | 0 | 0.01189 | 0.347686 | 0.001422 | 0 | 0.158392 |
| 4795-081 | 0 | 0.362329 | 0 | 0 | 0 | 0.007779 | 0 | 0.350895 | 0.00012 | 0 | 0.016689 |
| 4795-087 | 0 | 0.366073 | 0 | 0 | 0 | 0 | 0.005147 | 0.346256 | 0 | 0 | 0 |
| 4795-092 | 0 | 0.341868 | 0 | 0 | 0 | 0 | 0 | 0.397714 | 0 | 0 | 0.029479 |
| 4795-096 | 0 | 0.369715 | 0 | 0 | 0 | 0.012602 | 0.110321 | 0.295533 | 0 | 0 | 0 |
| 4797-008 | 0 | 0.370103 | 0 | 0 | 0 | 0 | 0 | 0.360942 | 0.000181 | 0 | 0.088881 |
| 4792-005 | 0.036127 | 0.254221 | 0 | 0 | 0 | 0.026125 | 0.012123 | 0.353699 | 0 | 0 | 0.177151 |
| 4790-040 | 0 | 0.376578 | 0 | 0 | 0 | 0.007356 | 0 | 0.387265 | 0 | 0 | 0.030936 |
| 4792-010 | 0.014367 | 0.381152 | 0 | 0 | 0 | 0.005548 | 0.00911 | 0.295916 | 0 | 0 | 0.065927 |
| 4238-002 | 0.002377 | 0.273032 | 0 | 0 | 0 | 0 | 0 | 0.450177 | 0.000241 | 0 | 0.14106 |
| 4795-012 | 0 | 0.308239 | 0 | 0 | 0 | 0 | 0.006128 | 0.433411 | 0 | 0 | 0 |
| 4790-019 | 0 | 0.24543 | 0 | 0 | 0 | 0 | 0 | 0.430284 | 0 | 0 | 0.169968 |
| 4790-028 | 0 | 0.358218 | 0 | 0 | 0 | 0 | 0.002151 | 0.453814 | 0 | 0 | 0.013246 |
| 4797-009 | 0 | 0.341045 | 0 | 0 | 0 | 0 | 0 | 0.392442 | 0.000154 | 0 | 0.001674 |
| 4797-011 | 0 | 0.496923 | 0 | 0 | 0 | 0 | 0 | 0.247175 | 0 | 0 | 0 |
| 4797-002 | 0 | 0.468645 | 0 | 0 | 0 | 0 | 0.010336 | 0.417911 | 0 | 0 | 0 |
| 4797-003 | 0 | 0.389721 | 0 | 0 | 0 | 0 | 0 | 0.348058 | 0.000219 | 0 | 0.059132 |
| 4238-004 | 0 | 0.474465 | 0 | 0 | 0 | 0 | 0 | 0.314273 | 0.000531 | 0 | 0 |
| 4790-003 | 0 | 0.437294 | 0 | 0 | 0 | 0 | 0.005221 | 0.381711 | 0 | 0 | 0.013118 |
| 4790-001 | 0.010742 | 0.432407 | 0 | 0 | 0 | 0.000448 | 0.031989 | 0.310872 | 0 | 0 | 0 |
| 4795-010 | 0 | 0.466736 | 0 | 0 | 0 | 0 | 0.024906 | 0.286587 | 0 | 0 | 0 |
| 4714-001 | 0 | 0.21707 | 0 | 0 | 0 | 0 | 0.032748 | 0.463756 | 0 | 0 | 0.036847 |
| 4796-001 | 0 | 0.350752 | 0 | 0 | 0 | 0.004988 | 0.015355 | 0.405518 | 0 | 0 | 0.034783 |
| 4790-002 | 0 | 0.298951 | 0 | 0 | 0 | 0.007792 | 0.002477 | 0.373034 | 0 | 0 | 0.113116 |
| 4794-001 | 0 | 0.49146 | 0 | 0 | 0 | 0.006425 | 0.000943 | 0.313846 | 0 | 0 | 0 |
| 4791-002 | 0 | 0.395805 | 0 | 0 | 0 | 0.017692 | 0.028275 | 0.318149 | 0 | 0 | 0 |
| 4794-002 | 0 | 0.282841 | 0 | 0 | 0 | 0.009163 | 0.004304 | 0.39601 | 0.000392 | 0 | 0.106446 |
| 4792-001 | 0.009107 | 0.323843 | 0 | 0 | 0 | 0.050157 | 0 | 0.332412 | 6.18E−05 | 0 | 0 |
| 4797-010 | 0 | 0.43227 | 0 | 0 | 0 | 0.013944 | 0.016014 | 0.329228 | 0 | 0 | 0 |
| 4795-002 | 0 | 0.369272 | 0 | 0 | 0 | 0 | 0.057638 | 0.404978 | 0 | 0 | 0 |
| 4438-004 | 0.009451 | 0.367843 | 0 | 0 | 0 | 0 | 0.000559 | 0.48803 | 0 | 0 | 0 |
| 4438-005 | 0 | 0.397176 | 0 | 0 | 0 | 0 | 0.002044 | 0.417391 | 0 | 0 | 0 |
| 4796-050 | 0 | 0.443554 | 0 | 0 | 0 | 0.013452 | 0.028431 | 0.315203 | 0 | 0 | 0 |
| 4795-051 | 0 | 0.287473 | 0 | 0 | 0 | 0 | 0.000798 | 0.40226 | 0 | 0 | 0.139418 |
| 4791-003 | 0 | 0.427104 | 0 | 0 | 0 | 0 | 0 | 0.316271 | 0.00023 | 0 | 0 |
| 4795-004 | 0 | 0.287172 | 0 | 0 | 0 | 0 | 0 | 0.374063 | 0.001136 | 0 | 0.123883 |
| 4202-004 | 0 | 0.329434 | 0 | 0 | 0 | 0.00371 | 0.00327 | 0.416358 | 0.00185 | 0 | 0.104965 |
| 4202-006 | 0 | 0.395398 | 0 | 0 | 0 | 0 | 0 | 0.363478 | 0 | 0 | 0.023205 |
| 4202-012 | 0 | 0.367615 | 0 | 0 | 0 | 0 | 0.02934 | 0.36574 | 0.001527 | 0 | 0.057163 |
| 4238-018 | 0 | 0.403689 | 0 | 0 | 0 | 0 | 0 | 0.349353 | 0.000668 | 0 | 0 |
| 4438-003 | 0 | 0.359288 | 0 | 0 | 0 | 0 | 0.006358 | 0.381961 | 0 | 0 | 0.030076 |
| 4438-026 | 0 | 0.352813 | 0 | 0 | 0 | 0 | 0.000484 | 0.363954 | 0 | 0 | 0.028732 |
| 4795-005 | 0 | 0.240605 | 0 | 0 | 0 | 0 | 0.000463 | 0.400334 | 0 | 0 | 0.141357 |
| 4795-007 | 0 | 0.313746 | 0 | 0 | 0 | 0 | 0 | 0.40681 | 0.000291 | 0 | 0.056951 |
| 4795-008 | 0 | 0.442851 | 0 | 0 | 0 | 0 | 0.017266 | 0.313007 | 0 | 0 | 0 |
| 4795-011 | 0 | 0.318448 | 0 | 0 | 0 | 0 | 0 | 0.344448 | 0 | 0 | 0.121685 |
| 4795-014 | 0 | 0.355076 | 0 | 0 | 0 | 0 | 0.003975 | 0.342398 | 0 | 0 | 0.118673 |
| 4796-045 | 0.0067 | 0.40726 | 0 | 0 | 0 | 0.000428 | 0.000134 | 0.350199 | 0 | 0 | 0.054012 |
| 4795-059 | 0 | 0.142106 | 0 | 0 | 0 | 0 | 0 | 0.426825 | 0 | 0 | 0.260221 |
| 4795-038 | 0 | 0.29369 | 0 | 0 | 0 | 0 | 0 | 0.379276 | 0.000187 | 0 | 0.109737 |
| 4238-012 | 0 | 0.256264 | 0 | 0 | 0 | 0.01261 | 0.000103 | 0.362385 | 0 | 0 | 0.164751 |
| 4795-080 | 0 | 0.326041 | 0 | 0 | 0 | 0 | 0 | 0.422482 | 0 | 0 | 0.132115 |
| 4796-018 | 0 | 0.417648 | 0 | 0 | 0 | 0.003483 | 0.001413 | 0.379176 | 0 | 0 | 0.022177 |
| 4796-016 | 0 | 0.37674 | 0 | 0 | 0 | 2.81E−05 | 0 | 0.350909 | 0 | 0 | 0.127785 |
| 4796-004 | 0 | 0.353873 | 0 | 0 | 0 | 0 | 0 | 0.336759 | 0 | 0 | 0.122775 |
| 4238-016 | 0 | 0.45953 | 0 | 0 | 0 | 0 | 0 | 0.309415 | 0 | 0 | 0 |
| 4714-005 | 0 | 0.292677 | 0 | 0 | 0 | 0 | 0.00995 | 0.350665 | 0.000683 | 0 | 0.11889 |
| 4796-059 | 0 | 0.284267 | 0 | 0 | 0 | 0 | 0.003254 | 0.376167 | 0.001286 | 0 | 0.103327 |
| 4796-058 | 0 | 0.292306 | 0 | 0 | 0 | 0 | 0 | 0.381949 | 0 | 0 | 0.134534 |
| 4202-016 | 0 | 0.378032 | 0 | 0 | 0 | 0.004578 | 0.027228 | 0.332542 | 0 | 0 | 0.026741 |
| 4714-013 | 0 | 0.38076 | 0 | 0 | 0 | 0 | 0.015628 | 0.307875 | 0.002045 | 0 | 0 |
| 4714-012 | 0 | 0.178611 | 0 | 0 | 0 | 0 | 0 | 0.460641 | 0.000432 | 0 | 0.159399 |
| 4714-009 | 0 | 0.311591 | 0 | 0 | 0 | 0 | 0.013777 | 0.376354 | 0.007626 | 0 | 0.10404 |
| 4714-007 | 0 | 0.327095 | 0 | 0 | 0 | 0 | 0.002342 | 0.376097 | 0.000529 | 0 | 0.003766 |
| 4790-030 | 0 | 0.367965 | 0 | 0 | 0 | 0 | 0 | 0.333044 | 0.000118 | 0 | 0.025965 |
| 4796-073 | 0.00976 | 0.452009 | 0 | 0 | 0 | 0 | 0.000776 | 0.344336 | 0 | 0 | 0 |
| 4796-041 | 0 | 0.347922 | 0 | 0 | 0 | 0 | 0.000936 | 0.379876 | 0 | 0 | 0.111739 |
| 4790-046 | 0.034798 | 0.405139 | 0 | 0 | 0 | 0 | 0 | 0.293865 | 0 | 0 | 0.043575 |
| 4790-038 | 0 | 0.33664 | 0 | 0 | 0 | 0.001296 | 0 | 0.364217 | 0 | 0 | 0.13467 |

-continued

| | | | | | | | | | | |
|---|---|---|---|---|---|---|---|---|---|---|
| 4790-037 | 0 | 0.304859 | 0 | 0 | 0 | 0 | 0 | 0.365995 | 0.000258 | 0 | 0.117151 |
| 4790-059 | 0 | 0.421681 | 0 | 0 | 0 | 0 | 0.006822 | 0.368961 | 0 | 0 | 0 |
| 4790-057 | 0 | 0.317662 | 0 | 0 | 0 | 0 | 0 | 0.351269 | 0 | 0 | 0.086195 |
| 4790-052 | 0 | 0.302404 | 0 | 0 | 0 | 0 | 0.032654 | 0.37647 | 0 | 0 | 0.112478 |
| 4438-037 | 0 | 0.397715 | 0 | 0 | 0 | 0 | 0 | 0.307994 | 0 | 0 | 0.064399 |
| 4797-029 | 0 | 0.363795 | 0 | 0 | 0 | 0.000706 | 0.009079 | 0.291632 | 0 | 0 | 0.079949 |
| 4438-052 | 0.000265 | 0.337726 | 0 | 0 | 0 | 0 | 0.022629 | 0.348924 | 0 | 0 | 0.034975 |
| 4793-039 | 0.01678 | 0.243826 | 0 | 0 | 0 | 0 | 0.158929 | 0.349132 | 0 | 0 | 0 |
| 4796-080 | 0.00594 | 0.356132 | 0 | 0 | 0 | 0.014297 | 0.041703 | 0.382123 | 0 | 0 | 0 |
| 4438-056 | 0 | 0.481142 | 0 | 0 | 0 | 0.007616 | 0 | 0.292689 | 0 | 0 | 0 |
| 4790-074 | 0 | 0.398126 | 0 | 0 | 0 | 0.010182 | 0.03333 | 0.358958 | 0 | 0 | 0 |
| 4790-073 | 0 | 0.501482 | 0 | 0 | 0 | 0 | 0 | 0.301912 | 0 | 0 | 0 |
| 4790-070 | 0 | 0.439774 | 0 | 0 | 0 | 0.004449 | 0.002356 | 0.368842 | 0 | 0 | 0 |
| 4790-063 | 0 | 0.250054 | 0 | 0 | 0 | 0.01031 | 0.059161 | 0.421548 | 0 | 0 | 0 |
| 4793-006 | 0 | 0.320182 | 0 | 0 | 0 | 0 | 0.001262 | 0.380313 | 0 | 0 | 0 |
| 4438-051 | 0.010644 | 0.302414 | 0 | 0 | 0 | 0.028323 | 0.01445 | 0.379755 | 0 | 0 | 0.056155 |
| 4793-021 | 0 | 0.460327 | 0 | 0 | 0 | 0 | 0.002954 | 0.321969 | 0 | 0 | 0 |
| 4793-013 | 0.005272 | 0.250683 | 0 | 0 | 0.001242 | 0.005111 | 0.008769 | 0.504088 | 0 | 0 | 0.051195 |
| 4793-035 | 0 | 0.347839 | 0 | 0 | 0 | 0.003818 | 0.002751 | 0.27072 | 0 | 0 | 0.119697 |
| 4793-028 | 0.009349 | 0.304635 | 0 | 0 | 0 | 0 | 0.0077 | 0.412996 | 0 | 0 | 0.123581 |
| 4793-027 | 0.031311 | 0.339009 | 0 | 0 | 0 | 0.008999 | 0.006996 | 0.367151 | 0 | 0 | 0 |
| 4714-023 | 0 | 0.311748 | 0 | 0 | 0 | 0 | 0.045575 | 0.351836 | 0 | 0 | 0.011952 |
| 4238-037 | 0.032951 | 0.350638 | 0 | 0 | 0 | 0.005022 | 0.007476 | 0.327675 | 0 | 0 | 0.103261 |
| 4796-095 | 0.017226 | 0.272482 | 0 | 0 | 0 | 0.005638 | 0 | 0.35856 | 0 | 0 | 0.130723 |
| 4796-091 | 0 | 0.357641 | 0 | 0 | 0 | 0.000494 | 0.002518 | 0.303713 | 0 | 0 | 0.123557 |
| 4238-038 | 0 | 0.392684 | 0 | 0 | 0 | 0.005909 | 0.00355 | 0.336883 | 0 | 0 | 0.074015 |
| 4790-080 | 0 | 0.421005 | 0 | 0 | 0 | 0.008927 | 0.004845 | 0.294808 | 0 | 0 | 0.050431 |
| 4790-084 | 0.055523 | 0.29054 | 0 | 0 | 0 | 0 | 0 | 0.339917 | 0 | 0 | 0.129382 |
| 4796-108 | 0 | 0.317003 | 0 | 0 | 0 | 0 | 0.000914 | 0.311409 | 0 | 0 | 0.143786 |
| 4438-073 | 0 | 0.374862 | 0 | 0 | 0 | 0 | 0 | 0.310132 | 0 | 0 | 0.118519 |
| 4790-081 | 0 | 0.319497 | 0 | 0 | 0 | 0.004491 | 0 | 0.375671 | 5.80E−05 | 0 | 0.110742 |
| 4796-112 | 0.040733 | 0.401084 | 0 | 0 | 0 | 0 | 0 | 0.334721 | 0 | 0 | 0 |
| 4438-066 | 0 | 0.343789 | 0 | 0 | 0 | 0.000791 | 0 | 0.385247 | 0 | 0 | 0.133562 |
| 4791-006 | 0 | 0.431511 | 0 | 0 | 0 | 0 | 0 | 0.379138 | 0 | 0 | 0 |
| 4790-077 | 0.00052 | 0.163884 | 0 | 0 | 0 | 0 | 0 | 0.410768 | 0 | 0 | 0.247763 |
| 4438-068 | 0.00137 | 0.423047 | 0 | 0 | 0 | 0 | 0.000195 | 0.346245 | 0 | 0 | 0.02618 |
| 4202-033 | 0 | 0.302481 | 0 | 0 | 0 | 0.020042 | 0.033719 | 0.39406 | 0 | 0 | 0.012445 |
| 4202-002 | 0 | 0.415808 | 0 | 0 | 0 | 0 | 0.007827 | 0.312331 | 0 | 0 | 0 |
| 4797-014 | 0.00643 | 0.361225 | 0 | 0 | 0 | 0.013189 | 0.005143 | 0.368531 | 0 | 0 | 0.017147 |
| 4797-005 | 0 | 0.407275 | 0 | 0 | 0 | 0 | 0 | 0.357309 | 0.000142 | 0 | 0.028691 |

What is claimed herein is:

1. A method comprising detecting the level of expression of one or more genes selected from at least one of:
 at least one gene of Group A, at least one gene of Group B, at least one gene of Group C,
 at least one gene of Group D, and at least one gene of Group E;
 in a bronchial brushing, nasal brushing, or sputum sample obtained from a subject; and
 the level of expression products of no more than 100 other genes is determined;
wherein:
 i) the at least one gene of Group A comprises Zinc Finger Protein 493 (ZNF493);
 ii) the at least one gene of Group B comprises Fat Atypical Cadherin 2 (FAT2);
 iii) the at least one gene of Group C comprises at least one of: Argininosuccinate Lyase (ASL) and Coiled-Coil Domain Containing 160 (CCDC160);
 iv) the at least one gene of Group D comprises at least one of: Long Intergenic Non-Protein Coding RNA 888 (LINC00888) and F-Box Protein 16 (FBX016); or
 v) the at least one gene of Group E comprises DnaJ Heat Shock Protein Family Member C22 (DNAJC22); and
wherein Group A consists of:
 ZNF493; ZNF519; ENSG00000271430; MYH7B; MKRNSP; ENSG00000270574;
 VN1R83P; ENSG00000268555; ZNF577; NBPF11; SCUBE2; SGK1; BNIPL;
 ENSG00000271533; PCDHGB6; LRP1; PCDHGB7; ENSG00000262877; ABCC5;
 PMS2P4; TTC28-AS1; PRR24; CD81; RGL3; PTPRS; ENSG00000271011; ZNF286B;
 GNB1L; PCDHGA12; SLC16A10; ZNF66; ENSG00000261584; ZNF311; ZNF718;
 ENSG00000223745; RAB40A; ENSG00000268119; PCDHGA4; ENSG00000270589;
 ENSG00000256142; DLL1; BRAFP1; PCDHGA11; FTX; FLYWCH1; NOVA1;
 KANSL1; ZNF826P; ENSG00000196295; ENSG00000229036; TLE3; KLF8; LONRF2;
 PCDHGB8P; ENSG00000259326; AOC2; RAPGEFL1; ARL10; ADAMTS10;
 ENSG00000250303; TSHZ2; CRYM-AS1; ENSG00000213971; TVP23CP2;
 ENSG00000234978; ZBTB12; PCDHGA9; RPS3AP29; KSR2; ENOSF1;
 ENSG00000233175; ENSG00000260729; LINC00664; ZNF257; POU5F1P5; FN3K;
 ZNF814; CYP2C19; ENSG00000270096; PDE11A; FAM13A-AS1; KCNMA1;
 ENSG00000247270; ENSG00000270019; ENSG00000270154; ENSG00000248445;
 ENSG00000234129; ENSG00000267169; ENSG00000261423; C1RL-AS1; NONOP2;
 SLC26A5; STX18-AS1; AMT; ENSG00000232626; ENSG00000235834; RN7SL648P;
 ENSG00000254634; ENSG00000236144; ACAP2-IT1; ENSG00000268472; TDRD6;
 ENSG00000272563; SUDS3P1; PCDHGB4; FOXO3B; ENSG00000272977;

LINC00176; MYO15A; GHRLOS; TTC28; ENSG00000271840; NBPF20; VANGL2;
JMJD7-PLA2G4B; ENSG00000267940; OGDHL; ENSG00000206195; KLF11;
TAPT1-AS1; TMEM59L; ACKR3; ENSG00000184441; KAT2A; SULT1A3; SIPA1L2;
RPL5P4; CTSF; ZNF208; CYP2E1; L3MBTL1; BENDS; ACACB; ENSG00000261087;
NFATC4; CES4A; ZFP2; BSN; ENSG00000254469; ZNF514; ENSG00000176593;
ENSG00000232116; OTX1; ENSG00000269918; AVIL; ENSG00000271971; MICU3;
GRAMD1A; C1QTNF6; KIF3C; ZACN; RPL7P46; PLA2G4F; SLX1A-SULT1A3;
ZNF135; OR2A9P; TMEM63C; TG; ENSG00000261502; ARLSB-AS1; ZNF705E;
PCDHGC5; GOLGA8A; PLEKHH1; PPAP2B; ENSG00000267481; OR7E7P;
ENSG00000259585; ENSG00000225210; TSSK1B; ENSG00000215022; STRC;
ENSG00000250290; UBAP1L; ENSG00000264112; LINC00959; SPATA41; CRYGS;
ZNF862; ENSG00000225032; PCED1B; SMAD6; ENSG00000264538; FRS3;
ENSG00000256139; NSUN5P1; LTBP4; ENSG00000267053; ENSG00000171282;
PCDHGA7; GREB1; ADAM1A; ENSG00000251323; ENSG00000271917;
ENSG00000253366; ENSG00000225241; IL11RA; PCDHB18; FAM85A; UPK3BP1;
ACADL; ENSG00000236055; ZNF285; and ENSG00000239665;
wherein Group B consists of:
LRP4; ZNF578; FAT2; FGFR3; MCC; SLC26A9; MKL2; AGKP1; KRT15; CSRNP3;
PKP1; FSTL3; NEURL1; JAG2; DACT2; TRO; NDRG1; ADCY2; IGSF3; NLGN4Y;
SALL2; SUSD4; ARSG; BCL11A; RNF165; TP63; UGT1A7; CACNA1A; PAPPA;
SULF2; RGS17; PIK3R1; SNX31; COL4A5; SNAI2; UGT1A5; SYNGR1;
ENSG00000213963; SV2A; FGFR2; KANK1; WNT5A; FZD7; SRRM3; SEMA5A;
ZNF471; HYKK; PPM1L; ARHGAP28; UGT1A8; ARHGEF10; MT1X; FOXN1;
NTF3; SMOC2; USP44; FBXL16; EPAS1; EGFR; PTPRG; NEB; GDNF-AS1;
FAM117B; RERG; ZBTB47; ADAMTS9-AS2; PAPLN; NCKAP5; STK32A; FAT4;
LGR6; TPTE2P1; SLITRK6; TNC; EVPLL; POMGNT1; KCTD15; WSCD1; KIF7;
KIF1A; FRAS1; KRT5; ENSG00000174171; CDH11; ZFP28; GPRASP1; PRKY;
COL4A6; LSAMP; SYDE1; ENSG00000271880; RGMA; BOC; SLC2A9; WNT2B;
CDHR1; ENSG00000248705; TGFB2; NCAM1; LTB4R; TLE2; AP3B2; LRRC2;
MEGF6; RNF212; FBLN1; SLCO4C1; WNT3A; ZNF665; ESYT3; FREM2;
ARHGEF4; LURAP1; SETP21; COL7A1; B4GALNT4; FBN1; ZNF90; LRP1B;
ABCC9; ENSG00000256995; S1PR5; EFS; NPTX1; ENSG00000260197; UGT1A2P;
SLC16A2; MAN1C1; MARVELD1; FGF9; CIB2; LGR5; KIRREL; LTB4R2; SPTB;
ITPRIPL1; PHLDB1; SPRY1; DEPTOR; EPHA4; TTTY10; TET1; ZNF667; EPHB6;
ENSG00000250685; ENSG00000271738; IGFBP4; ARHGEF25; TRPV6; KCNB2;
SPRY2; DLK2; and CLUL1;
wherein Group C consists of:
ENSG00000258545; ENSG00000257512; ASL; CCDC160; SMIM6; PLCB1;
TMEM125; C20orf201; CD38; ENSG00000268129; TSPAN2; DAPP1; IDH2; APOL4;
HRASLS2; C9orf66; BFSP1; DLG1-AS1; C16orf54; LAMP3; LYSMD2; PSMB9;
NR5A2; ENSG00000005189; COCH; CCDC67; XK; OR7E14P; LINC00589; F5;
PDE3A; RTP4; ENSG00000253474; ANTXR2; HCG4P3; FATE1; FBLN5;
ENSG00000259153; NMI; ENSG00000231901; PSMB8; SERF1A; MOCOS; GSTM1;
RAMP1; LINC00643; PRKG1; ENSG00000225335; LMO3; ENSG00000270659;
CNTF; ENSG00000272463; ENSG00000260552; FHL1; KIF18A; RARRES3;
TNFAIP8L3; PSMB10; ENSG00000227053; DPF1; GSTT2; TMEM176B; RPL7AP64;
CDKN2D; ENSG00000196826; MUC12; ENSG00000260806; GLIPR2; USP18;
ENSG00000238837; C19orf38; ABCC2; VWA5A; SGOL2; PKIB; KLB; TMEM200C;
and SHH;
wherein Group D consists of:
LINC00888; FBXO16; SCRN1; ENSG00000259508; LINC00467; MPC2; KIAA0895;
SEPW1; CALML4; ERICH2; SLC51B; FAM69A; ENSG00000259802;
ENSG00000249241; MRPS31; CCDC176; DUSP14; TMEM17; VIM-AS1; GSTP1;
CCT6B; RUVBL1; ENSG00000267325; AAED1; SLC25A4; C1orf192; DYRK3;
ELK3; ENSG00000272092; LINC00326; B9D2; LINC00240; IFT43; CPNE8; SMIM22;
PHTF1; C11orf70; APOO; SPAG1; CCDC65; DPCD; CCDC104; RABL5;
ENSG00000263450; DNPH1; ENSG00000234478; ENSG00000233170; LINC01132;
IQCK; ENSG00000257698; ROPN1L; AHSA1; C21orf59; C15orf65;
ENSG00000271133; IL7; LXN; DNAL4; C6orf99; MAPS; C1orf189; LINC00948;
DHX40; GFM2; LRRC34; SPA17; ENSG00000261465; C21orf119; TUBA1A; GJB7;
TOMM34; NUDT7; LINC00908; C10orf107; C20orf85; ARL3; DNAL1; CNTN5;
MYCBP; ENSG00000266916; ENSG00000260057; CYSTM1; ENSG00000236028;
UFC1; C9orf135; ENSG00000263011; DSTN; IFT57; C9orf116; MORN2; PPIL6;
LCA5L; DPY30; CEP97; AKAP14; ENSG00000272514; CAPSL; CC2D2A; OSCP1;
DYX1C1; PNLDC1; SPATA4; ZNF165; IGFBP7; CXorf58; C15orf26;
ENSG00000224049; TCTEX1D2; TCEAL3; ENSG00000258940; DYNC2LI1; and
PKIG; and
wherein Group E consists of:
C8orf76; DNAJC22; ENSG00000250508; SEC23B; SLC35B1; KRT23; MRPL47; NIP7;
NDUFV2; KCTD14; GTF3C6; ISOC2; SAP30; HSBP1; PSMA5; ENSG00000262823;

SEC61B; TIMM17A; CLIC5; RPN1; LACC1; MRPL54; PSMB5; UCHL3; C14orf166;
C2orf47; PPP1R2; C5orf15; DNAJA1; HIGD1A; MIF; RAB9A; CASP7; POMP;
SERHL2; BCCIP; GRK5; UBB; PARK7; CHCHD2; FAR2; DNAJC12; NT5C3A;
UFM1; CDK7; CCDC167; CCT2; MORF4L2; CALM2; C4orf19; PSENEN; HSPA8;
GTF2B; NDUFAB1; DAD1; SMS; KBTBD4; AGR3; GPR160; TCP1; PSMA3; STS;
LAMTOR5; COX17; UGCG; PSMA6; COX6A1; SLC41A2; HSP90B1; PDIA4; NXT2;
LACTB2; RFK; DYNLT1; COX7A2; BOLA3; MTFP1; FOLH1; PSMD10; NDUFB4;
MRPL39; C1orf122; MMADHC; SEC61G; NDUFB3; SSR4; NRIP1; ANG; WBP5;
ABRACL; BIK; MRPS36; MOSPD1; SLIRP; MRPL13; CD24P4; ENSG00000113811;
LINC00493; SOD1; IGFBP6; PRDX4; ACTR6; SDF2L1; C19orf10; IL23A; BZW1P2;
CXCL17; and USMG5.

2. The method of claim 1, wherein the sample obtained from the subject is a bronchial brushing or nasal brushing sample.

3. A method of treating airway dysfunction, the method comprising administering:
a) a chest CT, smoking cessation, and/or avoiding aspiration risk and inhalational injury to a subject determined to have a decreased level of expression of at least one of:
at least one gene of Group A, and at least one gene of Group B; and/or
an increased level of expression of at least one of:
at least one gene of Group C, at least one gene of Group D, and at least one gene of Group E;
b) an immunosuppressant and/or a more aggressive immunosuppressant regimen to a subject who had previously received and lung transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; or
c) an immunosuppressant and/or a more aggressive immunosuppressant regimen to a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E;
d) an inhibitor of dipeptidyl peptidase 1 (DPP1) to a subject who had previously received a bone marrow or blood stem cell transplant and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; and/or
e) an inhibitor of DPP1 to a subject who has chronic obstructive pulmonary disease (COPD), asthma, or rheumatoid arthritis and was determined to have a decreased level of expression of at least one of:
at least one gene of Group A, and at least one gene of Group B; and/or
an increased level of expression of at least one of:
at least one gene of Group C, at least one gene of Group D, and at least one gene of Group E; and
wherein a decreased level of expression is decreased relative to the level of the at least one gene in a population of subject who do not have or are not diagnosed as having, and/or do not exhibit signs or symptoms of airway dysfunction, and an increased level of expression is increased relative to the level of the at least one gene in a population of subject who do not have or are not diagnosed as having, and/or do not exhibit signs or symptoms of airway dysfunction;
wherein Group A consists of:
ZNF493; ZNF519; ENSG00000271430; MYH7B; MKRN5P; ENSG00000270574;
VN1R83P; ENSG00000268555; ZNF577; NBPF11; SCUBE2; SGK2; BNIPL;
ENSG00000271533; PCDHGB6; LRP1; PCDHGB7; ENSG00000262877; ABCC5;
PMS2134; TTC28-AS1; PRR24; CD81; RGL3; PTPRS; ENSG00000271011; ZNF286B;
GNB1L; PCDHGA12; SLC16A10; ZNF66; ENSG00000261584; ZNF311; ZNF718;
ENSG00000223745; RAB40A; ENSG00000268119; PCDHGA4; ENSG00000270589;
ENSG00000256142; DLL1; BRAFP1; PCDHGA11; FTX; FLYWCH1; NOVA1;
KANSL1; ZNF826P; ENSG00000196295; ENSG00000229036; TLE3; KLF8; LONRF2;
PCDHGB8P; ENSG00000259326; A0C2; RAPGEFL1; ARL10; ADAMTS10;
ENSG00000250303; TSHZ2; CRYM-AS1; ENSG00000213971; TVP23CP2;
ENSG00000234978; ZBTB12; PCDHGA9; RPS3AP29; KSR2; ENOSF1;
ENSG00000233175; ENSG00000260729; LINC00664; ZNF257; POU5F1P5; FN3K;
ZNF814; CYP2C19; ENSG00000270096; PDE11A; FAM13A-AS1; KCNMA1;
ENSG00000247270; ENSG00000270019; ENSG00000270154; ENSG00000248445;
ENSG00000234129; ENSG00000267169; ENSG00000261423; C1RL-AS1; NONOP2;
SLC26A5; STX18-AS1; AMT; ENSG00000232626; ENSG00000235834; RN7SL648P;
ENSG00000254634; ENSG00000236144; ACAP2-IT1; ENSG00000268472; TDRD6;
ENSG00000272563; SUDS3P1; PCDHGB4; FOXO3B; ENSG00000272977;
LINC00176; MY015A; GHRLOS; TTC28; ENSG00000271840; NBPF20; VANGL2;
JMID7-PLA2G4B; ENSG00000267940; OGDHL; ENSG00000206195; KLF11;
TAPT1-AS1; TMEM59L; ACKR3; ENSG00000184441; KAT2A; SULT1A3; SIPA1L2;
RPL5134; CTSF; ZNF208; CYP2E1; L3MBTL1; BEND5; ACACB; ENSG00000261087;
NFATC4; CES4A; ZFP2; BSN; ENSG00000254469; ZNF514; ENSG00000176593;
ENSG00000232116; OTX1; ENSG00000269918; AVIL; ENSG00000271971; MICU3;
GRAMD1A; C1QTNF6; KIF3C; ZACN; RPL7P46; PLA2G4F; SLX1A-SULT1A3;

ZNF135; OR2A9P; TMEM63C; TG; ENSG00000261502; ARL5B-AS1; ZNF705E;

PCDHGC5; GOLGA8A; PLEKH111; PPAP2B; ENSG00000267481; OR7E71P;

ENSG00000259585; ENSG00000225210; TSSK1B; ENSG00000215022; STRC;

ENSG00000250290; UBAP1L; ENSG00000264112; LINC00959; SPATA41; CRYGS;

ZNF862; ENSG00000225032; PCED1B; SMAD6; ENSG00000264538; FRS3;

ENSG00000256139; NSUN5P1; LTB134; ENSG00000267053; ENSG00000171282;

PCDHGA7; GREB1; ADAM1A; ENSG00000251323; ENSG00000271917;

ENSG00000253366; ENSG00000225241; IL11RA; PCDHB18; FAM85A; UPK3BP1;

ACADL; ENSG00000236055; ZNF285; and ENSG00000239665;

wherein Group B consists of:
LRP4; ZNF578; FAT2; FGFR3; MCC; SLC26A9; MKL2; AGKP1; KRT15; CSRNP3;
PKP1; FSTL3; NEURL1; JAG2; DACT2; TRO; NDRG1; ADCY2; IGSF3; NLGN4Y;
SALL2; SUSD4; ARSG; BCL11A; RNF165; TP63; UGT1A7; CACNA1A; PAPPA;
SULF2; RGS17; PIK3R1; SNX31; COL4A5; SNAI2; UGT1A5; SYNGR1;
ENSG00000213963; SV2A; FGFR2; KANK1; WNT5A; FZD7; SRRM3; SEMA5A;
ZNF471; HYKK; PPM1L; ARHGAP28; UGT1A8; ARHGEF10; MT1X; FOXN1;
NTF3; SMOC2; USP44; FBXL16; EPAS1; EGFR; PTPRG; NEB; GDNF-AS1;
FAM117B; RERG; ZBTB47; ADAMTS9-AS2; PAPLN; NCKAP5 STK32A; FAT4;
LGR6; TPTE2P1; SLITRK6; EVPLL; POMGNT1; KCTD15; WSCD1; KIF7; KIF1A;
FRAS1; KRT5 ENSG00000174171; CDH11; ZFP28; GPRASP1; PRKY; COL4A6;
LSAMP; SYDE1; ENSG00000271880; RGMA; BOC; SLC2A9; WNT2B; CDHR1;
ENSG00000248705; TGFB2; NCAM1; LTB4R; TLE2; AP3B2; LRRC2; MEGF6;
RNF212; FBLN1; SLCO4C1; WNT3A; ZNF665; ESYT3; FREM2; ARHGEF4;
LURAP1; SETP21; COL7A1; B4GALNT4; FBN1; ZNF90; LRP1B; ABCC9;
ENSG00000256995; S1PR5; EFS; NPTX1; ENSG00000260197; UGT1A2P; SLC16A2;
MAN1C1; MARVELD1; FGF9; CIB2; LGR5; KIRREL; LTB4R2; SPTB; ITPRIPL1;
PHLDB1; SPRY1; DEPTOR; EPHA4; TTTY10; TET1; ZNF667; EPHB6;
ENSG00000250685; ENSG00000271738; IGFBP4; ARHGEF25; TRPV6; KCNB2;
SPRY2; DLK2; and CLUL1;

wherein Group C consists of:
ENSG00000258545; ENSG00000257512; ASL; CCDC160; SMIM6; PLCB1;
TMEM125; C20orf201; CD38; ENSG00000268129; TSPAN2; DAPP1; IDH2; APOL4;
HRASLS2; C9orf66; BFSP1; DLG1-AS1; C16orf54; LAMP3; LYSMD2; PSMB9;
NR5A2; ENSG00000005189; COCH; CCDC67; XK; OR7E14P; LINC00589; F5;
PDE3A; RTP4; ENSG00000253474; ANTXR2; HCG4P3; FATE1; FBLN5

ENSG00000259153; NMI; ENSG00000231901; PSMB8 SERF1A; MOCOS; GSTM1;
RAMP1; LINC00643; PRKG1; ENSG00000225335; ENSG00000270659; CNTF;
ENSG00000272463; ENSG00000260552; FHL1; KIF18A; RARRES3; TNFAIP8L3;
PSMB10; ENSG00000227053; DPF1; GSTT2; TMEM176B; RPL7AP64; CDKN2D;
ENSG00000196826; MUC12; ENSG00000260806; GLIPR2; USP18;
ENSG00000238837; C19orf38; ABCC2; VWA5A; SGOL2; PKIB; KLB; TMEM200C;
and SHH;

wherein Group D consists of:
LINC00888; FBX016; SCRN1; ENSG00000259508; LINC00467; MPC2; KIAA0895;
SEPW1; CALML4; ERICH2; SLC51B; FAM69A; ENSG00000259802;
ENSG00000249241; MRPS31; CCDC176; DUSP14; TMEM17; VIM-AS1; GSTP1;
CCT6B; RUVBL1; ENSG00000267325; AAED1; SLC25A4; C1orf192; DYRK3;
ELK3; ENSG00000272092; LINC00326; B9D2; LINC00240; IFT43; CPNE8; SMIM22;
PHTF1; C11orf70; APOO; SPAG1; CCDC65; DPCD; CCDC104; RABL5;
ENSG00000263450; DNPH1; ENSG00000234478; ENSG00000233170; LINC01132;
IQCK; ENSG00000257698; ROPN1L; AHSA1; C21orf59; C15orf65;
ENSG00000271133; IL7; LXN; DNAL4; C6orf99; MAPS; C1orf189; LINC00948;
DHX40; GFM2; LRRC34; SPA17; ENSG00000261465; C21orf119; TUBA1A; GJB7;
TOMM34; NUDT7; LINC00908; C10orf107; C20orf85; ARL3; DNAL1; CNTN5
MYCBP; ENSG00000266916; ENSG00000260057; CYSTM1; ENSG00000236028;
UFC1; C9orf135; ENSG00000263011; DSTN; IFT57; C9orf116; MORN2; PPIL6;
LCA5L; DPY30; CEP97; AKAP14; ENSG00000272514; CAPSL; CC2D2A; OSCP1;
DYX1C1; PNLDC1; SPATA4; ZNF165; IGFBP7; CXorf58; C15orf26;
ENSG00000224049; TCTEX1D2; TCEAL3; ENSG00000258940; DYNC2l11; and
PKIG; and wherein Group E consists of:
C8orf76; DNAJC22; ENSG00000250508; SEC23B; SLC35B1; KRT23; MRPL47; NIP7;
NDUFV2; KCTD14; GTF3C6; ISOC2; SAP30; HSBP1; PSMA5; ENSG00000262823;
SEC61B; TIMM17A; CLIC5; RPN1; LACC1; MRPL54; PSMB5; UCHL3; C14orf166;
C2orf47; PPP1R2; C5orf15; DNAJA1; HIGD1A; MIF; RAB9A; CASP7; POMP;
SERHL2; BCCIP; GRK5; UBB; PARK7; CHCHD2; FAR2; DNAJC12; NT5C3A;
UFM1; CDK7; CCDC167; CCT2; MORF4L2; CALM2; C4orf19; PSENEN; HSPA8;
GTF2B; NDUFAB1; DAD1; SMS; KBTBD4; AGR3; GPR160; TCP1; PSMA3; STS;
LAMTOR5 COX17; UGCG; PSMA6; COX6A1; SLC41A2; HSP90B1; PDIA4; NXT2;
LACTB2; RFK; DYNLT1; COX7A2; BOLA3; MTFP1; FOLH1; PSMD10; NDUFB4;

MRPL39; C1orf122; MMADHC; SEC61G; NDUFB3; SSR4; NRIP1; ANG; WBP5
ABRACL; BIK; MRPS36; MOSPD1; SLIRP; MRPL13; CD24P4; ENSG00000113811;
LINC00493; SOD1; IGFBP6; PRDX4; ACTR6; SDF2L1; C19orf10; IL23A; BZW1P2;
CXCL17; and USMG5; and
wherein the airway dysfunction is COPD, asthma, bronchiolitis, bronchiectasis, lung transplant rejection, rheumatoid arthritis, graft versus host disease (GvHD), or autoimmune pneumonitis.

4. The method of claim 3, wherein the subject is determined to have a decreased level of expression of one or more genes selected from Group B and/or an increased level of expression of one or more genes selected from Group C; wherein a decreased level of expression is decreased relative to the level of the at least one gene in a population of subject who do not have or are not diagnosed as having, and/or do not exhibit signs or symptoms of airway dysfunction, and an increased level of expression is increased relative to the level of the at least one gene in a population of subject who do not have or are not diagnosed as having, and/or do not exhibit signs or symptoms of airway dysfunction.

5. The method of claim 3, wherein the DPP1 inhibitor is AZD7986.

6. The method of claim 3, wherein the airway dysfunction is bronchial enlargement or dilation.

7. The method of claim 3, wherein the level of expression is the level in a sample obtained from the subject.

8. The method of claim 7, wherein the sample is a bronchial brushing, nasal brushing, sputum, or peripheral blood sample.

9. The method of claim 1, wherein the method comprises determining the level of expression of, at least one gene of Group A, at least one gene of Group B, at least one gene of Group C, at least one gene of Group D, and at least one gene of Group E.

10. The method of claim 1, wherein the method comprises determining the level of expression of, at least one gene of Group A, at least one gene of Group C, at least one gene of Group D, and at least one gene of Group E.

11. The method of claim 1, wherein the method comprises determining the level of expression of, at least one gene of Group A, at least one gene of Group C, and at least one gene of Group E.

12. The method of claim 1, wherein the method comprises determining the level of expression of, at least one gene of Group B and at least one gene of Group C.

13. The method of claim 1, wherein the at least one gene of Group A comprises at least one of: Zinc Finger Protein 493 (ZNF493) and Zinc Finger Protein 519 (ZNF519).

14. The method of claim 1, wherein the at least one gene of Group A is comprises ZNF493 and ZNF519.

15. The method of claim 1, wherein the at least one gene of Group A is comprises ZNF493.

16. The method of claim 1, wherein the at least one gene of Group B comprises is at least one of: Low Density Lipoprotein Receptor Related Protein 4 (LRP4) and Fat Atypical Cadherin 2 (FAT2).

17. The method of claim 1, wherein the at least one gene of Group B comprises LRP4 and FAT2.

18. The method of claim 1, wherein the at least one gene of Group C comprises at least one of: Argininosuccinate Lyase (ASL) and Coiled-Coil Domain Containing 160 (CCDC160).

19. The method of claim 1, wherein the at least one gene of Group C comprises ASL and CCDC160.

20. The method of claim 1, wherein the at least one gene of Group C comprises ASL.

21. The method of claim 1, wherein the at least one gene of Group D comprises at least one of: Long Intergenic Non-Protein Coding RNA 888 (LINC00888) and F-Box Protein 16 (FBXO16).

22. The method of claim 1, wherein the at least one gene of Group D comprises LINC00888 and FBXO16.

23. The method of claim 1, wherein the at least one gene of Group D comprises LINC00888.

24. The method of claim 1, wherein the at least one gene of Group E comprises at least one of: Chromosome 8 Open Reading Frame 76 (C8orf76) and DnaJ Heat Shock Protein Family Member C22 (DNAJC22).

25. The method of claim 1, wherein the at least one gene of Group E comprises C8orf76 and DNAJC22.

26. The method of claim 1, wherein the at least one gene of Group E comprises C8orf76.

27. The method of claim 1, wherein the level of expression is the level of mRNA.

28. The method of claim 3, wherein the sample obtained from the subject is a bronchial brushing or nasal brushing sample.

* * * * *